US008222404B2

(12) United States Patent
Dragovich et al.

(10) Patent No.: US 8,222,404 B2
(45) Date of Patent: Jul. 17, 2012

(54) [1,2,4]THIADIAZIN-3-YL ACETIC ACID COMPOUND AND METHODS OF MAKING THE ACETIC ACID COMPOUND

(75) Inventors: Peter Dragovich, San Diego, CA (US); Douglas Eric Murphy, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/349,705

(22) Filed: Jan. 13, 2012

(65) Prior Publication Data

US 2012/0116077 A1    May 10, 2012

Related U.S. Application Data

(62) Division of application No. 12/481,391, filed on Jun. 9, 2009, now Pat. No. 8,097,613.

(60) Provisional application No. 61/091,620, filed on Aug. 25, 2008, provisional application No. 61/060,295, filed on Jun. 10, 2008.

(51) Int. Cl.
*C07D 513/04* (2006.01)

(52) U.S. Cl. .......................................... 544/10; 544/12

(58) Field of Classification Search ................... 544/10, 544/12
See application file for complete search history.

(56) References Cited

U.S. PATENT DOCUMENTS

| | | | |
|---|---|---|---|
| 6,329,367 B1 * | 12/2001 | Hansen et al. | ............. 514/222.8 |
| 7,582,626 B2 | 9/2009 | Tran et al. | |
| 7,834,009 B2 | 11/2010 | Ellis et al. | |
| 7,939,524 B2 | 5/2011 | Tran et al. | |
| 2005/0075331 A1 | 4/2005 | Pratt et al. | |
| 2005/0153877 A1 | 7/2005 | Miao et al. | |
| 2006/0040927 A1 | 2/2006 | Blake et al. | |
| 2006/0189602 A1 | 8/2006 | Zhou et al. | |
| 2006/0211695 A1 | 9/2006 | Borzilleri et al. | |
| 2006/0252785 A1 | 11/2006 | Blake et al. | |

FOREIGN PATENT DOCUMENTS

| | | |
|---|---|---|
| WO | WO 01/85172 | 11/2001 |
| WO | WO 02/098424 | 12/2002 |
| WO | WO 03/059356 | 7/2003 |
| WO | WO 2006/066079 | 6/2006 |
| WO | WO 2006115221 | 11/2006 |

OTHER PUBLICATIONS

U.S. Appl. No. 11/766,668, filed Apr. 17, 2008, Ellis et al.
U.S. Appl. No. 11/898,334, filed Nov. 6, 2008, Zhou et al.
U.S. Appl. No. 11/861,678, filed Aug. 7, 2008, Dragovich et al.
U.S. Appl. No. 11/955,144, filed Apr. 30, 2009, Tran et al.
U.S. Appl. No. 11/955,193, filed Sep. 4, 2008, Ruebsam et al.
U.S. Appl. No. 12/048,933, filed Sep. 18, 2008, Ruebsam et al.
U.S. Appl. No. 12/061,499, filed Feb. 11, 2010, Tran et al.
U.S. Appl. No. 11/845,515, filed Mar. 5, 2009, Ellis et al.
Wang et al., "Non-nucleoside Analogue Inhibitors Bind to an Allosteric Site on HCV NS5B Polymerase," The Journal of Biological Chemistry, vol. 278, No. 11, pp. 9489-9495, Mar. 14, 2003, Abstract; p. 9491-9493.
International Search Report for WO 2009/152166 (PCT/US09/46772) dated Oct. 15, 2009.
Pogam et al., Selection and Characterization of Replicon Variants Dually Resistant to Thumb- and Palm-Binding Nonnucleoside Polymerase Inhibitors of the Hepatitis C Virus, Journal of Virology, Jun. 2006, vol. 80, No. 12, pp. 6146-6154.
Int'l Search Report and Written Opinion of Int'l Appl. No. PCT/US08/59164 dated Jun. 27, 2008.
Int'l Search Report of Int'l Appl. No. PCT/US05/45588 dated Oct. 13, 2006.
Tedesco et al., 3-(1,2,4)-benzothiadiazin-3-yl-4-hydroxy-2(1H)-quinolines, Potent Inhibitors of Hepatitis C Virus RNA-Dependent RNA Polymerase, J. Med. Chem. 49:971-983 (2006).
Int'l Search Report and Written Opinion of Int'l Appl. No. PCT/US07/87272 dated Apr. 16, 2008.
Int'l Search Report and Written Opinion of Int'l Appl. No. PCT/US07/87288 dated Apr. 17, 2008.
Fisyuk et al., Synthesis of 5,6-Dihydropyridin-2(1H)-ones, 1,5,6,8,8a-Hexahydroisoquinolin-3(2H)-ones and 4a,5,6,7,8,8a-Hexahydroquinolin-2(1H)-ones by Intramolecular Wittig Reaction. Molecules, Feb. 28, 2002, vol. 7, pp. 124-128.

* cited by examiner

*Primary Examiner* — Kahsay T Habte
(74) *Attorney, Agent, or Firm* — Connolly Bove Lodge & Hutz LLP

(57) ABSTRACT

The invention is directed to a [7-methanesulfonylamino-methyl)-1,1-dioxo-1,4-dihydro-1$\lambda^6$-thieno[2,3-e][1,2,4]thiadiazin-3-yl]-acetic acid compound and to methods of making the same.

10 Claims, No Drawings

[1,2,4]THIADIAZIN-3-YL ACETIC ACID COMPOUND AND METHODS OF MAKING THE ACETIC ACID COMPOUND

This application is a divisional of U.S. application Ser. No. 12/481,391 which claims the benefit of U.S. Provisional Application No. 61/060,295 filed Jun. 10, 2008 and U.S. Provisional Application No. 61/091,620 filed Aug. 25, 2008, both of which are hereby incorporated in their entireties.

FIELD OF THE INVENTION

The invention is directed to [1,2,4]thiadiazine 1,1-dioxide compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately $10,000/year. These drugs have difficult dosing problems and side-effects that preclude their use in almost half of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; approximately one third of patients do not respond. Of those who do respond, a large fraction relapses within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects.

A number of publications have described NS5B inhibitors useful in the treatment of hepatitis C infection. See, e.g., U.S. Patent Application Publication No. US 2008/0031852 (describing [1,2-b]pyridazinone compounds); U.S. Patent Application Publication No. US 2006/0189602 (disclosing certain pyridazinones); U.S. Patent Application Publication No. US 2006/0252785 (disclosing selected heterocyclics); and International Publication Nos. WO 03/059356, WO 02/098424, and WO 01/85172 (each describing a particular class of substituted thiadiazines).

While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel [1,2,4]thiadiazine 1,1-dioxide compounds and pharmaceutically acceptable salts thereof, which are useful in treating or preventing a hepatitis C virus infection in a patient in need thereof comprising administering to the patient a therapeutically or prophylactically effective amount of a [1,2,4]thiadiazine 1,1-dioxide compound.

In a general aspect, the invention relates to compounds of Formula I

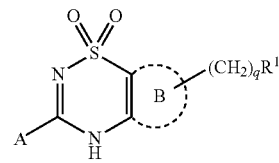

wherein

Ring B is

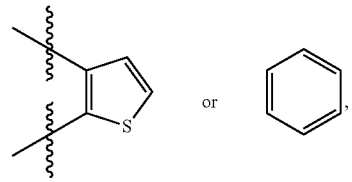

A is

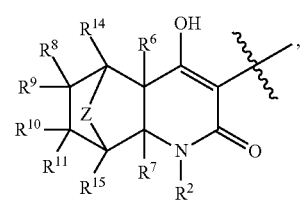

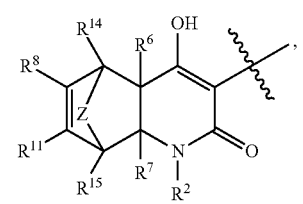

II(c)

II(d)

II(e)

$R^1$ is H, halo, hydroxy, —$CHR^3$—$S(O)_2R^4$, —$C(S(O)_2R^4)$=$CHR^3$—, —$NR^4R^5$, —$NR^3S(O)_2R^4$, or —$NR^3S(O)_2NR^4R^5$, wherein $R^3$, $R^4$, and $R^5$ are independently H, $C_1$-$C_6$ alkyl, $C_3$-$C_8$ cycloalkyl, C(O)O—($C_1$-$C_6$ alkyl), aryl, or heterocyclyl, or $R^3$ and $R^4$ or $R^4$ and $R^5$ combine with the atom(s) to which they are attached to form a 5- or 6-membered heterocyclyl ring, $R^2$ is H, $C_1$-$C_6$ alkyl, $C_3$-$C_8$ cycloalkyl, —$C_1$-$C_6$ alkylene($C_3$-$C_8$ cycloalkyl), —$C_1$-$C_6$ alkylene(aryl), —$C_1$-$C_6$ alkylene(heterocyclyl), aryl, or heterocyclyl, or —$NR^{16}R^{17}$, wherein $R^{16}$ and $R^{17}$ are independently H, $C_1$-$C_6$ alkyl, $C_3$-$C_8$ cycloalkyl, or $C_2$-$C_6$ alkenyl, Z is —$(CR^{12}R^{13})_n$—, or O, n is 1, 2 or 3, Y is —$(CR^{12}R^{13})_m$—, m is 2, 3, or 4, q is 0 or 1, provided that when q is 0, then $R^2$ is —$NR^{16}R^{17}$, Ring B is phenyl and A is not II(c), II(d) or II (e), $R^6$ and $R^7$ are independently H or $C_1$-$C_6$ alkyl, $R^8$, $R^9$, $R^{10}$, $R^{11}$, $R^{12}$, $R^{13}$, $R^{14}$, and $R^{15}$ are independently H, $C_1$-$C_6$ alkyl, hydroxy, or halo, or $R^8$ and $R^{10}$ or $R^8$ and $R^{11}$ or $R^9$ and $R^{10}$ or $R^9$ and $R^{11}$ can combine with the atom(s) to which they are attached to form a 3- to 6-membered cycloalkyl ring when A is II(a), or $R^{12}$ and $R^{13}$ can combine with the atom(s) to which they are attached to form a 3- to 6-membered spirocyclic ring when Z is —$(CR^{12}R^{13})_n$—and n is 1, or $R^{12}$ and $R^{13}$ can combine with the atom(s) to which they are attached to form a 3- to 6-membered cycloalkyl ring when Z is —$(CR^{12}R^{13})_n$— and n is 2, $R^{18}$, $R^{19}$, $R^{20}$, and $R^{21}$ are independently H, halo, cyano, hydroxyl, $C_1$-$C_6$ hydroxyalkyl, $C_1$-$C_6$ alkoxy, amino, $C_1$-$C_6$ alkylamine, $C_1$-$C_6$ dialkylamine, $C_1$-$C_6$ alkyl, $C_3$-$C_8$ cycloalkyl, $C_1$-$C_6$ alkylene(cycloalkyl), $C_2$-$C_6$ alkenyl, $C_2$-$C_6$ alkynyl, aryl, $C_1$-$C_6$ alkylene(aryl), heterocyclyl, or $C_1$-$C_6$ alkylene(heterocyclyl), or $R^{18}$ and $R^{19}$ or $R^{20}$ and $R^{21}$ can combine with the atom(s) to which they are attached to form a 3- to 6-membered spiro cycloalkyl ring, or $R^{20}$ and $R^2$ or $R^{21}$ and $R^2$ can combine with the atom(s) to which they are attached to form a 4- to 6-membered heterocyclyl ring, $R^{22}$ is H, $C_1$-$C_6$ alkyl, $C_3$-$C_8$ cycloalkyl, aryl, or heterocyclyl, wherein the above alkyl, alkylene, aryl, cycloalkyl, or heterocyclyl moieties provided in $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, keto, nitro, —C(O)OH, —C(O)$NH_2$, —C(O)($C_1$-$C_6$ alkylamine), —C(O)($C_1$-$C_6$ dialkylamine), —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl, wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, or a pharmaceutically acceptable salt, hydrate, solvate, tautomer or stereoisomer thereof.

In one embodiment, the invention relates to compounds of Formula I wherein $R^1$ is —$NR^3S(O)_2R^4$ and $R^3$ and $R^4$ are independently H, $C_1$-$C_6$ alkyl or $C_3$-$C_8$ cycloalkyl.

In another embodiment, the invention relates to compounds of Formula I wherein $R^1$ is In one embodiment, the invention relates to compounds of Formula I wherein q is 1 and $R^2$ is selected from

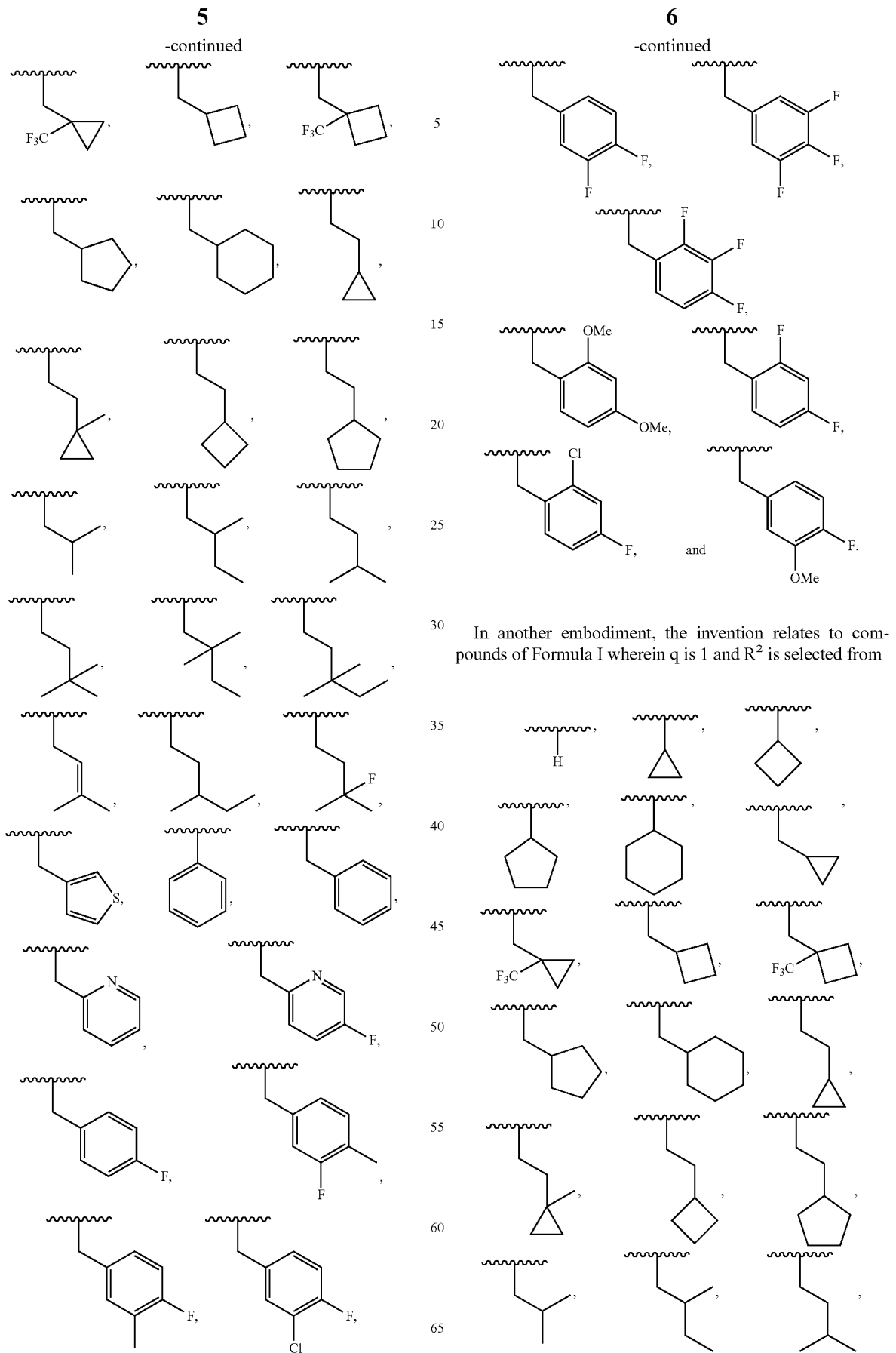
In another embodiment, the invention relates to compounds of Formula I wherein q is 1 and R² is selected from

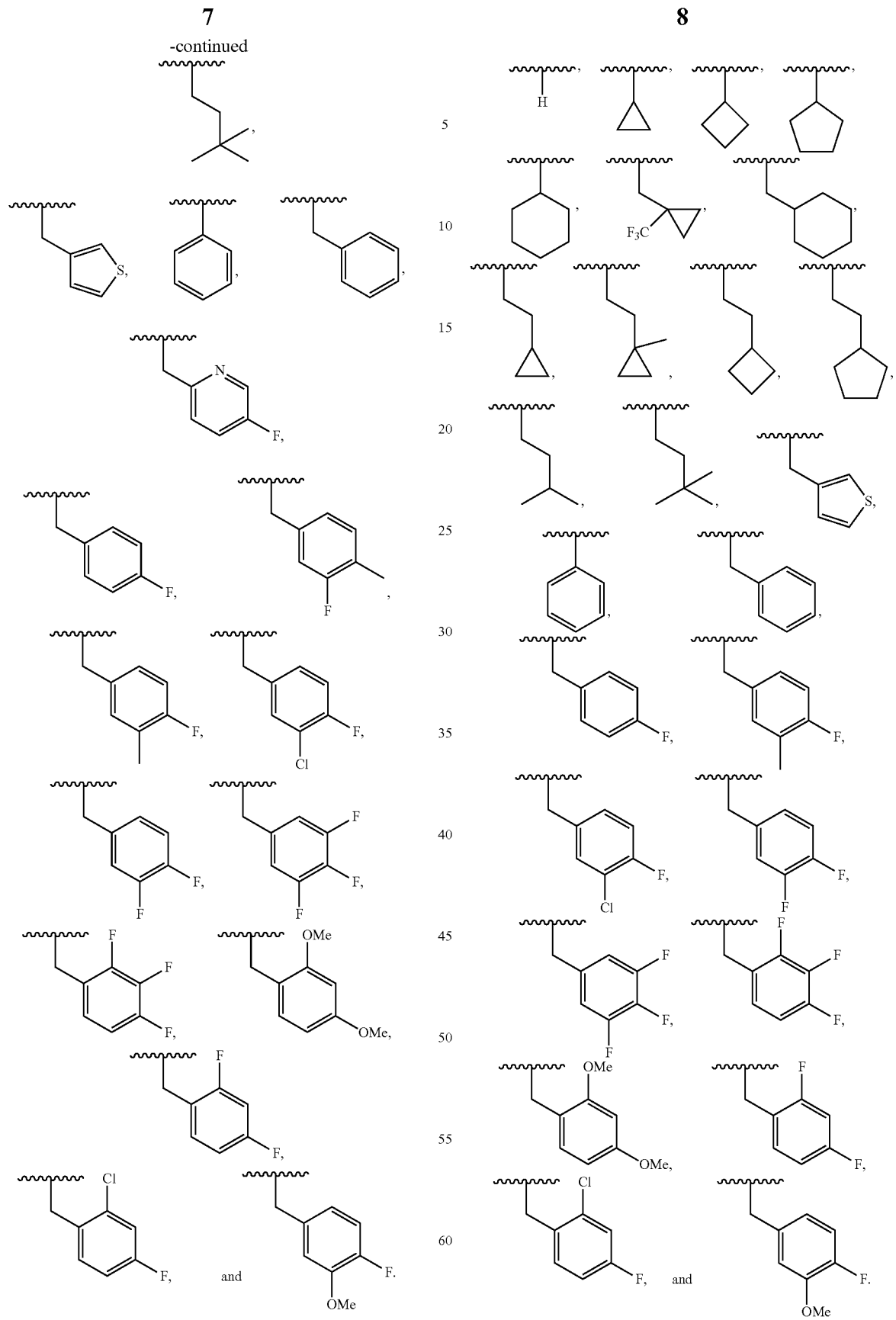
In yet another embodiment, the invention relates to compounds of Formula I wherein q is 1 and $R^2$ is selected from
In one embodiment, the invention relates to compounds of Formula I wherein q is 0 and $R^2$ is selected from

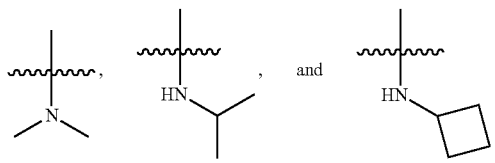

In another embodiment, the invention relates to compounds of Formula I wherein q is 0 and $R^2$ is

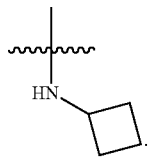

In one embodiment, the invention relates to compounds of Formula I wherein $R^6$ and $R^7$ are H.

In one embodiment, the invention relates to compounds of Formula I wherein $R^8$, $R^9$, $R^{10}$, $R^{11}$, $R^{12}$, $R^{13}$, $R^{14}$, and $R^{15}$ are independently selected from

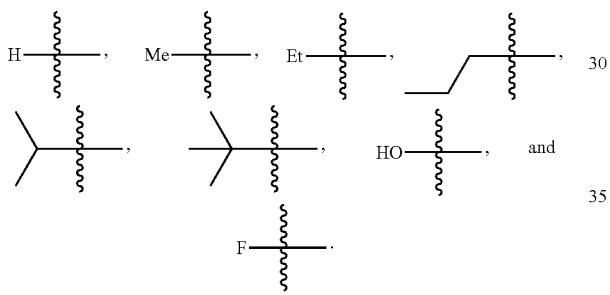

In another embodiment, the invention relates to compounds of Formula I wherein $R^8$, $R^9$, $R^{10}$, $R^{11}$, $R^{12}$, $R^{13}$, $R^{14}$, and $R^{15}$ are H.

In a further embodiment, the invention relates to compounds of Formula I wherein A is II(a) and $R^8$ and $R^{10}$ or $R^8$ and $R^{11}$ or $R^9$ and $R^{10}$ or $R^9$ and $R^{11}$ can combine with the atom(s) to which they are attached to form a 3-membered cycloalkyl ring.

In a yet another embodiment, the invention relates to compounds of Formula I wherein Z is $-(CR^{12}R^{13})_n-$, and n is 2 and $R^{12}$ and $R^{13}$ can combine with the atom(s) to which they are attached to form a 3-membered cycloalkyl ring, In one embodiment, the invention relates to compounds of Formula I wherein $R^{18}$, $R^{19}$, $R^{20}$, and $R^{21}$ are independently H, halo, cyano, $C_1-C_6$ hydroxyalkyl, $C_1-C_6$ alkoxy, $C_1-C_6$ alkyl, $C_3-C_8$ cycloalkyl, $C_1-C_6$ alkylene(cycloalkyl), $C_2-C_6$ alkenyl, $C_2-C_6$ alkynyl, aryl, $C_1-C_6$ alkylene(aryl), heterocyclyl, or $C_1-C_6$ alkylene(heterocyclyl), or $R^{18}$ and $R^{19}$ or $R^{20}$ and $R^{21}$ can combine with the atom(s) to which they are attached to form a 3- to 6-membered spiro cycloalkyl ring, or $R^{20}$ and $R^2$ or $R^{21}$ and $R^2$ can combine with the atom(s) to which they are attached to form a 4- to 6-membered heterocyclyl ring.

In another embodiment, the invention relates to compounds of Formula I wherein $R^{18}$, $R^{19}$, $R^{20}$, and $R^{21}$ are independently selected from

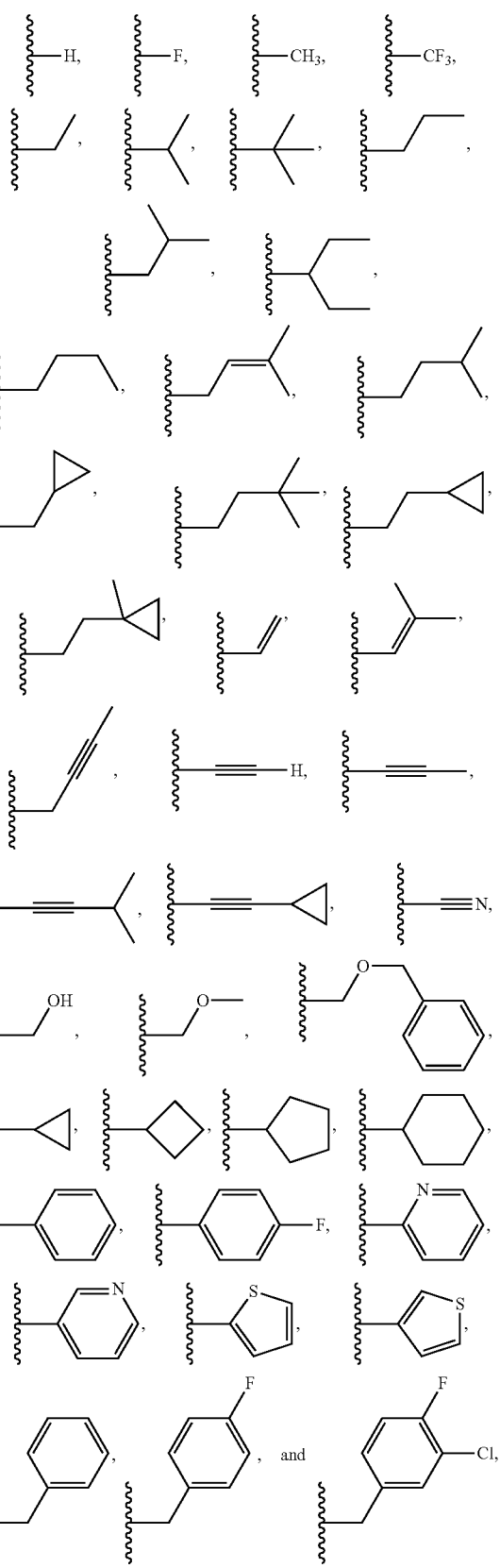

or $R^{18}$ and $R^{19}$ or $R^{20}$ and $R^{21}$ can combine with the atom(s) to which they are attached to form spiro rings selected from

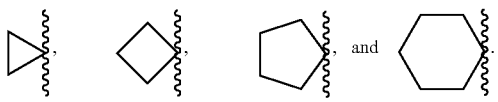

In a further embodiment, the invention relates to compounds of Formula I wherein $R^{18}$, $R^{19}$, $R^{20}$, and $R^{21}$ are independently selected from

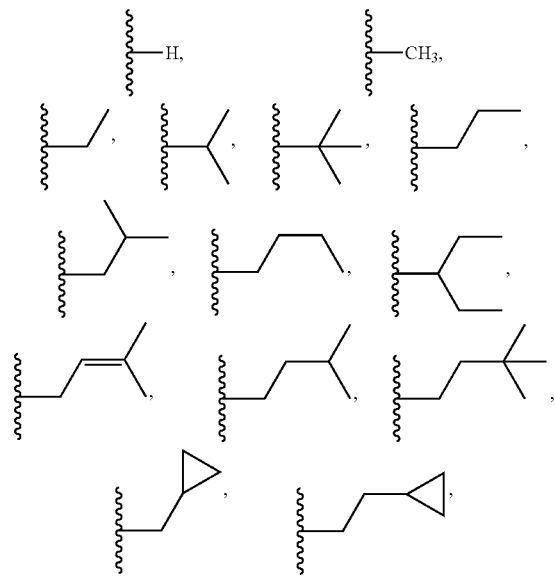

or $R^{18}$ and $R^{19}$ or $R^{20}$ and $R^{21}$ can combine with the atom(s) to which they are attached to form spiro rings selected from

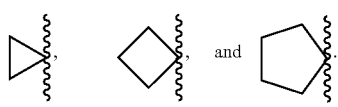

In a further embodiment, the invention relates to compounds of Formula I wherein $R^{18}$, $R^{19}$, $R^{20}$, and $R^{21}$ are independently selected from

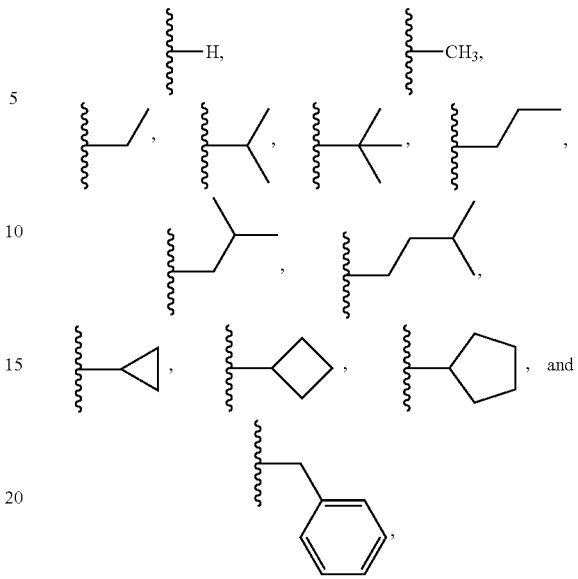

or $R^{18}$ and $R^{19}$ or $R^{20}$ and $R^{21}$ can combine with the atom(s) to which they are attached to form spiro rings selected from

In yet another embodiment, the invention relates to compounds of Formula I wherein $R^{20}$ and $R^2$ or $R^{21}$ and $R^2$ combine to form a 4- to 6-membered heterocyclyl ring.

In one embodiment, the invention relates to compounds of Formula I wherein $R^{22}$ is $C_1$-$C_6$ alkyl, $C_3$-$C_8$ cycloalkyl, aryl, or heterocyclyl, In another embodiment, the invention relates to compounds of Formula I wherein $R^{22}$ is

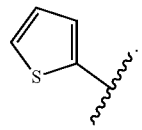

In another embodiment, the invention relates to compounds selected from (1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-methanesulfonamide;

(rac-cis)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-thieno[2,3-e][1,2,4]thiadiazin-7-ylmethyl}-methanesulfonamide;

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-ylmethyl}-methanesulfonamide;

rac-N-{3-[6-Cyclopropyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-2-oxo-6-propyl-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[6-Cyclobutyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-6-isobutyl-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-6-isopropyl-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[6-Cyclopentyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-5-methyl-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

N-{3-[5-(4-Fluoro-benzyl)-8-hydroxy-6-oxo-5-aza-spiro[2.5]oct-7-en-7-yl]-1,1-dioxo-1,4-dihydro-1$\lambda^6$-thieno[2,3-e][1,2,4]thiadiazin-7-ylmethyl}-methanesulfonamide;

rac-N-{3-[5-Benzyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-5-isopropyl-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[5-tert-Butyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-2-oxo-5-propyl-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[5-Cyclopentyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-(4-Fluoro-benzyl)-4-hydroxy-5-isobutyl-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[5-Ethyl-1-(4-fluoro-benzyl)-4-hydroxy-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-Cyclopropyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-Cyclobutyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

rac-N-{3-[1-Cyclopentyl-4-hydroxy-5-methyl-5-(3-methyl-butyl)-2-oxo-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

(rac-di-endo)-N-{3-[3-(4-Fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1$\lambda^6$-thieno[2,3-e][1,2,4]thiadiazin-7-ylmethyl}-methanesulfonamide;

(rac-di-exo)-N-{3-[3-(4-Fluoro-benzyl)-6-hydroxy-4-oxo-3-aza-tetracyclo [6.3.2.0$^{2,7}$.0$^{9,11}$]tridec-5-en-5-yl]-1,1-dioxo-1,4-dihydro-1$\lambda^6$-thieno[2,3-e][1,2,4]thiadiazin-7-ylmethyl}-methanesulfonamide;

(rac-di-endo)-N-{3-[3-(3,3-Dimethyl-butyl)-6-hydroxy-4-oxo-3-aza-tetracyclo [6.3.2.0$^{2,7}$.0$^{9,11}$]tridec-5-en-5-yl]-1,1-dioxo-1,4-dihydro-1$\lambda^6$-thieno[2,3-e][1,2,4]thiadiazin-7-ylmethyl}-methanesulfonamide;

(rac-di-exo)-N-{3-[3-(3,3-Dimethyl-butyl)-6-hydroxy-4-oxo-3-aza-tetracyclo [6.3.2.0$^{2,7}$.0$^{9,11}$]tridec-5-en-5-yl]-1,1-dioxo-1,4-dihydro-1$\lambda^6$-thieno[2,3-e][1,2,4]thiadiazin-7-ylmethyl}-methanesulfonamide;

N-{3-[(1R,2S,7R,8S)-3-(2-Cyclobutyl-ethyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-methanesulfonamide;

(rac-cis)-N-[3-(1-Cyclobutylamino-4-hydroxy-2-oxo-2,4a,5,6,7,7a-hexahydro-1H-[1]pyrindin-3-yl)-1,1-dioxo-1,4-dihydro-1$\lambda^6$-thieno[2,3-e][1,2,4]thiadiazin-7-ylmethyl]-methanesulfonamide;

N-{3-[5-Hydroxy-2-(3-methyl-butyl)-3-oxo-6-thiophen-2-yl-2,3-dihydro-pyridazin-4-yl]-1,1-dioxo-1,4-dihydro-1$\lambda^6$-thieno[2,3-e][1,2,4]thiadiazin-7-ylmethyl}-methanesulfonamide;

N-{3-[(1R,2S,7R,8S)-6-Hydroxy-4-oxo-3-(1-trifluoromethyl-cyclopropylmethyl)-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-methanesulfonamide;

N-{3-[(1R,2S,7R,8S)-3-(2-Cyclopentyl-ethyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-methanesulfonamide;

N-{3-[4-Hydroxy-5-methyl-5-(3-methyl-butyl)-2-oxo-1-phenyl-1,2,5,6-tetrahydro-pyridin-3-yl]-1,1-dioxo-1,4-dihydro-1$\lambda^6$-thieno[2,3-e][1,2,4]thiadiazin-7-ylmethyl}-methanesulfonamide;

(rac-di-exo, di-exo)-N-{3-[3-(4-Fluoro-benzyl)-6-hydroxy-4-oxo-3-aza-tetracyclo [6.3.1.0$^{2,7}$.0$^{9,11}$]dodec-5-en-5-yl]-1,1-dioxo-1,4-dihydro-1$\lambda^6$-thieno[2,3-e][1,2,4]thiadiazin-7-ylmethyl}-methanesulfonamide;

Cyclopropanesulfonic acid {3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-amide;

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-sulfamide;

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-acetamide;

N-{3-[(2S,7R)-3-(4-Fluoro-3-methoxy-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-thieno[2,3-e][1,2,4]thiadiazin-7-ylmethyl}-methanesulfonamide;

N-{3-[(1R,2S,7R,8S)-3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-methanesulfonamide;

N-{3-[(1R,2S,7R,8S)-3-(4-Fluoro-3-methoxy-benzyl)-6-hydroxy-4-oxo-3-aza-tricyclo[6.2.1.0$^{2,7}$]undec-5-en-5- yl]-1,1-dioxo-1,4-dihydro-1λ$^6$-thieno[2,3-e][1,2,4]thiadiazin-7-ylmethyl}-methanesulfonamide;

N-[3-((1S,2S,7R,8R)-3-Benzyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-{3-[(1S,2S,7R,8R)-3-(2,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-3-(4-Fluoro-3-methoxy-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

(rac-di-exo)-N-[3-(3-Benzyl-6-hydroxy-4-oxo-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

(rac-di-exo)-N-[3-(3-Benzyl-6-hydroxy-4-oxo-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide;

(rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide;

N-[3-((2S,7R)-3-Benzyl-6-hydroxy-4-oxo-3-aza-tricyclo[6.2.2.0$^{2,7}$]dodec-5-en-5-yl)-1,1-dioxo-1,4-dihydro-1λ$^6$-thieno[2,3-e][1,2,4]thiadiazin-7-ylmethyl]-methanesulfonamide;

N-{3-[(1R,2S,7R,8S)-3-(2,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-[3-((1R,2S,7R,8S)-3-Benzyl-6-hydroxy-4-oxo-3-aza-tricyclo[6.2.1.0$^{2,7}$]undec-5-en-5-yl)-1,1-dihydro-1λ$^6$-thieno[2,3-e][1,2,4]thiadiazin-7-ylmethyl]-methanesulfonamide;

N-{3-[(2S,7R)-3-(2,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-[3-((1R,2S,7R,8S)-6-Hydroxy-4-oxo-3-(3,4,5-trifluoro-benzyl)-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-[(1R,2S,7R,8S)-3-(6-Hydroxy-4-oxo-3-thiophen-3-ylmethyl-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-{3-[(1S,2S,7R,8R)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-6-Hydroxy-4-oxo-3-(3,4,5-trifluoro-benzyl)-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-[3-((1S,2S,7R,8R)-6-Hydroxy-4-oxo-3-thiophen-3-ylmethyl-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-{3-[(1S,2S,7R,8R)-3-(3,3-Dimethyl-butyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-[3-[(1S,7R)-6-Hydroxy-4-oxo-3-thiophen-3-ylmethyl-3-aza-tricyclo[6.2.2.0$^{2,7}$]dodec-5-en-5-yl)-1,1-dioxo-1,4-dihydro-1λ$^6$-thieno[2,3-e][1,2,4]thiadiazin-7-ylmethyl]-methanesulfonamide;

(rac-di-exo)-N-[3-(6-Hydroxy-4-oxo-3-thiophen-3-ylmethyl-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

(rac-di-exo)-N-{3-[3-(3,3-Dimethyl-butyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

(rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

(rac-di-exo)-N-[3-(6-Hydroxy-4-oxo-3-thiophen-3-ylmethyl-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide;

(rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide;

(rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide;

N-{3-[(1R,2S,7R,8S)-3-(3,3-Dimethyl-butyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1R,2S,7R,8S)-6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-6-Hydroxy-4-oxo-3-(3,4,5-trifluoro-benzyl)-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-6-Hydroxy-3-(3-methyl-butyl)-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(1R,2S,7R,8S)-3-(2,4-Dimethoxy-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-3-(2,4-Dimethoxy-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(2,4-Dimethoxy-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

(rac-di-exo)-N-{3-[3-(2,4-Dimethoxy-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

(rac-di-exo)-N-{3-[3-(2,4-Dimethoxy-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide;

(4aR,7aS)-N-{3-[1-(2,4-Dimethoxy-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide;

(rac-cis)-N-{3-[1-(2,4-Dimethoxy-benzyl)-4-hydroxy-2-oxo-1,2,4a,5,6,7,8,8a-octahydro-quinolin-3-yl]-1,1-dioxo-1,4-dihydro-1λ$^6$-thieno[2,3-e][1,2,4]thiadiazin-7-ylmethyl}-methanesulfonamide;

(rac-cis)-N-{3-[1-(2,4-Dimethoxy-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide;

N-[3-((1R,2S,7R,8S)-6-Hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-[3-((1S,2S,7R,8R)-6-Hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-[3-((2S,7R)-6-Hydroxy-4-oxo-3-aza-tricyclo[6.2.2.0$^{2,7}$]dodec-5-en-5-yl)-1,1-dioxo-1,4-dihydro-1λ$^6$-thieno[2,3-e][1,2,4]thiadiazin-7-ylmethyl]-methanesulfonamide;

(rac-di-exo)-N-[3-(6-Hydroxy-4-oxo-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

(rac-di-exo)-N-[3-(6-Hydroxy-4-oxo-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide;

(4aR,7aS)-N-[3-(4-Hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide;

(rac-cis)-N-[3-(4-Hydroxy-2-oxo-1,2,4a,5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide;

(rac-cis)-N-[3-(4-Hydroxy-2-oxo-2,4a,5,6,7,8,9,9a-octahydro-1H-cyclohepta[b]pyridin-3-yl)-1,1-dioxo-1,4-dihydro-1λ$^6$-thieno[2,3-e][1,2,4]thiadiazin-7-ylmethyl}-methanesulfonamide;

N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

(rac-di-exo)-N-{3-[3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(3,3-Dimethyl-butyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-{3-[(1R,2S,7R,8S)-3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(1S,2S,7R,8R)-3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide;

N-{3-[(2S,7R)-3-(2-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide;

N-[3-((1R,2S,7R,8S)-3-Cyclohexyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-[3-((1S,2S,7R,8R)-3-Cyclohexyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

(4aR,7aS)-N-[3-(1-Cyclohexyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide;

(rac-cis)-N-[3-(1-Cyclohexyl-4-hydroxy-2-oxo-1,2,4a,5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide;

N-[3-((1R,2S,7R,8S)-3-Cyclohexylmethyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

N-[3-((1S,2S,7R,8R)-3-Cyclohexylmethyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide;

(4aR,7aS)-N-[3-(1-Cyclohexylmethyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide;

(rac-cis)-N-[3-(1-Cyclohexylmethyl-4-hydroxy-2-oxo-1,2,
4a,5,6,7,8,8a-octahydro-quinolin-3-yl)-1,1-dioxo-1,4-di-
hydro-1λ⁶-thieno[2,3-e][1,2,4]thiadiazin-7-ylmethyl]-
methanesulfonamide;

(rac-cis)-N-[3-(1-Cyclohexylmethyl-4-hydroxy-2-oxo-2,4a,
5,6,7,8,9,9a-octahydro-1H-cyclohepta[b]pyridin-3-yl)-1,
1-dioxo-1,4-dihydro-1λ⁶-thieno[2,3-e][1,2,4]thiadiazin-
7-ylmethyl]-methanesulfonamide;

N-{3-[(1R,2S,7R,8S)-3-(2-Cyclopropyl-ethyl)-6-hydroxy-
4-oxo-3-aza-tricyclo[6.2.1.0²,⁷]undec-5-en-5-yl]-1,1-di-
oxo-1,4-dihydro-1λ⁶-thieno[2,3-e][1,2,4]thiadiazin-7-yl-
methyl}-methanesulfonamide;

N-{3-[(1S,2S,7R,8R)-3-(2-Cyclopropyl-ethyl)-6-hydroxy-
4-oxo-3-aza-tricyclo[6.2.1.0²,⁷]undec-5-en-5-yl]-1,1-di-
oxo-1,4-dihydro-1λ⁶-thieno[2,3-e][1,2,4]thiadiazin-7-yl-
methyl}-methanesulfonamide;

N-{3-[3-(2-Cyclopropyl-ethyl)-6-hydroxy-4-oxo-3-aza-tri-
cyclo[6.2.2.0²,⁷]dodec-5-en-5-yl]-1,1-dioxo-1,4-dihydro-
1λ⁶-thieno[2,3-e][1,2,4]thiadiazin-7-ylmethyl}-methane-
sulfonamide;

N-(3-{6-Hydroxy-3-[2-(1-methyl-cyclopropyl)-ethyl]-4-
oxo-3-aza-tricyclo[6.2.2.0²,⁷]dodec-5-en-5-yl}-1,1-di-
oxo-1,4-dihydro-1λ⁶-thieno[2,3-e][1,2,4]thiadiazin-7-yl-
methyl)-methanesulfonamide;

(4aR,7aS)-N-{3-[1-(4-Fluoro-benzyl)-4-hydroxy-2-oxo-2,
4a,5,6,7,7a-hexahydro-1H-[1]pyrindin-3-yl]-1,1-dioxo-1,
4-dihydro-1λ⁶-thieno[2,3-e][1,2,4]thiadiazin-7-ylm-
ethyl}-methanesulfonamide;

(4aR,7aS)-N-{3-[1-(2-Chloro-4-fluoro-benzyl)-4-hydroxy-
2-oxo-2,4-a,5,6,7,7a-hexahydro-1H-[1]pyrindin-3-yl]-1,
1-dioxo-1,4-dihydro-1λ⁶-thieno[2,3-e][1,2,4]thiadiazin-
7-ylmethyl}-methanesulfonamide;

(4aR,7aS)-N-{3-[1-(2,4-Difluoro-benzyl)-4-hydroxy-2-
oxo-2,4a,5,6,7,7a-hexahydro-1H-[1]pyrindin-3-yl]-1,1-
dioxo-1,4-dihydro-1λ⁶-thieno[2,3-e][1,2,4]thiadiazin-7-
ylmethyl}-methanesulfonamide;

(4aR,7aS)-N-{3-[1-(3-Chloro-4-fluoro-benzyl)-4-hydroxy-
2-oxo-2,4-a,5,6,7,7a-hexahydro-1H-[1]pyrindin-3-yl]-1,
1-dioxo-1,4-dihydro-1λ⁶-thieno[2,3-e][1,2,4]thiadiazin-
7-ylmethyl}-methanesulfonamide;

(4aR,7aS)-N-{3-[1-(4-Fluoro-3-methoxy-benzyl)-4-hy-
droxy-2-oxo-2,4a,5,6,7,7a-hexahydro-1H-[1]pyrindin-3-
yl]-1,1-dioxo-1,4-dihydro-1λ⁶-thieno[2,3-e][1,2,4]thiadi-
azin-7-ylmethyl}-methanesulfonamide;

(4aR,7aS)-N-{3-[4-Hydroxy-2-oxo-1-(2,3,4-trifluoro-ben-
zyl)-2,4a,5,6,7,7a-hexahydro-1H-[1]pyrindin-3-yl]-1,1-
dioxo-1,4-dihydro-1λ⁶-thieno[2,3-e][1,2,4]thiadiazin-7-
ylmethyl}-methanesulfonamide;

(rac-cis)-N-{3-[1-(4-Fluoro-benzyl)-4-hydroxy-2-oxo-1,2,
4a,5,6,7,8,8a-octahydro-quinolin-3-yl]-1,1-dioxo-1,4-di-
hydro-1λ⁶-thieno[2,3-e][1,2,4]thiadiazin-7-ylmethyl}-
methanesulfonamide;

(rac-cis)-N-{3-[1-(2-Chloro-4-fluoro-benzyl)-4-hydroxy-2-
oxo-1,2,4a,5,6,7,8,8a-octahydro-quinolin-3-yl]-1,1-di-
oxo-1,4-dihydro-1λ⁶-thieno[2,3-e][1,2,4]thiadiazin-7-yl-
methyl}-methanesulfonamide;

(rac-cis)-N-{3-[1-(2,4-Difluoro-benzyl)-4-hydroxy-2-oxo-
1,2,4a,5,6,7,8,8a-octahydro-quinolin-3-yl]-1,1-dioxo-1,
4-dihydro-1λ⁶-thieno[2,3-e][1,2,4]thiadiazin-7-ylm-
ethyl}-methanesulfonamide;

(rac-cis)-N-{3-[1-(3-Chloro-4-fluoro-benzyl)-4-hydroxy-2-
oxo-1,2,4a,5,6,7,8,8a-octahydro-quinolin-3-yl]-1,1-di-
oxo-1,4-dihydro-1λ⁶-thieno[2,3-e][1,2,4]thiadiazin-7-yl-
methyl}-methanesulfonamide;

(rac-cis)-N-{3-[1-(4-Fluoro-benzyl)-4-hydroxy-2-oxo-2,4a,
5,6,7,8,9,9a-octahydro-1H-cyclohepta[b]pyridin-3-yl]-1,
1-dioxo-1,4-dihydro-1λ⁶-thieno[2,3-e][1,2,4]thiadiazin-
7-ylmethyl}-methanesulfonamide;

(rac-cis)-N-{3-[1-(2-Chloro-4-fluoro-benzyl)-4-hydroxy-2-
oxo-2,4a,5,6,7,8,9,9a-octahydro-1H-cyclohepta[b]pyri-
din-3-yl]-1,1-dioxo-1,4-dihydro-1λ⁶-thieno[2,3-e][1,2,4]
thiadiazin-7-ylmethyl}-methanesulfonamide;

(rac-cis)-N-{3-[1-(2,4-Difluoro-benzyl)-4-hydroxy-2-oxo-
2,4a,5,6,7,8,9,9a-octahydro-1H-cyclohepta[b]pyridin-3-
yl]-1,1-dioxo-1,4-dihydro-1λ⁶-thieno[2,3-e][1,2,4]thiadi-
azin-7-ylmethyl}-methanesulfonamide;

(rac-cis)-N-{3-[1-(3-Chloro-4-fluoro-benzyl)-4-hydroxy-2-
oxo-2,4a,5,6,7,8,9,9a-octahydro-1H-cyclohepta[b]pyri-
din-3-yl]-1,1-dioxo-1,4-dihydro-1λ⁶-thieno[2,3-e][1,2,4]
thiadiazin-7-ylmethyl}-methanesulfonamide;

(4aR,7aS)-N-[3-(1-Benzyl-4-hydroxy-2-oxo-2,4a,5,6,7a-
hexahydro-1H-[1]pyrindin-3-yl)-1,1-dioxo-1,4-dihydro-
1λ⁶-thieno[2,3-e][1,2,4]thiadiazin-7-ylmethyl]-methane-
sulfonamide;

(4aR,7aS)-N-{3-[1-(3,4-Difluoro-benzyl)-4-hydroxy-2-
oxo-2,4a,5,6,7a-hexahydro-1H-[1]pyrindin-3-yl]-1,1-
dioxo-1,4-dihydro-1λ⁶-thieno[2,3-e][1,2,4]thiadiazin-7-
ylmethyl}-methanesulfonamide;

(4aR,7aS)-N-{3-[1-(4-Fluoro-3-methyl-benzyl)-4-hydroxy-
2-oxo-2,4a,5,6,7a-hexahydro-1H-[1]pyrindin-3-yl]-1,1-
dioxo-1,4-dihydro-1λ⁶-thieno[2,3-e][1,2,4]thiadiazin-7-
ylmethyl}-methanesulfonamide;

(4aR,7aS)-N-[3-(4-Hydroxy-2-oxo-1-thiophen-3-ylmethyl-
2,4a,5,6,7a-hexahydro-1H-[1]pyrindin-3-yl)-1,1-dioxo-
1,4-dihydro-1λ⁶-thieno[2,3-e][1,2,4]thiadiazin-7-ylm-
ethyl]-methanesulfonamide;

(4aR,7aS)-N-{3-[4-Hydroxy-1-(3-methyl-butyl)-2-oxo-2,
4a,5,6,7a-hexahydro-1H-[1]pyrindin-3-yl]-1,1-dioxo-1,
4-dihydro-1λ⁶-thieno[2,3-e][1,2,4]thiadiazin-7-ylm-
ethyl}-methanesulfonamide;

(4aR,7aS)-N-{3-[1-(3,3-Dimethyl-butyl)-4-hydroxy-2-oxo-
2,4a,5,6,7a-hexahydro-1H-[1]pyrindin-3-yl]-1,1-dioxo-
1,4-dihydro-1λ⁶-thieno[2,3-e][1,2,4]thiadiazin-7-ylm-
ethyl}-methanesulfonamide;

(rac-cis)-N-[3-(1-Benzyl-4-hydroxy-2-oxo-1,2,4a,5,6,7,8,
8a-octahydro-quinolin-3-yl)-1,1-dioxo-1,4-dihydro-1λ⁶-
thieno[2,3-e][1,2,4]thiadiazin-7-ylmethyl]-methane-
sulfonamide;

(rac-cis)-N-{3-[1-(4-Fluoro-3-methyl-benzyl)-4-hydroxy-2-
oxo-1,2,4a,5,6,7,8,8a-octahydro-quinolin-3-yl]-1,1-di-
oxo-1,4-dihydro-1λ⁶-thieno[2,3-e][1,2,4]thiadiazin-7-yl-
methyl}-methanesulfonamide;

(rac-cis)-N-{3-[4-Hydroxy-1-(3-methyl-butyl)-2-oxo-1,2,
4a,5,6,7,8,8a-octahydro-quinolin-3-yl]-1,1-dioxo-1,4-di-
hydro-1λ⁶-thieno[2,3-e][1,2,4]thiadiazin-7-ylmethyl}-
methanesulfonamide;

(rac-cis)-N-{3-[1-(3,3-Dimethyl-butyl)-4-hydroxy-2-oxo-1,
2,4a,5,6,7,8,8a-octahydro-quinolin-3-yl]-1,1-dioxo-1,4-
dihydro-1λ⁶-thieno[2,3-e][1,2,4]thiadiazin-7-ylmethyl}-
methanesulfonamide;

(rac-cis)-N-{3-[1-(3,4-Difluoro-benzyl)-4-hydroxy-2-oxo-
1,2,4a,5,6,7,8,8a-octahydro-quinolin-3-yl]-1,1-dioxo-1,
4-dihydro-1λ⁶-thieno[2,3-e][1,2,4]thiadiazin-7-ylm-
ethyl}-methanesulfonamide;

(rac-cis)-N-[3-(4-Hydroxy-2-oxo-1-thiophen-3-ylmethyl-1,
2,4a,5,6,7,8,8a-octahydro-quinolin-3-yl)-1,1-dioxo-1,4-
dihydro-1λ⁶-thieno[2,3-e][1,2,4]thiadiazin-7-ylmethyl]-
methanesulfonamide;

(rac-cis)-N-[3-(1-Benzyl-4-hydroxy-2-oxo-2,4a,5,6,7,8,9,
9a-octahydro-1H-cyclohepta[b]pyridin-3-yl)-1,1-dioxo-
1,4-dihydro-1λ⁶-thieno[2,3-e][1,2,4]thiadiazin-7-ylm-
ethyl]-methanesulfonamide;

(rac-cis)-N-{3-[1-(3,4-Difluoro-benzyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-thieno[2,3-e][1,2,4]thiadiazin-7-ylmethyl}-methanesulfonamide;

(rac-cis)-N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1$\lambda^6$-thieno[2,3-e][1,2,4]thiadiazin-7-ylmethyl}-methanesulfonamide;

(rac-cis)-N-{3-[1-(4-Fluoro-3-methyl-benzyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-thieno[2,3-e][1,2,4]thiadiazin-7-ylmethyl}-methanesulfonamide;

(rac-cis)-N-{3-[4-Hydroxy-2-oxo-1-(3,4,5-trifluoro-benzyl)-2,4a,5,6,7,8,9,9a-octahydro-1H-cyclohepta[b]pyridin-3-yl]-1,1-dioxo-1,4-dihydro-1$\lambda^6$-thieno[2,3-e][1,2,4]thiadiazin-7-ylmethyl}-methanesulfonamide, (rac-cis)-N-[3-(4-Hydroxy-2-oxo-1-thiophen-3-ylmethyl-2,4a,5,6,7,8,9,9a-octahydro-1H-cyclohepta[b]pyridin-3-yl)-1,1-dioxo-1,4-dihydro-1$\lambda^6$-thieno[2,3-e][1,2,4]thiadiazin-7-ylmethyl]-methanesulfonamide, and (rac-di-exo)-N-{3-[3-(4-Fluoro-benzyl)-6-hydroxy-4-oxo-3-aza-tricyclo[6.3.2.0$^{2,7}$]tridec-5-en-5-yl]-1,1-dioxo-1,4-dihydro-1$\lambda^6$-thieno[2,3-e][1,2,4]thiadiazin-7-ylmethyl}-methanesulfonamide.

The invention is also directed to pharmaceutically acceptable salts and pharmaceutically acceptable solvates of the compounds of Formula I. Advantageous methods of making the compounds of Formula I are also described.

In one aspect, the invention encompasses a method for treating or preventing hepatitis C virus infection in a mammal in need thereof, preferably in a human in need thereof, comprising administering to the patient a therapeutically or prophylactically effective amount of a Formula I compound. In one embodiment, the invention encompasses a method for treating or preventing hepatitis C virus infection by administering to a patient in need thereof a therapeutically or prophylactically effective amount of a Formula I compound that is an inhibitor of HCV NS5B polymerase.

In another aspect, the invention encompasses a method for treating or preventing hepatitis C virus infection in a patient in need thereof, comprising administering to the patient a therapeutically or prophylactically effective amount of a compound of Formula I and a pharmaceutically acceptable excipient, carrier, or vehicle.

In another aspect, the invention encompasses a method for treating or preventing hepatitis C virus infection in a patient in need thereof, comprising administering to the patient a therapeutically or prophylactically effective amount of a compound of Formula I and an additional therapeutic agent, preferably an additional antiviral agent or an immunomodulatory agent.

DETAILED DESCRIPTION OF THE INVENTION

Where the following terms are used in this specification, they are used as defined below:

The terms "comprising," "having" and "including" are used herein in their open, non-limiting sense.

The term "alkyl", as used herein, unless otherwise indicated, includes 1-6 saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkylene", as used herein, unless otherwise indicated, includes a divalent radical derived from alkyl, as exemplified by —CH$_2$CH$_2$CH$_2$CH$_2$—.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

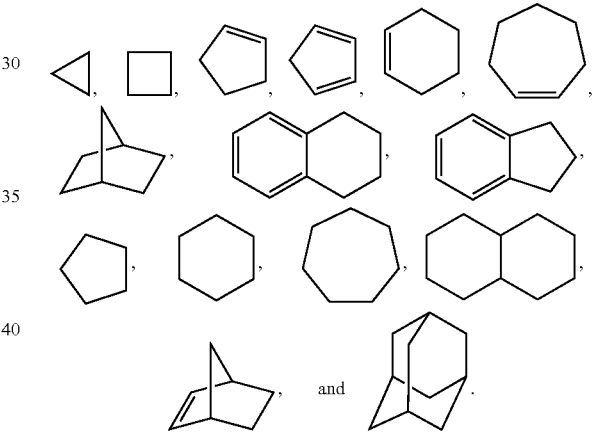

The term "aryl", as used herein, unless otherwise indicated, includes an organic radical derived from an aromatic hydrocarbon by removal of one hydrogen, and has from 6-14 carbon atoms in its ring system, such as phenyl or naphthyl.

The term "heterocyclic" or "heterocyclyl", as used herein, unless otherwise indicated, includes aromatic (e.g., heteroaryls) and non-aromatic heterocyclic groups containing one to four heteroatoms each selected from O, S and N, wherein each heterocyclic group has from 4-10 atoms in its ring system, and with the proviso that the ring of said group does not contain two adjacent O atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

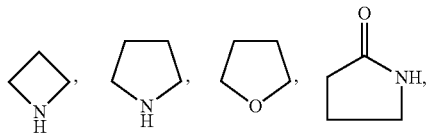

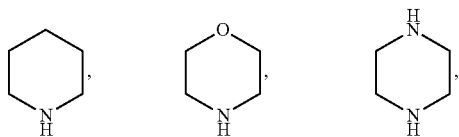

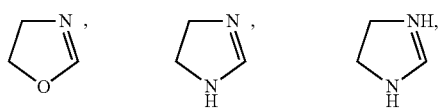

-continued

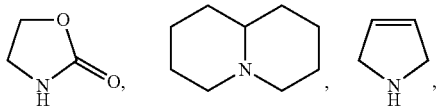

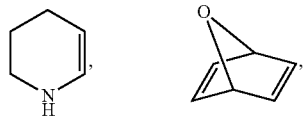

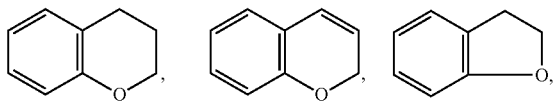

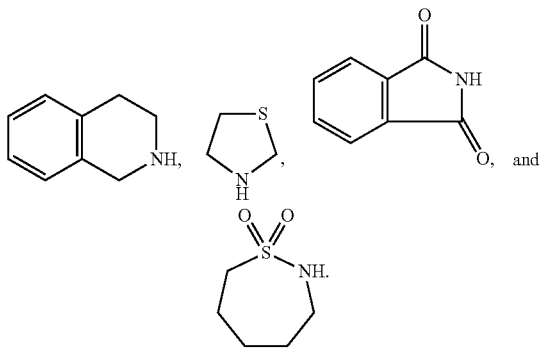

Unless defined otherwise, "alkyl," "alkylene," "alkenyl," "alkynyl," "aryl," "cycloalkyl," or "heterocyclyl" are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —C(O)OH, —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl, wherein each of these optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey, chimpanzee or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac- (or racem-) or by the symbols RS and SR.

The terms "endo" and "exo" are descriptors of the relative orientation of substituents attached to non-bridgehead atoms in a bicyclo[x.y.z]alkane (x≧y>z>0).

The terms "syn" and "anti" are descriptors of the relative orientation of substituents attached to bridgehead atoms in a bicyclo[x.y.]alkane (x≧y>z>0).

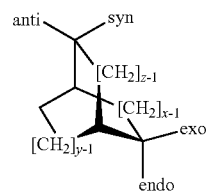

The term "exo" is given to a substituent (e.g., Br attached to C-2 in the example below) that is oriented towards the highest numbered bridge (z bridge, e.g., C-7 in example below); if the substituent is oriented away from the highest numbered bridge it is given the description "endo".

The term "syn" is given to a substituent attached to the highest numbered bridge (z bridge, e.g., F attached to C-7 in the example below) and is oriented towards the lowest numbered bridge (x bridge, e.g., C-2 and C-3 in example below); if the substituent is oriented away from the lowest numbered bridge it is given the description "anti."

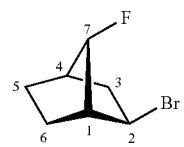

2-exo-bromo-7-syn-fluoro-bicyclo[2.2.1]heptane

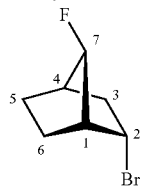

2-endo-bromo-7-anti-fluoro-bicyclo[2.2.1]heptane

The terms "cis" and "trans" are descriptors which show the relationship between two ligands attached to separate atoms that are connected by a double bond or are contained in a ring. The two ligands are said to be located cis to each other if they lie on the same side of a plane. If they are on opposite sides, their relative position is described as trans. The appropriate reference plane of a double bond is perpendicular to that of the relevant σ-bonds and passes through the double bond. For a ring it is the mean plane of the ring(s).

The compounds of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings. For illustration, and in no way limiting the range of tautomers, the compounds of Formula I may exist as the following:

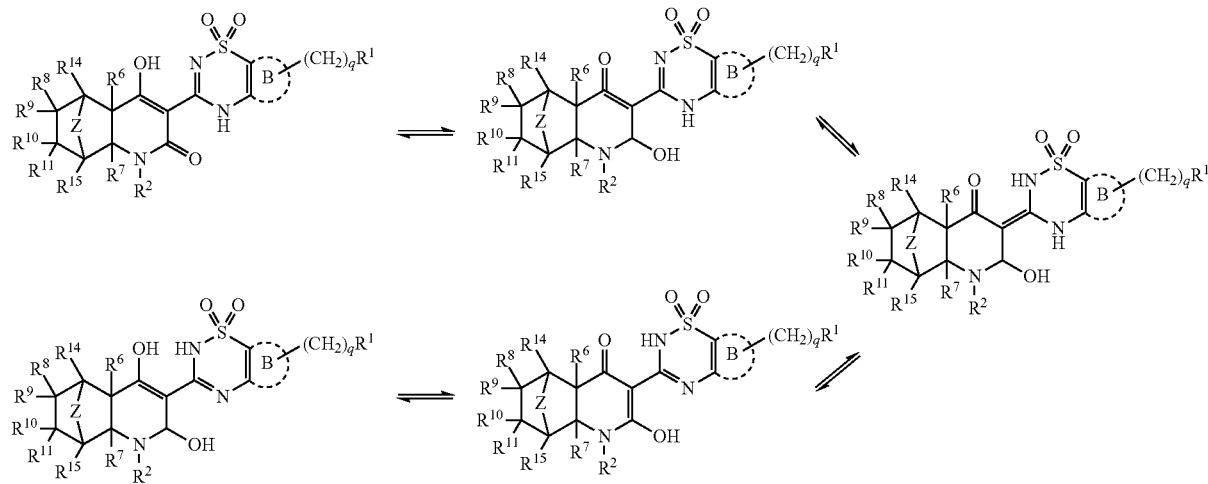
Or, the compounds of Formula I may exist as the following:
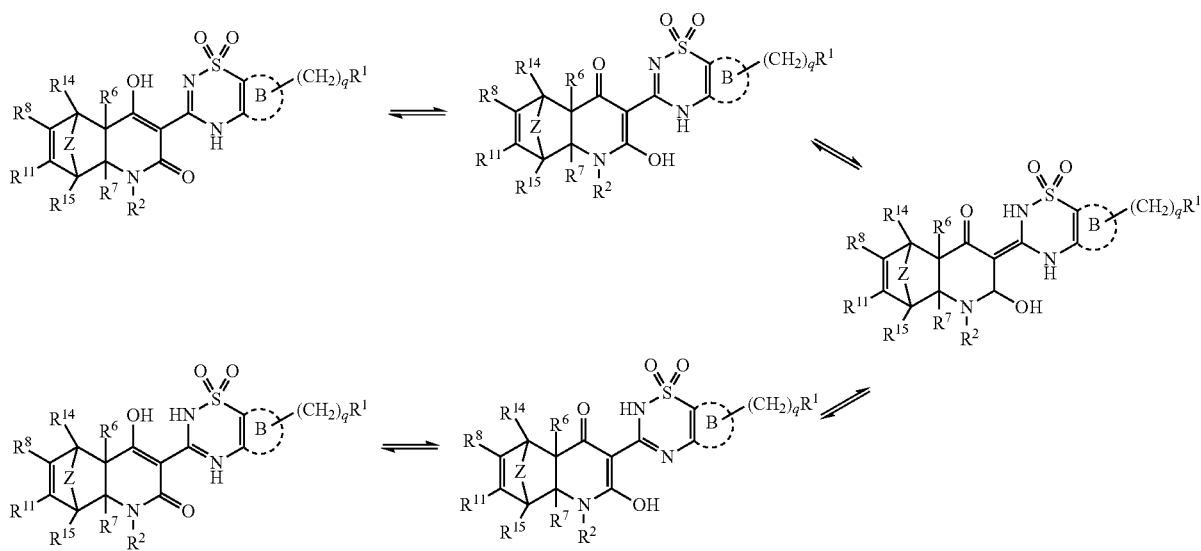

Or, the compounds of Formula I may exist as the following:
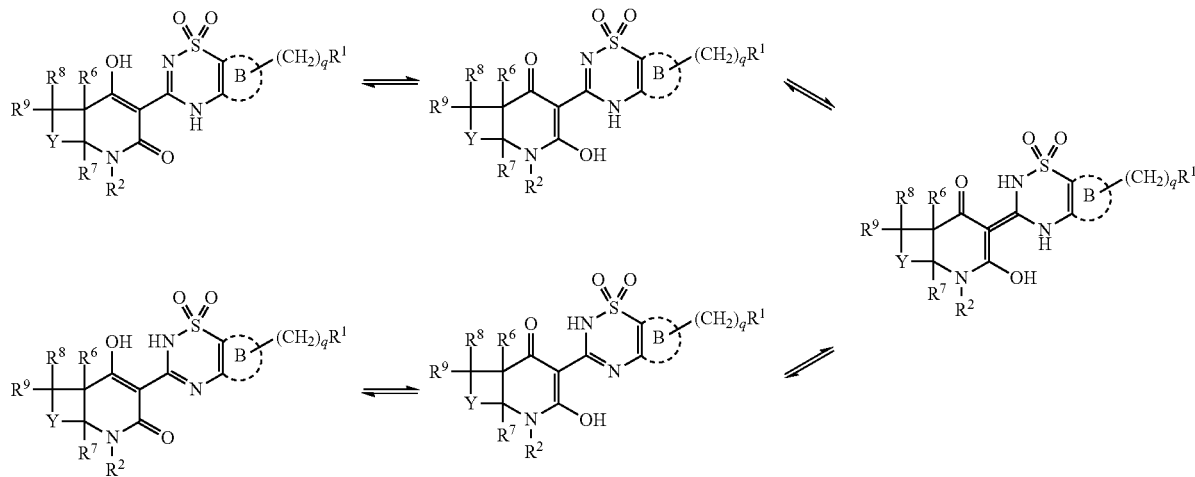
Or, the compounds of Formula I may exist as the following:
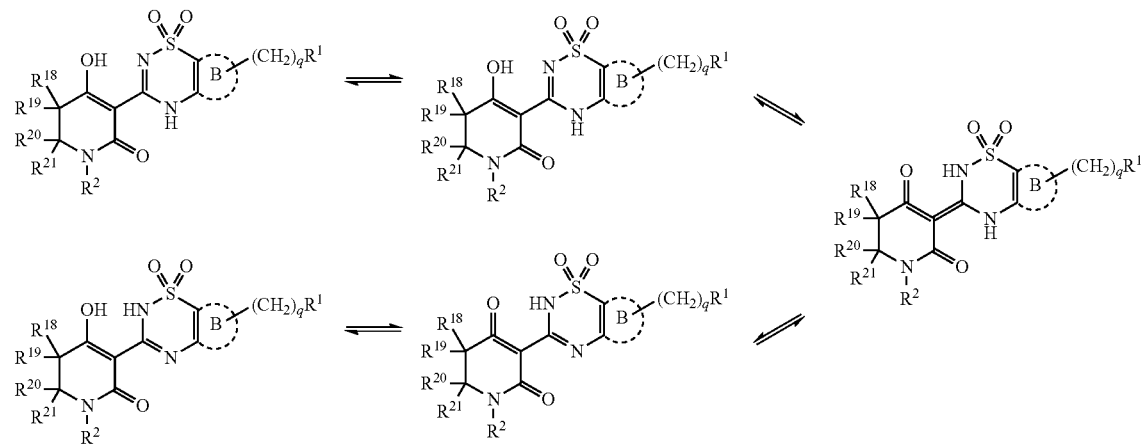
Or, the compounds of Formula I may exist as the following:
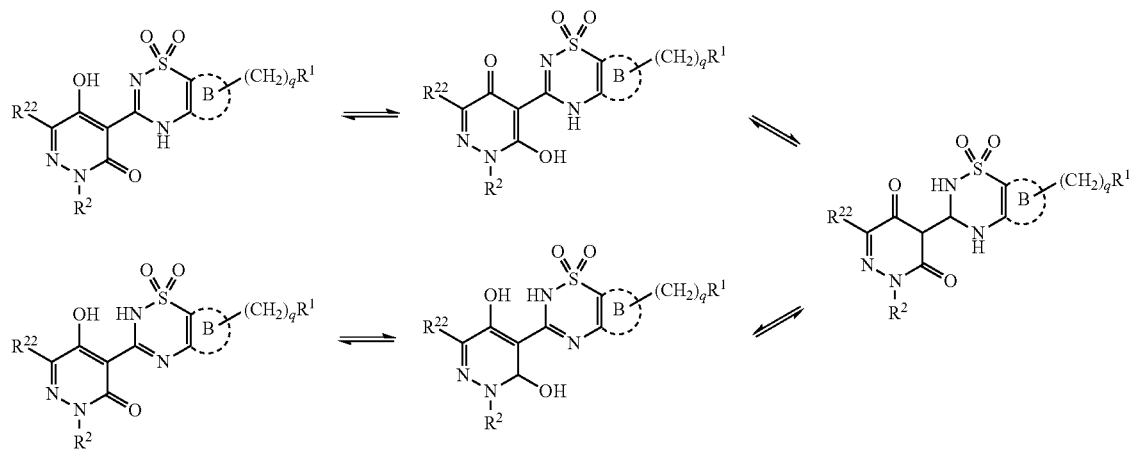

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, pentyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect(s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal, co-crystal, or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to polymerase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $EC_{50}$ (i.e., the concentration of the test compound that provokes a response half way between the baseline and maximum response) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug, in instances where the compound to be tested is a prodrug. Compounds for use in methods of the invention can be tested in suitable animal model systems prior to testing in humans, including but not limited to in rats, mice, chicken, cows, monkeys, chimpanzees, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient.

Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 1 mg to 12 g per day, more preferably from 100 mg to 8000 mg per day.

Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll-like receptor modulators. In one embodiment the invention encompasses the administration of an additional therapeutic agent that is HCV specific or demonstrates anti-HCV activity.

The compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The compounds of the invention can be administered or formulated in combination with an antidepressant. Suitable antidepressants include, but are not limited to, binedaline, caroxazone, citalopram, dimethazan, fencamine, indalpine, indeloxazine hydrochloride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The compounds of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The compounds of the invention can be administered or formulated in combination with another antiviral agent. Useful antiviral agents include, but are not limited to, protease inhibitors, nucleoside polymerase inhibitors, non-nucleoside polymerase inhibitors and nucleoside analogs. The antiviral agents include but are not limited to ribavirin, the α-interferons, and β-interferons.

The compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll-like receptor (TLR) modulators (e.g., ANA773, PF-04878691). Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN-α, Albuferon, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-αantibodies, anti-IL-1β antibodies, anti-IL-6 antibodies, anti-IL-8 antibodies (e.g., ABX-IL-8 (Abgenix)), and anti-IL-12 antibodies).

The compounds of the invention can be administered or formulated in combination with an agent which inhibits viral enzymes, including but not limited to inhibitors of HCV protease, such as ABT-450, VX-500, VX-813, VBY-376, BMS-650032, MK-7009, TMC-435350, SCH-503034 (Boceprevir), ITMN-191, IDX-136, IDX-316, or VX-950 (Telaprevir); inhibitors of NS5B polymerase such as GS-9190, MK-3281, VCH-222, VCH-759, VCH-916, ABT-333, ABT-072, BMS-791325, PF-00868554 (Filibuvir), BI 207127, IDX-184, IDX-375, R7128, or R1626; and inhibitors of the NS5A protein, such as BMS-790052 or A-831.

The compounds of the invention can be administered or formulated in combination with an indirect antiviral agent which inhibits HCV infection, including but not limited to Debio 025, NIM811, Nitazoxanide, or Taribavirin.

The compounds of the invention can be administered or formulated in combination with an agent which inhibits HCV polymerase such as those described in Wu, *Curr Drug Targets Infect Disord.* 2003, 3(3), 207-19 or in combination with compounds that inhibit the helicase function of the virus such as those described in Bretner M, et al. *Nucleosides Nucleotides Nucleic Acids.* 2003, 22(5-8), 1531, or with inhibitors of other HCV specific targets such as those described in Zhang X., *IDrugs* 2002, 5(2), 154-8.

The compounds of the invention can be administered or formulated in combination with an agent which inhibits viral replication.

The compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, IFN-β, and IFN-γ).

The compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The compounds of the invention can be administered or formulated in combination with β-interferons which include, but are not limited to, interferon β-1a, and interferon β-1b.

The compounds of the invention can be administered or formulated in combination with α-interferons which include, but are not limited to, interferon α-1, interferon α-2a (roferon), interferon α-2b, intron, Peg-Intron, Pegasys, consensus interferon (infergen) and albuferon.

The compounds of the invention can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.*, 7, 1-33, which is hereby incorporated by reference in its entirety. Other known absorption enhancers can also be used. Thus, the invention also encompasses a pharmaceutical composition comprising one or more compounds of the invention and one or more absorption enhancers.

The compounds of the invention can be administered or formulated in combination with a cytochrome P450 monooxygenase inhibitor, such as, but not limited to, ritonavir or a pharmaceutically acceptable salt, ester, and prodrug thereof to improve the pharmacokinetics (e.g., increased half-life, increased time to peak plasma concentration, increased blood levels) of a compound of the invention that is metabolized by cytochrome P450 monooxygenase. Thus, the invention also encompasses a pharmaceutical composition comprising compounds of the invention and one or more cytochrome P450 monooxygenase inhibitors.

The compounds of the invention can be administered in combination with food to enhance absorption of the compounds of the invention in the gastrointestinal tract and to increase the bioavailability of the compounds of the invention.

The compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more compounds of the invention without an additional therapeutic agent.

Pharmaceutical Compositions and Dosage Forms

Pharmaceutical compositions and single unit dosage forms comprising a compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The compounds of the invention may also be administered directly to the lung by inhalation. For administration by inhalation, a compound of the invention can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound of the invention directly to the lung. MDI devices are available from a number of suppliers such as 3M Corporation, Aventis, Boehringer Ingelheim, Forest Laboratories, Glaxo-Wellcome, Schering Plough and Vectura.

Alternatively, a Dry Powder Inhaler (DPI) device can be used to administer a compound of the invention to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, WAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver compounds of the invention to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the compounds of the invention formulation may be important parameters to optimize when delivering this drug to the lung with an EHD aerosol device and such optimization is routinely performed by one of skill in the art. EHD aerosol devices may more efficiently deliver drugs to the lung than existing pulmonary delivery technologies. Other methods of intra-pulmonary delivery of compounds of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the compound of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598; Biesalski, 5,556,611, which are herein incorporated by reference) A compound of the invention can also be formulated in rectal or vaginal compositions such as suppositories or retention enemas, e.g., containing conventional suppository bases such as cocoa butter or other glycerides.

In addition to the formulations described previously, a compound of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes, emulsions, self-emulsifying (SEDDS), and self micro-emulsifying systems (SMEDDS) are well known examples of delivery vehicles that can be used to deliver compositions of the invention. Such systems can also contain fatty acids, bile salts and mixtures of mono-, di- and triglycerides to ameliorate potential food effects. Other functional lipid excipients include esters of glycerol, PEG-esters, propylene glycol esters and polyglycerol esters. Certain organic solvents such as dimethylsulfoxide can also be employed, although usually at the cost of greater toxicity. A compound of the invention can also be delivered in a controlled release system. In one embodiment, a pump can be used (Sefton, *CRC Crit. Ref Biomed Eng.*, 1987, 14, 201; Buchwald et al., *Surgery*, 1980, 88, 507; Saudek et al., *N Engl. J. Med.*, 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25,351; Howard et al., *J. Neurosurg.*, 71, 105 (1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release, supra*, vol. 2, pp. 115 (1984)). Other controlled-release systems can be used (see, e.g., Langer, *Science*, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a compound of the invention useful for the treatment or prevention of a Hepatitis C virus infection. In other embodiments, the invention provides a pharmaceutical pack or kit comprising one or more containers comprising a compound of the invention useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS or HPLC and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous sodium sulfate and/or magnesium sulfate prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, Teledyne Isco flash-chromatography using prepacked RediSep silica gel columns, or Analogix flash column chromatography using prepacked SuperFlash silica gel columns Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm)

when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wavenumbers (cm$^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures utilize many common chemical abbreviations, 2,2-DMP (2,2-dimethoxypropane), Ac (acetyl), ACN (acetonitrile), Bn (benzyl), BnOH (benzyl alcohol), Boc (tert-butoxycarbonyl), Boc$_2$O (di-tert-butyl dicarbonate), Bz (benzoyl), CSA (camphorsulfonic acid), CSI (chlorosulfonyl isocyanate), DBU (1,8-diazabicyclo[5,4,0]undec-7-ene), DCC (N,N'-dicyclohexylcarbodiimide), DCE (1,2-dichloroethane), DCM (dichloromethane), DEAD (diethylazodicarboxylate), DIBAL (diisobutylaluminum hydride), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOAc (acetic acid), HOBT (1-hydroxybenzotriazole hydrate), HPLC (high pressure liquid chromatography), IPA (isopropyl alcohol), KHMDS (potassium bis(trimethylsilyl)amide), KN (TMS)$_2$ (potassium bis(trimethylsilyl)amide), KO$^t$Bu (potassium tert-butoxide), LDA (lithium diisopropylamine), MCPBA (3-chloroperbenzoic acid), Me (methyl), MeCN (acetonitrile), MeOH (methanol), NaCNBH$_3$ (sodium cyanoborohydride), NaH (sodium hydride), NaN (TMS)$_2$ (sodium bis(trimethylsilyl)amide), NaOAc (sodium acetate), NaOEt (sodium ethoxide), NEt$_3$ (triethylamine), NMM (N-methylmorpholine), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Scheme 1 provides a general procedure that can be used to prepare saturated [1,2,4]thiadiazine 1,1-dioxide compounds of Formula I.

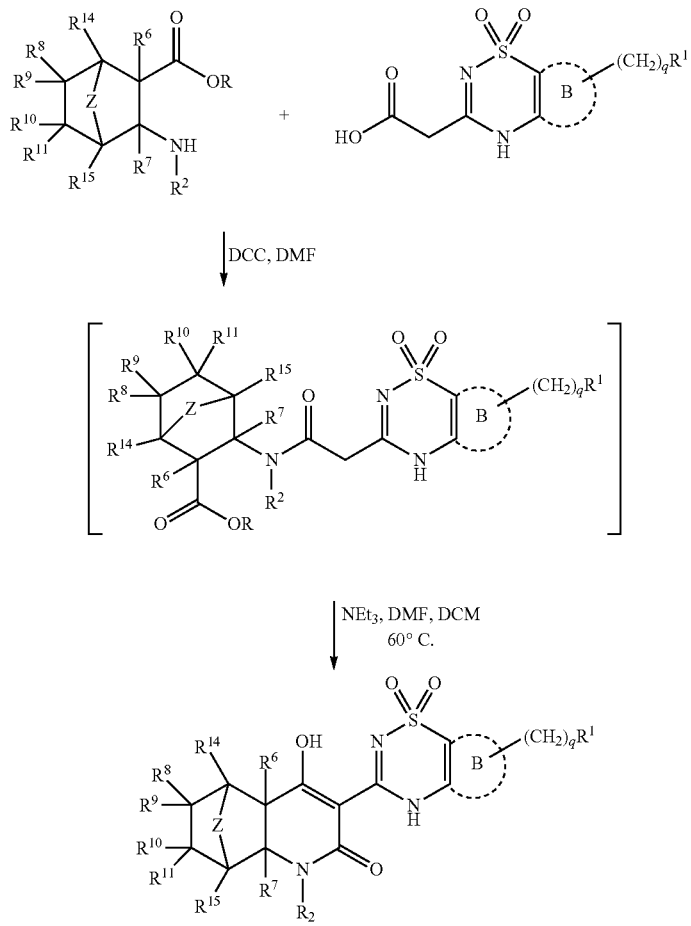

R = an aliphatic or aromatic leaving group

The saturated cyclic N-substituted-β-amino acid ester intermediates, which can be obtained as described by one of the methods in Schemes 2-8 can be condensed with a carboxylic acid intermediate (or a salt thereof, e.g., sodium salt) using standard peptide coupling conditions used for the formation of amide bonds, such as DCC, to yield the shown amide. This intermediate can be cyclized with or without isolation in the presence of a base (e.g., triethylamine) to give the desired saturated [1,2,4]thiadiazine 1,1-dioxide compounds.

Scheme 2 provides a general procedure that can be used to prepare saturated cyclic N-substituted-β-amino acid ester intermediates from saturated anhydrides.

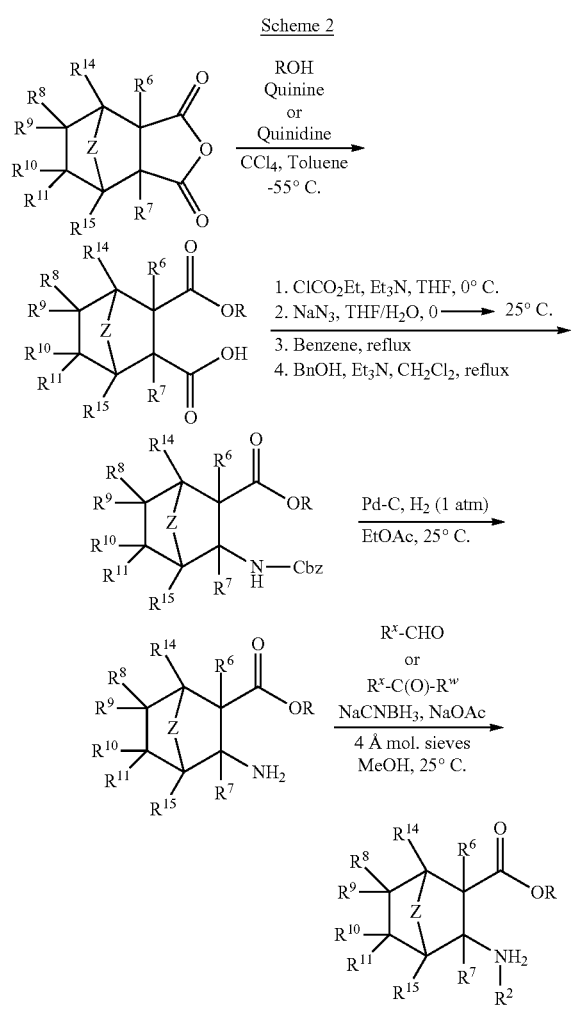

Commercially available saturated cyclic meso-anhydrides can be desymmetrized with the help of enzymes or chiral reagents, such as cinchona alkaloids (e.g., quinine or quinidine) as described in the literature to provide optically active saturated cyclic dicarboxylic acid monoesters (with R as defined in Scheme 1). See *J. Org. Chem.*, 65, 6984-6991 (2000); *Synthesis*, 11, 1719-1730 (2001), and references cited therein.

These intermediates can be further elaborated into protected optically active saturated cyclic β-amino acid esters (e.g., Cbz-protected) via a rearrangement reaction, such as the Curtius rearrangement (shown) or a Hofmann degradation. Hydrogenation of the protected saturated cyclic β-amino acid esters under standard conditions can be used to remove the protecting group and furnish the optically active saturated cyclic β-amino acid esters, which can be isolated (and used) as either the free bases or their corresponding salts. The optically active saturated cyclic β-amino acid esters (or their salts) can then be treated with aldehydes or ketones, where $R^x$ and $R^w$ are independently $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene (aryl), —$C_1$-$C_5$ alkylene(heterocyclyl), aryl, or heterocyclyl, or $R^w$ can combine with $R^x$ to form a 3- to 8-membered ring, in the presence of a reducing agent (such as sodium cyanoborohydride) to afford the desired optically active saturated cyclic N-substituted-β-amino acid ester intermediates. Alternatively, the reaction sequence described above can be performed without enzymes or chiral reagents leading to the corresponding achiral intermediates and products.

Scheme 3 provides a general procedure that can be used to prepare saturated cyclic N-substituted-β-amino acid ester intermediates from unsaturated anhydrides.

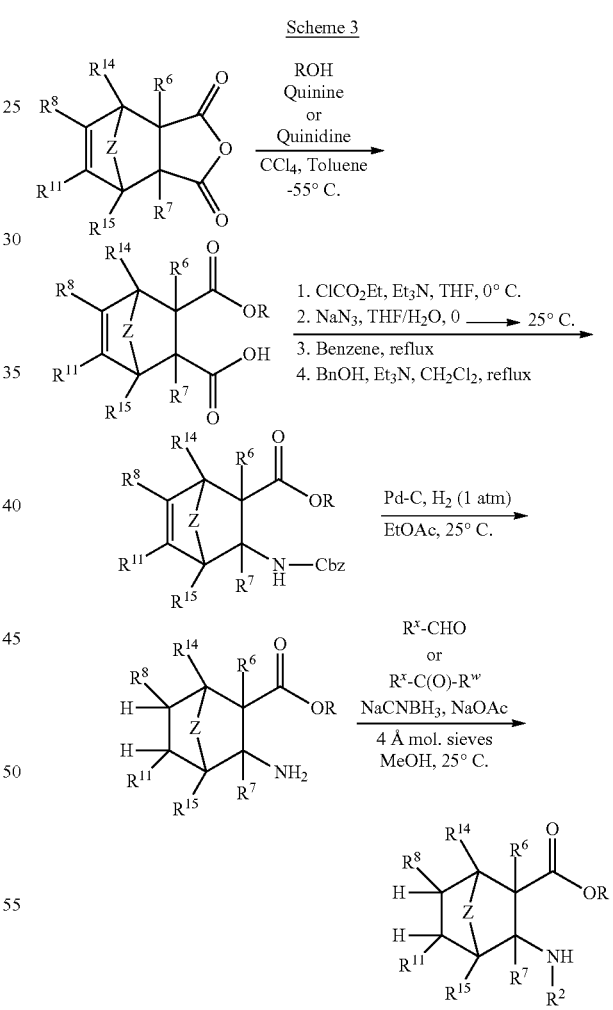

Commercially available unsaturated cyclic meso-anhydrides can be desymmetrized as described above (Scheme 2) to provide optically active unsaturated cyclic dicarboxylic acid monoesters (with R as defined in Scheme 1). These intermediates can be further elaborated into protected optically active unsaturated cyclic β-amino acid esters (e.g., Cbz-protected) via a rearrangement reaction, such as the Curtius rearrangement (shown) or a Hofmann degradation. Hydrogenation of the protected optically active unsaturated cyclic β-amino acid esters under standard conditions removes the protecting group and reduces the olefin to furnish the optically active saturated cyclic β-amino acid esters, which can be isolated (and used) as either the free bases or their corresponding salts.

The optically active saturated cyclic β-amino acid esters (or their salts) can then be treated with aldehydes or ketones (with $R^x$ and $R^w$ as defined in Scheme 2) in the presence of a reducing agent (such as sodium cyanoborohydride) to afford the desired optically active saturated cyclic N-substituted-β-amino acid ester intermediates. Alternatively, the reaction sequence described above can be performed without enzymes or chiral reagents leading to the corresponding achiral intermediates and products.

Scheme 4 provides an alternate general procedure that can be used to prepare saturated cyclic N-substituted-β-amino acid ester intermediates.

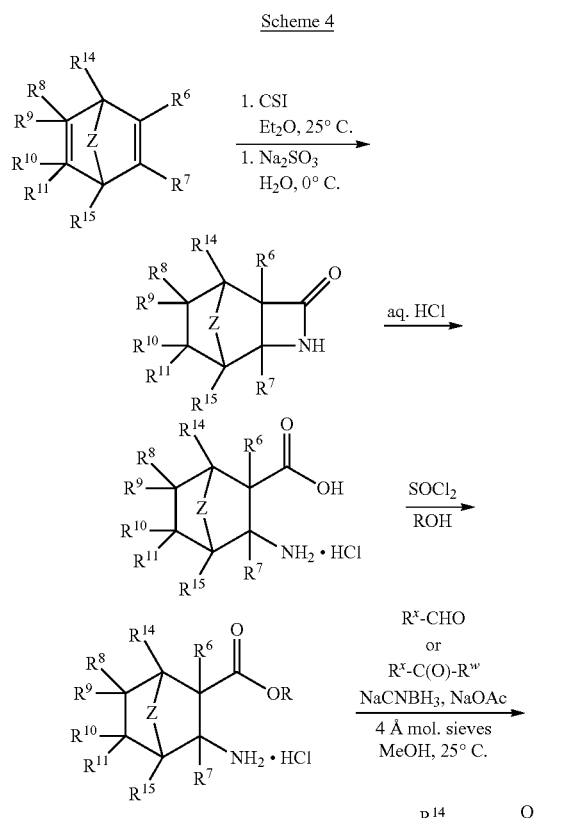

Bicyclic olefins, such as norbornene, can be reacted with chlorosulfonyl isocyanate to yield the β-lactams shown. These intermediates can be hydrolyzed in the presence of a strong acid (such as hydrochloric acid) to afford the saturated cyclic β-amino acids (or their salts), which can then be further elaborated into the corresponding esters using standard conditions (with R as defined in Scheme 1). The saturated cyclic β-amino acid esters can then be treated with aldehydes or ketones (with $R^x$ and $R^w$ as defined in Scheme 2) in the presence of a reducing agent, such as sodium cyanoborohydride, to afford the desired saturated cyclic N-substituted-β-amino acid ester intermediates.

Scheme 5 provides a general scheme describing a method that can be used to resolve the di-exo enantiomers by diastereomeric crystallization

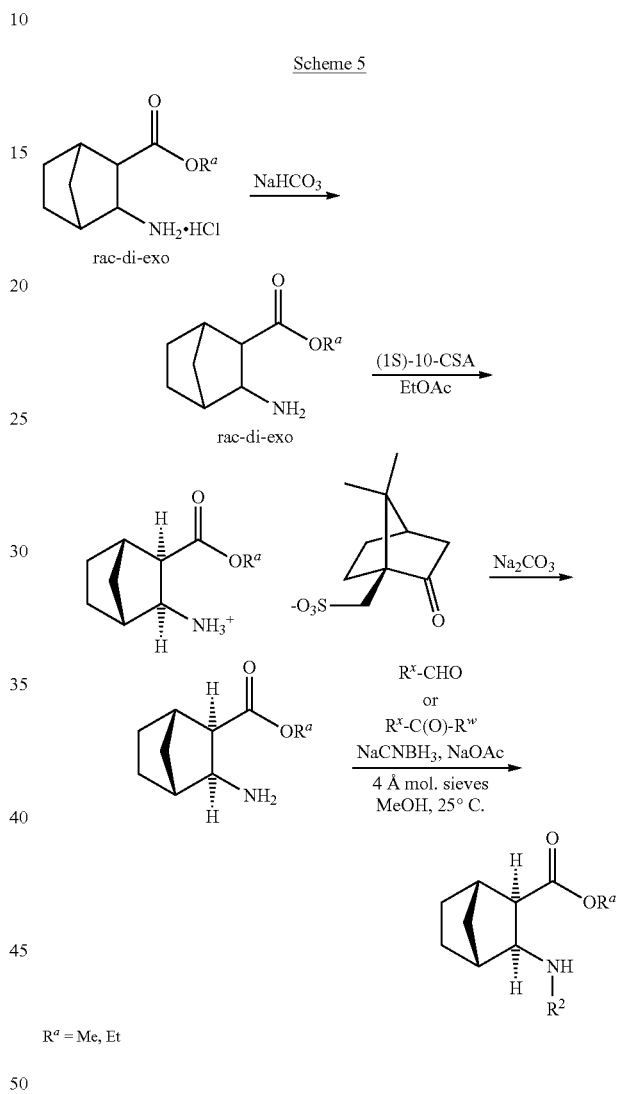

The racemic di-exo-β-amino acid ester derivatives obtained from norbornene as described above (Scheme 4), can be resolved by forming diastereomeric salts with an optically pure acid, such as (1S)-(+)-10-camphorsulfonic acid. The (1R,2R,3S,4S)-β-amino acid ester derivatives form a crystalline salt with (1S)-(+)-10-camphorsulfonic acid that can be selectively isolated by filtration from an appropriate solvent (e.g., ethyl acetate) and treated with a base, such as sodium carbonate, to afford the free enantiomerically pure cyclic (1R,2R,3S,4S)-β-amino acid esters. The optically pure cyclic (1R,2R,3S,4S)-β-amino acid esters (or their salts) can then be treated with aldehydes or ketones (with $R^x$ and $R^w$ as defined in Scheme 2) in the presence of a reducing agent, such as sodium cyanoborohydride, to afford the desired optically pure saturated cyclic N-substituted-(1R,2R,3S,4S)-β-amino acid ester intermediates.

Scheme 6 provides an alternative procedure that can be used to prepare enantiomerically pure saturated cyclic N-substituted-β-amino acid ester intermediates.

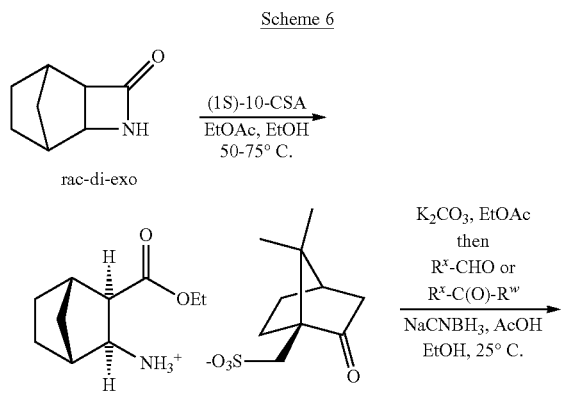

The β-lactam (prepared as described in Scheme 4) can be opened and resolved by forming diastereomeric salts with an optically pure acid, such as (1S)-(+)-10-camphorsulfonic acid (as described in Scheme 5) in the presence of an alcohol (e.g., ethanol) to directly afford the diastereomerically pure (1R,2R,3S,4S)-β-amino acid ester as a salt with (1S)-(+)-10-camphorsulfonic acid. Treatment with a base, such as potassium carbonate, followed by reductive alkylation with aldehydes or ketones (with $R^x$ and $R^w$ as defined in Scheme 2) in the presence of a reducing agent, such as sodium cyanoborohydride, affords the desired enantiomerically pure saturated cyclic N-substituted-(1R,2R,3S,4S)-β-amino acid ester intermediates.

Scheme 7 provides a general procedure that can be used to prepare saturated cyclic N-substituted-β-amino acid ester intermediates.

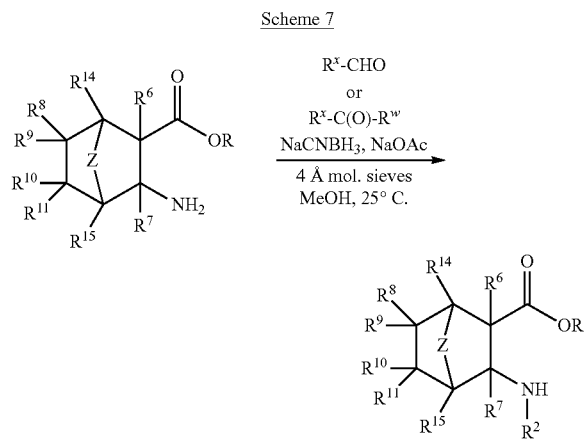

The saturated cyclic β-amino acid esters (or their salts, with R as defined in Scheme 1) can be purchased, prepared from the corresponding commercially available saturated cyclic β-amino acids, or can be prepared by methods described in Schemes 2, 3, 4, 5 or 6. The saturated cyclic β-amino acid esters can then be treated with aldehydes or ketones (with $R^x$ and $R^w$ as defined in Scheme 2) in the presence of a reducing agent, such as sodium cyanoborohydride, to afford the desired saturated cyclic N-substituted-β-amino acid ester intermediates. In each case the saturated cyclic β-amino acid esters or the desired saturated cyclic N-substituted-β-amino acid ester intermediates may be optically active.

Scheme 8 provides an alternative general procedure that can be used to prepare saturated cyclic N-substituted-β-amino acid ester intermediates.

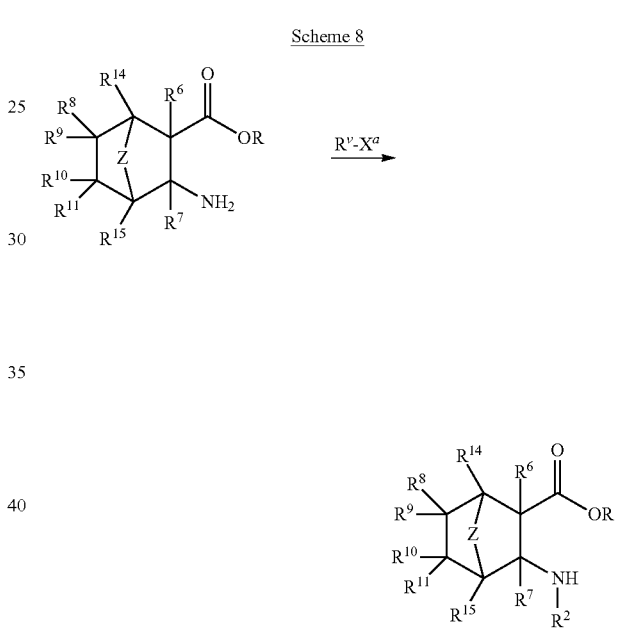

The saturated cyclic β-amino acid esters (or their salts, with R as defined in Scheme 1) can be purchased, prepared from the corresponding commercially available saturated cyclic β-amino acids, or can be prepared by the method described in Schemes 2, 3, 4, 5 or 6. The saturated cyclic β-amino acid esters can then be treated with halides or pseudohalides $X^a$ (e.g., bromides, iodides or triflates), where $R^v$ is aryl or heterocyclyl, in the presence of metal catalyst such as copper (e.g., under Ullmann reaction conditions) or palladium (e.g., under Buchwald-Hartwig reaction conditions), to afford the desired saturated cyclic N-substituted-β-amino acid ester intermediates. In each case the saturated cyclic β-amino acid esters or the desired saturated cyclic N-substituted-β-amino acid ester intermediates may be optically active.

Scheme 9 provides a general procedure that can be used to prepare unsaturated [1,2,4]thiadiazine 1,1-dioxide compounds of Formula I.

Scheme 9

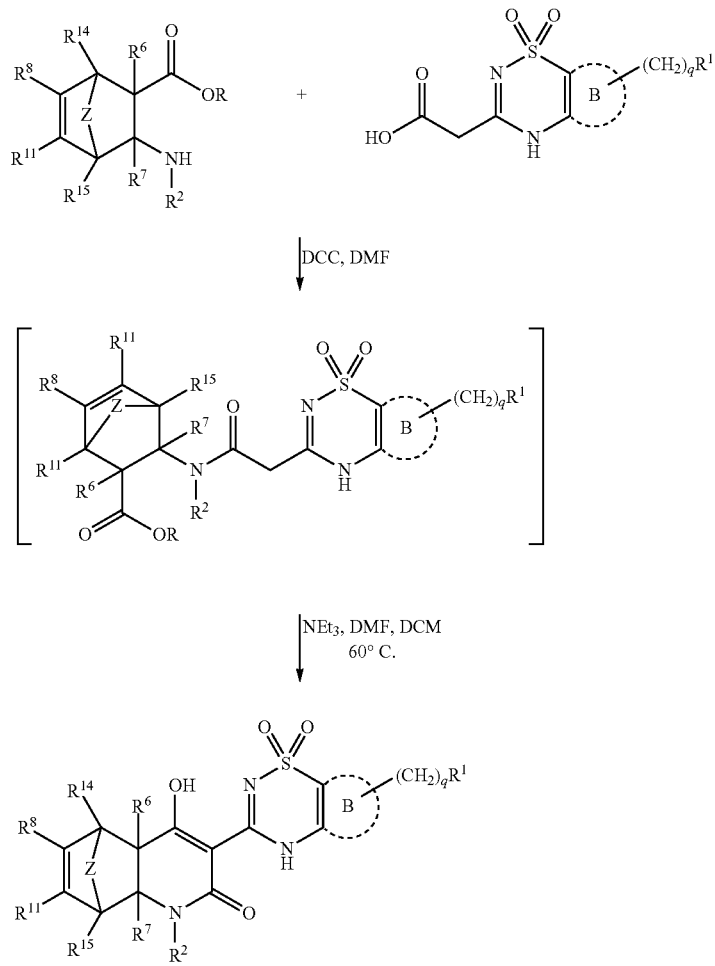

The unsaturated cyclic N-substituted-β-amino acid ester intermediates (with R as defined in Scheme 1), which can be obtained as described by one of the methods in Schemes 10, 11 or 12, can be condensed with a carboxylic acid intermediate (or a salt thereof, e.g., sodium salt) using standard peptide coupling conditions used for the formation of amide bonds, such as DCC, to yield the shown amide. This intermediate can be cyclized with or without isolation in the presence of a base (e.g., triethylamine) to give the desired unsaturated [1,2,4]thiadiazine 1,1-dioxide compounds.

Scheme 10 provides a general procedure that can be used to prepare unsaturated cyclic N-substituted-β-amino acid ester intermediates from unsaturated anhydrides.

Scheme 10

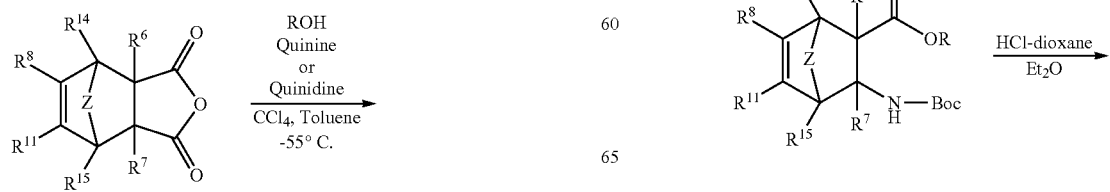

-continued

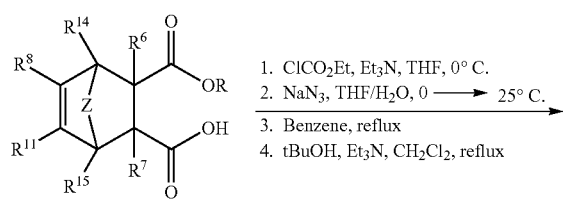

1. ClCO$_2$Et, Et$_3$N, THF, 0° C.
2. NaN$_3$, THF/H$_2$O, 0 ⟶ 25° C.
3. Benzene, reflux
4. tBuOH, Et$_3$N, CH$_2$Cl$_2$, reflux

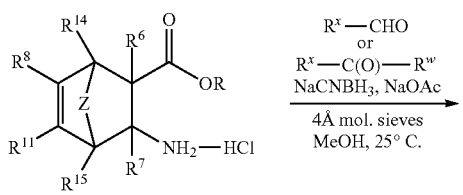 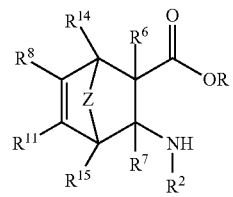

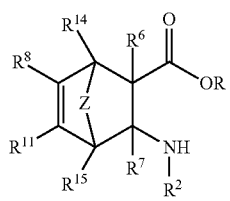

Commercially available unsaturated cyclic meso-anhydrides can be desymmetrized as described above (Scheme 2) to provide optically active unsaturated cyclic dicarboxylic acid monoesters (with R as defined in Scheme 1). These intermediates can be further elaborated into protected optically active unsaturated cyclic β-amino acid esters (e.g., Boc-protected) via a rearrangement reaction, such as the Curtius rearrangement (shown) or a Hofmann degradation. The Boc protecting group can then be selectively removed in the presence of the olefin, thus leading to the optically active unsaturated cyclic β-amino acid ester intermediates, which can be isolated (and used) as either the salts or their corresponding free bases.

The optically active unsaturated cyclic β-amino acid esters (or their salts) can then be treated with aldehydes or ketones (with $R^x$ and $R^w$ as defined in Scheme 2) in the presence of a reducing agent (such as sodium cyanoborohydride) to afford the desired optically active unsaturated cyclic N-substituted-β-amino acid ester intermediates. Alternatively, the reaction sequence described above can be performed without enzymes or chiral reagents leading to the corresponding achiral intermediates and products.

Scheme 11 provides a general procedure that can be used to prepare unsaturated cyclic N-substituted-β-amino acid ester intermediates.

Scheme 11

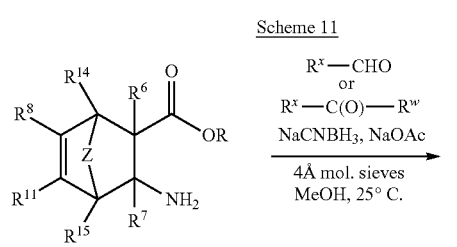

The unsaturated cyclic β-amino acid esters (or their salts, with R as defined in Scheme 1) can be purchased, prepared from the corresponding commercially available unsaturated cyclic β-amino acids, or can be prepared by the method described in Scheme 10. The unsaturated cyclic β-amino acid esters can then be treated with aldehydes or ketones (with $R^x$ and $R^w$ as defined in Scheme 2) in the presence of a reducing agent, such as sodium cyanoborohydride, to afford the desired unsaturated cyclic N-substituted-β-amino acid ester intermediates. In each case the unsaturated cyclic β-amino acid esters or the desired unsaturated cyclic N-substituted-β-amino acid ester intermediates may be optically active.

Scheme 12 provides an alternative general procedure that can be used to prepare unsaturated cyclic N-substituted-β-amino acid ester intermediates.

Scheme 12

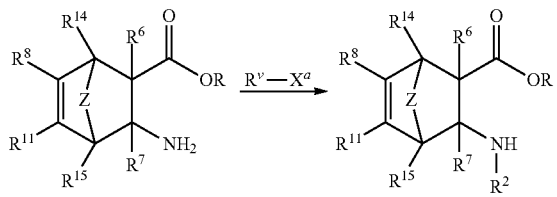

The unsaturated cyclic β-amino acid esters (or their salts, with R as defined in Scheme 1) can be purchased, prepared from the corresponding commercially available unsaturated cyclic β-amino acids, or can be prepared by the method described in Scheme 10. The unsaturated cyclic β-amino acid esters can then be treated with halides or pseudohalides $X^a$ (e.g., bromides, iodides or triflates), where $R^v$ is aryl or heterocyclyl, in the presence of metal catalyst such as copper (e.g., under Ullmann reaction conditions), to afford the desired unsaturated cyclic N-substituted-β-amino acid ester intermediates. In each case the unsaturated cyclic β-amino acid esters or the desired unsaturated cyclic N-substituted-β-amino acid ester intermediates may be optically active.

Scheme 13 provides a general procedure that can be used to prepare [1,2,4]thiadiazine 1,1-dioxide compounds of Formula I.

Scheme 13

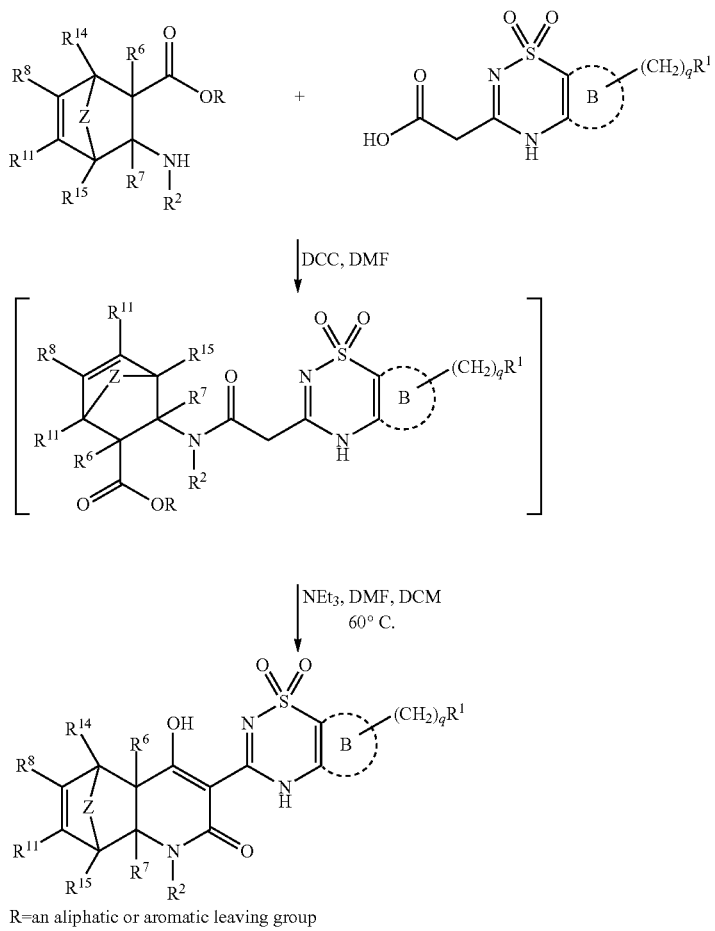

R=an aliphatic or aromatic leaving group

The β-amino acid ester intermediate, which can be obtained as described by one of the methods in Schemes 14 to 19, can be condensed with a carboxylic acid intermediate using standard peptide coupling conditions used for the formation of amide bonds, such as DCC, to yield the shown amide. This intermediate can be cyclized without isolation in the presence of a base (e.g., triethylamine) to give the desired [1,2,4]thiadiazine 1,1-dioxide compounds.

Scheme 14 provides a general procedure that can be used to prepare the β-amino acid ester intermediates.

Scheme 14

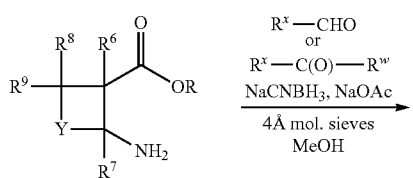

$R^x$—CHO
or
$R^x$—C(O)—$R^w$
NaCNBH$_3$, NaOAc
4Å mol. sieves
MeOH

-continued

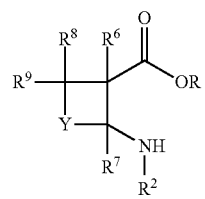

In cases where the cyclic β-amino acid esters (or their salts, e.g., hydrochlorides) are not commercially available, the commercially available cyclic β-amino acids, where Y is —$(CR^{13}R^{14})_n$— and n is 4 or 5, can be converted to an ester, such as a methyl ester, using known methods for the formation of esters from carboxylic acids (e.g., TMS-diazomethane). Also, in some cases the optically active cyclic β-amino acids are commercially available. The cyclic β-amino acid ester can then be treated with aldehydes or ketones, where $R^x$ and $R^w$ are $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene (aryl), —$C_1$-$C_5$ alkylene(heterocyclyl), aryl, or heterocyclyl, or $R^w$ can combine with $R^x$ to form a 3-to 8-membered ring, in the presence of a reducing agent (such as sodium cyanoborohydride) to afford the desired β-amino acid ester intermediates.

Scheme 15 provides a general procedure that can be used to prepare the β-amino acid ester intermediates.

Scheme 15

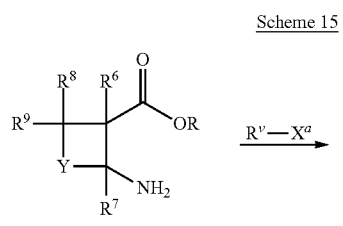

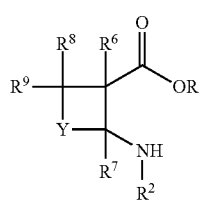

In cases where the cyclic β-amino acid esters (or their salts, e.g., hydrochlorides) are not commercially available, the commercially available cyclic β-amino acids, where Y is —$(CR^{13}R^{14})_n$— and n is 4 or 5, can be converted to an ester, such as a methyl ester, using known methods for the formation of esters from carboxylic acids (e.g., TMS-diazomethane). Also, in some cases the optically active cyclic β-amino acids are commercially available. The cyclic β-amino acid ester can then be treated with halides or pseudohalides $X^a$ (e.g., chlorides, bromides, iodides, mesylates, tosylates or triflates), where $R^v$ is aryl or heterocyclyl, in the presence of metal catalyst such as copper (e.g., under Ullmann reaction conditions) or palladium (e.g., under Buchwald-Hartwig reaction conditions), to afford the desired β-amino acid ester intermediates.

Scheme 16 provides an alternate general procedure that can be used to prepare the β-amino acid ester intermediates.

Scheme 16

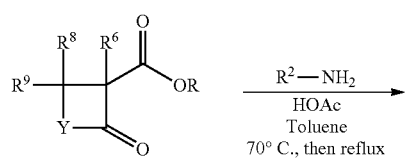

-continued

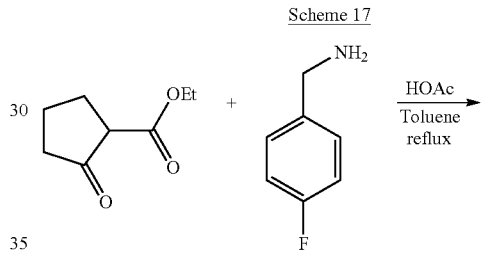

Alternatively, commercially available β-ketoesters can be treated with a primary amine to form enamines. The enamines can then be reduced to the desired corresponding amine compounds using standard methods for the reduction of a C—N double bond, such as sodium triacetoxyborohydride, yielding predominantly the cis isomers. The other isomer (trans) can be separated and isolated by chromatography.

Scheme 17 provides a specific procedure that was used to prepare the β-amino acid ester intermediates.

Scheme 17

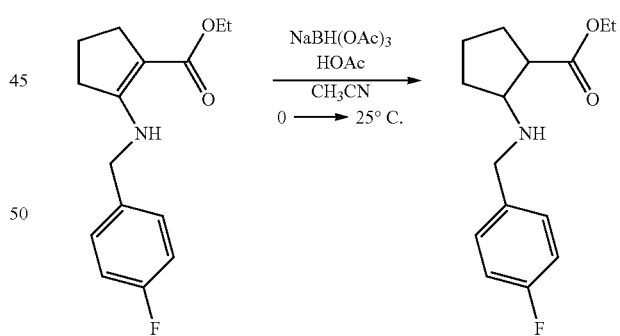

The commercially available β-ketoesters can be treated with a primary amine, such as an aliphatic or benzylic amine, to form enamines. The enamines can then be reduced to the desired corresponding amine compounds using standard methods for the reduction of a C—N double bond, such as sodium triacetoxyborohydride.

Scheme 18 provides a general procedure that can be used to prepare [1,2,4]thiadiazine 1,1-dioxide compounds of Formula I.

Scheme 18

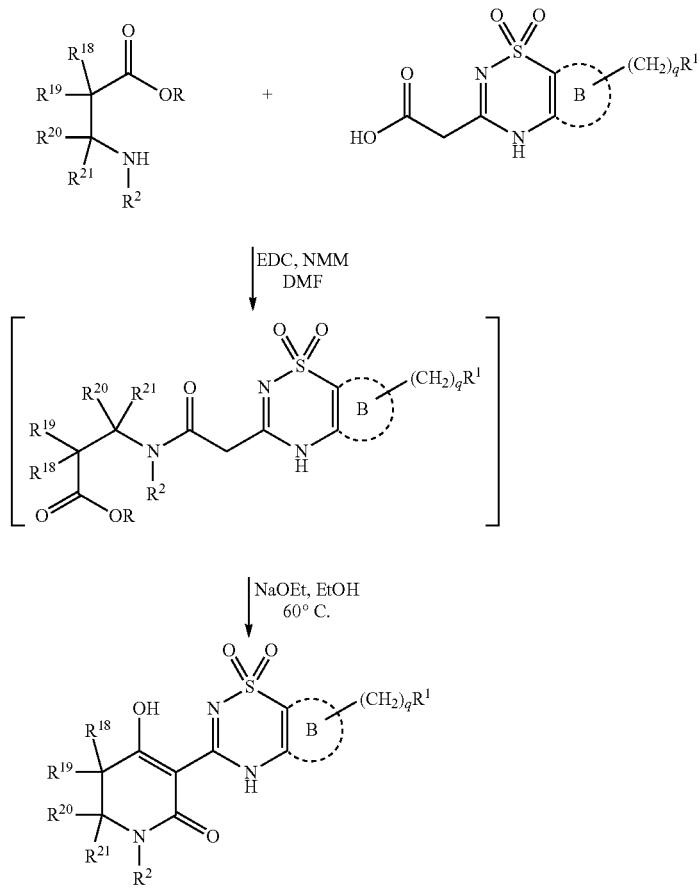

R = an aliphatic or aromatic leaving group

The N-monoalkylated β-amino acid ester intermediate, which can be obtained as described by one of the methods in Schemes 19 to 24, can be condensed with a carboxylic acid intermediate using standard peptide coupling conditions used for the formation of amide bonds, such as EDC, to yield the shown amide. This intermediate can be cyclized without isolation in the presence of a base (e.g., sodium ethoxide) to give the desired [1,2,4]thiadiazine 1,1-dioxide compounds.

Scheme 19 provides a general procedure that can be used to prepare N-monoalkylated α-monosubstituted β-amino ester intermediates.

Scheme 19

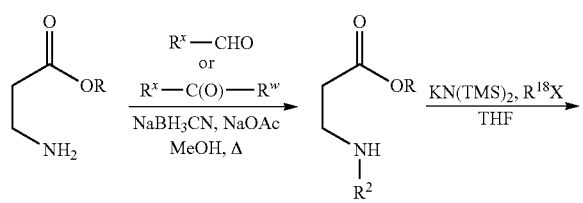

-continued

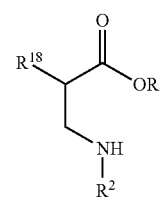

R = alkyl
$R^2 = R^xCH_2\text{-, } R^xR^wCH\text{-}$

β-Amino esters (or their salts, such as hydrochlorides) can undergo reactions with aldehydes or ketones, where $R^x$ and $R^w$ are $C_1$-$C_5$ alkyl, $C_3$-$C_8$ cycloalkyl, $C_1$-$C_5$ alkylene($C_3$-$C_8$ cycloalkyl), $C_1$-$C_5$ alkylene(aryl), $C_1$-$C_5$ alkylene(heterocyclyl), aryl, or heterocyclyl, or $R^w$ can combine with $R^x$ to form a 3- to 6-membered ring to give intermediate imines or enamines that can undergo subsequent reduction with reducing agents, such as sodium cyanoborohydride, to provide N-monoalkylated β-amino esters. Treatment of β-amino esters of this type with a strong base, such as potassium bis(trimethylsilyl)amide, followed by treatment with an appropriate alkylating agent, such as an alkyl halide, gives the desired N-monoalkylated α-monosubstituted β-amino ester intermediates.

Scheme 20 provides a general procedure that can be used to prepare N-monoalkylated α,α'-disubstituted β-amino ester intermediates.

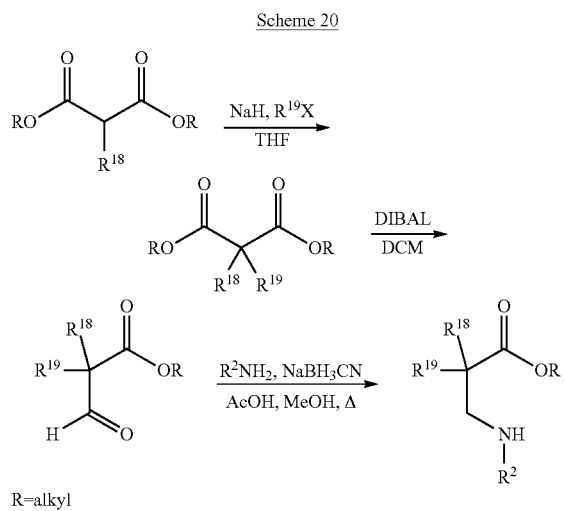

Commercially available 2-monoalkyl malonates can be alkylated with a strong base, such as sodium hydride, and a suitable alkylating agent, such as an alkyl halide. Dialkyl malonates can undergo de-symmetrization by treatment with a reducing agent, such as diisobutylaluminum hydride, to provide the corresponding β-formylesters. Also, in some cases 2,2-disubstituted dialkyl malonates are commercially available, and can undergo the reduction described above to furnish the corresponding β-formylesters. Treatment of the resulting β-formylesters with a primary amine gives imines that can undergo subsequent reduction with a reducing agent, such as sodium cyanoborohydride, to provide the desired N-monoalkylated α,α'-disubstituted β-amino ester intermediates.

Scheme 21 provides a general procedure that can be used to prepare N-monoalkylated α,α'-disubstituted β-amino ester intermediates.

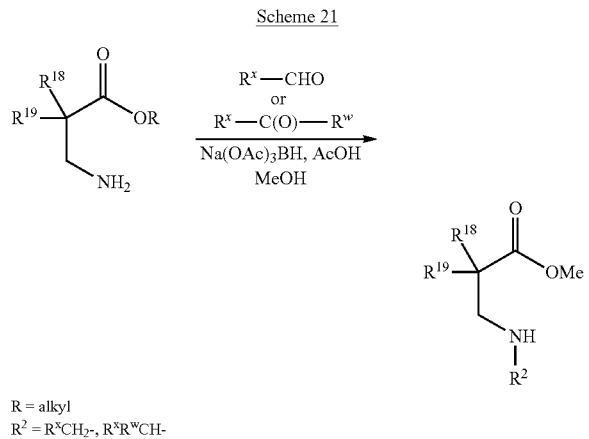

Commercially available α,α'-disubstituted β-amino acids (or their salts, such as hydrochlorides), wherein $R^{18}$ and $R^{19}$ combine to form a 3- to 6-membered cycloalkyl ring, can be converted to their corresponding β-amino esters, such as methyl esters, using standard conditions, such as (trimethylsilyl)diazomethane. The resulting β-amino esters can then be treated with aldehydes or ketones, where $R^x$ and $R^w$ are independently $C_1$-$C_5$ alkyl, $C_3$-$C_8$ cycloalkyl, —$C_1$-$C_5$ alkylene ($C_3$-$C_8$ cycloalkyl), —$C_1$-$C_5$ alkylene(aryl), —$C_1$-$C_5$ alkylene(heterocyclyl), aryl, or heterocyclyl, or $R^w$ can combine with $R^x$ to form a 3- to 6-membered ring, in the presence of a reducing agent, such as sodium triacetoxyborohydride or sodium cyanoborohydride, to provide the desired N-monoalkylated α,α'-disubstituted β-amino ester intermediates.

Scheme 22 provides a general procedure that can be used to prepare N-monoalkylated β,β'-disubstituted β-amino ester intermediates.

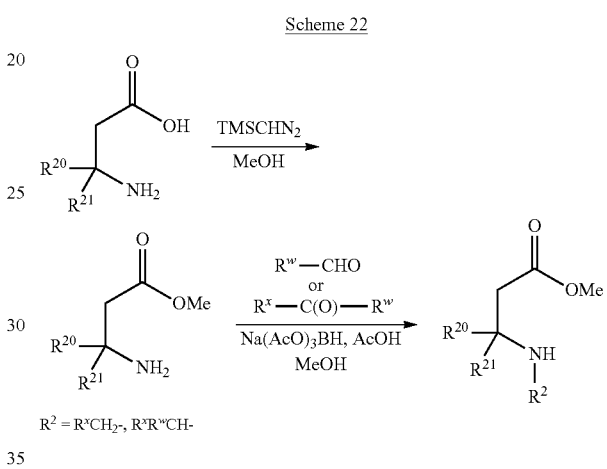

Commercially available β,β'-disubstituted β-amino acids (or their salts, such as hydrochlorides), some of which are optically active, can be converted to their corresponding β-amino esters, such as methyl esters, using standard conditions, such as (trimethylsilyl)diazomethane. The resulting β-amino esters can then be treated with aldehydes or ketones, where $R^x$ and $R^w$ are independently $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene(aryl), —$C_1$-$C_5$ alkylene(heterocyclyl), aryl, or heterocyclyl, or $R^w$ can combine with $R^x$ to form a 3-to 6-membered ring, in the presence of a reducing agent, such as sodium triacetoxyborohydride or sodium cyanoborohydride, to provide the desired N-monoalkylated β,β'-disubstituted β-amino ester intermediates.

Scheme 23 provides a general procedure that can be used to prepare α,α'-disubstituted cyclic β-amino ester intermediates with a 4- to 6-membered heterocyclyl ring.

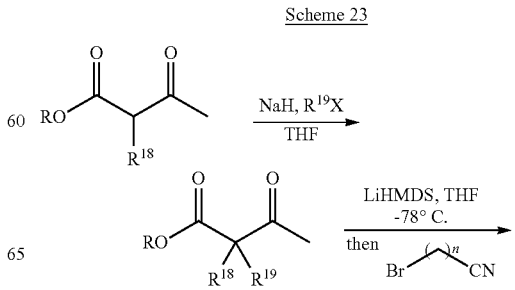

-continued

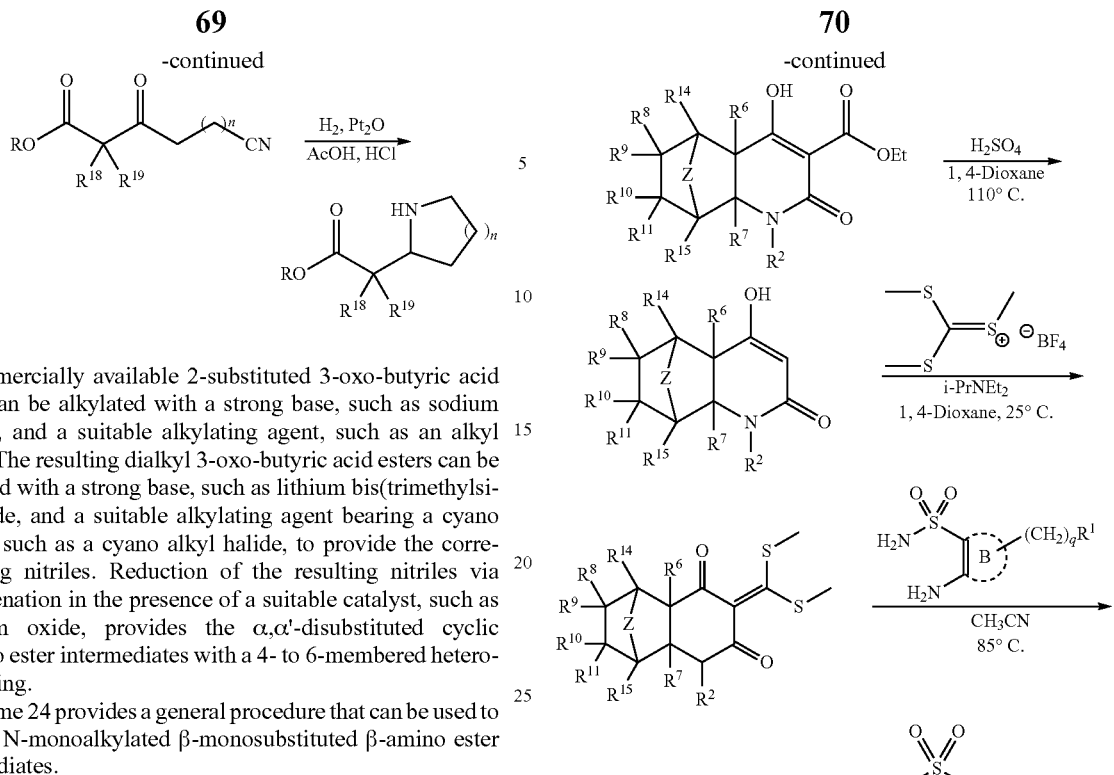

Commercially available 2-substituted 3-oxo-butyric acid esters can be alkylated with a strong base, such as sodium hydride, and a suitable alkylating agent, such as an alkyl halide. The resulting dialkyl 3-oxo-butyric acid esters can be alkylated with a strong base, such as lithium bis(trimethylsilyl)amide, and a suitable alkylating agent bearing a cyano moiety, such as a cyano alkyl halide, to provide the corresponding nitriles. Reduction of the resulting nitriles via hydrogenation in the presence of a suitable catalyst, such as platinum oxide, provides the α,α'-disubstituted cyclic β-amino ester intermediates with a 4- to 6-membered heterocyclyl ring.

Scheme 24 provides a general procedure that can be used to prepare N-monoalkylated β-monosubstituted β-amino ester intermediates.

Scheme 24

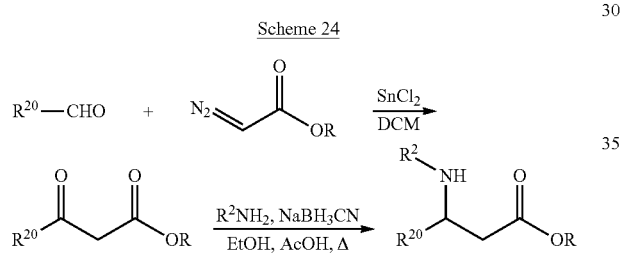

Commercially available aldehydes can be treated with diazo-acetic acid esters in the presence of a Lewis acid, such as tin (II) chloride, to provide β-ketoesters. In cases where the desired aldehydes are not available, they can be prepared via oxidation of the corresponding alcohols using known methods, such as a Swern oxidation. Treatment of the resulting β-ketoesters with a primary amine gives imines that can undergo subsequent hydrogenation with a reducing agent, such as sodium cyanoborohydride, to provide the desired N-monoalkylated β-monosubstituted β-amino ester intermediates.

Scheme 25 provides a general procedure that can be used to prepare the desired saturated [1,2,4]thiadiazine 1,1-dioxide compounds of Formula I.

Scheme 25

1.

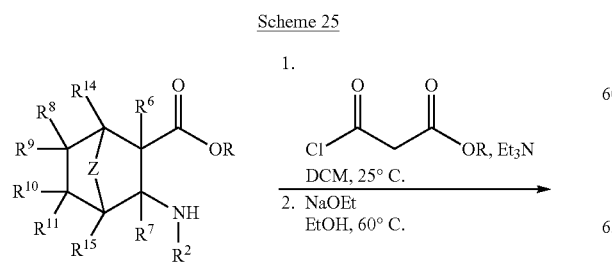

The saturated cyclic β-amino acid ester intermediates can be acylated using an alkyl malonylchloride (e.g., methyl or ethyl malonylchloride) in the presence of a base, such as triethylamine. Subsequent cyclization using a base (e.g., sodium ethoxide) affords the ester intermediate, which can then be decarboxylated in the presence of a strong acid. Treatment with (bis-methylsulfanyl-methylene)-methyl-sulfonium tetrafluoro borate salt, followed by the addition of the ortho-amino sulfonic acid amide intermediate, affords the desired saturated [1,2,4]thiadiazine 1,1-dioxide compounds.

Scheme 26 provides a specific procedure that was used to prepare a desired saturated [1,2,4]thiadiazine 1,1-dioxide compound of Formula I.

Scheme 26

1.

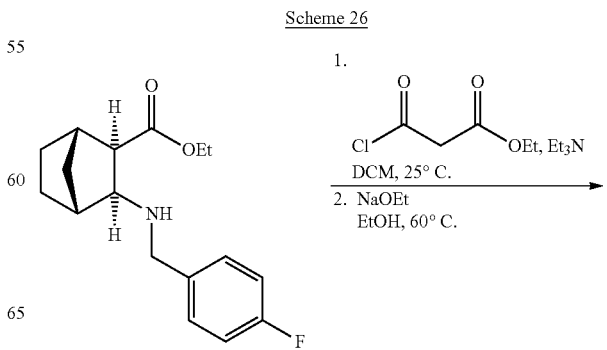

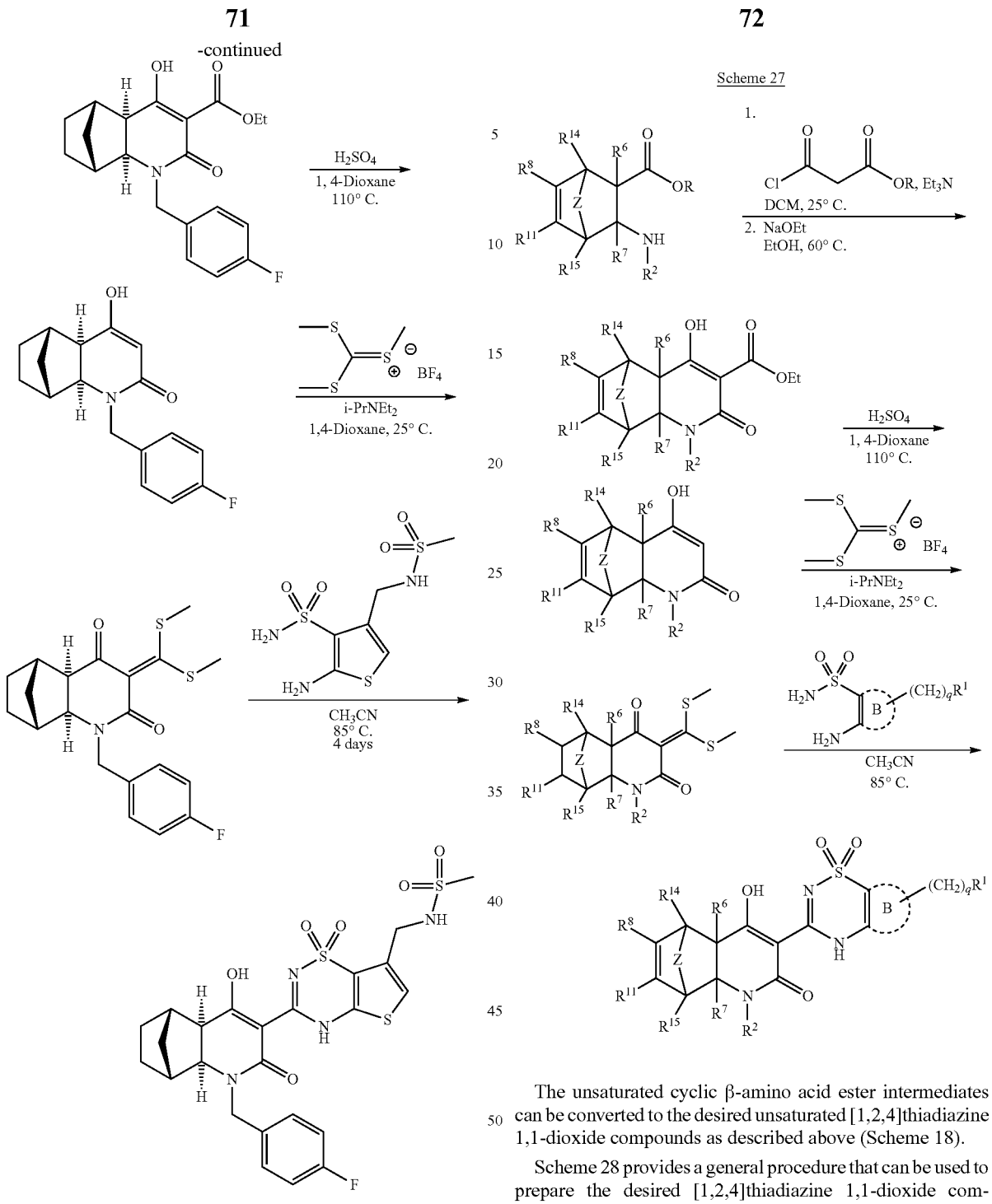

The saturated cyclic β-amino acid ester intermediate was acylated using ethyl malonylchloride in the presence of triethylamine. Subsequent cyclization using sodium ethoxide afforded the ester intermediate, which was then decarboxylated in the presence of sulfuric acid. Treatment with (bis-methylsulfanyl-methylene)-methyl-sulfonium tetrafluoro borate salt, followed by the addition of the 2-amino-4-(methanesulfonylamino-methyl)-thiophene-3-sulfonic acid amide intermediate, afforded the desired saturated [1,2,4]thiadiazine 1,1-dioxide compound shown.

Scheme 27 provides a general procedure that can be used to prepare the desired unsaturated [1,2,4]thiadiazine 1,1-dioxide compounds.

The unsaturated cyclic β-amino acid ester intermediates can be converted to the desired unsaturated [1,2,4]thiadiazine 1,1-dioxide compounds as described above (Scheme 18).

Scheme 28 provides a general procedure that can be used to prepare the desired [1,2,4]thiadiazine 1,1-dioxide compounds.

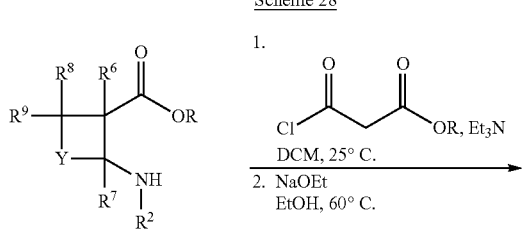

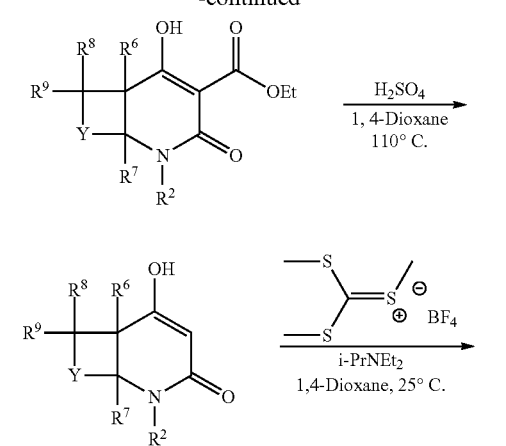

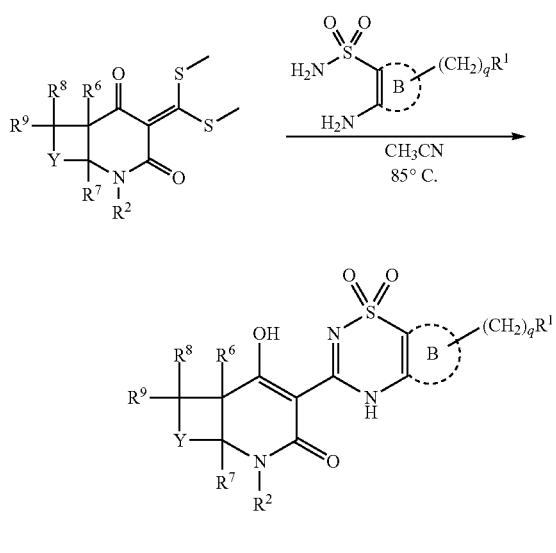

The cyclic β-amino acid ester intermediates can be converted to the desired [1,2,4]thiadiazine 1,1-dioxide compounds as described above (Schemes 18 and 20).

Scheme 29 provides a specific procedure that was used to prepare a desired saturated [1,2,4]thiadiazine 1,1-dioxide compound of Formula I.

Scheme 29

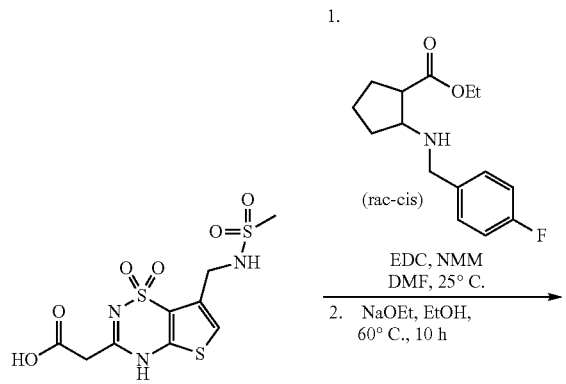

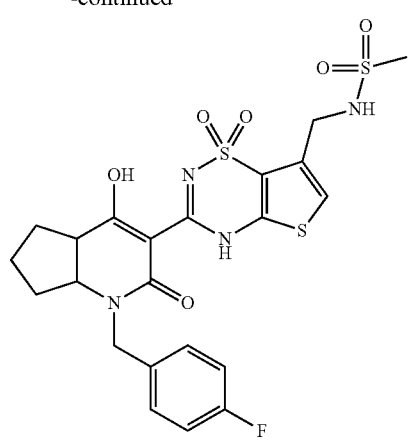

The 2-amino-4-(methanesulfonylamino-methyl)-thiophene-3-sulfonic acid amide intermediate was coupled to the N-substituted cyclic β-amino acid ester intermediate shown using standard peptide coupling conditions (e.g., 1-(3-dimethylaminopropyl)-3-ethylcarbodiimide hydrochloride in the presence of a N-methylmorpholine) to afford the corresponding amide intermediate. Subsequent cyclization using sodium ethoxide afforded the desired saturated [1,2,4] thiadiazine 1,1-dioxide compound.

Scheme 30 provides a general procedure that can be used to prepare the desired saturated [1,2,4]thiadiazine 1,1-dioxide compounds of Formula I.

Scheme 30

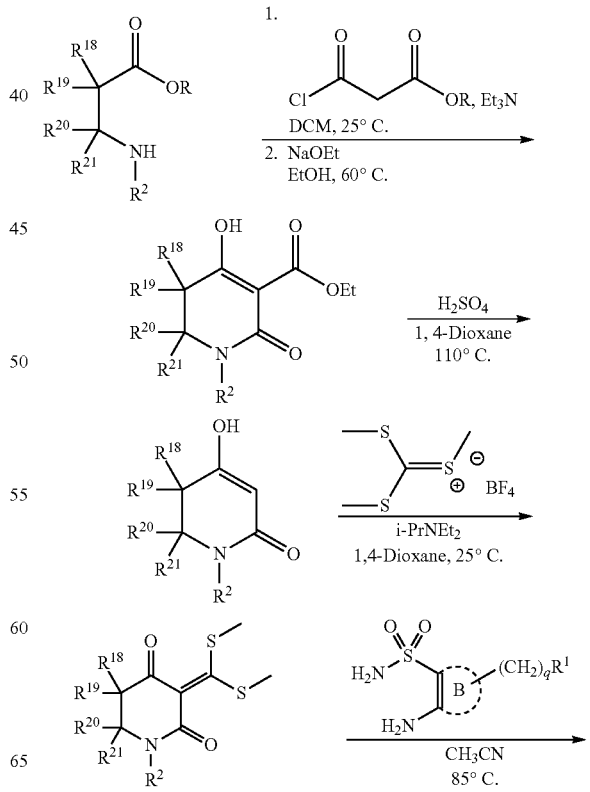

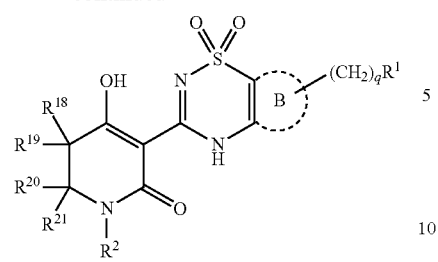

The saturated cyclic β-amino acid ester intermediates can be acylated using an alkyl malonylchloride (e.g., methyl or ethyl malonylchloride) in the presence of a base, such as triethylamine. Subsequent cyclization using a base (e.g., sodium ethoxide) affords the ester intermediate, which can then be decarboxylated in the presence of a strong acid. Treatment with (bis-methylsulfanyl-methylene)-methyl-sulfonium tetrafluoro borate salt, followed by the addition of the ortho-amino sulfonic acid amide intermediate, affords the desired saturated [1,2,4]thiadiazine 1,1-dioxide compounds.

Scheme 31 provides a specific procedure that was used to prepare the 2-amino-4-(methanesulfonylamino-methyl)-thiophene-3-sulfonic acid amide intermediate.

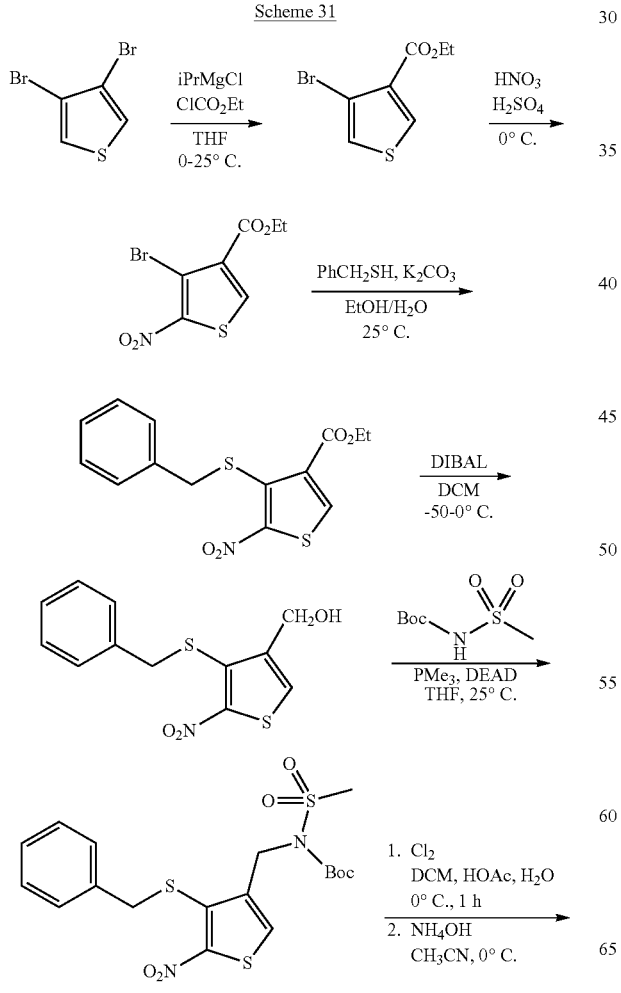

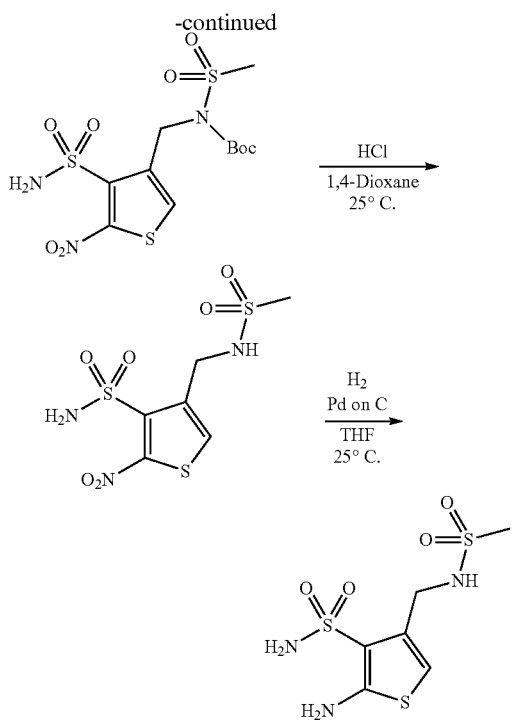

3,4-Dibromothiophene was converted to the 2-amino-4-(methanesulfonylamino-methyl)-thiophene-3-sulfonic acid amide intermediate as described in WO 2008/011337.

Scheme 32 provides a specific procedure that was used to prepare the [7-(methanesulfonylamino-methyl)-1,1-dioxo-1,4-dihydro-1λ⁶-thieno[2,3-e][1,2,4]thiadiazin-3-yl]-acetic acid intermediate.

The 2-amino-4-(methanesulfonylamino-methyl)-thiophene-3-sulfonic acid amide intermediate was acylated with methyl malonylchloride to afford the amide intermediate. Treatment with sodium hydroxide affected the cyclization and ester hydrolysis to afford the desired [7-(methanesulfonylamino-methyl)-1,1-dioxo-1,4-dihydro-1λ⁶-thieno[2,3-e][1,2,4]thiadiazin-3-yl]-acetic acid intermediate.

Scheme 33 provides an alternative specific procedure that was used to prepare the [7-(methanesulfonylamino-methyl)-1,1-dioxo-1,4-dihydro-1λ⁶-thieno[2,3-e][1,2,4]thiadiazin-3-yl]-acetic acid intermediate.

Scheme 33

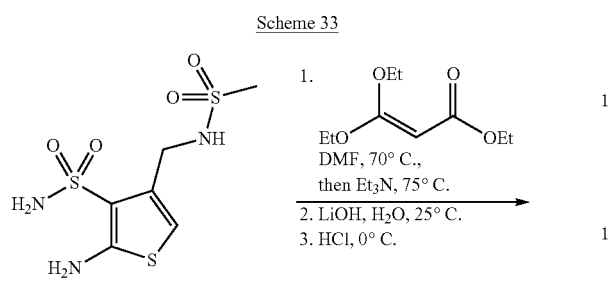

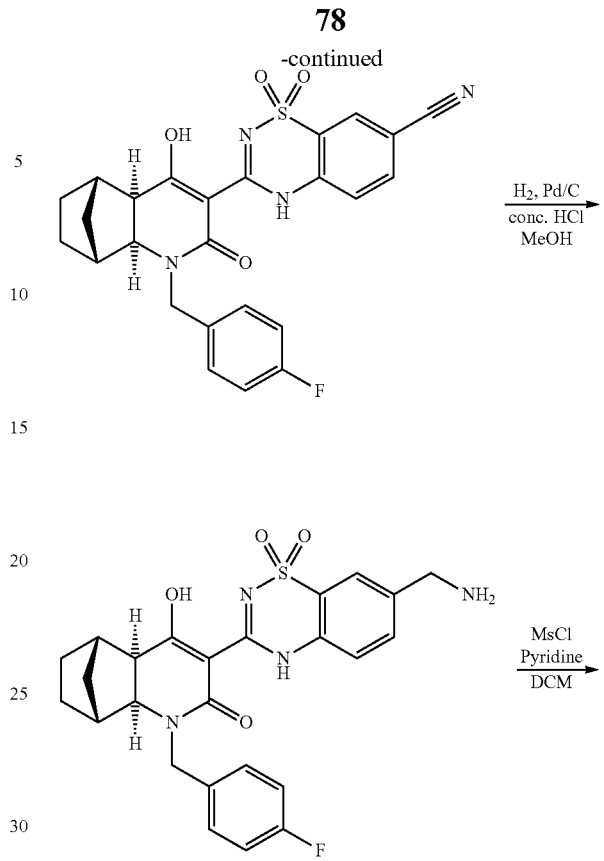

The 2-amino-4-(methanesulfonylamino-methyl)-thiophene-3-sulfonic acid amide intermediate was treated with 3,3-diethoxy-acrylic acid ethyl ester followed by triethylamine to afford the cyclic ester intermediate. The ester was hydrolysed with lithium hydroxide and after treatment with aqueous hydrochloric acid solution, the desired [7-(methanesulfonylamino-methyl)-1,1-dioxo-1,4-dihydro-1λ⁶-thieno[2,3-e][1,2,4]thiadiazin-3-yl]-acetic acid intermediate was obtained.

Scheme 34 provides a specific procedure that was used to prepare a saturated [1,2,4]thiadiazine 1,1-dioxide compound of Formula I.

Scheme 34

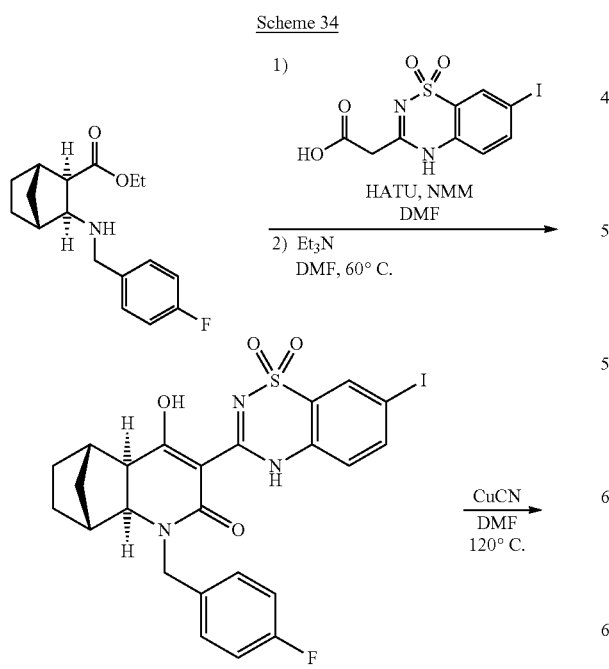

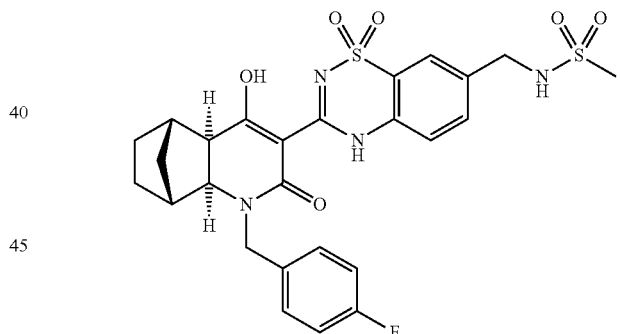

The N-substituted cyclic β-amino acid ester intermediate shown was coupled to (7-iodo-1,1-dioxo-1,4-dihydro-1λ⁶-benzo[1,2,4]thiadiazin-3-yl)-acetic acid (prepared as described in WO2007150001A1) in the presence of)-(7-aza-benzotriazol-1-yl)-1,1,3,3-tetramethyluronium hexafluorophosphate and N-methylmorpholine to afford the amide intermediate which was cyclized in the presence of triethylamine to afford the desired cyclic intermediate. Displacement of the iodo moiety with copper (I) cyanide gave the desired nitrile intermediate. Reduction of the nitrile under standard hydrogenation conditions yielded the desired benzyl amine derivative which was then treated with methanesulfonyl chloride to afford the desired [1,2,4]thiadiazine 1,1-dioxide compound.

Scheme 35 provides a general procedure that can be used to prepare the saturated [1,2,4]thiadiazine 1,1-dioxide compounds of Formula I.

Scheme 35

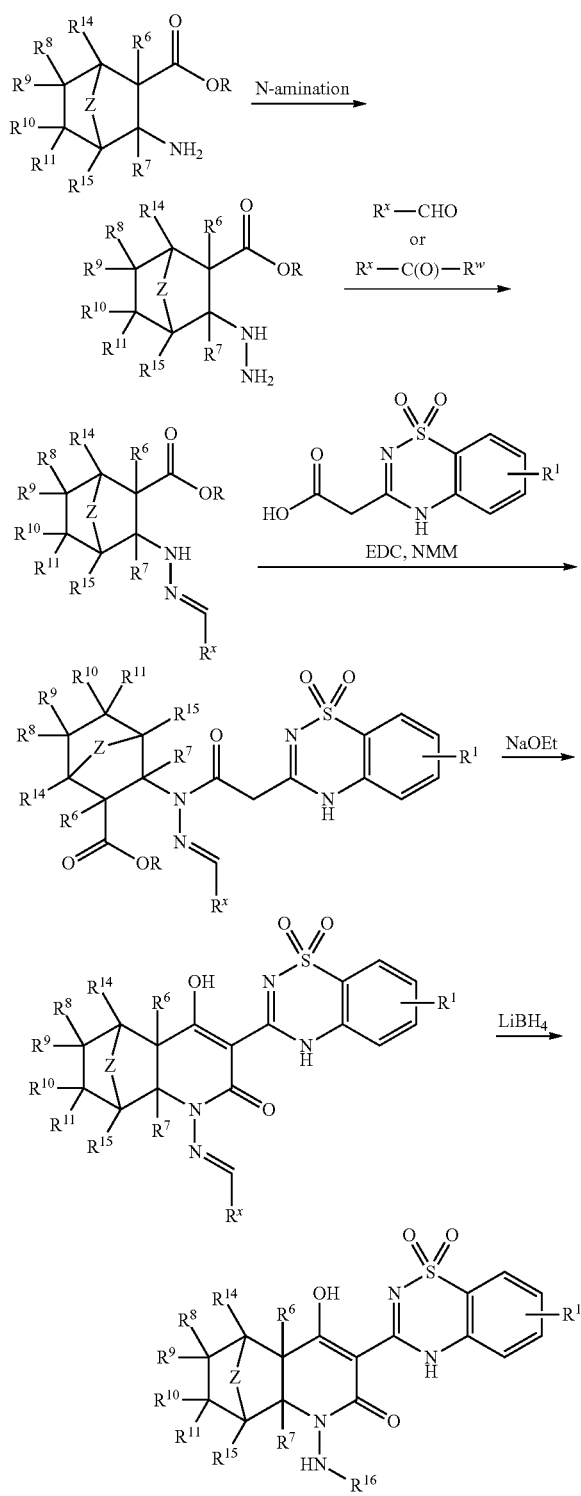

The saturated cyclic β-amino acid ester intermediates (with R as defined in Scheme 1, which can be purchased, prepared from the corresponding commercially available saturated cyclic β-amino acids, or can be prepared by methods described in Schemes 2, 3, 4, 5 or 6) can undergo an N-amination reaction using known reagents such as hydroxylamine-O-sulfonic acid to afford the corresponding hydrazines. These can be reacted with an aldehyde or a ketone (with $R^x$ and $R^w$ as defined in Scheme 2) to form the hydrazone intermediates (for simplicity only the product derived from an aldehyde is shown in the scheme) which can be coupled to the acid intermediates (prepared as described in WO2007150001A1) to form the hydrazide intermediates. Subsequent cyclization in the presence of a base (e.g., sodium ethoxide) can be used to yield the cyclic intermediates. Reduction of the hydrazone bond with a reducing agent, such as lithium borohydride, can be used to afford the desired saturated [1,2,4]thiadiazine 1,1-dioxide compounds of Formula I.

Scheme 36 provides a general procedure that can be used to prepare the unsaturated [1,2,4]thiadiazine 1,1-dioxide compounds of Formula I.

Scheme 36

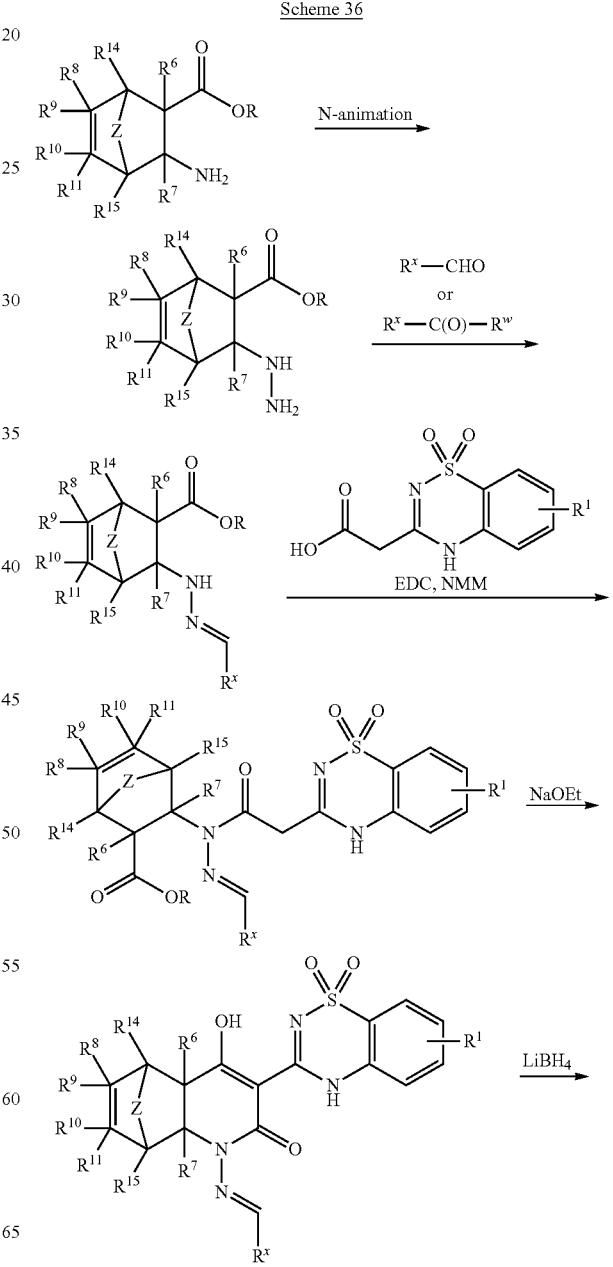

-continued

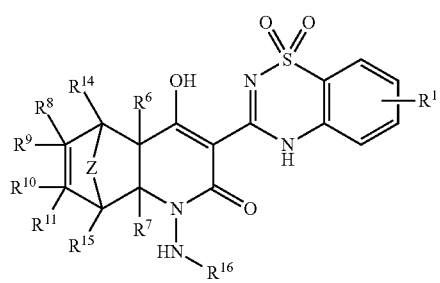

-continued

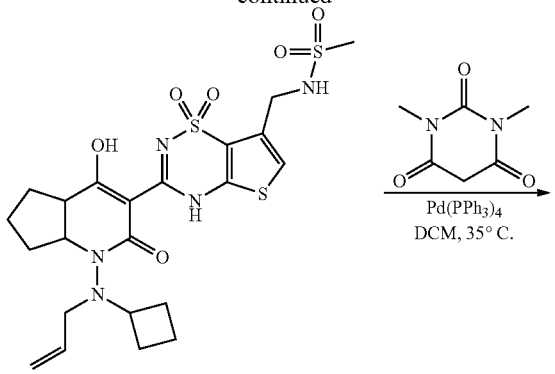

The unsaturated cyclic β-amino acid ester intermediates (with R as defined in Scheme 1, which can be purchased, prepared from the corresponding commercially available unsaturated cyclic β-amino acids, or can be prepared by the method described in Scheme 10) can undergo an N-amination reaction using known reagents such as hydroxylamine-O-sulfonic acid to afford the corresponding hydrazines. These can be reacted with an aldehyde or a ketone (with $R^x$ and $R^w$ as defined in Scheme 2) to form the hydrazone intermediates (for simplicity only the product derived from an aldehyde is shown in the scheme) which can be coupled to the acid intermediates (prepared as described in WO2007150001A1) to form the hydrazide intermediates. Subsequent cyclization in the presence of a base (e.g., sodium ethoxide) can be used to yield the cyclic intermediates. Reduction of the hydrazone bond with a reducing agent, such as lithium borohydride, can be used to afford the desired unsaturated [1,2,4]thiadiazine 1,1-dioxide compounds of Formula I.

Scheme 37 provides a specific procedure that was used to prepare a desired [1,2,4]thiadiazine 1,1-dioxide compound of Formula I.

2-(N'-Allyl-N'-cyclobutyl-hydrazino)-cyclopentanecarboxylic acid ethyl ester (prepared as described in WO2008/073982) was coupled to [7-(methanesulfonylamino-methyl)-1,1-dioxo-1,4-dihydro-1$\lambda^6$-thieno[2,3-e][1,2,4]thiadiazin-3-yl]-acetic acid in the presence of 1-(3-dimethylaminopropyl)-3-ethylcarbodiimide hydrochloride and N-methylmorpholine to afford the amide intermediate which was cyclized in the presence of sodium ethoxide to afford the desired cyclic intermediate. Deprotection with tetrakis(triphenylphosphine)palladium(0) and N,N'-dimethylbarbituric acid afforded the desired [1,2,4]thiadiazine 1,1-dioxide compound.

Scheme 38 provides a specific procedure that was used to prepare a desired [1,2,4]thiadiazine 1,1-dioxide compound of Formula I.

Scheme 37

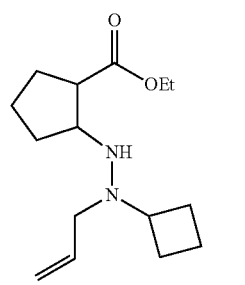

Scheme 38

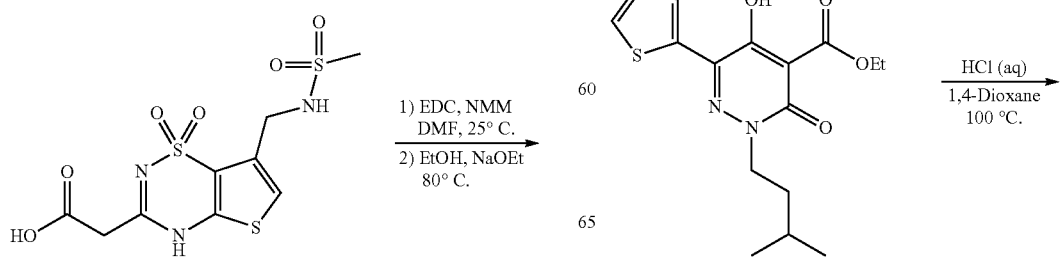

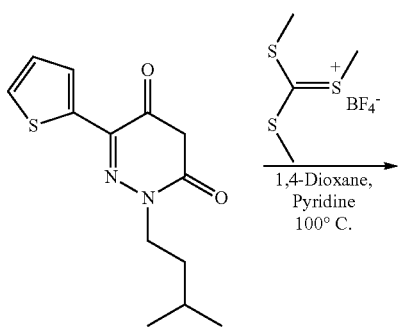

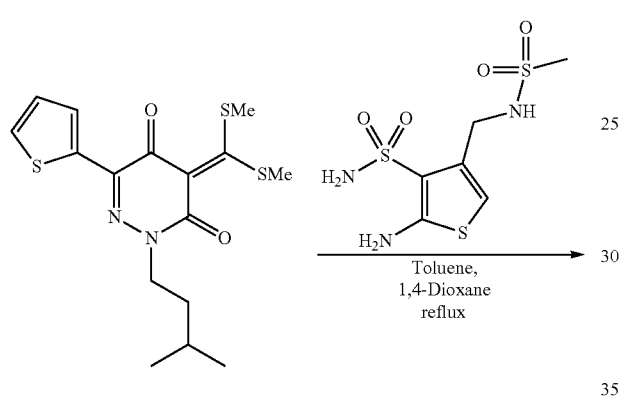

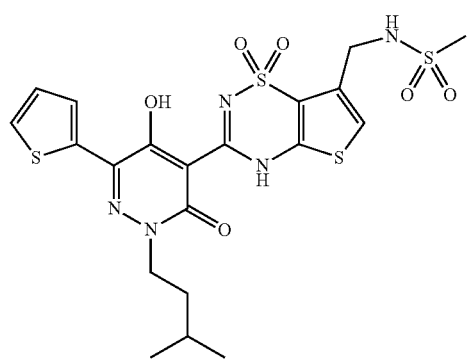

5-Hydroxy-2-(3-methyl-butyl)-3-oxo-6-thiophen-2-yl-2,3-dihydro-pyridazine-4-carboxylic acid ethyl ester (prepared as described in WO06066079A2) was decarboxylated in the presence of aqueous hydrochloric acid solution. The intermediate was treated with (bis-methylsulfanyl-methylene)-methyl-sulfonium tetrafluoro borate salt (prepared as described in WO 2008/011337) and the obtained intermediate was subsequently reacted with 2-amino-4-(methanesulfonylamino-methyl)-thiophene-3-sulfonic acid amide to afford the desired [1,2,4]thiadiazine 1,1-dioxide compound.

Example 1

(1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

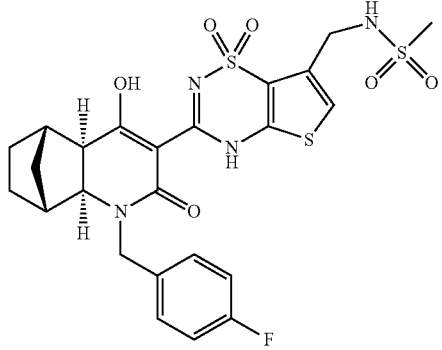

a) 4-Bromo-thiophene-3-carboxylic acid ethyl ester

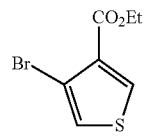

Isopropylmagnesium chloride (263 mL of a 2.0 M solution in tetrahydrofuran, 0.527 mol) was added via cannula over 35 min to a solution of 3,4-dibromo-thiophene (102 g, 0.421 mol) in tetrahydrofuran (600 mL) at 0° C. The mixture was allowed to warm to 25° C. and was stirred at that temperature for 18 h. Water (25 mL) was added, and the mixture was stirred at 25° C. for 15 min, and then was concentrated in vacuo to ~200 mL volume. The concentrate was partitioned between 1.0 M aqueous hydrochloric acid solution (400 mL) and ethyl acetate (2×350 mL). The combined organic layers were dried over sodium sulfate, filtered and were concentrated in vacuo to afford the crude product, 4-bromo-thiophene-3-carboxylic acid ethyl ester (91.9 g, 0.391 mol, 93%), as a yellow/brown oil. $^1$H NMR (400 MHz, CDCl$_3$) δ: 1.40 (3H, t, J=7.5 Hz), 4.36 (2H, q, J=7.3 Hz), 7.31 (1H, d, J=3.9 Hz), 8.10 (1H, d, J=3.0 Hz).

b) 4-Bromo-5-nitro-thiophene-3-carboxylic acid ethyl ester

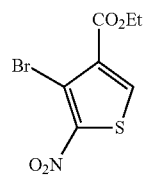

4-Bromo-thiophene-3-carboxylic acid ethyl ester (97.6 g, 0.415 mol) was added over 10 min via pipette to 18.0 M sulfuric acid (660 mL) at 0° C. After stirring 5 min at 0° C., fuming nitric acid (18 mL) dissolved in 18.0 M sulfuric acid (130 mL) was added via addition funnel over 30 min. After the addition was completed, the reaction mixture was stirred for 5 min at 0° C., and then was poured onto ice (3.5 kg). The resulting precipitate was collected by filtration and was washed sequentially with water (300 mL), 10% aqueous sodium bicarbonate solution (400 mL) and water (300 mL). The brown/yellow solid thus obtained was dried in a vacuum oven overnight at 40° C. to afford the crude product, 4-bromo-5-nitro-thiophene-3-carboxylic acid ethyl ester (97.9 g, 0.350 mol, 84%). This material was further purified by flash column chromatography (Merck silica gel 60, 40-63 μm; 25% hexanes in dichloromethane) in 20 g portions prior to use in the next step (recovery=80-90%). $^1$H NMR (400 MHz, DMSO-$d_6$) δ: 1.31 (3H, t, J=7.0 Hz), 4.30 (4H, q, J=7.0 Hz), 8.68 (1H, s).

c) 4-Benzylsulfanyl-5-nitro-thiophene-3-carboxylic acid ethyl ester

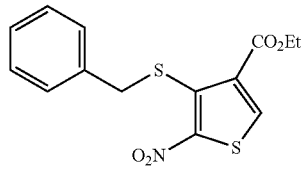

An aqueous solution of potassium carbonate (9.90 g, 71.6 mmol, dissolved in 40 mL water) was added to a suspension of 4-bromo-5-nitro-thiophene-3-carboxylic acid ethyl ester (20.06 g, 71.6 mmol) in ethanol at 25° C. Benzyl mercaptan (8.41 mL, 71.6 mmol) was added via pipette, and the dark red reaction mixture was stirred at 25° C. for 4 h and then was concentrated in vacuo to near-dryness. The remaining orange-brown solid was triturated with water (200 mL) and was collected by filtration. After washing with water (200 mL), the resulting solid was air-dried overnight to afford the desired product, 4-benzylsulfanyl-5-nitro-thiophene-3-carboxylic acid ethyl ester (22.63 g, 70.0 mmol, 98%), as a yellow/brown solid. $^1$H NMR (400 MHz, CDCl$_3$) δ: 1.41 (3H, t, J=7.1 Hz), 4.25 (2H, s), 4.39 (2H, q, J=7.0 Hz), 7.18-7.23 (5H, m), 8.07 (1H, s).

d)
(4-Benzylsulfanyl-5-nitro-thiophen-3-yl)-methanol

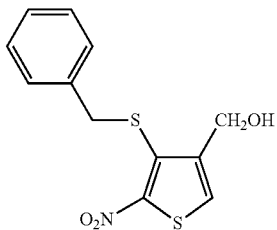

Diisobutylaluminum hydride (154 mL of a 1.0 M solution in dichloromethane, 154 mmol) was added via cannula over 25 min to a solution of 4-benzylsulfanyl-5-nitro-thiophene-3-carboxylic acid ethyl ester (22.63 g, 70.0 mmol) at −50° C. The reaction mixture was stirred at −50° C. for 2 h, then was warmed to 0° C. and was maintained at that temperature for 35 min. Water (200 mL) was added via addition funnel over 15 min and the resulting suspension was warmed to 25° C. whereupon additional water (200 mL) and D/L-tartaric acid (20 g) were added. After stirring vigorously at 25° C. for 30 min, the reaction mixture was partitioned between 1.0 M aqueous hydrochloric acid solution (300 mL) and dichloromethane (2×400 mL). The combined organic layers were dried over sodium sulfate, filtered and were concentrated in vacuo. Purification of the residue by flash column chromatography (Merck silica gel 60, 40-63 μm; 10-50% ethyl acetate in hexanes) afforded the desired product, (4-benzylsulfanyl-5-nitro-thiophen-3-yl)-methanol (10.52 g, 37.4 mmol, 53%), as a dark brown oil. $^1$H NMR (400 MHz, CDCl$_3$) δ: 4.21 (2H, s), 4.40 (2H, s), 7.09-7.12 (1H, m), 7.21-7.24 (4H, m), 7.39 (1H, s).

e) Boc-N-(4-Benzylsulfanyl-5-nitro-thiophen-3-ylmethyl)-methanesulfonamide

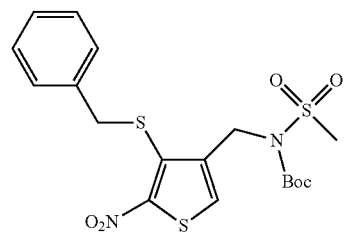

Triethylamine (22.0 mL, 158 mmol), di-tert-butyl dicarbonate (27.5 g, 126 mmol), and 4-(N,N-dimethylamino)pyridine (1.28 g, 10.5 mmol) were added sequentially to a solution of methanesulfonamide (10.0 g, 105 mmol) in dichloromethane (300 mL) at 25° C. The mixture was stirred at 25° C. for 2 h, and then was concentrated in vacuo to ~40 mL volume. Ethyl acetate (350 mL) was added and the mixture was washed with 1.0 M aqueous hydrochloric acid solution (300 mL). The aqueous layer was extracted with ethyl acetate (250 mL) and the combined organic layers were dried over sodium sulfate, filtered and were concentrated in vacuo to afford Boc-N-methanesulfonamide (17.1 g, 87.6 mmol, 83%) as a white solid. $^1$H NMR (400 MHz, CDCl$_3$) δ: 1.53 (9H, s), 3.27 (3H, s).

Boc-N-methanesulfonamide (11.0 g, 56.3 mmol), trimethylphosphine (56.1 mL of a 1.0 M solution in tetrahydrofuran, 56.1 mmol), and a 40 wt. % solution of diethyl azodicarboxylate in toluene (25.6 mL, 56.0 mmol) were added sequentially to a solution of (4-benzylsulfanyl-5-nitro-thiophen-3-yl)-methanol (10.52 g, 37.4 mmol) in tetrahydrofuran (300 mL) at 25° C. The mixture was stirred for 3.5 h at 25° C., and then was concentrated in vacuo. Purification of the residue by flash column chromatography (Merck silica gel 60, 40-63 μm; 20% ethyl acetate in hexanes) afforded the desired product, Boc-N-(4-benzylsulfanyl-5-nitro-thiophen-3-ylmethyl)-methanesulfonamide (9.79 g, 21.3 mmol, 57%), as a dark brown oil. $^1$H NMR (400 MHz, CDCl$_3$) δ: 1.50 (9H, s), 3.29 (3H, s), 4.19 (2H, s), 4.68 (2H, s), 7.15-7.18 (2H, m), 7.22-7.25 (3H, m), 7.40 (1H, s).

f) Boc-4-(Methanesulfonylamino-methyl)-2-nitro-thiophene-3-sulfonic acid amide

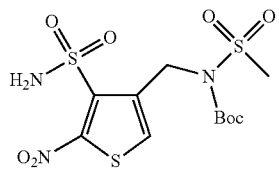

Boc-N-(4-Benzylsulfanyl-5-nitro-thiophen-3-ylmethyl)-methanesulfonamide (4.90 g, 10.7 mmol) was dissolved in dichloromethane (65 mL) and the dark brown solution was cooled to 0° C. A mixture of glacial acetic acid (15 mL) and water (20 mL) was then added slowly, producing a biphasic mixture. Chlorine gas was bubbled through this mixture at 0° C. for 5 min using a pipette. The resulting yellow biphasic mixture was stirred at 0° C. for an additional 35 min, then was poured into a separatory funnel and the layers separated. The aqueous layer was extracted with dichloromethane (1×50 mL) and the combined organic layers were washed with water (1×50 mL), dried over sodium sulfate, filtered and concentrated in vacuo to ~25 mL volume. Heptane (80 mL) was then added to this solution via addition funnel over 30 min. The resulting orange precipitate was collected by filtration, washed with heptane (2×20 mL), and air-dried to afford Boc-4-(methanesulfonylamino-methyl)-2-nitro-thiophene-3-sulfonyl chloride (2.45 g, 5.63 mmol, 53%).

Concentrated aqueous ammonium hydroxide solution (3 mL) was added to a solution of Boc-4-(methanesulfonylamino-methyl)-2-nitro-thiophene-3-sulfonyl chloride (3.30 g, 7.59 mmol) in acetonitrile (90 mL) at 0° C. The mixture was stirred at 0° C. for 45 min, and then was partitioned between half-saturated aqueous sodium bicarbonate solution (150 mL) and ethyl acetate (2×150 mL). The combined organic layers were dried over sodium sulfate, filtered and were concentrated in vacuo. Purification of the residue by flash column chromatography (Teledyne Isco RediSep column; 20-90% ethyl acetate in hexanes) afforded the desired product, Boc-4-(methanesulfonylamino-methyl)-2-nitro-thiophene-3-sulfonic acid amide (2.64 g, 6.35 mmol, 84%), as a yellow solid. $^1$H NMR (400 MHz, CDCl$_3$) δ: 1.54 (9H, s), 3.35 (3H, s), 5.12 (2H, s), 5.81 (2H, bs), 7.61 (1H, s).

g) 4-(Methanesulfonylamino-methyl)-2-nitro-thiophene-3-sulfonic acid amide

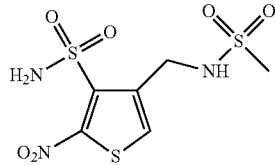

Hydrogen chloride (20 mL of a 4.0 M solution in 1,4-dioxane) was added to a solution of Boc-4-(methanesulfonylamino-methyl)-2-nitro-thiophene-3-sulfonic acid amide (0.600 g, 1.44 mmol) in 1,4-dioxane (10 mL) at 25° C. The mixture was stirred at 25° C. for 18 h, and then was partitioned between half-saturated aqueous sodium bicarbonate solution (150 mL) and ethyl acetate (2×150 mL). The combined organic layers were dried over sodium sulfate, filtered and were concentrated in vacuo. Purification of the residue by flash column chromatography (Teledyne Isco RediSep column; 60-100% ethyl acetate in hexanes) provided a yellow oil. This material was triturated with dichloromethane to afford a yellow solid that was collected by filtration to afford the desired product, 4-(methanesulfonylamino-methyl)-2-nitro-thiophene-3-sulfonic acid amide (0.400 g, 1.27 mmol, 88%). $^1$H NMR (400 MHz, DMSO-d$_6$) δ: 2.96 (3H, s), 3.31 (2H, s), 4.35 (1H, d, J=5.4 Hz), 7.61 (1H, t, J=6.2 Hz), 7.85 (1H, s), 7.87 (2H, bs).

h) 2-Amino-4-(methanesulfonylamino-methyl)-thiophene-3-sulfonic acid amide

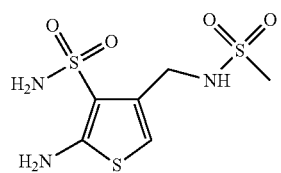

Palladium on carbon (10%, 0.150 g, dry) was added to a solution of 4-(methanesulfonylamino-methyl)-2-nitro-thiophene-3-sulfonic acid amide (0.156 g, 0.495 mmol) in tetrahydrofuran (12 mL) at 25° C. The flask was degassed and backfilled with hydrogen gas via balloon and the mixture was stirred under a positive pressure of hydrogen (2 balloons) for 17 h. The mixture was then filtered through Celite and the Celite was washed with tetrahydrofuran (3×20 mL). The combined filtrate and washings were concentrated in vacuo to afford the crude product, 2-amino-4-(methanesulfonylamino-methyl)-thiophene-3-sulfonic acid amide, as a yellow oil. This material was used in subsequent synthetic transformations without additional purification.

i) (rac-di-exo)-3-Aza-tricyclo[4.2.1.0$^{2,5}$]nonan-4-one

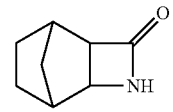

rac-di-exo

Bicyclo[2.2.1]hept-2-ene (1000 g, 10.6 mol) was dissolved in ethyl acetate (1.7 L) and the resulting solution was cooled to 0° C. Chlorosulfonyl isocyanate (969 mL, 11.1 mol) was added at 0-20° C. over 30 min. The mixture was allowed to warm to 25° C. and stirred for 4 h, then cooled to 0° C. A mixture of sodium sulfite (1500 g, 11.9 mol) in water (6 L) was added at 0-20° C. The milky suspension was stirred at 25° C. for 30 min and cooled to 0° C. A 50% aqueous sodium hydroxide solution (1.6 L, 30.3 mol) was added at 0-15° C. to adjust to pH 7. A saturated aqueous sodium carbonate solution (300 mL) was added to adjust the pH to 7.5-8.0. The mixture was filtered and the solid was washed with ethyl acetate (3×2 L) and the solid was discarded. The combined ethyl acetate extracts were washed with saturated aqueous brine solution (2 L), dried over magnesium sulfate and filtered. The solution was concentrated in vacuo to dryness to afford the desired product, (rac-di-exo)-3-aza-tricyclo

[4.2.1.0²,⁵]nonan-4-one (1220 g, 8.9 mol, 84%), as a white glassy solid. ¹H NMR (400 MHz, CDCl₃) δ 1.02-1.11 (2H, m), 1.24 (1H, dt, J1=10.9 Hz, J2=1.6 Hz), 1.51-1.72 (3H, m), 2.37-2.37 (1H, m), 2.43-2.44 (1H, m), 2.99-3.00 (1H, m), 3.40 (1H, d, J=3.4 Hz), 5.73 (1H, bs).

j) (rac-di-exo)-3-Amino-bicyclo[2.2.1]heptane-2-carboxylic acid hydrochloride

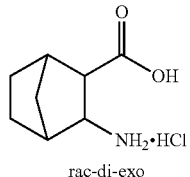

rac-di-exo

To (rac-di-exo)-3-aza-tricyclo[4.2.1.0²,⁵]nonan-4-one (23.37 g, 170.4 mmol) was added a 12.0 M aqueous hydrochloric acid solution (150 mL). The mixture was stirred at 25° C. for 12 h. The solvent was evaporated in vacuo and the crude compound was dried under high vacuum for 0.5 h. The crude compound was triturated with acetone and filtered to afford (rac-di-exo)-3-amino-bicyclo[2.2.1]heptane-2-carboxylic acid hydrochloride (28.43 g, 148.3 mmol, 87%), as a white solid. ¹H NMR (400 MHz, DMSO-d6) 1.15-1.26 (3H, m), 1.42-1.59 (2H, m), 1.87 (1H, d, J=10.3 Hz), 2.33 (1H, d, J=3.4 Hz), 2.45 (1H, d, J=2.3 Hz), 2.67 (1H, d, J=7.6 Hz), 3.23-3.26 (1H, m), 7.93 (3H, bs), 12.73 (1H, bs).

k) (rac-di-exo)-3-Amino-bicyclo[2.2.1]heptane-2-carboxylic acid ethyl ester hydrochloride

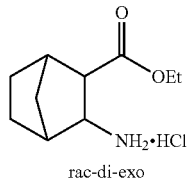

rac-di-exo

To absolute ethanol (75 mL) at −10° C. was added thionyl chloride (4.1 mL, 54.5 mmol) dropwise followed by (rac-di-exo)-3-amino-bicyclo[2.2.1]heptane-2-carboxylic acid hydrochloride (9.60 g, 50.1 mmol). The mixture was stirred at 0° C. for 1 h, at 25° C. for 4 h, and heated at reflux for 0.5 h. The solution was concentrated in vacuo and dried under high vacuum to afford the crude (rac-di-exo)-3-amino-bicyclo[2.2.1]heptane-2-carboxylic acid ethyl ester hydrochloride (11.01 g, 50.1 mmol, 100%), as an off-white solid. ¹H NMR (400 MHz, DMSO-d6) 1.17-1.27 (3H, m), 1.21 (3H, t, J=7.0 Hz), 1.43-1.57 (2H, m), 1.91 (1H, d, J=10.0 Hz), 2.36 (1H, d, J=3.9 Hz), 2.42 (1H, d, J=3.0 Hz), 2.72 (1H, d, J=7.6 Hz), 3.28 (1H, d, J=8.3 Hz), 4.00-4.13 (2H, m), 8.06 (3H, bs).

1) (rac-di-exo)-3-Amino-bicyclo[2.2.1]heptane-2-carboxylic acid ethyl ester

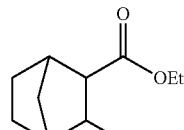

rac-di-exo

To (rac-di-exo)-3-amino-bicyclo[2.2.1]heptane-2-carboxylic acid ethyl ester hydrochloride (11.01 g, 50.1 mmol) was added saturated aqueous sodium bicarbonate solution (50 mL) and the mixture was stirred at 25° C. for 0.5 h. The crude product was extracted with ethyl acetate (3×100 mL). The solution was dried over magnesium sulfate, filtered, and concentrated in vacuo and dried under high vacuum for 2 h to afford the crude (rac-di-exo)-3-amino-bicyclo[2.2.1]heptane-2-carboxylic acid ethyl ester (8.17 g, 44.6 mmol, 89%), as a brown oil. ¹H NMR (400 MHz, CDCl₃) 1.10-1.26 (3H, m), 1.29 (3H, t, J=7.0 Hz), 1.45-1.62 (2H, m), 1.86 (2H, bs), 1.95 (1H, dt, J1=10.3 Hz, J2=1.9 Hz), 2.09 (1H, d, J=4.5 Hz), 2.49 (1H, d, J=4.2 Hz), 2.56 (1H, d, J=9.0 Hz), 3.24 (1H, d, J=7.7 Hz), 4.09-4.21 (2H, m).

m) (1R,2S,3R,4S)-3-Ethoxycarbonyl-bicyclo[2.2.1]hept-2-yl-aminium (1'S)-(+)-10-camphorsulfonate

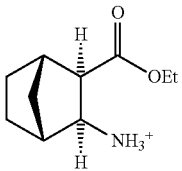 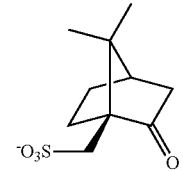

To a solution of (rac-di-exo)-3-amino-bicyclo[2.2.1]heptane-2-carboxylic acid ethyl ester (408.47 g, 2.98 mol) in ethyl acetate (500 mL) was added a solution of (1S)-(+)-10-camphorsulfonic acid (691.70 g, 2.98 mol) in ethanol (800 mL) at 50-75° C. over 30 min. The resulting solution was stirred at 70° C. for 1 h. More ethyl acetate (2.7 L) was added at >55° C. The solution was allowed to cool to 50° C. and seeded with (1R,2S,3R,4S)-3-ethoxycarbonyl-bicyclo[2.2.1]hept-2-yl-aminium (1'S)-(+)-10-camphorsulfonate (ca. 20 mg). The mixture was allowed to cool to 25° C. and stirred for 16 h. The suspension was filtered and the wet filter cake was washed with ethyl acetate (2×500 mL). The crude salt was recrystallized from ethanol (600 mL) and ethyl acetate (3 L) to afford the desired product, (1R,2S,3R,4S)-3-ethoxycarbonyl-bicyclo[2.2.1]hept-2-yl-aminium (1'S)-(+)-10-camphorsulfonate (334.84 g, 0.806 mol, 27%, >99.5% de), as a white solid. ¹H NMR (400 MHz, CDCl₃) δ 0.84 (3H, s), 1.08 (3H, s), 1.30 (3H, t, J=6.9 Hz), 1.32-1.43 (4H, m), 1.58-1.75 (3H, m), 1.89 (1H, d, J=17.7 Hz), 1.95-2.07 (3H, m), 2.33 (1H, dt, J₁=18.4 Hz, J₂=3.9 Hz), 2.53 (1H, s), 2.58-2.65 (1H, m), 2.69 (1H, d, J=2.9 Hz), 2.76-2.79 (2H, m), 3.26 (1H, d, J=14.1 Hz), 3.60 (1H, d, J=7.4 Hz), 4.14-4.27 (2H, m), 7.80 (3H, bs).

Alternatively, (1R,2S,3R,4S)-3-ethoxycarbonyl-bicyclo[2.2.1]hept-2-yl-aminium (1'S)-(+)-10-camphorsulfonate can be prepared as follows:

(rac-di-exo)-3-Aza-tricyclo[4.2.1.0²,⁵]nonan-4-one (prepared as described in Example 1i, 1220 g, 8.9 mol) was dissolved in ethyl acetate (1.7 L). The solution was heated to n) (1S,2R,3S,4R)-3-Amino-bicyclo[2.2.1]heptane-2-carboxylic acid ethyl ester

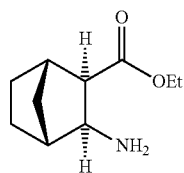

To (1R,2S,3R,4S)-3-ethoxycarbonyl-bicyclo[2.2.1]hept-2-yl-aminium (1'S)-(+)-10-camphorsulfonate (2.76 g, 6.64 mmol) was added ethyl acetate (28 mL) and saturated aqueous sodium carbonate solution (28 mL) and the mixture was stirred at 25° C. for 0.5 h. The organic layer was separated and the aqueous layer was extracted with ethyl acetate (2×50 mL). The solution was dried over magnesium sulfate, filtered, and concentrated in vacuo and dried under high vacuum for 1 h to afford (1S,2R,3S,4R)-3-amino-bicyclo[2.2.1]heptane-2-carboxylic acid ethyl ester (1.15 g, 6.28 mmol, 95%), as a colorless oil. $^1$H NMR (400 MHz, CDCl$_3$) 1.10-1.26 (3H, m), 1.29 (3H, t, J=7.0 Hz), 1.45-1.62 (2H, m), 1.86 (2H, bs), 1.95 (1H, dt, J1=10.3 Hz, J2=1.9 Hz), 2.09 (1H, d, J=4.5 Hz), 2.49 (1H, d, J=4.2 Hz), 2.56 (1H, d, J=9.0 Hz), 3.24 (1H, d, J=7.7 Hz), 4.09-4.21 (2H, m).

In order to determine the enantiomeric excess, (1S,2R,3S,4R)-3-amino-bicyclo[2.2.1]heptane-2-carboxylic acid ethyl ester was derivatized to the (S)-mandelate salt as follows: To a solution of (1S,2R,3S,4R)-3-amino-bicyclo[2.2.1]heptane-2-carboxylic acid ethyl ester (34.2 mg, 0.187 mmol) in ethyl acetate (1 mL) was added (S)-α-hydroxyphenylacetic acid (28.7 mg, 0.187 mmol) and the mixture was stirred at 25° C. for 0.5 h. The solid was filtered and dried under high vacuum to afford (1R,2S,3R,4S)-3-ethoxycarbonyl-bicyclo[2.2.1]hept-2-yl-aminium (S)-α-hydroxyphenylacetate (11.4 mg, 0.034 mmol, 18%, de=97%), as a white solid. 1H NMR (400 MHz, CDCl$_3$) 1.08-1.20 (3H, m), 1.28 (3H, t, J=7.1 Hz), 1.50-1.59 (2H, m), 1.79 (1H, d, J=10.9 Hz), 2.23 (1H, s), 2.46-2.48 (2H, m), 3.04 (1H, d, J=7.8 Hz), 4.05-4.18 (2H, m), 4.89 (1H, s), 5.49 (3H, bs), 7.22-7.31 (3H, m), 7.43 (2H, d, J=6.9 Hz).

o) (1S,2R,3S,4R)-3-(4-Fluorobenzylamino)-bicyclo[2.2.1]heptane-2-carboxylic acid ethyl ester

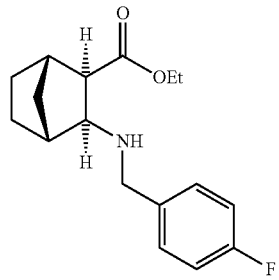

To a solution of (1S,2R,3S,4R)-3-amino-bicyclo[2.2.1]heptane-2-carboxylic acid ethyl ester (1.15 g, 6.28 mmol) in ethanol (30 mL) was added 4-fluorobenzaldehyde (0.68 mL, 6.31 mmol), glacial acetic acid (0.4 mL, 6.99 mmol), and sodium cyanoborohydride (1.04 g, 15.7 mmol) at 25° C. After stirring for 3 h, the mixture was diluted with ethyl acetate (50 mL) and quenched with saturated aqueous sodium bicarbonate solution (50 mL) for 0.5 h. The mixture was filtered through Celite. The organic layer was separated and the aqueous layer was extracted with ethyl acetate (2×50 mL). When all solvent was removed, a solid was formed. The solid was filtered, washed with water, and dried in vacuo to afford the desired product, (1S,2R,3S,4R)-3-(4-fluorobenzylamino)-bicyclo[2.2.1]heptane-2-carboxylic acid ethyl ester (1.74 g, 5.97 mmol, 95%), as a white solid. $^1$H NMR (400 MHz, CDCl$_3$) δ 1.05-1.16 (2H, m), 1.21 (1H, dt, J$_1$=8.0 Hz, J$_2$=1.6 Hz), 1.27 (3H, t, J=7.4 Hz), 1.45-1.61 (2H, m), 1.94 (1H, dt, J$_1$=10.1 Hz, J$_2$=1.9 Hz), 2.28 (1H, d, J=3.9 Hz), 2.43 (1H, d, J=3.3 Hz), 2.60 (1H, dd, J$_1$=8.8 Hz, J$_2$=1.5 Hz), 2.94 (1H, d, J=7.8 Hz), 3.66 (1H, d, J=13.2 Hz), 3.80 (1H, d, J=13.5 Hz), 4.13 (2H, q, J=7.0 Hz), 6.97 (2H, t, J=8.5 Hz), 7.26 (2H, t, J=7.1 Hz).

Alternatively, (1S,2R,3S,4R)-3-(4-Fluorobenzylamino)-bicyclo[2.2.1]heptane-2-carboxylic acid ethyl ester can be prepared as follows:

(1R,2S,3R,4S)-3-ethoxycarbonyl-bicyclo[2.2.1]hept-2-yl-aminium (1'S)-(+)-10-camphorsulfonate (prepared as described in Example 1m, 2000 g, 4.81 mol) and powdered potassium carbonate (1320 g, 9.62 mol) were suspended in ethyl acetate (20 L). The suspension was stirred at 25° C. for 16 h and filtered. The ethyl acetate filtrate was concentrated in vacuo to afford the free amine (1050 g) as a liquid. The liquid was dissolved in ethanol (10 L), and 4-fluorobenzaldehyde (558 mL, 5.3 mol) and acetic acid (362 mL, 6.3 mol) were added, causing the temperature to rise to 28-30° C. The solution was allowed to cool to 25° C. and stirred for 30 min. A cloudy solution of sodium cyanoborohydride (756 g, 12.03 mol) in ethanol (5 L) was added in 20 min, causing the temperature to rise to 45-50° C. The mixture was allowed to cool to 25° C. and stirred for 16 h. The mixture was concentrated in vacuo to a volume of about 13-14 L. Water (1-2 L) was added, and the resulting mixture was further concentrated in vacuo. A saturated aqueous sodium bicarbonate solution (4 L) and water (4 L) were added with stirring. The pH was adjusted to 8.0-8.5 by adding additional saturated aqueous sodium bicarbonate solution (~500 mL). The mixture was stirred for 1 h before the solids were collected by filtration and the wet filter cake was washed with water (2 L). The solid was dried in vacuo at 35° C. for 64 h to afford the desired product, (1S,2R,3S,4R)-3-(4-fluoro-benzylamino)-bicyclo[2.2.1]heptane-2-carboxylic acid ethyl ester (1350 g, 4.63 mol, 96%), as a white solid.

p) (1R,2S,7R,8S)-3-(4-Fluoro-benzyl)-6-hydroxy-4-oxo-3-aza-tricyclo[6.2.1.0$^{2,7}$]undec-5-ene-5-carboxylic acid ethyl ester

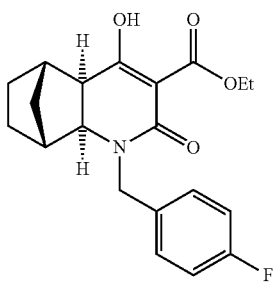

Triethylamine (4.22 mL, 30.3 mmol) and ethyl malonyl chloride (1.91 mL, 15.2 mmol) were added sequentially to a solution of (1S,2R,3S,4R)-3-(4-fluorobenzylamino)-bicyclo[2.2.1]heptane-2-carboxylic acid ethyl ester (4.21 g, 14.4 mmol) in dichloromethane at 25° C. The mixture was stirred at 25° C. for 1 h, and then was partitioned between 1.0 M aqueous hydrochloric acid solution (150 mL) and ethyl acetate (2×150 mL). The combined organic layers were dried over sodium sulfate, filtered and were concentrated in vacuo to afford a yellow/orange oil.

This material was dissolved in absolute ethanol (80 mL) at 25° C. and a 21 wt. % solution of sodium ethoxide in ethanol (14.0 mL, 43.2 mmol) was added. The mixture was heated to 60° C. for 45 min, and then was allowed to cool to 25° C. The mixture was then concentrated in vacuo and the resulting orange/brown solid was partitioned between 1.0 M aqueous hydrochloric acid solution (150 mL) and ethyl acetate (2×150 mL). The combined organic layers were dried over sodium sulfate, filtered and were concentrated in vacuo. Purification of the residue by flash column chromatography (Teledyne Isco RediSep column; 10-80% ethyl acetate in hexanes) afforded the desired product, (1R,2S,7R,8S)-3-(4-fluoro-benzyl)-6-hydroxy-4-oxo-3-aza-tricyclo[6.2.1.0$^{2,7}$]undec-5-ene-5-carboxylic acid ethyl ester, as a pale yellow oil. This material was used directly in the next synthetic step.

q) (1R,2S,7R,8S)-3-(4-Fluoro-benzyl)-6-hydroxy-3-aza-tricyclo[6.2.1.0$^{2,7}$]undec-5-en-4-one

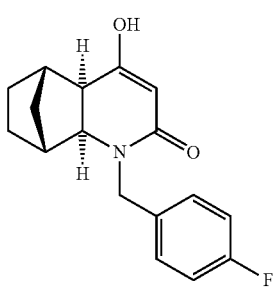

(1R,2S,7R,8S)-3-(4-fluoro-benzyl)-6-hydroxy-4-oxo-3-aza-tricyclo[6.2.1.0$^{2,7}$]undec-5-ene-5-carboxylic acid ethyl ester was suspended in a 1/1 mixture of 1,4-dioxane and 1.0 M aqueous sulfuric acid solution (200 mL). The mixture was heated to 110° C. for 40 min, and then was allowed to cool to 25° C. The cooled mixture was poured into a separatory funnel and was extracted with ethyl acetate (2×150 mL). The combined organic layers were dried over sodium sulfate, filtered and were concentrated in vacuo to afford a white solid. This material was triturated with hexanes and was collected by filtration, washed with hexanes (2×15 mL) and air-dried to afford the desired product, (1R,2S,7R,8S)-3-(4-fluoro-benzyl)-6-hydroxy-3-aza-tricyclo[6.2.1.0$^{2,7}$]undec-5-en-4-one (2.24 g, 7.80 mmol, 54% over three steps), as a white solid. $^1$H NMR (major tautomer, 400 MHz, CDCl$_3$) δ: 1.11-1.16 (1H, m), 1.20-1.39 (3H, m), 1.57-1.69 (2H, m), 2.53 (1H, d, J=8.4 Hz), 2.63 (1H, bs), 2.73 (1H, bs), 3.39 (1H, d, J=4.1 Hz), 3.51 (1H, d, J=9.5 Hz), 4.29 (1H, d, J=14.9 Hz), 5.20 (1H, d, J=14.9 Hz), 6.98-7.04 (2H, m), 7.19-7.24 (2H, m).

r) (1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

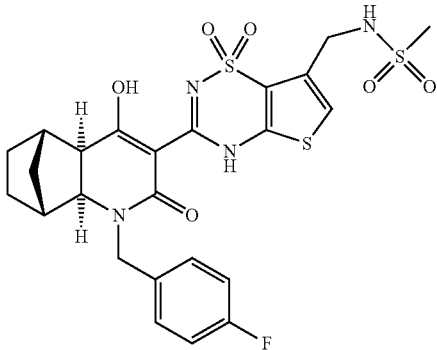

N,N-Diisopropylethylamine (0.974 mL, 5.59 mL) and (bis-methylsulfanyl-methylene)-methyl-sulfonium tetrafluoro borate salt (prepared as described in WO 2008/solution of (1R,2S,7R,8S)-3-(4-fluoro-benzyl)-6-hydroxy-3-aza-tricyclo[6.2.1.0$^{2,7}$]undec-5-en-4-one (0.197 g, 0.686 mmol) in 1,4-dioxane (50 mL) at 25° C. The orange mixture was stirred at 25° C. for 2 h, and then was partitioned between water (100 mL) and ethyl acetate (2×100 mL). The combined organic layers were dried over sodium sulfate, filtered and were concentrated in vacuo to afford an orange oil.

This material was dissolved in acetonitrile (8 mL) and was added to a solution of crude 2-amino-4-(methanesulfonylamino-methyl)-thiophene-3-sulfonic acid amide (prepared 011337, 0.466 g, 1.94 mmol) were added sequentially to a as described in Example 1h, 0.495 mmol) in acetonitrile (4 mL) at 85° C. The mixture was maintained at 85° C. for 4 days, then was allowed to cool to 25° C. and was concentrated in vacuo. The residue was purified by prep-HPLC [Column Thomson ODS-A 100 Å 5μ, 150×21.2 mm, 30%-100% in 11.5 min @ 22 mL/min flow rate, 0.05% trifluoroacetic acid in acetonitrile/0.05% trifluoroacetic acid in water] to afford the crude product. Purification of this material by flash column chromatography (Teledyne Isco RediSep column; 50-100% ethyl acetate in hexanes) afforded the desired product, (1R,2S,7R,8S)—N-{3-[3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.060 g, 0.103 mmol, 21%), as an off-white solid. $^1$H NMR (400 MHz, DMSO-d$_6$) δ: 0.84-0.90 (1H, m), 1.08-1.60 (5H, m), 1.99 (1H, s), 2.61 (1H, bs), 2.96 (3H, s), 3.50 (1H, d, J=9.4 Hz), 3.96-3.99 (1H, m), 4.24 (1H, d, J=5.7 Hz), 4.38 (1H, d, J=14.8 Hz), 4.93 (1H, d, J=15.7 Hz), 7.11-7.16 (2H, m), 7.27 (1H, s), 7.29-7.33 (2H, m), 7.65 (1H, t, J=5.9 Hz). LC-MS (ESI) calculated for C$_{24}$H$_{25}$FN$_4$O$_6$S$_3$ 580.09. found 581.1 [M+H$^+$].

Example 2

(rac-cis)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

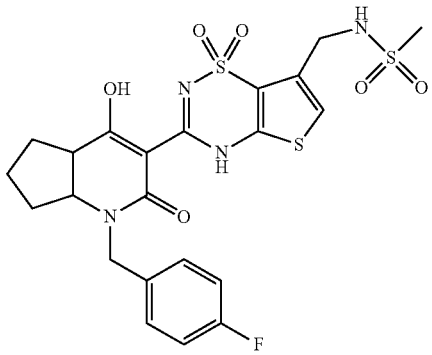

a)
2-(4-Fluoro-benzylamino)-cyclopent-1-enecarboxylic acid ethyl ester

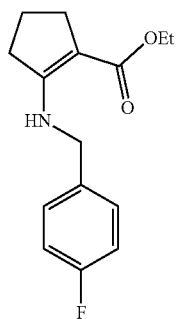

4-Fluorobenzylamine (12.1 g, 97.5 mmol) was added to a solution of 2-oxo-cyclopentanecarboxylic acid ethyl ester (15.25 g, 97.6 mmol) in toluene (225 mL) at 23° C. Glacial acetic acid (6.15 mL, 107 mmol) was then added, producing a large amount of white solid. The reaction mixture was heated to 70° C. in an oil bath, whereupon most of the solids dissolved. After stirring for 2 h at 70° C., a Dean-Stark apparatus and reflux condenser were fitted to the reaction flask and approximately 40 mL of liquid (predominantly toluene) was removed by distillation over 45 min (oil bath temperature=145° C.). The mixture was allowed to cool to 23° C. and was used in the next step. A small aliquot of the crude reaction mixture was concentrated in vacuo to afford the desired product, 2-(4-fluoro-benzylamino)-cyclopent-1-enecarboxylic acid ethyl ester as an orange oil: $^1$H NMR (CDCl$_3$) δ: 1.28 (3H, t, J=7.5), 1.79-1.86 (2H, m), 2.51-2.56 (4H, m), 4.15 (2H, q, J=6.9), 4.34-4.36 (2H, m), 6.98-7.03 (2H, m), 7.19-7.23 (2H, m), 7.73 (1H, bs).

b)
2-(4-Fluoro-benzylamino)-cyclopentanecarboxylic acid ethyl ester

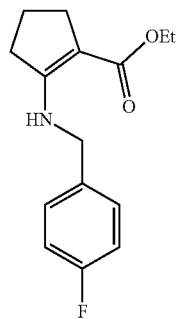

Sodium triacetoxyborohydride (62.1 g, 293 mmol) was suspended in a 1:1 mixture of glacial acetic acid and acetonitrile (200 mL) at 0° C. The crude 2-(4-fluoro-benzylamino)-cyclopent-1-enecarboxylic acid ethyl ester was added via cannula over 15 min and the resulting orange/brown suspension was allowed to warm to 23° C. over 19 h. A 4.0 M aqueous hydrochloric acid solution (60 mL) was then carefully added and the mixture was stirred at 23° C. for 20 min. The mixture was transferred to a large Erlenmeyer flask containing a stir bar and was cooled to 0° C. Aqueous sodium hydroxide (98 g dissolved in 350 mL; approx. 8.0 M) was then added over 20 min with gentle stirring and continued external cooling (large exotherm noted; melted ice was replenished). After the exotherm subsided, the mixture was transferred to a separatory funnel and the phases were separated. The aqueous phase was extracted with ethyl acetate (1×300 mL) and the combined organic layers were washed with half-saturated aqueous sodium bicarbonate solution (1×200 mL), dried over sodium sulfate, filtered and were concentrated in vacuo. Purification of the residue by flash chromatography (Teledyne Isco RediSep Column; 15-40% ethyl acetate in hexanes) afforded the desired product, cis-2-(4-fluoro-benzylamino)-cyclopentanecarboxylic acid ethyl ester (19.9 g, 77% over two steps), as a pale yellow oil. $^1$H NMR (CDCl$_3$) δ: 1.27 (3H, t, J=7.0), 1.55-1.71 (2H, m), 1.81-1.91 (4H, m), 1.98-2.06 (1H, m), 2.90-2.96 (1H, m), 3.26-3.31 (1H, m), 3.73 (1H, d, J=13.1), 3.77 (1H, d, J=13.2), 4.15 (2H, q, J=7.3), 6.94-7.00 (2H, m), 7.24-7.28 (2H, m).

$^{13}$C NMR (CDCl$_3$) δ: 14.8, 22.7, 27.9, 32.2, 48.0, 51.9, 60.5, 61.7, 115.2 (d, J=21.5), 129.6 (d, J=8.4), 136.5 (d, J=3.1), 161.9 (d, J=243.8), 174.7. Anal. calculated for C$_{15}$H$_{20}$FNO$_2$, C, 67.90; H, 7.60; N, 5.28. found: C, 67.92; H, 7.88; N, 5.55. Continued elution of the silica gel column with increasing amounts of ethyl acetate (up to 100% of eluent concentration) afforded trans-2-(4-fluoro-benzylamino)-cyclopentanecarboxylic acid ethyl ester (3.2 g, 12%) as a dark orange oil. $^1$H NMR (CDCl$_3$) δ: 1.26 (3H, t, J=7.0), 1.40-1.49 (1H, m), 1.67-1.77 (2H, m), 1.82-1.91 (1H, m), 1.97-2.05 (2H, m), 2.58 (1H, q, J=7.9), 3.31 (1H, q, J=7.3), 3.72 (1H, d, J=13.2), 3.77 (1H, d, J=12.5), 4.14 (2H, q, J=7.0), 6.96-7.01 (2H, m), 7.24-7.29 (2H, m).

c) [7-(Methanesulfonylamino-methyl)-1,1-dioxo-1,4-dihydro-1λ$^6$-thieno[2,3-e][1,2,4]thiadiazin-3-yl]-acetic acid

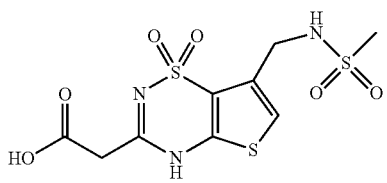

Methyl malonyl chloride (0.208 mL, 1.94 mmol) was added to a solution of crude 2-amino-4-(methanesulfonylamino-methyl)-thiophene-3-sulfonic acid amide (prepared as described in Example 1h, 1.76 mmol) in tetrahydrofuran at 25° C. The mixture was stirred at 25° C. for 1.5 h, then was partitioned between half-saturated aqueous sodium bicarbonate solution (100 mL) and ethyl acetate (2×100 mL). The organic layers were dried over sodium sulfate, filtered and were concentrated in vacuo to afford an orange solid.

This material was dissolved in aqueous sodium hydroxide (0.220 g dissolved in 25 mL water) and the resulting solution was heated to 100° C. for 30 min. After cooling to 25° C., the mixture was partitioned between 1.0 M aqueous hydrochloric acid solution (150 mL) and ethyl acetate (2×150 mL). The organic layers were dried over sodium sulfate, filtered and were concentrated in vacuo to afford an orange-brown oil. This material was triturated with a 10/10/1 mixture of dichloromethane/diethyl ether/methanol to afford a solid that was collected by filtration, washed with diethyl ether (2×10 mL), and air-dried to afford the desired product, [7-(methanesulfonylamino-methyl)-1,1-dioxo-1,4-dihydro-1λ$^6$-thieno[2,3-e][1,2,4]thiadiazin-3-yl]-acetic acid (0.177 g, 0.501 mmol, 26%). $^1$H NMR (400 MHz, DMSO-d$_6$) δ: 2.95 (3H, s), 3.59 (2H, s), 4.22 (2H, d, J=5.5 Hz), 7.23 (1H, s), 7.65 (1H, t, J=6.3 Hz).

Alternatively, [7-(methanesulfonylamino-methyl)-1,1-dioxo-1,4-dihydro-1λ$^6$-thieno[2,3-e][1,2,4]thiadiazin-3-yl]-acetic acid can be prepared as follows:

a') [7-(Methanesulfonylamino-methyl)-1,1-dioxo-1,4-dihydro-1λ$^6$-thieno[2,3-e][1,2,4]thiadiazin-3-yl]-acetic acid ethyl ester

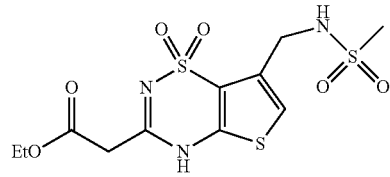

Palladium on carbon (12 g, 10%, activated, Aldrich) was added to a solution of 4-(methanesulfonylamino-methyl)-2-nitro-thiophene-3-sulfonic acid amide (prepared as described in Example 1g; 15 g, 47.6 mmol) dissolved in tetrahydrofuran (150 mL). The flask was degassed and backfilled with hydrogen gas. The mixture stirred under an atmosphere of hydrogen gas (balloon) for 20 h at 25° C. and then was filtered through Celite. The filtrate was concentrated in vacuo to afford 2-amino-4-(methanesulfonylamino-methyl)-thiophene-3-sulfonic acid amide as a thick golden oil. The oil was dissolved in N,N-dimethylformamide (150 mL) and 3,3-diethoxy-acrylic acid ethyl ester (10.62 g, 56.4 mmol) was added. A slow stream of nitrogen gas was applied to the atmosphere above the reaction mixture and the solution stirred at 70° C. for 5 h. Triethylamine (19 g, 188 mmol) was added directly to the reaction mixture and the solution continued to stir for 1 h. Upon cooling, the solution was concentrated in vacuo to reduce the total volume to 25 mL. The mixture was diluted with ethyl acetate (150 mL) and washed with 1.0 M aqueous hydrochloric acid solution (1×50 mL) followed by saturated aqueous brine solution (1×50 mL). The aqueous phase was back extracted with ethyl acetate (1×25 mL). The organic phases were combined, passed through a plug of silica gel (Merck silica gel 60, 40-63 µm) and concentrated in vacuo to afford a thick oil. The oil was dissolved in ethyl acetate (30 mL) and was stored at 25° C. for 16 h. The resulting solid was collected by vacuum filtration (10.75 g). The filtrate was concentrated in vacuo to afford a thick oil. The residue was purified by flash column chromatography (Teledyne Isco RediSep column; 40-100% ethyl acetate in hexanes) to afford a solid (3.23 g) which was combined with the solid from above followed to afford [7-(methanesulfonylamino-methyl)-1,1-dioxo-1,4-dihydro-1λ$^6$-thieno[2,3-e][1,2,4]thiadiazin-3-yl]-acetic acid ethyl ester (13.98 g, 3.7 mmol, 77%) as a beige powder.

b') [7-(Methanesulfonylamino-methyl)-1,1-dioxo-1,4-dihydro-1λ$^6$-thieno[2,3-e][1,2,4]thiadiazin-3-yl]-acetic acid

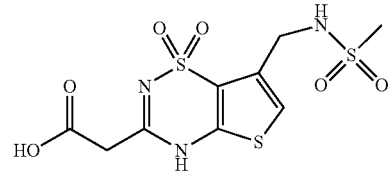

[7-(Methanesulfonylamino-methyl)-1,1-dioxo-1,4-dihydro-1λ⁶-thieno[2,3-e][1,2,4]thiadiazin-3-yl]-acetic acid ethyl ester (10 g, 26.2 mmol) and solid lithium hydroxide monohydrate (5.5 g, 131 mmol) were combined and then dissolved in water (40 mL). The resulting solution stirred at 25° C. for 30 min and then was then chilled to 0° C. While stirring, a 6.0 M aqueous hydrochloric acid solution (40 mL, 240 mmol) was added. Immediate precipitation was observed. The mixture continued to stir at 0° C. for 30 min. The solids were collected by vacuum filtration, rinsed with water (15 mL), filtered and dried in vacuo to afford a beige powder (8.4 g). The filtrate was concentrated in vacuo to reduce the volume to 10 mL. Additional solids precipitated over a period of 3 h. The solids were collected by vacuum filtration, rinsed with water (2 mL), filtered and dried in vacuo to afford a beige powder (0.37 g). The solids were combined to afford [7-(methanesulfonylamino-methyl)-1,1-dioxo-1,4-dihydro-1λ⁶-thieno[2,3-e][1,2,4]thiadiazin-3-yl]-acetic acid (8.77 g, 24.8 mmol, 95%). ¹H NMR (400 MHz, DMSO-d₆) δ: 3.59 (2H, s), 4.22 (2H, d, J=6.3 Hz), 7.23 (1H, s), 7.65 (1H, t, J=6.3 Hz), 13.08 (1H, bs).

d) (rac-cis)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide

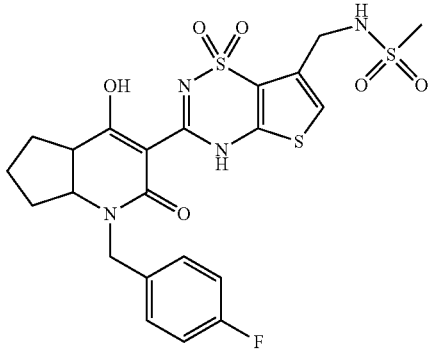

[7-(Methanesulfonylamino-methyl)-1,1-dioxo-1,4-dihydro-1 6-thieno[2,3-e][1,2,4]thiadiazin-3-yl]-acetic acid (0.155 g, 0.439 mmol), 1-(3-dimethylaminopropyl)-3-ethylcarbodiimide hydrochloride (0.084 g, 0.438 mmol) and 4-methylmorpholine (0.100 mL, 0.909 mmol) were added sequentially to a solution of cis-2-(4-fluoro-benzylamino)-cyclopentanecarboxylic acid ethyl ester (prepared as described in Example 2b, 0.106 g, 0.400 mmol) in N,N-dimethylformamide (4 mL) at 25° C. The reaction mixture was stirred at 25° C. for 2 h, and then was partitioned between 1.0 M aqueous hydrochloric acid solution (100 mL) and ethyl acetate (2×100 mL). The organic layers were dried over sodium sulfate, filtered and were concentrated in vacuo. The residue was dissolved in ethanol (30 mL) at 25° C. A 21 wt. % solution of sodium ethoxide in ethanol (0.518 mL, 1.60 mmol) was added and the reaction mixture was heated to 60° C. for 8 h. After cooling to 25° C., the reaction mixture was partitioned between 1.0 M aqueous hydrochloric acid solution (150 mL) and ethyl acetate (2×150 mL). The organic layers were dried over sodium sulfate, filtered and were concentrated in vacuo. The residue was purified by flash column chromatography (Teledyne Isco RediSep column; 40-100% ethyl acetate in hexanes) to afford the desired product, (rac-cis)-N-{3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (0.109 g, 0.197 mmol, 49%), as an off-white solid. ¹H NMR (400 MHz, DMSO-d₆) δ: 0.79-0.89 (1H, m), 1.08-1.30 (2H, m), 1.48 (2H, bs), 1.86 (1H, bs), 1.98 (1H, s), 2.11 (2H, bs), 2.95 (3H, s), 3.74 (1H, bs), 3.96-4.02 (1H, m), 4.25 (1H, bs), 4.43 (1H, d, J=14.7 Hz), 4.82 (1H, d, J=14.8 Hz), 7.11-7.16 (2H, m), 7.35 (2H, bs), 7.59 (1H, bs). LC-MS (ESI) calculated for C₂₂H₂₃FN₄O₆S₃ 554.08. found 555.0 [M+H⁺].

Example 3

N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-ylmethyl}-methanesulfonamide

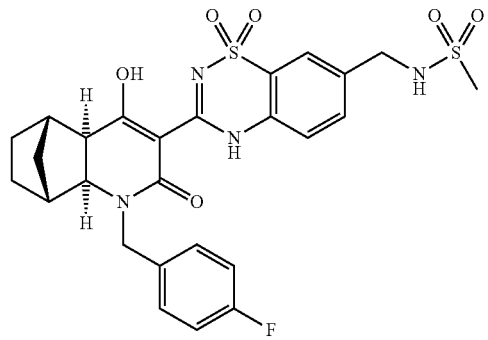

a) (1R,2S,7R,8S)-3-(4-Fluoro-benzyl)-6-hydroxy-5-(7-iodo-1,1-dioxo-1,4-dihydro-1λ⁶-benzo[1,2,4]thiadiazin-3-yl)-3-aza-tricyclo[6.2.1.0²,⁷]undec-5-en-4-one

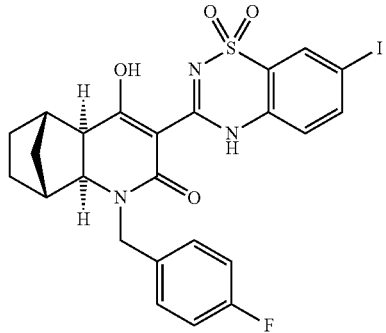

(7-Iodo-1,1-dioxo-1,4-dihydro-1λ⁶-benzo[1,2,4]thiadiazin-3-yl)-acetic acid (prepared as described in US patent application US 2008/0031852; 2.51 g, 6.86 mmol), (1S,2R,3S,4R)-3-(4-fluoro-benzylamino)-bicyclo[2.2.1]heptane-2-carboxylic acid ethyl ester (2 g, 6.86 mmol) and O-(7-azabenzotriazol-1-yl)-N,N,N',N'-tetramethyluronium hexafluorophosphate (2.74 g, 7.2 mmol) were combined and dissolved in anhydrous N,N-dimethylformamide (18 mL). N-Methylmorpholine (3 mL, 27.44 mmol) was added and the mixture was stirred at 25° C. for 2 h. Triethylamine (3.82 mL, 27.44 mmol) was added and the mixture stirred at 60° C. for 16 h. Upon cooling, the mixture was slowly added to a 1.0 M aqueous hydrochloric acid solution (200 mL) while stirring. The product precipitated immediately. Stirring was continued for 5 min. The solid was collected by vacuum filtration, rinsed with water (2×60 mL) and dried in vacuo for 16 h to afford the desired product, (1S,2R,3S,4R)-3-(4-fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (1.94 g, 3.27 mmol, 48%), as a white, brittle foam. $^1$H NMR (400 MHz, DMSO-d$_6$) δ: 1.20-1.23 (1H, m), 1.38-1.61 (5H, m), 2.50-2.53 (1H, m), 2.62 (1H, d, J=3.2 Hz), 2.98 (1H, d, J=9.3 Hz), 3.52 (1H, d, J=9.4 Hz), 4.40 (1H, d, J=15.7 Hz), 4.95 (1H, d, J=14.9 Hz), 7.12-7.16 (2H, m), 7.30-7.34 (3H, m), 7.97 (1H, dd, J$_1$=8.6 Hz, J$_2$=1.4 Hz), 8.07 (1H, d, J=1.7 Hz).

b) (1R,2S,7R,8S)-3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazine-7-carbonitrile

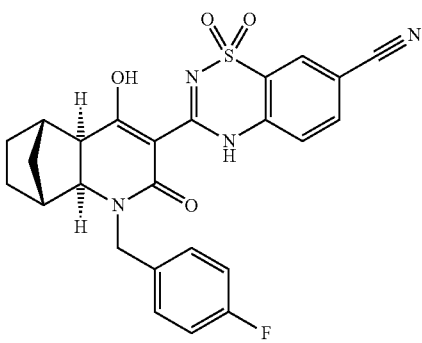

(1R,2S,7R,8S)-3-(4-Fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (0.5 g, 0.84 mmol) and copper(I) cyanide (0.151 g, 1.7 mmol) were suspended anhydrous N,N-dimethylformamide (4 mL). The mixture was stirred at 120° C., under nitrogen for 24 h. Upon cooling, the mixture was diluted with ethyl acetate (20 mL) and washed with saturated aqueous ammonium chloride solution (3×15 mL). The organic phase was passed through a short plug of Celite followed by a short plug of silica gel (Merck silica gel 60, 40-63 μm), eluting with ethyl acetate. The filtrate was concentrated in vacuo to afford a yellow solid. Purification by flash column chromatography (Teledyne Isco RediSep column; 25-100% ethyl acetate in hexanes) followed by concentration in vacuo afforded the desired product, (1R,2S,7R,8S)-3-[3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazine-7-carbonitrile (0.398 g, 0.808 mmol, 96%), as a white, brittle foam. $^1$H NMR (400 MHz, DMSO-d$_6$) δ: 1.15-1.15 (1H, m), 1.34-1.61 (5H, m), 2.48-2.48 (1H, m), 2.60 (1H, d, J=3.3 Hz), 2.90 (1H, d, J=9.4 Hz), 3.48 (1H, d, J=9.4 Hz), 4.38 (1H, d, J=15.6 Hz), 4.96 (1H, d, J=15.4 Hz), 7.11-7.16 (2H, m), 7.31 (2H, dd, J$_1$=8.6 Hz, J$_2$=5.4 Hz), 7.60 (1H, d, J=8.6 Hz), 8.02 (1H, dd, J$_1$=8.6 Hz, J$_2$=2.5 Hz), 8.37 (1H, s). LC-MS (ESI) calculated for C$_{25}$H$_{21}$FN$_4$O$_4$S 492.13. found 493.1 [M+H$^+$].

c) (1R,2S,7R,8S)-5-(7-Aminomethyl-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one hydrochloride

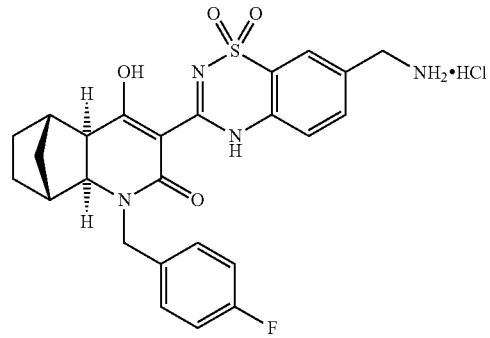

(1R,2S,7R,8S)-3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazine-7-carbonitrile (0.38 g, 0.77 mmol) was dissolved in methanol (required gentle heating via heat gun). Concentrated aqueous hydrochloric acid solution (5 mL) was added followed by 10% palladium on carbon (~150 mg). The mixture was degassed and backfilled with hydrogen gas via balloon. The mixture stirred at 25° C. for 3 h. The mixture was passed through a plug of Celite, eluting with additional methanol (200 mL). The filtrate was concentrated in vacuo to afford the desired product, (1R,2S,7R,8S)-5-(7-aminomethyl-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one hydrochloride (~0.77 mmol), as a pale yellow solid. The solid was used directly in the next step without further purification or characterization. LC-MS (ESI) calculated for C$_{25}$H$_{25}$FN$_4$O$_4$S 496.16. found 497.3 [M+H$^+$].

d) N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-ylmethyl}-methanesulfonamide

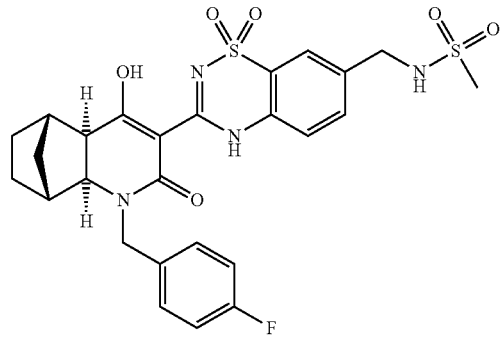

(1R,2S,7R,8S)-5-(7-Aminomethyl-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one hydrochloride (crude from previous step, ~0.77 mmol) was dissolved in methylene chloride (10 mL). Triethylamine (2 mL) and pyridine (2 mL) were added. Methane sulfonyl chloride (2 mL) was added and the mixture stirred at 25° C. for 20 min Water (50 mL) was added and the mixture stirred for 5 min. The solution was diluted with ethyl acetate (200 mL) and washed with 1.0 M aqueous hydrochloric acid solution (3×300 mL), saturated aqueous ammonium chloride solution (2×200 mL) and saturated aqueous brine solution (200 mL). The organic phase was dried over magnesium sulfate, filtered and concentrated in vacuo to afford a clear oil. Purification by flash column chromatography (Teledyne Isco RediSep column; 25-100% ethyl acetate in hexanes) followed by concentration in vacuo afforded the desired product, N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-ylmethyl}-methanesulfonamide (0.139 g, 0.238 mmol, 31%) as a white, brittle foam. ¹H NMR (400 MHz, DMSO-d₆) δ: 1.19-1.25 (1H, m), 1.40-1.64 (5H, m), 2.50-2.54 (1H, m), 2.64 (1H, d, J=2.5 Hz), 2.92 (3H, s), 3.04 (1H, d, J=8.8 Hz), 3.53 (1H, d, J=9.5 Hz), 4.25 (2H, d, J=6.2 Hz), 4.42 (1H, d, J=15.8 Hz), 4.97 (1H, d, J=14.7 Hz), 7.12-7.17 (2H, m), 7.33 (2H, dd, J₁=7.7 Hz, J₂=5.4 Hz), 7.52 (1H, d, J=8.7 Hz), 7.63-7.70 (2H, m), 7.81 (1H, s). LC-MS (ESI) calculated for $C_{26}H_{27}FN_4O_6S_2$ 574.14. found 575.3 [M+H⁺].

Example 4 rac-N-{3-[6-Cyclopropyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

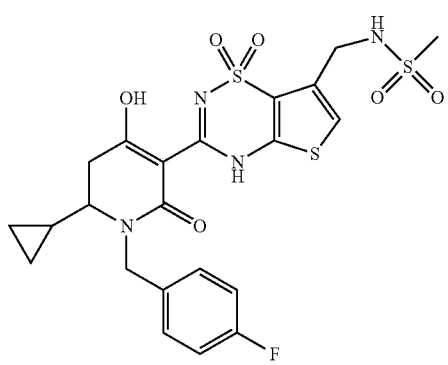

a) rac-3-Cyclopropyl-3-(4-fluoro-benzylamino)-propionic acid ethyl ester

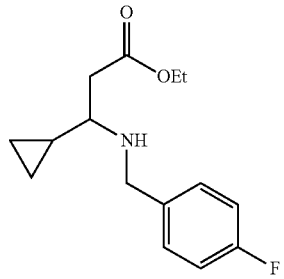

4-Fluorobenzaldehyde (0.565 mL, 5.27 mmol), sodium acetate (0.864 g, 10.5 mmol), powdered/activated 4 Å molecular sieves (1.0 g) and sodium cyanoborohydride (0.662 g, 10.5 mmol) were added sequentially to a solution of racemic 3-amino-3-cyclopropyl-propionic acid ethyl ester hydrochloride (1.02 g, 5.27 mmol) in methanol (25 mL) at 25° C. The mixture was stirred at 25° C. for 17 h, and then was filtered through Celite. The Celite was washed with methanol (2×30 mL) and the combined filtrate and washings were partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-80% ethyl acetate in hexanes) to afford rac-3-cyclopropyl-3-(4-fluoro-benzylamino)-propionic acid ethyl ester (0.75 g, 2.83 mmol, 53%) as a colorless oil. ¹H NMR (400 MHz, CDCl₃) δ: 0.00-0.06 (1H, m), 0.16-0.22 (1H, m), 0.36-0.43 (1H, m), 0.50-0.57 (1H, m), 0.75-0.84 (1H, m), 1.18 (3H, t, J=7.0 Hz), 2.17-2.23 (1H, m), 2.53 (2H, d, J=6.1 Hz), 3.74 (1H, d, J=12.4 Hz), 3.87 (1H, d, J=12.3 Hz), 4.05 (2H, q, J=7.0 Hz), 6.88-6.96 (2H, m), 7.21-7.25 (2H, m).

b) rac-N-{3-[6-Cyclopropyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

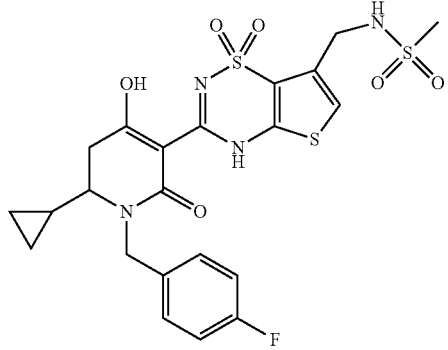

[7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.089 g, 0.252 mmol), O-(7-azabenzotriazol-1-yl)-N,N,N',N'-tetramethyluronium hexafluorophosphate (0.106 g, 0.279 mmol) and 4-methyl-morpholine (0.055 mL, 0.500 mmol) were added sequentially to a solution of 3-cyclopropyl-3-(4-fluoro-benzylamino)-propionic acid ethyl ester (0.067 g, 0.252 mmol) in N,N-dimethylformamide (4 mL) at 25° C. The reaction mixture was stirred at 25° C. for 17 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (25 mL) at 25° C. A 21 wt. % solution of sodium ethoxide in ethanol (0.327 mL, 1.01 mmol) was added and the reaction mixture was heated to 60° C. for 3 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 40-100% ethyl acetate in hexanes) to afford (after trituration with diethylether) rac-N-{3-[6-cyclopropyl-1-(4-fluoro-benzyl)-4-hydroxy-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide (0.045 g, 0.081 mmol, 32%) as a pale yellow solid. $^1$H NMR (400 MHz, DMSO-d$_6$) δ: −0.03-0.01 (1H, m), 0.25-0.39 (2H, m), 0.67-0.74 (1H, m), 0.93-0.96 (1H, m), 0.98-1.06 (1H, m), 2.48 (1H, d, J=17.0 Hz), 2.76-2.79 (1H, m), 2.81 (3H, s), 3.02 (1H, dd, J$_1$=6.9 Hz, J$_2$=17.0 Hz), 4.10 (2H, d, J=6.1 Hz), 4.21 (1H, d, J=15.5 Hz), 4.94 (1H, d, J=15.8 Hz), 6.96-7.12 (2H, m), 7.12 (1H, s), 7.19-7.22 (2H, m), 7.51 (1H, t, J=6.3 Hz). LC-MS (ESI) calculated for $C_{22}H_{23}FN_4O_6S_3$ 554.08. found 555.1 [M+H$^+$].

Example 5 rac-N-{3-[1-(4-Fluoro-benzyl)-4-hydroxy-2-oxo-6-propyl-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

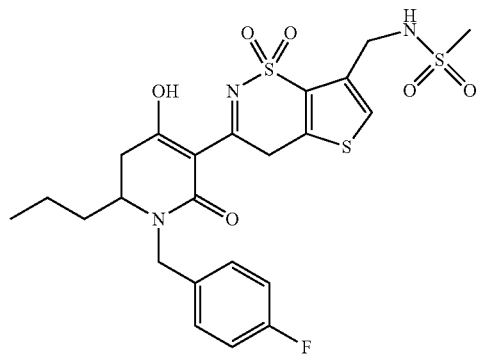

a) rac-3-(4-Fluoro-benzylamino)-hexanoic acid ethyl ester

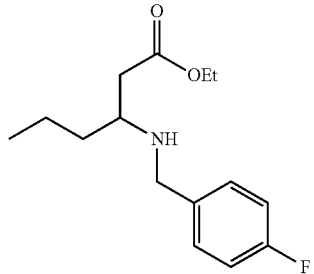

4-Fluorobenzaldehyde (0.287 mL, 2.68 mmol), sodium acetate (0.439 g, 5.35 mmol), powdered/activated 4 Å molecular sieves (0.72 g) and sodium cyanoborohydride (0.336 g, 5.35 mmol) were added sequentially to a solution of racemic 3-amino-hexanoic acid ethyl ester hydrochloride (0.524 g, 2.68 mmol) in methanol (10 mL) at 25° C. The mixture was stirred at 25° C. for 2 h, and then was filtered through Celite. The Celite was washed with ethyl acetate (2×30 mL) and the combined filtrate and washings were partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 10-80% ethyl acetate in hexanes) to afford rac-3-(4-fluoro-benzylamino)-hexanoic acid ethyl ester (0.43 g, 1.61 mmol, 60%) as a colorless oil. $^1$H NMR (400 MHz, CDCl$_3$) δ: 0.92 (3H, t, J=7.4 Hz), 1.26 (3H, t, J=7.1 Hz), 1.32-1.43 (2H, m), 1.45-1.52 (1H, m), 1.53-1.62 (1H, m), 2.51 (2H, d, J=6.3 Hz), 3.03-3.09 (1H, m), 3.77-3.84 (2H, m), 4.14 (2H, q, J=7.1 Hz), 6.97-7.02 (2H, m), 7.31-7.34 (2H, m).

b) rac-N-{3-[1-(4-Fluoro-benzyl)-4-hydroxy-2-oxo-6-propyl-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

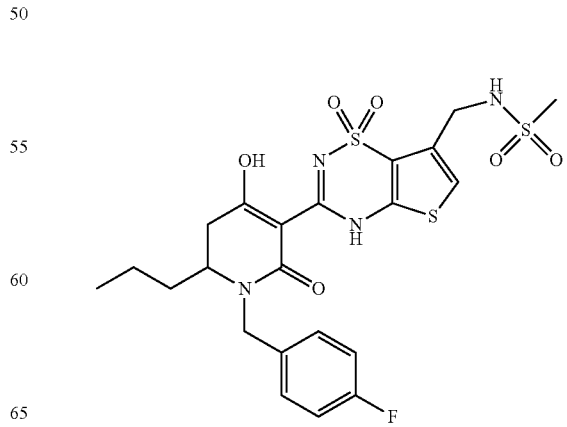

[7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.103 g, 0.291 mmol), O-(7-azabenzotriazol-1-yl)-N,N,N',N'-tetramethyluronium hexafluorophosphate (0.122 g, 0.321 mmol) and 4-methylmorpholine (0.064 mL, 0.582 mmol) were added sequentially to a solution of rac-3-(4-fluoro-benzylamino)-hexanoic acid ethyl ester (0.078 g, 0.292 mmol) in N,N-dimethylformamide (4 mL) at 25° C. The reaction mixture was stirred at 25° C. for 17 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (25 mL) at 25° C. A 21 wt. % solution of sodium ethoxide in ethanol (0.378 mL, 1.17 mmol) was added and the reaction mixture was heated to 60° C. for 4 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 40-100% ethyl acetate in hexanes) to afford (after trituration with diethyl ether) rac-N-{3-[1-(4-fluoro-benzyl)-4-hydroxy-2-oxo-6-propyl-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide (0.027 g, 0.049 mmol, 17%) as a pale yellow solid. $^1$H NMR (400 MHz, DMSO-d$_6$) δ: 0.85 (3H, t, J=7.2 Hz), 1.15-1.38 (2H, m), 1.54-1.60 (2H, m), 2.51 (1H, d, J=15.1 Hz), 2.96 (3H, s), 3.12 (1H, dd, J$_1$=6.5 Hz, J$_2$=16.8 Hz), 3.54-3.58 (1H, m), 4.19 (1H, d, J=15.2 Hz), 4.24 (2H, d, J=6.1 Hz), 5.04 (1H, d, J=15.5 Hz), 7.13-7.17 (2H, m), 7.25 (1H, s), 7.36-7.39 (2H, m), 7.64 (1H, t, J=6.3 Hz). LC-MS (ESI) calculated for $C_{22}H_{25}FN_4O_6S_3$ 556.09. found 557.3 [M+H$^+$].

Example 6 rac-N-{3-[6-Cyclobutyl-1-(4-fluoro-benzyl)-4-hydroxy-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide a) rac-3-Cyclobutyl-3-(4-fluoro-benzylamino)-propionic acid methyl ester

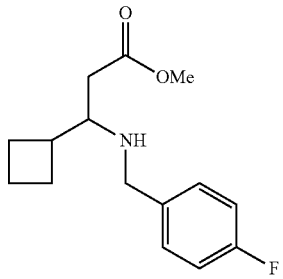

(Trimethylsilyl)diazomethane (3.65 mL of a 1.0 M solution in diethyl ether, 7.3 mmol) was added over 2 min to a solution of racemic 3-tert-butoxycarbonylamino-3-cyclobutyl-propionic acid (0.89 g, 3.66 mmol) in a 1:1 mixture of methanol/benzene (50 mL) at 0° C. The resulting yellow solution was stirred at 0° C. for 40 min, then was concentrated in vacuo. The residue was dissolved in 1,4-dioxane (10 mL) at 25° C. and a 4.0 M solution of hydrochloric acid in 1,4-dioxane (10 mL) was subsequently added. After stirring at 25° C. for 3.5 h, the reaction mixture was concentrated in vacuo to afford a sticky oil. This material was dissolved in toluene (80 mL) and the solution was concentrated in vacuo (the process was then repeated). The resulting residue was dissolved in methanol (25 mL) at 25° C. and 4-fluorobenzaldehyde (0.393 mL, 3.66 mmol), sodium acetate (0.600 g, 7.31 mmol), powdered/activated 4 Å molecular sieves (0.85 g) and sodium cyanoborohydride (0.46 g, 7.32 mmol) were added sequentially. The mixture was stirred at 25° C. for 16 h, then was filtered through Celite. The Celite was washed with ethyl acetate (2×30 mL) and the combined filtrate and washings were partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-80% ethyl acetate in hexanes) to afford rac-3-cyclobutyl-3-(4-fluoro-benzylamino)-propionic acid methyl ester (0.424 g, 1.60 mmol, 44%) as a colorless oil. $^1$H NMR (400 MHz, CDCl$_3$) δ: 1.68-1.80 (2H, m), 1.82-1.89 (1H, m), 1.92-1.99 (1H, m), 2.04-2.11 (1H, m), 2.32-2.45 (2H, m), 2.94-2.99 (1H, m), 3.67 (3H, s), 3.76 (2H, d, J=6.8 Hz), 6.96-7.01 (2H, m), 7.25-7.30 (2H, m).

b) rac-N-{3-[6-Cyclobutyl-1-(4-fluoro-benzyl)-4-hydroxy-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

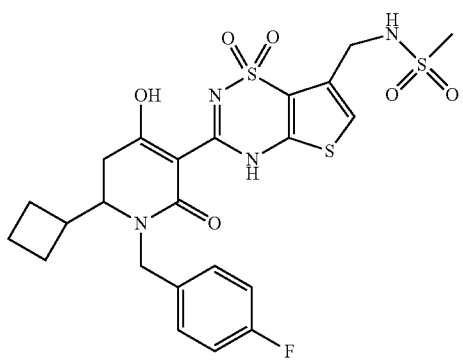

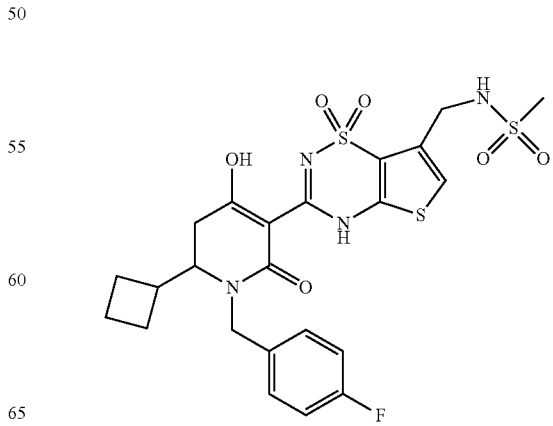

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.119 g, 0.337 mmol), O-(7-azabenzotriazol-1-yl)-N,N,N',N'-tetramethyluronium hexafluorophosphate (0.140 g, 0.368 mmol) and 4-methylmorpholine (0.074 mL, 0.673 mmol) were added sequentially to a solution of rac-3-cyclobutyl-3-(4-fluoro-benzylamino)-propionic acid methyl ester (0.089 g, 0.335 mmol) in N,N-dimethylformamide (5 mL) at 25° C. The reaction mixture was stirred at 25° C. for 22 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (5 mL) at 25° C. A 21 wt. % solution of sodium ethoxide in ethanol (0.46 mL, 1.42 mmol) was added and the reaction mixture was heated to 60° C. for 4 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 60-100% ethyl acetate in hexanes) to afford (after trituration with diethylether) rac-N-{3-[6-cyclobutyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.063 g, 0.111 mmol, 31%) as a tan solid. ¹H NMR (400 MHz, DMSO-d₆) δ: 1.64-1.94 (4H, m), 2.36 (1H, d, J=17.2 Hz), 2.64-2.71 (1H, m), 2.95 (3H, s), 3.03 (1H, dd, $J_1$=6.5 Hz, $J_2$=17.7 Hz), 3.53-3.57 (1H, m), 4.15 (1H, d, J=14.8 Hz), 4.24 (2H, d, J=6.2 Hz), 5.10 (1H, d, J=15.1 Hz), 7.12-7.16 (2H, m), 7.24 (1H, s), 7.34-7.38 (2H, m), 7.64 (1H, t, J=6.2 Hz). LC-MS (ESI) calculated for $C_{23}H_{25}FN_4O_6S_3$ 568.09. found 569.2 [M+H⁺].

Example 7 rac-N-{3-[1-(4-Fluoro-benzyl)-4-hydroxy-6-isobutyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

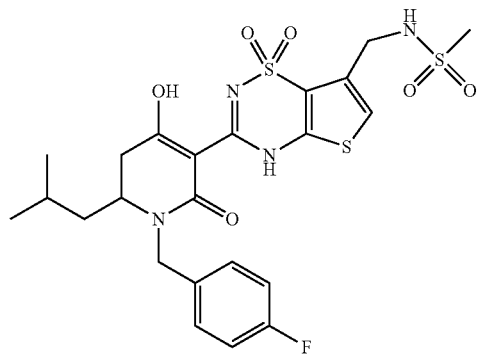

a) rac-3-(4-Fluoro-benzylamino)-5-methyl-hexanoic acid ethyl ester

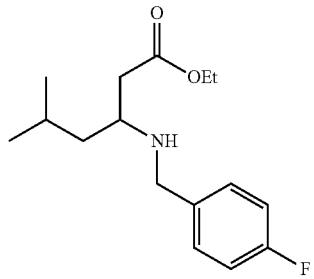

4-Fluorobenzaldehyde (0.500 mL, 4.66 mmol), sodium acetate (0.766 g, 9.34 mmol), powdered/activated 4 Å molecular sieves (1.0 g) and sodium cyanoborohydride (0.587 g, 9.34 mmol) were added sequentially to a solution of racemic 3-amino-5-methyl-hexanoic acid ethyl ester hydrochloride (0.979 g, 4.67 mmol) in methanol (25 mL) at 25° C. The mixture was stirred at 25° C. for 22 h, and then was filtered through Celite. The Celite was washed with ethyl acetate (2×30 mL) and the combined filtrate and washings were partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-80% ethyl acetate in hexanes) to afford rac-3-(4-fluoro-benzylamino)-5-methyl-hexanoic acid ethyl ester (0.616 g, 2.19 mmol, 47%) as a pale yellow oil. ¹H NMR (400 MHz, CDCl₃) δ: 0.88 (3H, d, J=3.8 Hz), 0.90 (3H, d, J=3.4 Hz), 1.26 (3H, t, J=7.0 Hz), 1.43-1.49 (1H, m), 1.66-1.76 (1H, m), 2.48 (2H, d, J=6.3 Hz), 3.04-3.11 (1H, m), 3.76 (1H, d, J=13.6 Hz), 3.80 (1H, d, J=12.2 Hz), 4.10-4.18 (2H, m), 6.97-7.01 (2H, m), 7.29-7.32 (2H, m).

b) rac-N-{3-[1-(4-Fluoro-benzyl)-4-hydroxy-6-isobutyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

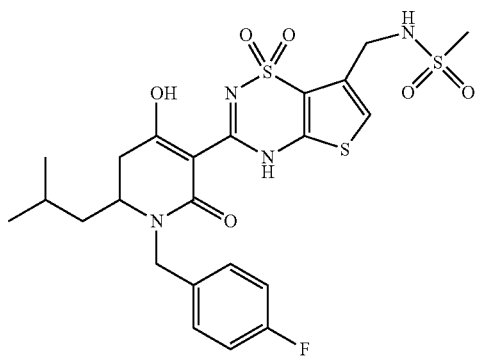

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.088 g, 0.249 mmol), O-(7-azabenzotriazol-1-yl)-N,N,N',N'-tetramethyluronium hexafluorophosphate (0.104 g, 0.274 mmol) and 4-methyl-morpholine (0.055 mL, 0.500 mmol) were added sequentially to a solution of rac-3-(4-fluoro-benzylamino)-5-methyl-hexanoic acid ethyl ester (0.070 g, 0.249 mmol) in N,N-dimethylformamide (4 mL) at 25° C. The reaction mixture was stirred at 25° C. for 20 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (5 mL) at 25° C. A 21 wt. % solution of sodium ethoxide in ethanol (0.322 mL, 0.994 mmol) was added and the reaction mixture was heated to 60° C. for 4 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethylether) rac-N-{3-[1-(4-fluoro-benzyl)-4-hydroxy-6-isobutyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.032 g, 0.056 mmol, 23%) as a tan solid. $^1$H NMR (400 MHz, DMSO-d₆) δ: 0.81 (3H, d, J=6.3 Hz), 0.87 (3H, d, J=6.2 Hz), 1.30-1.37 (1H, m), 1.50-1.60 (1H, m), 2.47 (1H, d, J=18.0 Hz), 2.96 (3H, s), 3.10 (1H, dd, $J_1$=6.4 Hz, $J_2$=16.3 Hz), 3.35-3.40 (1H, m), 3.51-3.55 (1H, m), 4.14 (1H, d, J=14.9 Hz), 4.24 (2H, d, J=5.5 Hz), 5.04 (1H, d, J=15.1 Hz), 7.13-7.18 (2H, m), 7.24 (1H, s), 7.36-7.39 (2H, m), 7.64 (1H, t, J=6.2 Hz). LC-MS (ESI) calculated for $C_{23}H_{27}FN_4O_6S_3$ 570.11. found 571.3 [M+H⁺].

Example 8 rac-N-{3-[1-(4-Fluoro-benzyl)-4-hydroxy-6-isopropyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

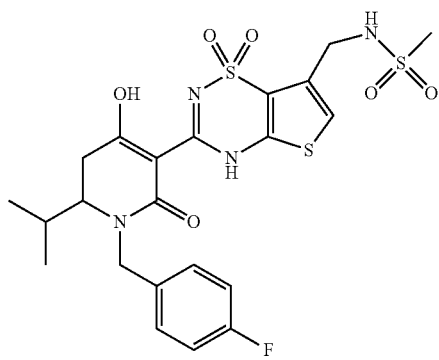

a) rac-3-(4-Fluoro-benzylamino)-4-methyl-pentanoic acid ethyl ester

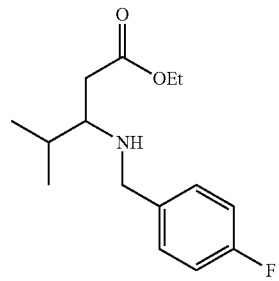

4-Fluorobenzaldehyde (0.547 mL, 5.10 mmol), sodium acetate (0.837 g, 10.2 mmol), powdered/activated 4 Å molecular sieves (1.0 g) and sodium cyanoborohydride (0.641 g, 10.2 mmol) were added sequentially to a solution of racemic 3-amino-4-methyl-pentanoic acid ethyl ester hydrochloride (0.998 g, 5.10 mmol) in methanol (25 mL) at 25° C. The mixture was stirred at 25° C. for 22 h, and then was filtered through Celite. The Celite was washed with ethyl acetate (2×30 mL) and the combined filtrate and washings were partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-70% ethyl acetate in hexanes) to afford rac-3-(4-fluoro-benzylamino)-4-methyl-pentanoic acid ethyl ester (0.723 g, 2.70 mmol, 53%) as a pale yellow oil. $^1$H NMR (400 MHz, CDCl₃) δ: 0.92 (6H, t (apparent), J=6.8 Hz), 1.26 (3H, t, J=7.1 Hz), 1.85-1.93 (1H, m), 2.35 (1H, dd, $J_1$=8.1 Hz, $J_2$=15.1 Hz), 2.45 (1H, dd, $J_1$=4.6 Hz, $J_2$=15.0 Hz), 2.87-2.92 (1H, m), 4.13 (2H, q, J=7.0 Hz), 6.96-7.00 (2H, m), 7.28-7.32 (2H, m).

b) rac-N-{3-[1-(4-Fluoro-benzyl)-4-hydroxy-6-isopropyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

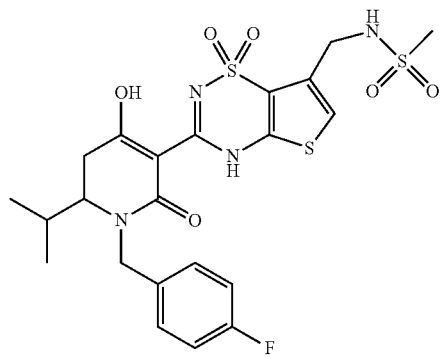

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.095 g, 0.269 mmol), O-(7-azabenzotriazol-1-yl)-N,N,N',N'-tetramethyluronium hexafluorophosphate (0.113 g, 0.297 mmol) and 4-methylmorpholine (0.059 mL, 0.537 mmol) were added sequentially to a solution of) rac-3-(4-fluoro-benzylamino)-4-methyl-pentanoic acid ethyl ester (0.072 g, 0.269 mmol) in N,N-dimethylformamide (4 mL) at 25° C. The reaction mixture was stirred at 25° C. for 20 h, then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (5 mL) at 25° C. A 21 wt. % solution of sodium ethoxide in ethanol (0.349 mL, 1.08 mmol) was added and the reaction mixture was heated to 60° C. for 4 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethylether) rac-N-{3-[1-(4-fluoro-benzyl)-4-hydroxy-6-isopropyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.020 g, 0.036 mmol, 13%) as a pale yellow solid. ¹H NMR (400 MHz, DMSO-d₆) δ: 0.86 (3H, d, J=7.0 Hz), 0.94 (3H, d, J=7.2 Hz), 2.04-2.09 (1H, m), 2.56 (1H, d, J=17.3 Hz), 2.95 (3H, s), 3.04-3.10 (1H, m), 3.38-3.41 (1H, m), 4.14 (1H, d, J=15.4 Hz), 4.23 (2H, d, J=5.7 Hz), 5.15 (1H, d, J=14.7 Hz), 7.11-7.16 (2H, m), 7.22 (1H, s), 7.35-7.38 (2H, m), 7.63 (1H, t, J=5.8 Hz). LC-MS (ESI) calculated for $C_{22}H_{25}FN_4O_6S_3$ 556.09. found 557.2 [M+H⁺].

Example 9 rac-N-{3-[6-Cyclopentyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

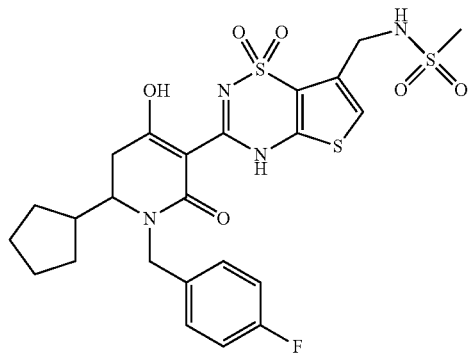

a) rac-3-Cyclopentyl-3-(4-fluoro-benzylamino)-propionic acid methyl ester

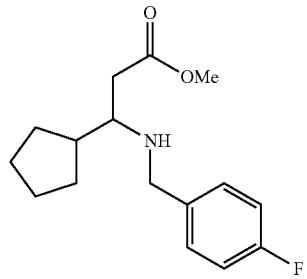

(Trimethylsilyl)diazomethane (10.3 mL of a 1.0 M solution in diethyl ether, 20.6 mmol) was added over 5 min to a solution of racemic 3-tert-butoxycarbonylamino-3-cyclopentyl-propionic acid (2.65 g, 10.3 mmol) in a 1:1 mixture of methanol/benzene (130 mL) at 0° C. The resulting yellow solution was allowed to warm to 25° C. over 3.5 h, and then was concentrated in vacuo. The residue was dissolved in 1,4-dioxane (20 mL) at 25° C. and a 4.0 M solution of hydrochloric acid in 1,4-dioxane (15 mL) was subsequently added. After stirring at 25° C. for 16 h, the reaction mixture was concentrated in vacuo to afford a sticky oil. This material was dissolved in toluene (80 mL) and the solution was concentrated in vacuo (the process was then repeated). The resulting residue was dissolved in methanol (75 mL) at 25° C. and 4-fluorobenzaldehyde (1.10 mL, 10.3 mmol), sodium acetate (1.69 g, 20.6 mmol), powdered/activated 4 Å molecular sieves (2.0 g) and sodium cyanoborohydride (1.29 g, 20.5 mmol) were added sequentially. The mixture was stirred at 25° C. for 23 h, and then was filtered through Celite. The filtrate was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-70% ethyl acetate in hexanes) to afford rac-3-cyclopentyl-3-(4-fluoro-benzylamino)-propionic acid methyl ester (0.812 g, 2.91 mmol, 28%) as a pale yellow oil. ¹H NMR (400 MHz, CDCl₃) δ: 1.16-1.30 (1H, m), 1.52-1.66 (2H, m), 1.69-1.76 (1H, m), 1.81-1.88 (1H, m), 1.95-2.03 (1H, m), 2.47 (1H, dd, J₁=7.0 Hz, J₂=14.9 Hz), 2.55 (1H, dd, J₁=4.6 Hz, J₂=14.8 Hz), 2.87-2.92 (1H, m), 3.68 (3H, s), 3.73 (1H, d, J=12.2 Hz), 3.81 (1H, d, J=12.1 Hz), 6.96-7.00 (2H, m), 7.27-7.31 (2H, m).

b) rac-N-{3-[6-Cyclopentyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

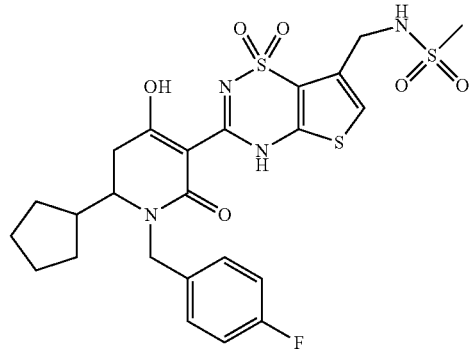

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.089 g, 0.252 mmol), O-(7-azabenzotriazol-1-yl)-N,N,N',N'-tetramethyluronium hexafluorophosphate (0.104 g, 0.274 mmol) and 4-methylmorpholine (0.055 mL, 0.500 mmol) were added sequentially to a solution of rac-3-cyclopentyl-3-(4-fluoro-benzylamino)-propionic acid methyl ester (0.070 g, 0.250 mmol) in N,N-dimethylformamide (4 mL) at 25° C. The reaction mixture was stirred at 25° C. for 18 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (5 mL) at 25° C. A 21 wt. % solution of sodium ethoxide in ethanol (0.324 mL, 1.00 mmol) was added and the reaction mixture was heated to 60° C. for 6 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethyl ether) rac-N-{3-[6-cyclopentyl-1-(4-fluoro-benzyl)-4-hydroxy-2-oxo-1,2,5,6-tetrahydropyridin-3-yl]-1,1-dioxo-1,4-dihydro-1λ⁶-thieno[2,3-e][1,2,4]thiadiazin-7-ylmethyl}-methanesulfonamide (0.018 g, 0.031 mmol, 12%) as a pale yellow solid. ¹H NMR (400 MHz, DMSO-d₆) δ: 1.07-1.17 (1H, m), 1.35-1.43 (1H, m), 1.45-1.68 (3H, m), 1.70-1.76 (1H, m), 2.20-2.26 (1H, m), 2.47 (1H, d, J=14.1 Hz), 2.95 (3H, s), 3.06-3.12 (1H, m), 3.43-3.47 (1H, m), 4.09 (1H, d, J=15.8 Hz), 4.23 (2H, d, J=6.3 Hz), 5.21 (1H, d, J=14.9 Hz), 7.11-7.15 (2H, m), 7.21 (1H, s), 7.34-7.38 (2H, m), 7.62 (1H, t, J=6.2 Hz). LC-MS (ESI) calculated for $C_{24}H_{27}FN_4O_6S_3$ 582.11. found 583.1 [M+H⁺].

Example 10 rac-N-{3-[1-(4-Fluoro-benzyl)-4-hydroxy-5-methyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

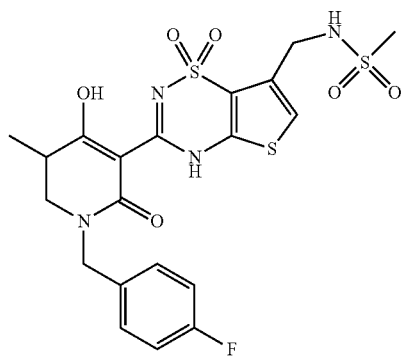

a) rac-3-(4-Fluoro-benzylamino)-2-methyl-propionic acid ethyl ester

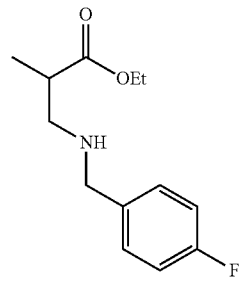

4-Fluorobenzaldehyde (0.622 mL, 5.80 mmol), sodium acetate (0.951 g, 11.6 mmol), powdered/activated 4 Å molecular sieves (2.0 g) and sodium cyanoborohydride (0.729 g, 11.6 mmol) were added sequentially to a solution of racemic 3-amino-2-methyl-propionic acid ethyl ester hydrochloride (0.972 g, 5.80 mmol) in methanol (30 mL) at 25° C. The mixture was stirred at 25° C. for 20 h, and then was filtered through Celite. The Celite was washed with methanol (2×30 mL) and the combined filtrate and washings were concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-80% ethyl acetate in hexanes) to afford rac-3-(4-fluoro-benzylamino)-2-methyl-propionic acid ethyl ester (0.821 g, 3.43 mmol, 59%) as a pale yellow oil. ¹H NMR (400 MHz, CDCl₃) δ: 1.18 (3H, d, J=7.2 Hz), 1.26 (3H, t, J=6.9 Hz), 2.63-2.72 (2H, m), 2.84-2.91 (1H, m), 3.75 (1H, d, J=13.3 Hz), 3.79 (1H, d, J=13.4 Hz), 4.14 (2H, q, J=6.9 Hz), 6.97-7.01 (2H, m), 7.25-7.29 (2H, m).

b) rac-N-{3-[1-(4-Fluoro-benzyl)-4-hydroxy-5-methyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

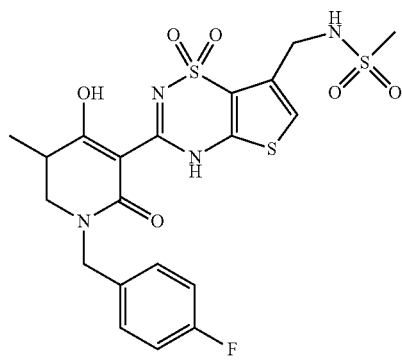

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.109 g, 0.308 mmol), O-(7-azabenzotriazol-1-yl)-N,N,N',N'-tetramethyluronium hexafluorophosphate (0.129 g, 0.339 mmol) and 4-methylmorpholine (0.068 mL, 0.618 mmol) were added sequentially to a solution of rac-3-(4-fluoro-benzylamino)-2-methyl-propionic acid ethyl ester (0.074 g, 0.309 mmol) in N,N-dimethylformamide (4 mL) at 25° C. The reaction mixture was stirred at 25° C. for 16 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (4 mL) at 25° C. A 21 wt. % solution of sodium ethoxide in ethanol (0.400 mL, 1.23 mmol) was added and the reaction mixture was heated to 60° C. for 4 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 60-100% ethyl acetate in hexanes) to afford (after trituration with diethylether) rac-N-{3-[1-(4-fluoro-benzyl)-4-hydroxy-5-methyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.040 g, 0.076 mmol, 25%) as a beige solid. ¹H NMR (400 MHz, DMSO-d₆) δ: 1.08 (3H, d, J=7.3 Hz), 2.84-2.86 (1H, m), 2.96 (3H, s), 3.17 (1H, dd, J₁=13.0 Hz, J₂=7.2 Hz), 3.55 (1H, dd, J₁=5.7 Hz, J₂=12.7 Hz), 4.24 (2H, d, J=5.4 Hz), 4.54 (1H, d, J=14.9 Hz), 4.69 (1H, d, J=14.8 Hz), 7.14-7.18 (2H, m), 7.26 (1H, s), 7.37 (2H, d, J=14.0 Hz), 7.65 (1H, t, J=6.3 Hz). LC-MS (ESI) calculated for $C_{20}H_{21}FN_4O_6S_3$ 528.06. found 529.2 [M+H⁺].

Example 11

N-{3-[5-(4-Fluoro-benzyl)-8-hydroxy-6-oxo-5-aza-spiro[2.5]oct-7-en-7-yl]-1,1-dioxo-1,4-dihydro-1λ⁶-thieno[2,3-e][1,2,4]thiadiazin-7-ylmethyl}-methanesulfonamide

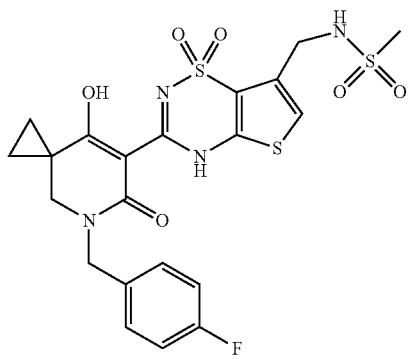

a) 1-[(4-Fluoro-benzylamino)-methyl]-cyclopropanecarboxylic acid methyl ester

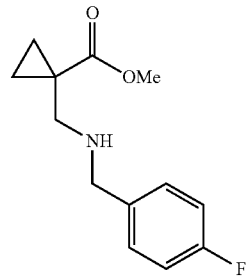

(Trimethylsilyl)diazomethane (4.41 mL of a 1.0 M solution in diethyl ether, 8.82 mmol) was added over 5 min to a solution of racemic 1-(tert-butoxycarbonylamino-methyl)-cyclopropanecarboxylic acid (0.95 g, 4.41 mmol) in a 1:1 mixture of methanol/benzene (30 mL) at 0° C. The resulting yellow solution was stirred at 0° C. for 1 h, and then was concentrated in vacuo. The residue was dissolved in 1,4-dioxane (20 mL) at 25° C. and a 4.0 M solution of hydrochloric acid in 1,4-dioxane (20 mL) was subsequently added. After stirring at 25° C. for 5 h, the reaction mixture was concentrated in vacuo to afford a sticky oil. This material was dissolved in toluene (80 mL) and the solution was concentrated in vacuo (the process was then repeated). The resulting residue was dissolved in methanol (30 mL) at 25° C. and 4-fluorobenzaldehyde (0.473 mL, 4.41 mmol), sodium acetate (0.723 g, 8.81 mmol), powdered/activated 4 Å molecular sieves (1.87 g) and sodium cyanoborohydride (0.554 g, 8.82 mmol) were added sequentially. The mixture was stirred at 25° C. for 19 h, then was filtered through Celite. The Celite was washed with methanol (2×30 mL) and the combined filtrate and washings were concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 50-100% ethyl acetate in hexanes) to afford 1-[(4-fluoro-benzylamino)-methyl]-cyclopropanecarboxylic acid methyl ester (0.050 g, 0.211 mmol, 5%) as a pale yellow oil. ¹H NMR (400 MHz, CDCl₃) δ: 0.79-0.82 (2H, m), 1.26-1.28 (2H, m), 2.70 (2H, s), 3.66 (3H, s), 3.79 (2H, s), 6.97-7.01 (2H, m), 7.28-7.31 (2H, m).

b)N-{3-[5-(4-Fluoro-benzyl)-8-hydroxy-6-oxo-5-aza-spiro[2.5]oct-7-en-7-yl]-1,1-dioxo-1,4-dihydro-1λ⁶-thieno[2,3-e][1,2,4]thiadiazin-7-ylmethyl]-methanesulfonamide

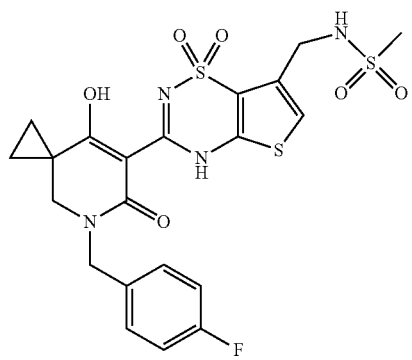

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.074 g, 0.209 mmol), O-(7-azabenzotriazol-1-yl)-N,N,N',N'-tetramethyluronium hexafluorophosphate (0.088 g, 0.231 mmol) and 4-methylmorpholine (0.046 mL, 0.418 mmol) were added sequentially to a solution of 1-[(4-fluoro-benzylamino)-methyl]-cyclopropanecarboxylic acid methyl ester (0.050 g, 0.211 mmol) in N,N-dimethylformamide (3 mL) at 25° C. The reaction mixture was stirred at 25° C. for 17 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (5 mL) at 25° C. A 21 wt. % solution of sodium ethoxide in ethanol (0.271 mL, 0.836 mmol) was added and the reaction mixture was heated to 60° C. for 24 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 60-100% ethyl acetate in hexanes) to afford (after trituration with diethylether) N-{3-[5-(4-fluoro-benzyl)-8-hydroxy-6-oxo-5-aza-spiro[2.5]oct-7-en-7-yl]-1,1-dioxo-1,4-dihydro-1λ⁶-thieno[2,3-e][1,2,4]thiadiazin-7-ylmethyl}-methanesulfonamide (0.015 g, 0.028 mmol, 13%) as a beige solid. ¹H NMR (400 MHz, DMSO-d₆) δ: 0.80-0.90 (2H, m), 1.20-1.26 (2H, m), 2.95 (3H, s), 3.31 (2H, bs), 4.23 (2H, d, J=6.1 Hz), 4.61 (2H, s), 7.14-7.18 (3H, m), 7.32-7.36 (2H, m), 7.61 (1H, t, J=5.4 Hz). LC-MS (ESI) calculated for $C_{21}H_{21}FN_4O_6S_3$ 540.06. found 541.1 [M+H⁺].

Example 12 rac-N-{3-[5-Benzyl-1-(4-fluoro-benzyl)-4-hydroxy-2-oxo-1,2,5,6-tetrahydro-pyridin-3-yl]-1,1-dioxo-1,4-dihydro-1λ⁶-thieno e][1,2,4]thiadiazin-7-ylmethyl}-methanesulfonamide

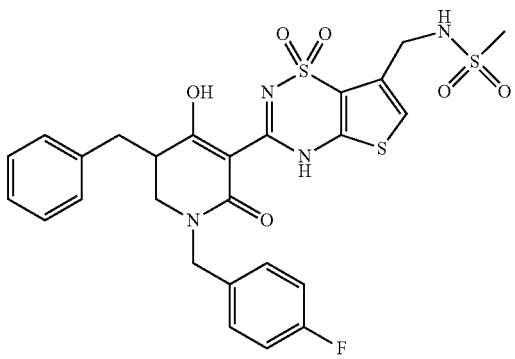

a) rac-2-Benzyl-3-(4-fluoro-benzylamino)-propionic acid ethyl ester

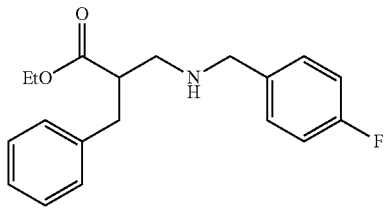

Diisobutylaluminum hydride (39 mL of a 1.0 M solution in toluene, 39 mmol) was added over 5 min to a solution of 2-benzyl-malonic acid diethyl ester (4.82 g, 19.3 mmol) in dichloromethane (45 mL) at −78° C. The reaction mixture was stirred at that temperature for 4 h, and then was quenched with saturated aqueous ammonium chloride (33 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford the crude product (0.96 g, 4.66 mmol, 24%). This material was dissolved in ethanol (20 mL) at 25° C. and 4-fluorobenzylamine (0.532 mL, 4.66 mmol), glacial acetic acid (1.5 mL), and sodium cyanoborohydride (0.585 g, 9.31 mmol) were added sequentially. The mixture was stirred at 25° C. for 17 h, and then was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 10-70% ethyl acetate in hexanes) to afford rac-2-benzyl-3-(4-fluoro-benzylamino)-propionic acid ethyl ester (0.643 g, 2.04 mmol, 44%) as a colorless oil. ¹H NMR (400 MHz, CDCl₃) δ: 1.18 (3H, t, J=7.0 Hz), 2.72-2.76 (1H, m), 2.81-3.02 (4H, m), 3.72 (1H, d, J=13.3 Hz), 3.79 (1H, d, J=13.2 Hz), 4.11 (2H, q, J=6.9 Hz), 6.96-7.00 (2H, m), 7.13-7.15 (2H, m), 7.17-7.21 (1H, m), 7.24-7.28 (4H, m).

b) rac-N-{3-[5-Benzyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

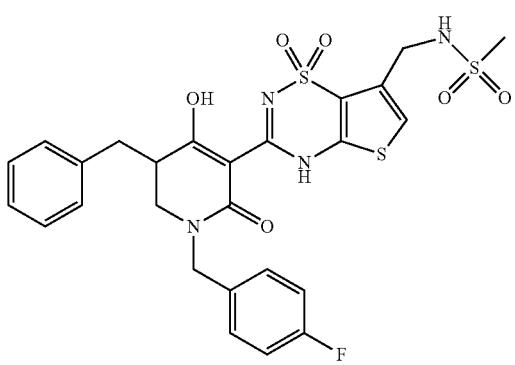

[7-(Methanesulfonylamino-methyl)-1,1-dioxo-1,4-dihydro-1λ[6]-thieno[2,3-e][1,2,4]thiadiazin-3-yl]-acetic acid (prepared as described in Example 2c; 0.108 g, 0.306 mmol), O-(7-azabenzotriazol-1-yl)-N,N,N',N'-tetramethyluronium hexafluorophosphate (0.128 g, 0.337 mmol) and 4-methylmorpholine (0.067 mL, 0.609 mmol) were added sequentially to a solution of rac-2-benzyl-3-(4-fluoro-benzylamino)-propionic acid ethyl ester (0.096 g, 0.304 mmol) in N,N-dimethylformamide (4 mL) at 25° C. The reaction mixture was stirred at 25° C. for 18 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (4 mL) at 25° C. A 21 wt. % solution of sodium ethoxide in ethanol (0.394 mL, 1.22 mmol) was added and the reaction mixture was heated to 60° C. for 20 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethylether) rac-N-{3-[5-benzyl-1-(4-fluoro-benzyl)-4-hydroxy-2-oxo-1,2,5,6-tetrahydro-pyridin-3-yl]-1,1-dioxo-1,4-dihydro-1λ[6]-thieno[2,3-e][1,2,4]thiadiazin-7-ylmethyl}-methanesulfonamide (0.058 g, 0.096 mmol, 32%) as a tan solid. $^1$H NMR (400 MHz, DMSO-$d_6$) δ: 2.46 (1H, d, J=11.1 Hz), 2.69-2.78 (1H, m), 2.92-2.98 (1H, m), 2.95 (3H, s), 3.01 (1H, d, J=3.9 Hz), 3.28-3.32 (1H, m), 4.24 (2H, d, J=5.5 Hz), 4.37 (1H, d, J=13.9 Hz), 4.66 (1H, d, J=14.9 Hz), 6.88-6.90 (2H, m), 7.13-7.20 (5H, m), 7.28-7.31 (2H, m), 7.58 (1H, t, J=6.3 Hz). LC-MS (ESI) calculated for $C_{26}H_{25}FN_4O_6S_3$ 604.09. found 605.4 [M+H$^+$].

Example 13 rac-N-{3-[1-(4-Fluoro-benzyl)-4-hydroxy-5-isopropyl-2-oxo-1,2,5,6-tetrahydro-pyridin-3-yl]-1,1-dioxo-1,4-dihydro-1λ[6]-thieno e][1,2,4]thiadiazin-7-ylmethyl}-methanesulfonamide

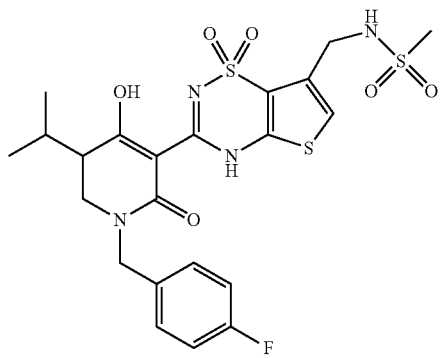

a) rac-2-[(4-Fluoro-benzylamino)-methyl]-3-methylbutyric acid ethyl ester

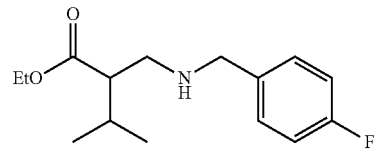

Diisobutylaluminum hydride (38 mL of a 1.0 M solution in toluene, 38 mmol) was added over 5 min to a solution of 2-isopropyl-malonic acid diethyl ester (3.84 g, 19.0 mmol) in dichloromethane (33 mL) at −78° C. The reaction mixture was stirred at that temperature for 3.5 h, and then was quenched with saturated aqueous ammonium chloride (33 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford crude product (1.92 g, 12.14 mmol, 64%). This material was dissolved in ethanol (40 mL) at 25° C. and 4-fluorobenzylamine (1.39 mL, 12.2 mmol), glacial acetic acid (1.5 mL), and sodium cyanoborohydride (1.52 g, 24.2 mmol) were added sequentially. The mixture was stirred at 25° C. for 17 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 10-80% ethyl acetate in hexanes) to afford rac-2-[(4-fluoro-benzylamino)-methyl]-3-methyl-butyric acid ethyl ester (1.36 g, 5.09 mmol, 42%) as a pale yellow oil. $^1$H NMR (400 MHz, CDCl$_3$) δ: 0.93 (6H, d, J=7.2 Hz), 1.27 (3H, t, J=7.0 Hz), 1.92-2.01 (1H, m), 2.35-2.46 (1H, m), 2.73 (1H, dd, J$_1$=3.8 Hz, J$_2$=11.6 Hz), 2.90 (1H, dd, J$_1$=10.2 Hz, J$_2$=11.7 Hz), 3.74 (1H, d, J=13.2 Hz), 3.82 (1H, d, J=13.5 Hz), 4.15-4.21 (2H, m), 6.97-7.01 (2H, m), 7.26-7.30 (2H, m).

b) rac-N-{3-[1-(4-Fluoro-benzyl)-4-hydroxy-5-isopropyl-2-oxo-1,2,5,6-tetrahydro-pyridin-3-yl]-1,1-dioxo-1,4-dihydro-1λ[6]-thieno[2,3-e][1,2,4]thiadiazin-7-ylmethyl}-methanesulfonamide

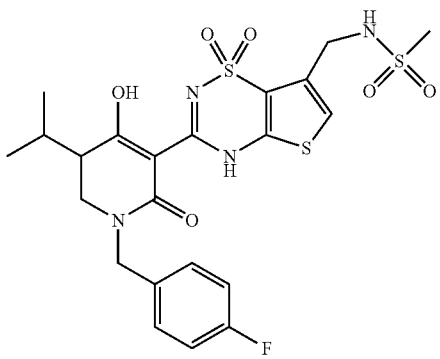

[7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.174 g, 0.492 mmol), O-(7-azabenzotriazol-1-yl)-N,N,N',N'-tetramethyluronium hexafluorophosphate (0.206 g, 0.542 mmol) and 4-methylmorpholine (0.109 mL, 0.990 mmol) were added sequentially to a solution of rac-2-[(4-fluoro-benzylamino)-methyl]-3-methyl-butyric acid ethyl ester (0.132 g, 0.494 mmol) in N,N-dimethylformamide (5 mL) at 25° C. The reaction mixture was stirred at 25° C. for 16 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (10 mL) at 25° C. A 21 wt. % solution of sodium ethoxide in ethanol (1.28 mL, 3.96 mmol) was added and the reaction mixture was heated to 70° C. for 38 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 10-80% ethyl acetate in hexanes) to afford (after trituration with diethylether) rac-N-{3-[1-(4-fluoro-benzyl)-4-hydroxy-5-isopropyl-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide (0.100 g, 0.180 mmol, 36%) as a beige solid. $^1$H NMR (400 MHz, DMSO-d$_6$) δ: 0.73 (3H, d, J=6.8 Hz), 0.90 (3H, d, J=6.8 Hz), 1.86-1.94 (1H, m), 2.35 (1H, bs), 2.96 (3H, s), 3.33 (1H, dd, J$_1$=3.5 Hz, J$_2$=13.0 Hz), 3.55 (1H, dd, J$_1$=5.6 Hz, J$_2$=13.3 Hz), 4.24 (2H, d, J=6.3 Hz), 4.52 (1H, d, J=14.8 Hz), 4.68 (1H, d, J=14.6 Hz), 7.14-7.19 (2H, m), 7.25 (1H, s), 7.37-7.41 (2H, m), 7.64 (1H, t, J=6.2 Hz). LC-MS (ESI) calculated for C$_{22}$H$_{25}$FN$_4$O$_6$S$_3$ 556.09. found 557.1 [M+H$^+$].

Example 14 rac-N-{3-[5-tert-Butyl-1-(4-fluoro-benzyl)-4-hydroxy-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

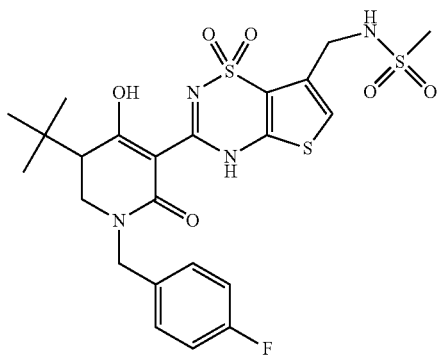

a) rac-2-[(4-Fluoro-benzylamino)-methyl]-3,3-dimethyl-butyric acid ethyl ester

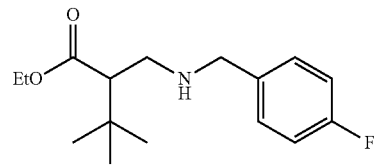

Diisobutylaluminum hydride (35.2 mL of a 1.0 M solution in toluene, 35.2 mmol) was added over 5 min to a solution of 2-tert-butyl-malonic acid diethyl ester (3.81 g, 17.6 mmol) in dichloromethane (33 mL) at −78° C. The reaction mixture was stirred at that temperature for 3.5 h, and then was quenched with saturated aqueous ammonium chloride (30 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford crude product (2.34 g, 13.6 mmol, 77%). This material was dissolved in ethanol (40 mL) at 25° C. and 4-fluorobenzylamine (1.55 mL, 13.6 mmol), glacial acetic acid (1.5 mL), and sodium cyanoborohydride (1.71 g, 27.2 mmol) were added sequentially. The mixture was stirred at 25° C. for 36 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 10-70% ethyl acetate in hexanes) to afford rac-2-[(4-fluoro-benzylamino)-methyl]-3-methyl-butyric acid ethyl ester (1.25 g, 4.44 mmol, 33%) as a colorless oil. $^1$H NMR (400 MHz, CDCl$_3$) δ: 0.96 (9H, s), 1.28 (3H, t, J=7.0 Hz), 2.39 (1H, dd, J$_1$=3.5 Hz, J$_2$=11.4 Hz), 2.46 (1H, dd, J$_1$=3.9 Hz, J$_2$=9.5 Hz), 2.73 (1H, dd, J$_1$=3.7 Hz, J$_2$=11.7 Hz), 3.71 (2H, d, J=13.2 Hz), 3.78 (1H, d, J=13.4 Hz), 4.14-4.20 (2H, m), 6.95-7.00 (2H, m), 7.22-7.26 (2H, m).

b) rac-N-{3-[5-tert-Butyl-1-(4-fluoro-benzyl)-4-hydroxy-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

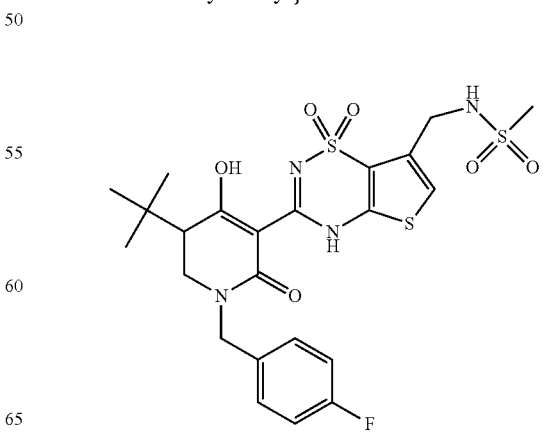

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.164 g, 0.464 mmol), O-(7-azabenzotriazol-1-yl)-N,N,N',N'-tetramethyluronium hexafluorophosphate (0.195 g, 0.513 mmol) and 4-methyl-morpholine (0.102 mL, 0.928 mmol) were added sequentially to a solution of rac-2-[(4-fluoro-benzylamino)-methyl]-3-methyl-butyric acid ethyl ester (0.131 g, 0.466 mmol) in N,N-dimethylformamide (5 mL) at 25° C. The reaction mixture was stirred at 25° C. for 16 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (10 mL) at 25° C. A 21 wt. % solution of sodium ethoxide in ethanol (1.81 mL, 5.58 mmol) was added and the reaction mixture was heated to 70° C. for 84 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 60-100% ethyl acetate in hexanes) to afford (after trituration with diethylether) rac-N-{3-[5-tert-butyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.111 g, 0.195 mmol, 42%) as a beige solid. ¹H NMR (400 MHz, DMSO-d₆) δ: 0.92 (9H, s), 2.36 (1H, bs), 2.96 (3H, s), 3.44 (1H, d, J=14.3 Hz), 3.59 (1H, dd, J₁=5.5 Hz, J₂=14.2 Hz), 4.25 (2H, d, J=6.1 Hz), 4.44 (1H, d, J=14.6 Hz), 4.79 (1H, d, J=13.9 Hz), 7.14-7.18 (2H, m), 7.27 (1H, s), 7.39-7.42 (2H, m), 7.65 (1H, t, J=6.2 Hz). LC-MS (ESI) calculated for C₂₃H₂₇FN₄O₆S₃ 570.11. found 571.2 [M+H⁺].

Example 15 rac-N-{3-[1-(4-Fluoro-benzyl)-4-hydroxy-2-oxo-5-propyl-1,2,5,6-tetrahydro-pyridin-3-yl]-1,1-dioxo-1λ⁶-thieno[2,3-e][1,2,4]thiadiazin-7-ylmethyl}-methanesulfonamide

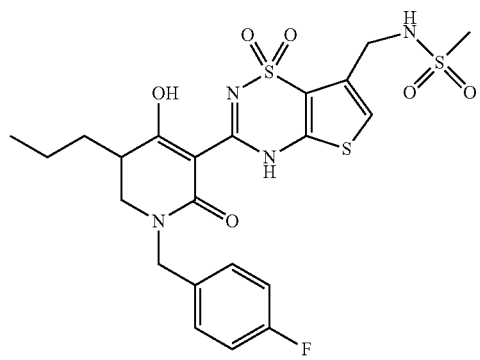

a) rac-2-[(4-Fluoro-benzylamino)-methyl]-pentanoic acid ethyl ester

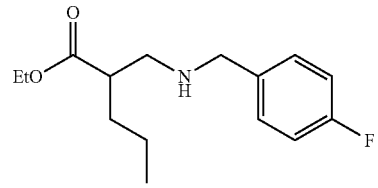

Diisobutylaluminum hydride (39.6 mL of a 1.0 M solution in toluene, 39.6 mmol) was added over 5 min to a solution of 2-propyl-malonic acid diethyl ester (4.00 g, 19.8 mmol) in dichloromethane (33 mL) at −78° C. The reaction mixture was stirred at that temperature for 3.5 h, and then was quenched with saturated aqueous ammonium chloride (33 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford crude product (1.18 g, 7.46 mmol, 38%). This material was dissolved in ethanol (20 mL) at 25° C. and 4-fluorobenzylamine (0.852 mL, 7.46 mmol), glacial acetic acid (1.5 mL), and sodium cyanoborohydride (0.937 g, 14.9 mmol) were added sequentially. The mixture was stirred at 25° C. for 17 h, and then was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 10-80% ethyl acetate in hexanes) to afford rac-2-[(4-fluoro-benzylamino)-methyl]-pentanoic acid ethyl ester (0.703 g, 2.63 mmol, 35%) as a colorless oil. ¹H NMR (400 MHz, CDCl₃) δ: 0.91 (3H, t, J=7.4 Hz), 1.26 (3H, t, J=7.1 Hz), 1.29-1.38 (2H, m), 1.44-1.51 (1H, m), 1.57-1.64 (1H, m), 2.57-2.64 (1H, m), 2.68 (1H, dd, J₁=4.7 Hz, J₂=11.7 Hz), 2.86 (1H, dd, J₁=9.2 Hz, J₂=11.7 Hz), 3.74 (1H, d, J=14.0 Hz), 3.79 (1H, d, J=13.2 Hz), 4.13-4.18 (2H, m), 6.96-7.01 (2H, m), 7.25-7.29 (2H, m).

b) rac-N-{3-[1-(4-Fluoro-benzyl)-4-hydroxy-2-oxo-5-propyl-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

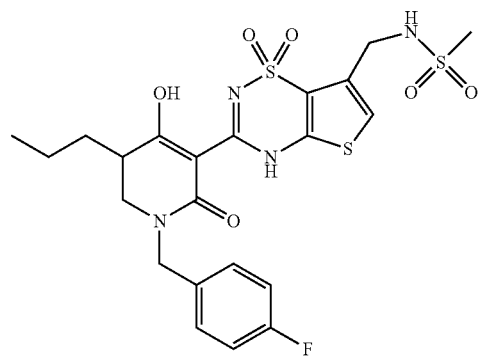

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.096 g, 0.272 mmol), O-(7-azabenzotriazol-1-yl)-N,N,N',N'-tetramethyluronium hexafluorophosphate (0.114 g, 0.300 mmol) and 4-methylmorpholine (0.060 mL, 0.546 mmol) were added sequentially to a solution of rac-2-[(4-fluoro-benzylamino)-methyl]-pentanoic acid ethyl ester (0.073 g, 0.273 mmol) in N,N-dimethylformamide (4 mL) at 25° C. The reaction mixture was stirred at 25° C. for 19 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (12 mL) at 25° C. A 21 wt. % solution of sodium ethoxide in ethanol (0.531 mL, 1.64 mmol) was added and the reaction mixture was heated to 70° C. for 48 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 60-100% ethyl acetate in hexanes) to afford (after trituration with diethylether) rac-N-{3-[1-(4-Fluoro-benzyl)-4-hydroxy-2-oxo-5-propyl-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.060 g, 0.108 mmol, 39%) as a beige solid. ¹H NMR (400 MHz, DMSO-d₆) δ: 0.75 (3H, t, J=7.1 Hz), 1.08-1.19 (2H, m), 1.21-1.28 (1H, m), 1.47-1.55 (1H, m), 2.53 (1H, bs), 2.95 (3H, s), 3.18 (1H, dd, J₁=3.8 Hz, J₂=13.2 Hz), 3.55 (1H, dd, J₁=4.5 Hz, J₂=12.9 Hz), 4.24 (2H, d, J=6.5 Hz), 4.39 (1H, d, J=14.7 Hz), 4.79 (1H, d, J=14.7 Hz), 7.14-7.18 (2H, m), 7.23 (1H, s), 7.36-7.39 (2H, m), 7.63 (1H, t, J=5.9 Hz). LC-MS (ESI) calculated for C₂₂H₂₅FN₄O₆S₃ 556.09. found 557.3 [M+H⁺].

Example 16 rac-N-}3-[5-Cyclopentyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

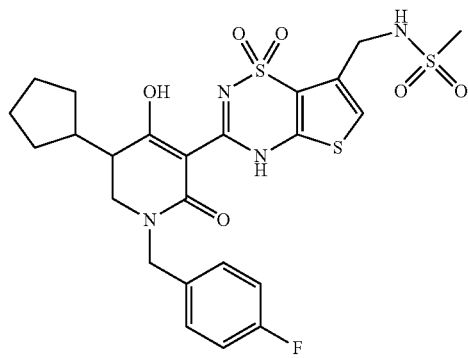

a) rac-2-Cyclopentyl-3-(4-fluoro-benzylamino)-propionic acid ethyl ester

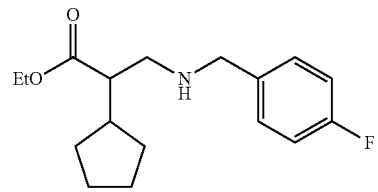

Diisobutylaluminum hydride (41.9 mL of a 1.0 M solution in toluene, 41.9 mmol) was added over 5 min to a solution of 2-cyclopentyl-malonic acid diethyl ester (4.78 g, 20.9 mmol) in dichloromethane (45 mL) at −78° C. The reaction mixture was stirred at that temperature for 3.5 h, and then was quenched with saturated aqueous ammonium chloride (33 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford crude product (1.67 g, 9.07 mmol, 43%). This material was dissolved in ethanol (30 mL) at 25° C. and 4-fluorobenzylamine (1.04 mL, 9.10 mmol), glacial acetic acid (1.5 mL), and sodium cyanoborohydride (1.14 g, 18.1.mmol) were added sequentially. The mixture was stirred at 25° C. for 17 h, then was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 10-80% ethyl acetate in hexanes) to afford rac-2-cyclopentyl-3-(4-fluoro-benzylamino)-propionic acid ethyl ester (1.33 g, 4.53 mmol, 50%) as a pale yellow oil. ¹H NMR (400 MHz, CDCl₃) δ: 1.10-1.22 (2H, m), 1.26 (3H, t, J=6.9 Hz), 1.47-1.79 (5H, m), 1.95-2.03 (1H, m), 2.40-2.46 (1H, m), 2.75 (1H, dd, J₁=3.8 Hz, J₂=11.5 Hz), 2.88 (1H, dd, J₁=10.2 Hz, J₂=11.7 Hz), 3.72 (1H, d, J=13.3 Hz), 3.80 (1H, d, J=14.0 Hz), 4.13-4.21 (2H, m), 6.96-7.00 (2H, m), 7.25-7.28 (2H, m).

b) rac-N-{3-[5-Cyclopentyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

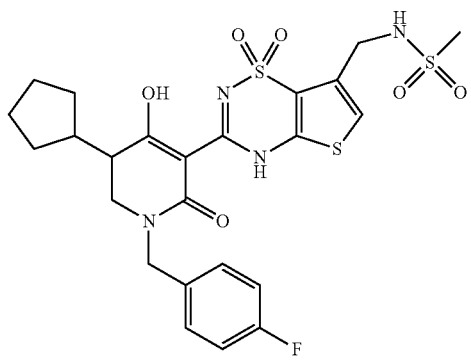

[7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.120 g, 0.340 mmol), O-(7-azabenzotriazol-1-yl)-N,N,N',N'-tetramethyluronium hexafluorophosphate (0.142 g, 0.373 mmol) and 4-methylmorpholine (0.075 mL, 0.682 mmol) were added sequentially to a solution of rac-2-cyclopentyl-3-(4-fluoro-benzylamino)-propionic acid ethyl ester (0.100 g, 0.341 mmol) in N,N-dimethylformamide (5 mL) at 25° C. The reaction mixture was stirred at 25° C. for 19 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (12 mL) at 25° C. A 21 wt. % solution of sodium ethoxide in ethanol (0.663 mL, 2.04 mmol) was added and the reaction mixture was heated to 70° C. for 66 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethylether)N-{3-[5-cyclopentyl-1-(4-fluoro-benzyl)-4-hydroxy-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide (0.036 g, 0.062 mmol, 18%) as a beige solid. $^1$H NMR (400 MHz, DMSO-d$_6$) δ: 1.07-1.12 (1H, m), 1.16-1.62 (7H, m), 1.76-1.86 (1H, m), 2.28-2.35 (1H, m), 2.95 (3H, s), 3.21 (1H, d, J=14.9 Hz), 3.63 (1H, dd, J$_1$=4.0 Hz, J$_2$=14.0 Hz), 4.24 (2H, d, J=6.3 Hz), 4.34 (1H, d, J=14.6 Hz), 4.85 (1H, d, J=14.2 Hz), 7.15-7.19 (2H, m), 7.25 (1H, s), 7.37-7.40 (2H, m), 7.64 (1H, t, J=6.4 Hz). LC-MS (ESI) calculated for C$_{24}$H$_{27}$FN$_4$O$_6$S$_3$ 582.11. found 583.1 [M+H$^+$].

Example 17 rac-N-{3-[1-(4-Fluoro-benzyl)-4-hydroxy-5-isobutyl-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

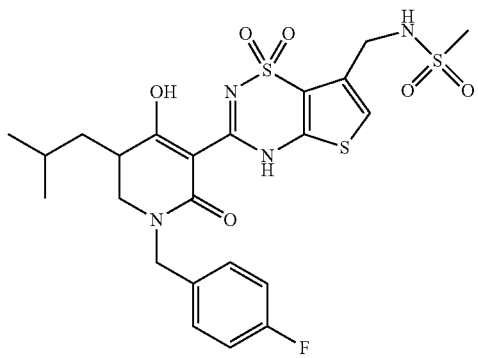

a) rac-2-[(4-Fluoro-benzylamino)-methyl]-4-methyl-pentanoic acid ethyl ester

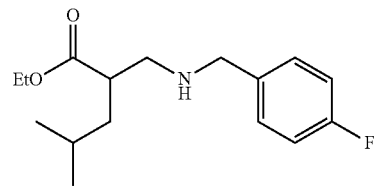

Diisobutylaluminum hydride (35.2 mL of a 1.0 M solution in toluene, 35.2 mmol) was added over 5 min to a solution of 2-isobutyl-malonic acid diethyl ester (3.81 g, 17.6 mmol) in dichloromethane (33 mL) at −78° C. The reaction mixture was stirred at that temperature for 4 h, and then was quenched with saturated aqueous ammonium chloride (35 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford crude product (2.20 g, 12.8 mmol, 73%). This material was dissolved in ethanol (40 mL) at 25° C. and 4-fluorobenzylamine (1.46 mL, 12.8 mmol), glacial acetic acid (1.5 mL), and sodium cyanoborohydride (1.61 g, 25.6 mmol) were added sequentially. The mixture was stirred at 25° C. for 18 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-70% ethyl acetate in hexanes) to afford rac-2-[(4-fluoro-benzylamino)-methyl]-4-methyl-pentanoic acid ethyl ester (0.995 g, 3.54 mmol, 28%) as a pale yellow oil. $^1$H NMR (400 MHz, CDCl$_3$) δ: 0.89 (3H, d, J=6.2 Hz), 0.91 (3H, d, J=6.0 Hz), 1.26 (3H, t, J=7.0 Hz), 1.54-1.61 (1H, m), 2.63-2.68 (2H, m), 2.83 (1H, dd, J$_1$=10.2 Hz, J$_2$=12.2 Hz), 3.72 (1H, d, J=13.3 Hz), 3.77 (1H, d, J=13.2 Hz), 4.13-4.18 (2H, m), 6.96-7.00 (2H, m), 7.23-7.27 (2H, m).

b) rac-N-{3-[1-(4-Fluoro-benzyl)-4-hydroxy-5-isobutyl-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

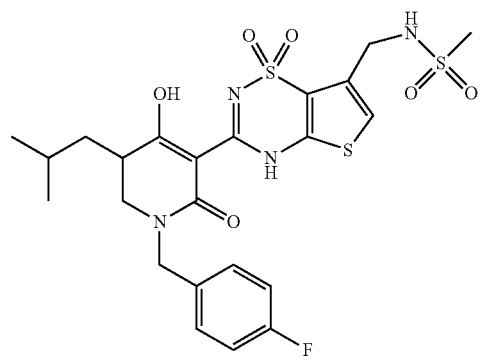

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.133 g, 0.376 mmol), O-(7-azabenzotriazol-1-yl)-N,N,N',N'-tetramethyluronium hexafluorophosphate (0.157 g, 0.413 mmol) and 4-methylmorpholine (0.083 mL, 0.755 mmol) were added sequentially to a solution of rac-2-[(4-fluoro-benzylamino)-methyl]-4-methyl-pentanoic acid ethyl ester (0.106 g, 0.377 mmol) in N,N-dimethylformamide (4 mL) at 25° C. The reaction mixture was stirred at 25° C. for 18 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (10 mL) at 25° C. A 21 wt. % solution of sodium ethoxide in ethanol (0.732 mL, 2.26 mmol) was added and the reaction mixture was heated to 70° C. for 22 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethylether) rac-N-{3-[1-(4-fluoro-benzyl)-4-hydroxy-5-isobutyl-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.097 g, 0.170 mmol, 45%) as a beige solid. ¹H NMR (400 MHz, DMSO-d₆) δ: 0.73 (3H, d, J=5.5 Hz), 0.77 (3H, d, J=5.5 Hz), 1.17-1.21 (1H, m), 1.31-1.33 (2H, m), 2.60 (1H, bs), 2.95 (3H, s), 3.16 (1H, d, J=13.3 Hz), 3.58 (1H, dd, J₁=4.8 Hz, J₂=12.5 Hz), 4.24 (2H, d, J=5.4 Hz), 4.34 (1H, d, J=15.0 Hz), 4.85 (1H, d, J=14.6 Hz), 7.15-7.19 (2H, m), 7.25 (1H, s), 7.37-7.40 (2H, m), 7.64 (1H, t, J=5.9 Hz). LC-MS (ESI) calculated for C₂₃H₂₇FN₄O₆S₃ 570.11. found 571.2 [M+H⁺].

Example 18 rac-N-{3-[5-Ethyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

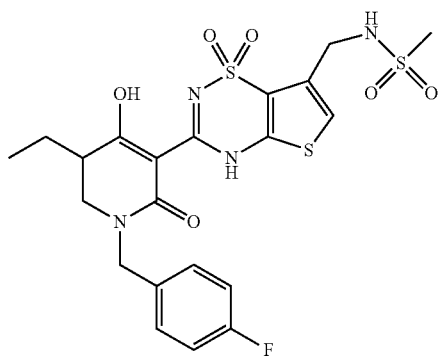

a) rac-2-[(4-Fluoro-benzylamino)-methyl]-butyric acid ethyl ester

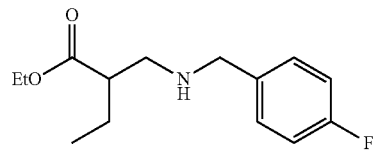

Diisobutylaluminum hydride (38.4 mL of a 1.0 M solution in toluene, 38.4 mmol) was added over 5 min to a solution of 2-ethyl-malonic acid diethyl ester (3.50 g, 19.2 mmol) in dichloromethane (35 mL) at −78° C. The reaction mixture was stirred at that temperature for 3.5 h, and then was quenched with saturated aqueous ammonium chloride (35 mL). The cold bath was removed, 1.0 M aqueous hydrochloric acid solution (90 mL) and DL-tartaric acid (4.25 g) were added sequentially, and the mixture was allowed to warm to 25° C. over 1.5 h with vigorous stirring. The biphasic mixture was then partitioned between 1.0 M aqueous hydrochloric acid solution (350 mL) and dichloromethane (350 mL). The organic layer was dried over sodium sulfate and was concentrated in vacuo to afford crude product (1.64 g, 11.4 mmol, 59%). This material was dissolved in ethanol (40 mL) at 25° C. and 4-fluorobenzylamine (1.30 mL, 11.4 mmol), glacial acetic acid (1.5 mL), and sodium cyanoborohydride (1.43 g, 22.8 mmol) were added sequentially. The mixture was stirred at 25° C. for 20 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (Teledyne Isco RediSep column; 0-60% ethyl acetate in hexanes) to afford rac-2-[(4-fluoro-benzylamino)-methyl]-butyric acid ethyl ester (0.630 g, 2.49 mmol, 22%) as a pale yellow oil. ¹H NMR (400 MHz, CDCl₃) δ: 0.92 (3H, t, J=7.4 Hz), 1.27 (3H, t, J=7.0 Hz), 1.52-1.69 (2H, m), 2.47-2.54 (1H, m), 2.68 (1H, dd, J₁=4.7 Hz, J₂=11.7 Hz), 2.86 (1H, dd, J₁=9.2 Hz, J₂=11.7 Hz), 3.73 (1H, d, J=13.2 Hz), 3.77 (1H, d, J=13.2 Hz), 4.12-4.20 (2H, m), 6.96-7.00 (2H, m), 7.24-7.27 (2H, m).

b) rac-N-{3-[5-Ethyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

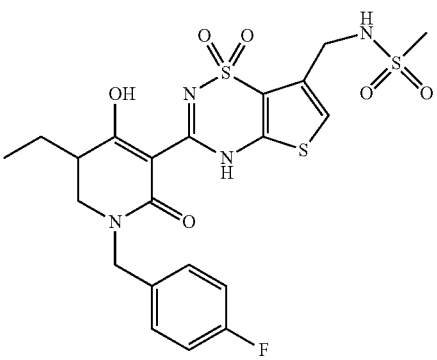

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.113 g, 0.320 mmol), O-(7-azabenzotriazol-1-yl)-N,N,N',N'-tetramethyluronium hexafluorophosphate (0.134 g, 0.352 mmol) and 4-methylmorpholine (0.070 mL, 0.637 mmol) were added sequentially to a solution of rac-2-[(4-fluoro-benzylamino)-methyl]-butyric acid ethyl ester (0.081 g, 0.320 mmol) in N,N-dimethylformamide (4 mL) at 25° C. The reaction mixture was stirred at 25° C. for 18 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (10 mL) at 25° C. A 21 wt. % solution of sodium ethoxide in ethanol (0.622 mL, 1.92 mmol) was added and the reaction mixture was heated to 70° C. for 18 h. After cooling to 25° C., the reaction mixture was partitioned between 1.0 M aqueous hydrochloric acid solution (100 mL) and ethyl acetate (2×100 mL). The organic layers were dried over sodium sulfate and were concentrated in vacuo. The residue was purified by flash chromatography (Teledyne Isco RediSep column; 50-100% ethyl acetate in hexanes) to afford (after trituration with diethylether) rac-N-{3-[5-ethyl-1-(4-fluoro-benzyl)-4-hydroxy-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.061 g, 0.112 mmol, 35%) as a white solid. ¹H NMR (400 MHz, DMSO-d₆) δ: 0.78 (3H, t, J=7.0 Hz), 1.30-1.38 (1H, m), 1.60-1.66 (1H, m), 2.95 (3H, s), 3.22 (1H, dd, J₁=4.5 Hz, J₂=12.1 Hz), 3.56 (1H, dd, J₁=4.2 Hz, J₂=12.8 Hz), 4.24 (2H, d, J=6.3 Hz), 4.45 (1H, d, J=14.7 Hz), 4.75 (1H, d, J=14.9 Hz), 7.14-7.18 (2H, m), 7.25 (1H, s), 7.36-7.39 (2H, m), 7.64 (1H, t, J=5.0 Hz). LC-MS (ESI) calculated for C₂₁H₂₃FN₄O₆S₃ 542.08. found 543.0 [M+H⁺].

Example 19 rac-N-{3-[1-Cyclopropyl-4-hydroxy-5-methyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

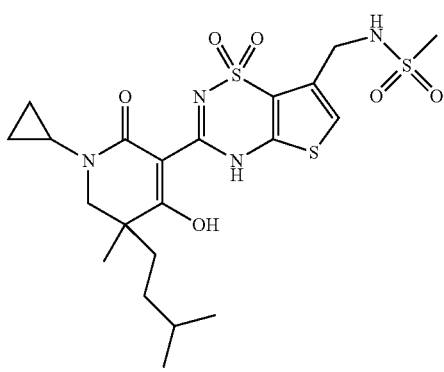

a) rac-2-Methyl-2-(3-methyl-but-2-enyl)-malonic acid diethyl ester

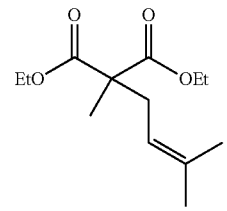

A solution of 2-methyl-malonic acid diethyl ester (20.0 g, 115 mmol) in tetrahydrofuran (50 mL) was added dropwise over 15 min to a suspension of sodium hydride (2.89 g, 120 mmol) in tetrahydrofuran (100 mL) at 0° C. The clear reaction mixture was stirred for 5 min at 0° C., then a solution of 1-bromo-3-methyl-but-2-ene (18.8 g, 126 mmol) in tetrahydrofuran (30 mL) was added over 10 min. The reaction mixture was allowed to warm to 25° C. and was stirred at that temperature for 22 h. After quenching with 1.0 M aqueous hydrochloric acid solution (20 mL), the mixture was partitioned between 1.0 M aqueous hydrochloric acid solution (150 mL) and ethyl acetate (2×150 mL). The organic layers were dried over sodium sulfate and were concentrated in vacuo. The residue was purified by flash chromatography (self packed glass column, gradient elution: 5-20% ethyl acetate in hexanes) to afford rac-2-methyl-2-(3-methyl-but-2-enyl)-malonic acid diethyl ester (22.15 g, 91.4 mmol, 79%) as a colorless oil. ¹H NMR (400 MHz, CDCl₃) δ: 1.25 (6H, t, J=7.0 Hz), 1.37 (3H, s), 1.62 (3H, s), 1.69 (3H, s), 2.57 (2H, d, J=7.0 Hz), 4.17 (4H, q, J=7.0 Hz), 4.99-5.03 (1H, m).

b) rac-2-Methyl-2-(3-methyl-butyl)-malonic acid diethyl ester

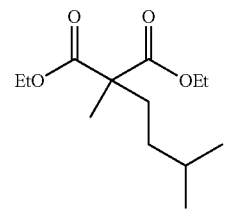

Palladium on carbon (4.26 g, 5%, "50% wet", Alfa) was added to a solution of rac-2-methyl-2-(3-methyl-but-2-enyl)-malonic acid diethyl ester (12.15 g, 50.1 mmol) in ethyl acetate (225 mL) at 25° C. The atmosphere above the reaction mixture was evacuated and replaced with hydrogen from a balloon (3 cycles). The reaction mixture was then stirred under an atmosphere of hydrogen (3 balloons) at 25° C. for 21 h, and then was filtered through Celite. The filtrate was concentrated in vacuo to afford rac-2-methyl-2-(3-methyl-butyl)-malonic acid diethyl ester (11.91 g, 48.7 mmol, 98%) as a colorless oil. ¹H NMR (400 MHz, CDCl₃) δ: 0.89 (6H, d, J=7.0 Hz), 1.07-1.13 (2H, m), 1.25 (6H, t, J=6.9 Hz), 1.39 (1H, s), 1.48-1.57 (1H, m), 1.84-1.88 (1H, m), 4.13-4.21 (2H, m).

c) rac-2-Formyl-2,5-dimethyl-hexanoic acid ethyl ester

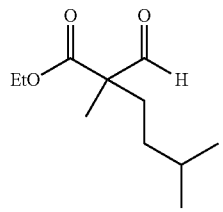

Diisobutylaluminum hydride (97.5 mL of a 1.0 M solution in toluene, 97.5 mmol) was added over 10 min to a solution of rac-2-methyl-2-(3-methyl-butyl)-malonic acid diethyl ester (11.91 g, 48.7 mmol) in dichloromethane (100 mL) at −78° C. The reaction mixture was stirred at that temperature for 4 h, and then was quenched with saturated aqueous ammonium chloride (100 mL). The cold bath was removed, 1.0 M aqueous hydrochloric acid solution (300 mL) and DL-tartaric acid (12 g) were added sequentially, and the mixture was allowed to warm to 25° C. over 2 h with vigorous stirring. The biphasic mixture was then partitioned between 1.0 M aqueous hydrochloric acid solution (150 mL) and dichloromethane (350 mL). The organic layer was dried over sodium sulfate and was concentrated in vacuo to afford the crude product, rac-2-formyl-2,5-dimethyl-hexanoic acid ethyl ester (8.80 g, 44 mmol, 90%).

d) rac-2-Cyclopropylaminomethyl-2,5-dimethyl-hexanoic acid ethyl ester

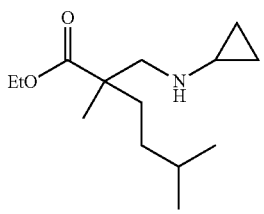

Cyclopropylamine (1.00 mL, 14.4 mmol), glacial acetic acid (1.0 mL), and sodium cyanoborohydride (1.82 g, 29.0 mmol) were added sequentially to a solution of crude rac-2-formyl-2,5-dimethyl-hexanoic acid ethyl ester (2.90 g, 14.5 mmol) in ethanol (40 mL) at 25° C. The mixture was stirred at 25° C. for 18 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (self-packed glass column, gradient elution: 20-30% ethyl acetate in hexanes) to afford rac-2-cyclopropylaminomethyl-2,5-dimethyl-hexanoic acid ethyl ester (1.33 g, 5.51 mmol, 38%) as a pale yellow oil. $^1$H NMR (400 MHz, CDCl$_3$) δ: 0.00-0.04 (2H, m), 0.12-0.16 (2H, m), 0.62 (6H, d, J=6.4 Hz), 0.76-0.86 (1H, m), 0.88 (3H, s), 1.00 (3H, t, J=6.9 Hz), 1.12-1.25 (2H, m), 1.30-1.38 (2H, m), 1.82-1.87 (1H, m), 2.38 (1H, d, J=11.7 Hz), 2.67 (1H, d, J=11.9 Hz), 3.86 (2H, q, J=6.9 Hz).

e) rac-N-{3-[1-Cyclopropyl-4-hydroxy-5-methyl-5-(3-methyl-butyl)-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide

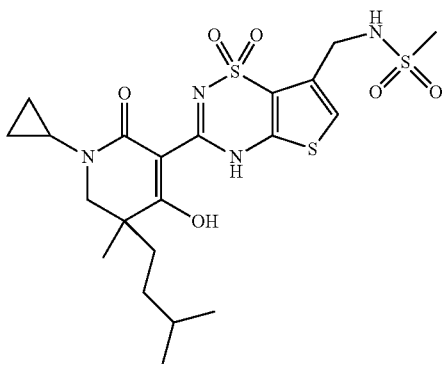

[7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.148 g, 0.419 mmol), O-(7-azabenzotriazol-1-yl)-N,N,N',N'-tetramethyluronium hexafluorophosphate (0.175 g, 0.460 mmol) and 4-methylmorpholine (0.092 mL, 0.837 mmol) were added sequentially to a solution of rac-2-cyclopropylaminomethyl-2,5-dimethyl-hexanoic acid ethyl ester (0.101 g, 0.418 mmol) in N,N-dimethylformamide (6 mL) at 25° C. The reaction mixture was stirred at 25° C. for 20 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (12 mL) at 25° C. A 21 wt. % solution of sodium ethoxide in ethanol (0.813 mL, 2.51 mmol) was added and the reaction mixture was heated to 70° C. for 26 h. After cooling to 25° C., the reaction mixture was partitioned between 1.0 M aqueous hydrochloric acid solution (150 mL) and ethyl acetate (2×150 mL). The organic layers were dried over sodium sulfate and were concentrated in vacuo. The residue was purified by flash chromatography (Teledyne Isco RediSep column; 50-100% ethyl acetate in hexanes) to afford rac-N-{3-[1-Cyclopropyl-4-hydroxy-5-methyl-5-(3-methyl-butyl)-2-oxo-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide (0.109 g, 0.205 mmol, 49%) as an orange oil. $^1$H NMR (400 MHz, DMSO-d$_6$) δ: 0.70 (4H, bs), 0.84-0.86 (6H, m), 1.09 (3H, s), 1.12-1.15 (2H, m), 1.50 (2H, bs), 2.81 (1H, bs), 2.95 (3H, s), 3.27 (1H, d, J=13.5 Hz), 4.23 (2H, d, J=5.4 Hz), 7.26 (1H, s), 7.65 (1H, t, J=6.2 Hz). LC-MS (ESI) calculated for C$_{21}$H$_{30}$N$_4$O$_6$S$_3$ 530.13. found 531.0 [M+H$^+$].

Example 20 rac-N-{3-[1-Cyclobutyl-4-hydroxy-5-methyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

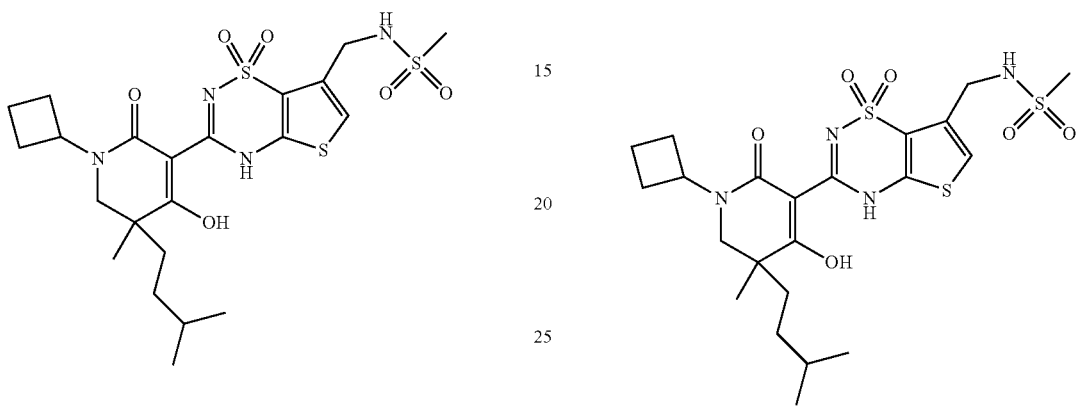

a) rac-2-Cyclobutylaminomethyl-2,5-dimethyl-hexanoic acid ethyl ester

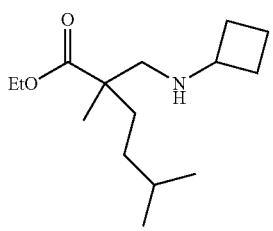

Cyclobutylamine (1.23 mL, 14.4 mmol), glacial acetic acid (1.5 mL), and sodium cyanoborohydride (1.81 g, 28.8 mmol) were added sequentially to a solution of crude rac-2-formyl-2,5-dimethyl-hexanoic acid ethyl ester (prepared as described in Example 19c; 2.88 g, 14.4 mmol) in ethanol (40 mL) at 25° C. The mixture was stirred at 25° C. for 18 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (self-packed glass column, gradient elution: 20-30% ethyl acetate in hexanes) to afford rac-2-cyclobutylaminomethyl-2,5-dimethyl-hexanoic acid ethyl ester (1.76 g, 6.89 mmol, 48%) as a pale yellow oil. $^1$H NMR (400 MHz, CDCl$_3$) δ: 0.87 (3H, d, J=3.0 Hz), 0.88 (3H, d, J=4.0 Hz), 0.99-1.07 (1H, m), 1.17 (3H, s), 1.26 (3H, t, J=7.5 Hz), 1.42-1.68 (4H, m), 2.43 (1H, d, J=11.7 Hz), 2.73 (1H, d, J=11.7 Hz), 3.15-3.23 (1H, m), 4.13 (2H, q, J=7.0 Hz).

b) rac-N-{3-[1-Cyclobutyl-4-hydroxy-5-ethyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.266 g, 0.753 mmol), O-(7-azabenzotriazol-1-yl)-N,N,N',N'-tetramethyluronium hexafluorophosphate (0.314 g, 0.826 mmol) and 4-methylmorpholine (0.165 mL, 1.50 mmol) were added sequentially to a solution of rac-2-cyclobutylaminomethyl-2,5-dimethyl-hexanoic acid ethyl ester (0.192 g, 0.752 mmol) in N,N-dimethylformamide (8 mL) at 25° C. The reaction mixture was stirred at 25° C. for 22 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (12 mL) at 25° C. A 21 wt. % solution of sodium ethoxide in ethanol (1.46 mL, 4.51 mmol) was added and the reaction mixture was heated to 70° C. for 24 h. After cooling to 25° C., the reaction mixture was partitioned between 1.0 M aqueous hydrochloric acid solution (150 mL) and ethyl acetate (2×150 mL). The organic layers were dried over sodium sulfate and were concentrated in vacuo. The residue was purified by flash chromatography (Teledyne Isco RediSep column; 50-100% ethyl acetate in hexanes) to afford rac-N-{3-[1-cyclobutyl-4-hydroxy-5-methyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.095 g, 0.174 mmol, 23%) as an orange oil. $^1$H NMR (400 MHz, DMSO-d$_6$) δ: 0.82-0.86 (6H, m), 0.94-0.99 (1H, m), 1.04 (3H, s), 1.07-1.23 (5H, m), 1.40-1.54 (2H, m), 1.65-1.70 (1H, m), 2.07 (1H, bs), 2.19-2.26 (1H, m), 2.95 (3H, s), 3.26-3.31 (1H, m), 3.46-3.51 (1H, m), 3.99-4.06 (1H, m), 4.23 (2H, d, J=6.1 Hz), 7.27 (1H, s), 7.65 (1H, t, J=6.3 Hz). LC-MS (ESI) calculated for C$_{22}$H$_{32}$N$_4$O$_6$S$_3$ 544.15. found 545.1 [M+H$^+$].

Example 21 rac-N-{3-[1-Cyclopentyl-4-hydroxy-5-methyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

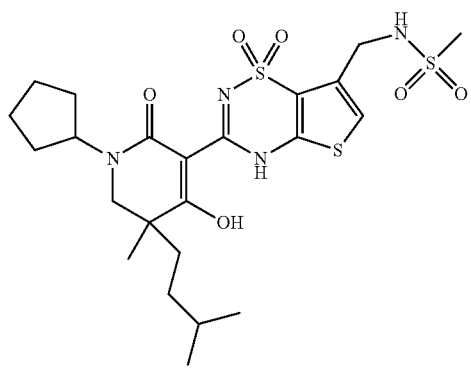

a)
rac-2-Cyclopentylaminomethyl-2,5-dimethyl-hexanoic acid ethyl ester

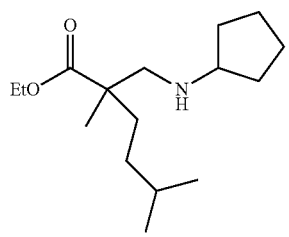

Cyclopentylamine (1.49 mL, 15.1 mmol), glacial acetic acid (1.5 mL), and sodium cyanoborohydride (1.90 g, 30.2 mmol) were added sequentially to a solution of crude rac-2-formyl-2,5-dimethyl-hexanoic acid ethyl ester (prepared as described in Example 19c; 3.02 g, 15.1 mmol) in ethanol (45 mL) at 25° C. The mixture was stirred at 25° C. for 18 h, and then was concentrated in vacuo. The residue was partitioned between half-saturated aqueous sodium bicarbonate solution (150 mL) and ethyl acetate (2×150 mL). The combined organic layers were dried over sodium sulfate and were concentrated in vacuo. The residue was purified by flash column chromatography (self-packed glass column, gradient elution: 20-30% ethyl acetate in hexanes) to afford rac-2-cyclopentylaminomethyl-2,5-dimethyl-hexanoic acid ethyl ester (1.60 g, 5.94 mmol, 39%) as a pale yellow oil. ¹H NMR (400 MHz, CDCl₃) δ: 0.87 (6H, d, J=6.9 Hz), 1.01-1.06 (1H, m), 1.16 (3H, s), 1.27 (3H, t, J=6.9 Hz), 1.27-1.33 (4H, m), 1.43-1.64 (8H, m), 2.51 (1H, d, J=11.7 Hz), 2.79 (1H, d, J=11.7 Hz), 2.96-3.02 (1H, m), 4.12 (2H, q, J=7.2 Hz).

b) rac-N-{3-[1-Cyclopentyl-4-hydroxy-5-methyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide

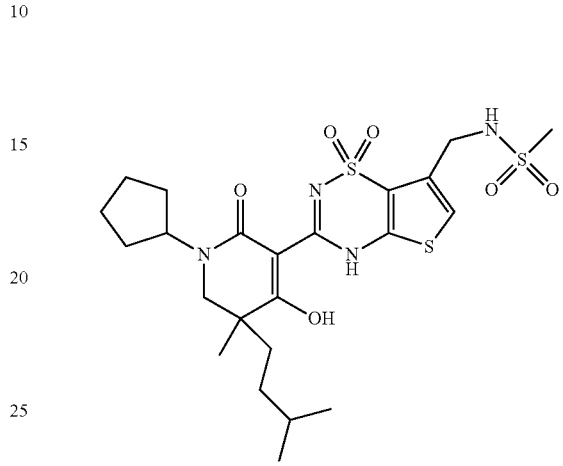

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.274 g, 0.775 mmol), O-(7-azabenzotriazol-1-yl)-N,N,N',N'-tetramethyluronium hexafluorophosphate (0.324 g, 0.853 mmol) and 4-methylmorpholine (0.171 mL, 1.55 mmol) were added sequentially to a solution of rac-2-cyclopentylaminomethyl-2,5-dimethyl-hexanoic acid ethyl ester (0.209 g, 0.776 mmol) in N,N-dimethylformamide (8 mL) at 25° C. The reaction mixture was stirred at 25° C. for 22 h, and then was concentrated in vacuo. The residue was partitioned between 1.0 M aqueous hydrochloric acid solution (100 mL) and ethyl acetate (2×100 mL). The organic layers were dried over sodium sulfate and were concentrated in vacuo. The residue was dissolved in ethanol (15 mL) at 25° C. A 21 wt. % solution of sodium ethoxide in ethanol (1.51 mL, 4.66 mmol) was added and the reaction mixture was heated to 70° C. for 24 h. After cooling to 25° C., the reaction mixture was partitioned between 1.0 M aqueous hydrochloric acid solution (150 mL) and ethyl acetate (2×150 mL). The organic layers were dried over sodium sulfate and were concentrated in vacuo. The residue was purified by flash chromatography (Teledyne Isco RediSep column; 40-100% ethyl acetate in hexanes) to afford rac-N-{3-[1-cyclopentyl-4-hydroxy-5-methyl-5-(3-methyl-butyl)-2-oxo-1,2,5,6-tetrahydro-pyridin-3-yl]-1,1-dioxo-1,4-dihydro-1λ⁶-thieno[2,3-e][1,2,4]thiadiazin-7-ylmethyl}-methanesulfonamide (0.032 g, 0.057 mmol, 7%) as an orange oil. ¹H NMR (400 MHz, DMSO-d₆) δ: 0.83-0.86 (6H, m), 0.88-0.91 (1H, m), 1.01 (3H, s), 1.08-1.17 (6H, m), 1.23-1.30 (2H, m), 1.41-1.51 (3H, m), 1.95-2.01 (1H, m), 2.95 (3H, s), 3.17-3.21 (1H, m), 3.46-3.51 (1H, m), 3.99-4.05 (1H, m), 4.23 (2H, d, J=5.4 Hz), 7.24 (1H, s), 7.64 (1H, bs). LC-MS (ESI) calculated for C₂₃H₃₄N₄O₆S₃ 558.16. found 559.1 [M+H⁺].

Example 22

(rac-di-endo)-N-{3-[3-(4-Fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide

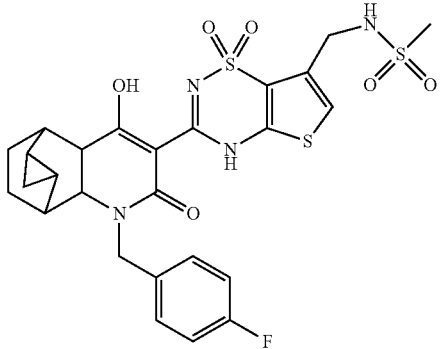

Methyl-(di-endo) 7 {[(benzyloxy)carbonyl]amino}tricyclo[3.2.2.0$^{2,4}$]non-8-ene-6-carboxylate (0.1 g, 0.43 mmol, prepared as described in WO08124450A1) was dissolved in methanol (4 mL). Sodium acetate (0.071 g, 0.86 mmol) was added followed by 4-fluoro benzaldehyde (0.053 g, 0.43 mmol) in methanol. The mixture was shaken for 15 min at 25° C. Sodium cyanoborohydride (0.054 g, 0.86 mmol) was added and the mixture was shaken at 25° C. for 16 h. Saturated aqueous sodium bicarbonate solution (2 mL) was added and the mixture was shaken for 1 h. The resulting suspension was partitioned between ethyl acetate (8 mL) and saturated aqueous sodium bicarbonate solution (4 mL). The organic phase was concentrated in vacuo to afford a thick oil which was dissolved in N,N-dimethylformamide (3 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.152 g, 0.43 mmol) was added followed by 1-(3-dimethylaminopropyl)-3-ethylcarbodiimide hydrochloride (0.124 g, 0.645 mmol. The mixture was shaken at 25° C. for 16 h. Triethylamine (0.6 mL, 2.16 mmol) was added and the mixture was shaken for at 75° C. for 24 h.

Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes). The resulting solid was triturated with diethyl ether, filtered and dried in vacuo to afford (rac-di-endo)-N-{3-[3-(4-fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide (0.012 g, 0.02 mmol, 4.7%) as an off-white powder. $^1$H NMR (400 MHz, DMSO-d$_6$) δ: 0.31-0.39 (1H, m), 0.58-0.63 (1H, m), 0.81-0.87 (2H, m), 1.12-1.23 (1H, m), 1.25-1.40 (3H, m), 2.28-2.31 (1H, m), 2.51-2.53 (1H, m), 2.95 (3H, s), 3.18-3.29 (1H, m), 3.79 (1H, d, J=10.9 Hz), 4.24 (2H, d, J=5.5 Hz), 4.46 (1H, d, J=15.8 Hz), 4.95 (1H, d, J=14.8 Hz), 7.14 (2H, t, J=9.1 Hz), 7.27 (1H, s), 7.37 (2H, dd, J$_1$=8.8 Hz, J$_2$=5.4 Hz), 7.65 (1H, t, J=6.3 Hz). LC-MS (ESI) calculated for C$_{26}$H$_{27}$FN$_4$O$_6$S$_3$ 606.10. found 607.0 [M+H$^+$].

Example 23

(rac-di-exo)-N-{3-[3-(4-Fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide

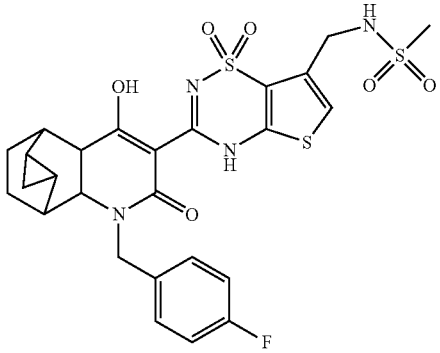

Methyl-(di-exo)-7-{[(benzyloxy)carbonyl]amino}tricyclo[3.2.2.0$^{2,4}$]non-8-ene-6-carboxylate (0.1 g, 0.43 mmol, prepared as described in WO08124450A1) was dissolved in methanol (4 mL). Sodium acetate (0.071 g, 0.86 mmol) was added followed by 4-fluoro benzaldehyde (0.053 g, 0.43 mmol) in methanol. The mixture was shaken for 15 min at 25° C. Sodium cyanoborohydride (0.054 g, 0.86 mmol) was added and the mixture was shaken at 25° C. for 16 h. Saturated aqueous sodium bicarbonate solution (2 mL) was added and the mixture was shaken for 1 h. The resulting suspension was partitioned between ethyl acetate (8 mL) and saturated aqueous sodium bicarbonate solution (4 mL). The organic phase was concentrated in vacuo to afford a thick oil which was dissolved in N,N-dimethylformamide (3 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.152 g, 0.43 mmol) was added followed by 1-(3-dimethylaminopropyl)-3-ethylcarbodiimide hydrochloride (0.124 g, 0.645 mmol. The mixture was shaken at 25° C. for 16 h. Triethylamine (0.6 mL, 2.16 mmol) was added and the mixture was shaken for at 75° C. for 24 h.

Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes). The resulting solid was triturated with diethyl ether, filtered and dried in vacuo to afford (rac-di-exo)-N-{3-[3-(4-fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide (0.011 g, 0.018 mmol, 4.2%) as an off-white powder. $^1$H NMR (400 MHz, DMSO-d$_6$) δ: 0.43-0.48 (1H, m), 0.71-0.75 (1H, m), 0.84-0.91 (1H, m), 1.05-1.12 (2H, m), 1.16-1.31 (3H, m), 2.25-2.31 (1H, m), 2.50-2.54 (1H, m), 2.96 (3H, s), 3.21-3.31 (1H, m), 3.81 (1H, d, J=12.0

Hz), 4.25 (2H, d, J=6.2 Hz), 4.38 (1H, d, J=14.7 Hz), 4.96 (1H, d, J=15.0 Hz), 7.14 (2H, t, J=8.7 Hz), 7.29 (1H, s), 7.38 (2H, dd, $J_1$=7.7 Hz, $J_2$=5.6 Hz), 7.66 (1H, t, J=6.2 Hz). LC-MS (ESI) calculated for $C_{26}H_{27}FN_4O_6S_3$ 606.10. found 606.9 [M+H$^+$].

Example 24

(rac-di-endo)-N-{3-[3-(3,3-Dimethyl-butyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide

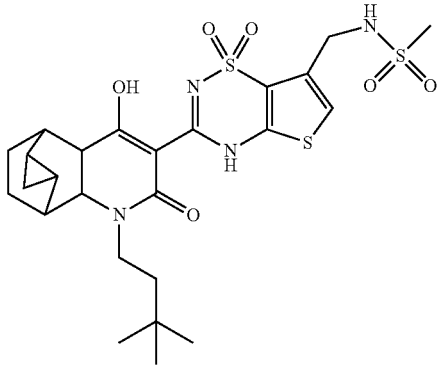

Methyl-(di-endo)-7-{[(benzyloxy)carbonyl]amino}tricyclo[3.2.2.0$^{2,4}$]non-8-ene-6-carboxylate (0.1 g, 0.43 mmol, prepared as described in WO08124450A1) was dissolved in methanol (4 mL). Sodium acetate (0.071 g, 0.86 mmol) was added followed by 3,3-dimethylbutyraldehyde (0.043 g, 0.43 mmol) in methanol. The mixture was shaken for 15 min at 25° C. Sodium cyanoborohydride (0.054 g, 0.86 mmol) was added and the mixture was shaken at 25° C. for 16 h. Saturated aqueous sodium bicarbonate solution (2 mL) was added and the mixture was shaken for 1 h. The resulting suspension was partitioned between ethyl acetate (8 mL) and saturated aqueous sodium bicarbonate solution (4 mL). The organic phase was concentrated in vacuo to afford a thick oil which was dissolved in N,N-dimethylformamide (3 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.152 g, 0.43 mmol) was added followed by 1-(3-dimethylaminopropyl)-3-ethylcarbodiimide hydrochloride (0.124 g, 0.645 mmol. The mixture was shaken at 25° C. for 16 h. Triethylamine (0.6 mL, 2.16 mmol) was added and the mixture was shaken for at 75° C. for 24 h.

Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes). The resulting solid was triturated with diethyl ether, filtered and dried in vacuo to afford N-{3-[3-(3,3-dimethyl-butyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide (0.026 g, 0.045 mmol, 10%) as an off-white powder. $^1$H NMR (400 MHz, DMSO-d$_6$) δ: 0.34-0.41 (1H, m), 0.62-0.68 (1H, m), 0.78-0.90 (3H, m), 0.94 (9H, s), 1.22-1.33 (1H, m), 1.33-1.44 (3H, m), 1.58-1.71 (1H, m), 2.26-2.32 (1H, m), 2.51-2.56 (1H, m), 2.95 (3H, s), 3.16-3.25 (2H, m), 3.56 (1H, dt, $J_1$=12.7 Hz, $J_2$=4.9 Hz), 3.89 (1H, d, J=10.2 Hz), 4.23 (2H, d, J=6.4 Hz), 7.28 (1H, s), 7.65 (1H, t, J=6.3 Hz). LC-MS (ESI) calculated for $C_{25}H_{34}N_4O_6S_3$ 582.16. found 583.1 [M+H$^+$].

Example 25

(rac-di-exo)-N-{3-[3-(3,3-Dimethyl-butyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide

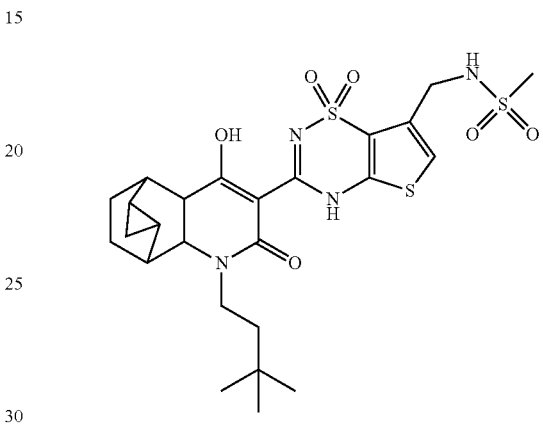

Methyl-(di-exo)-7-{[(benzyloxy)carbonyl]amino}tricyclo[3.2.2.0$^{2,4}$]non-8-ene-6-carboxylate (0.1 g, 0.43 mmol, prepared as described in WO08124450A1) was dissolved in methanol (4 mL). Sodium acetate (0.071 g, 0.86 mmol) was added followed by 3,3-dimethylbutyraldehyde (0.043 g, 0.43 mmol) in methanol. The mixture was shaken for 15 min at 25° C. Sodium cyanoborohydride (0.054 g, 0.86 mmol) was added and the mixture was shaken at 25° C. for 16 h. Saturated aqueous sodium bicarbonate solution (2 mL) was added and the mixture was shaken for 1 h. The resulting suspension was partitioned between ethyl acetate (8 mL) and saturated aqueous sodium bicarbonate solution (4 mL). The organic phase was concentrated in vacuo to afford a thick oil which was dissolved in N,N-dimethylformamide (3 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.152 g, 0.43 mmol) was added followed by 1-(3-dimethylaminopropyl)-3-ethylcarbodiimide hydrochloride (0.124 g, 0.645 mmol. The mixture was shaken at 25° C. for 16 h. Triethylamine (0.6 mL, 2.16 mmol) was added and the mixture was shaken for at 75° C. for 24 h.

Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes). The resulting solid was triturated with diethyl ether, filtered and dried in vacuo to afford (rac-di-exo)-N-{3-[3-(3,3-dimethyl-butyl)-6-hydroxy-4-oxo-3-aza-tetracyclo[6.3.2.0$^{2,7}$.0$^{9,11}$]tridec-5-en-5-yl]-1,1-dioxo-1,4-dihydro-1λ$^6$-thieno[2,3-e][1,2,4]thiadiazin-7-ylmethyl}-methanesulfonamide (0.036 g, 0.062 mmol, 14.4%) as an off-white powder. $^1$H NMR (400 MHz, DMSO-d$_6$) δ: 0.47-

0.52 (1H, m), 0.74-0.79 (1H, m), 0.94 (9H, s), 0.97-1.02 (1H, m), 1.09-1.43 (6H, m), 1.54-1.70 (1H, m), 2.21-2.32 (1H, m), 2.50-2.54 (1H, m), 2.88-3.25 (5H, m), 3.55 (1H, dt, $J_1$=12.5 Hz, $J_2$=4.8 Hz), 3.91 (1H, d, J=11.1 Hz), 4.24 (2H, d, J=5.2 Hz), 7.28 (1H, s), 7.66 (1H, t, J=6.3 Hz). LC-MS (ESI) calculated for $C_{25}H_{34}N_4O_6S_3$ 582.16. found 583.0 [M+H$^+$].

Example 26

N-{3-[(1R,2S,7R,8S)-3-(2-Cyclobutyl-ethyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

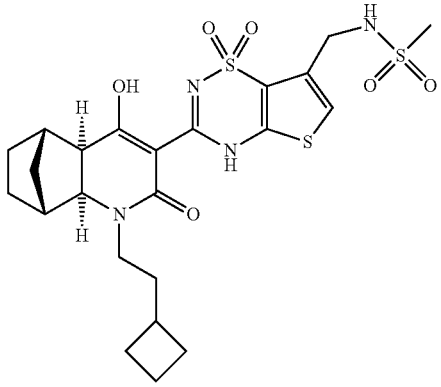

(1R,2R,3S,4S)-3-Amino-bicyclo[2.2.1]heptane-2-carboxylic acid ethyl ester (7,7-dimethyl-2-oxo-bicyclo[2.2.1]hept-1-yl)-methanesulfonate (0.15 g, 0.36 mmol, prepared as described in WO08124450A1) was dissolved in N,N-dimethylformamide (4 mL). Toluene-4-sulfonic acid 2-cyclobutyl-ethyl ester (0.182 g, 0.72 mmol) was added followed by triethylamine (0.109 g, 1.08 mmol) and potassium iodide (approximately 0.05 g, 0.03 mmol). The mixture was shaken for 40 h at 75° C. Upon cooling, [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.127 g, 0.36 mmol) was added followed by 1-(3-dimethylaminopropyl)-3-ethylcarbodiimide hydrochloride (0.104 g, 0.54 mmol. The mixture was shaken at 25° C. for 16 h. Triethylamine (0.145 g, 1.44 mmol) was added and the mixture was shaken for at 75° C. for 24 h.

Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes). The resulting solid was triturated with diethyl ether, filtered and dried in vacuo to afford N-{3-[(1R, 2S,7R,8S)-3-(2-cyclobutyl-ethyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.013 g, 0.023 mmol, 6.5%) as an off-white powder. $^1$H NMR (400 MHz, DMSO-d$_6$) δ: 1.25-1.31 (1H, m), 1.42-1.66 (8H, m), 1.75-1.85 (3H, m), 1.99-2.06 (2H, m), 2.22-2.30 (1H, m), 2.50-2.53 (1H, m), 2.57-2.62 (1H, m), 2.88-3.01 (4H, m), 3.54-3.66 (2H, m), 4.23 (2H, d, J=6.4 Hz), 7.27 (1H, s), 7.66 (1H, t, J=6.2 Hz). LC-MS (ESI) calculated for $C_{23}H_{30}N_4O_6S_3$ 554.1. found 555.2 [M+H$^+$].

Example 27

(rac-cis)-N-{3-(1-Cyclobutylamino-4-hydroxy-2-oxo-2,4a,5,6,7,7a-hexahydro-1H-[1]pyrindin-3-yl)-1, 1-dioxo-1,4-dihydro-1λ$^6$-thieno[2,3-e][1,2,4]thiadiazin-7-ylmethyl]-methanesulfonamide

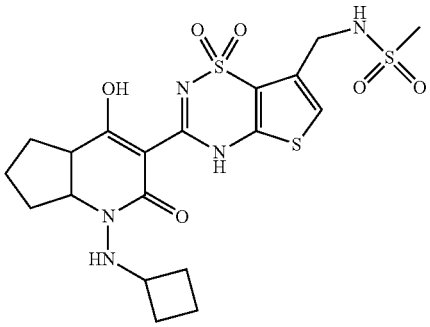

a) (rac-cis)-N-{3-[1-(Allyl-cyclobutyl-amino)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

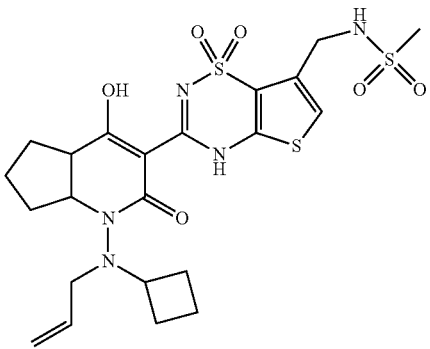

(rac-cis)-2-(N'-Allyl-N'-cyclobutyl-hydrazino)-cyclopentanecarboxylic acid ethyl ester (1.6 g, 6.2 mmol, prepared as described in WO2008/073982) was dissolved in N,N-dimethylformamide (20 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 2.52 g, 7.12 mmol) was added followed by 1-(3-dimethylaminopropyl)-3-ethylcarbodiimide hydrochloride (2.05 g, 10.7 mmol) and N-methyl morpholine (1.44 g, 14.26 mmol). The mixture stirred at 25° C. for 16 h. The reaction was quenched via addition of saturated aqueous sodium bicarbonate solution (40 mL). The mixture was extracted with ethyl acetate (3×60 mL). The organic layers were combined and washed with saturated aqueous brine solution (40 mL).

The resulting solution was dried over magnesium sulfate, filtered, and concentrated in vacuo to afford a golden oil. The oil was dissolved in ethanol (40 mL). A 21 wt. % solution of sodium ethoxide in ethanol (6.73 mL, 18 mmol) was added. The reaction was stirred at 80° C. for 16 h. The reaction was quenched via the addition of saturated aqueous ammonium chloride solution (50 mL). The mixture was extracted with ethyl acetate (3×100 mL). The organic layer was further washed with saturated aqueous sodium bicarbonate solution (2×50 mL), saturated aqueous brine solution (50 mL), dried over magnesium sulfate, filtered, and concentrated in vacuo to afford a clear oil. Purification by flash column chromatography (Teledyne Isco RediSep column; 0-100% ethyl acetate in hexanes) afford the desired product, (rac-cis)-N-{3-[1-(allyl-cyclobutyl-amino)-4-hydroxy-2-oxo-2,4a,5,6,7,7a-hexahydro-1H-[1]pyrindin-3-yl]-1,1-dioxo-1,4-dihydro-1$\lambda^6$-thieno[2,3-e][1,2,4]thiadiazin-7-ylmethyl}-methanesulfonamide (0.94 g, 1.69 mmol, 27%), as a golden, brittle foam. $^1$H NMR (400 MHz, DMSO-$d_6$) δ: 1.51-1.72 (4H, m), 1.75-2.02 (8H, m), 2.96 (3H, s), 3.02-4.11 (5H, m), 4.24 (2H, d, J=6.1 Hz), 5.02-5.11 (1H, m), 5.15-5.27 (1H, m), 5.78-5.93 (1H, m), 7.29 (1H, s), 7.66 (1H, t, J=6.3 Hz).

b) (rac-cis)-N-[3-(1-cyclobutylamino-4-hydroxy-2-oxo-2,4a,5,6,7,7a-hexahydro-1H-[1]pyrindin-3-yl)-1,1-dioxo-1,4-dihydro-1$\lambda^6$-thieno[2,3-e][1,2,4]thiadiazin-7-ylmethyl]-methanesulfonamide

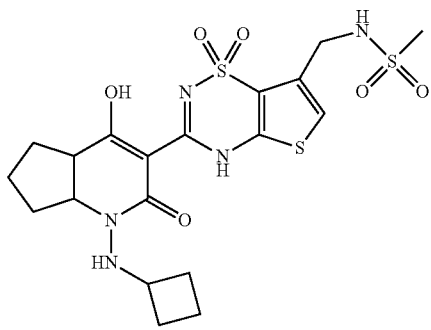

(rac-cis)-N-{3-[1-(Allyl-cyclobutyl-amino)-4-hydroxy-2-oxo-2,4a,5,6,7,7a-hexahydro-1H-[1]pyrindin-3-yl]-1,1-dioxo-1,4-dihydro-1$\lambda^6$-thieno[2,3-e][1,2,4]thiadiazin-7-ylmethyl}-methanesulfonamide (0.3 g, 0.54 mmol) was dissolved in dichloromethane (25 mL). The solution was degassed and backfilled with nitrogen. Tetrakis(triphenylphosphine)palladium(0) (0.063 mg, 0.054 mmol) and N,N'-dimethylbarbituric acid (0.252 g mg, 1.62 mmol) were added sequentially. The reaction was stirred at 35° C. for 18 h. The mixture was cooled to 25° C. and concentrated in vacuo. Purification by prep-HPLC [Column Luna 5µ C18 (2) 100 Å AXIA 150×21.2 mm, 5 micron, 25%-100% in 12 min @ 30 mL/min flow rate, 0.05% trifluoroacetic acid in acetonitrile/ 0.05% trifluoroacetic acid in water] afforded the desired product, (rac-cis)-N-[3-(1-cyclobutylamino-4-hydroxy-2-oxo-2,4a,5,6,7,7a-hexahydro-1H-[1]pyrindin-3-yl)-1,1-dioxo-1,4-dihydro-1$\lambda^6$-thieno[2,3-e][1,2,4]thiadiazin-7-ylmethyl]-methanesulfonamide (0.063 g, 0.122 mmol, 23%), as a white solid. $^1$H NMR (400 MHz, DMSO-$d_6$) δ: 1.52-1.70 (4H, m), 1.82-2.13 (8H, m), 2.95 (3H, s), 3.17-3.27 (1H, m), 3.55 (1H, quintet, J=8.0 Hz), 3.96-4.02 (1H, m), 4.24 (2H, d, J=6.2 Hz), 7.27 (1H, s), 7.66 (1H, t, J=6.3 Hz). LC-MS (ESI) calculated for $C_{19}H_{25}N_5O_6S_3$ 515.1. found 516.1 [M+H$^+$].

Example 28

N-{3-[5-Hydroxy-2-(3-methyl-butyl)-3-oxo-6-thiophen-2-yl-2,3-dihydro-pyridazin-4-yl]-1,1-dioxo-1,4-dihydro-1$\lambda^6$-thieno[2,3-e][1,2,4]thiadiazin-7-ylmethyl}-methanesulfonamide

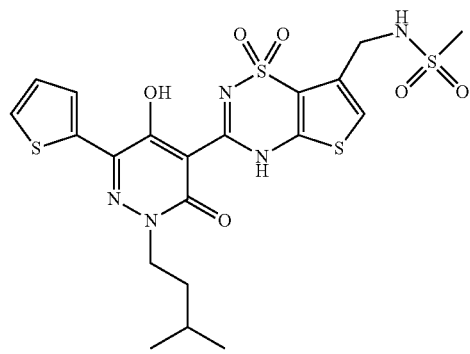

a) 2-(3-Methyl-butyl)-6-thiophen-2-yl-2H-pyridazine-3,5-dione

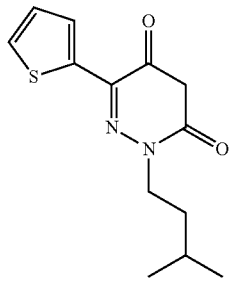

5-Hydroxy-2-(3-methyl-butyl)-3-oxo-6-thiophen-2-yl-2, 3-dihydro-pyridazine-4-carboxylic acid ethyl ester (0.3 g, 0.892 mmol, prepared as described in WO06066079A2) was dissolved in 1,4-dioxane (10 mL) and a 1.0 M aqueous hydrochloric acid solution (10 mL) was added. The mixture stirred in a sealed tube at 100° C. for 4 h. Upon cooling, the mixture was concentrated in vacuo to afford a thick oil. The oil was dissolved in dichloromethane (15 mL) and passed through a plug of silica gel (Merck silica gel 60, 40-63 µm), eluting with ethyl acetate. Upon concentrating, the desired product, 2-(3-methyl-butyl)-6-thiophen-2-yl-2H-pyridazine-3,5-dione (0.215 g, 0.814 mmol) was obtained as a thick oil. $^1$H NMR (400 MHz, DMSO-$d_6$) δ: 0.91 (6H, d, J=6.2 Hz), 1.49-1.61 (3H, m), 4.03 (2H, t, J=7.1 Hz), 6.09 (1H, s), 7.10 (1H, dd, $J_1$=8.6 Hz, $J_2$=0.0 Hz), 7.58 (1H, d, J=5.4 Hz), 7.77 (1H, dd, $J_1$=4.0 Hz, $J_2$=1.6 Hz), 12.02 (1H, s).

149 b) N-{3-[5-hydroxy-2-(3-methyl-butyl)-3-oxo-6-thiophen-2-yl-2,3-dihydro-pyridazin-4-yl]-1,1-dioxo-1,4-dihydro-1λ⁶-thieno[2,3-e][1,2,4]thiadiazin-7-ylmethyl}-methanesulfonaide

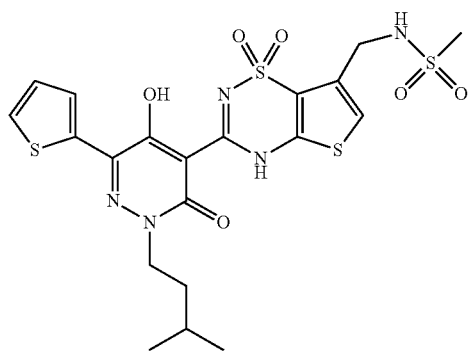

2-(3-Methyl-butyl)-6-thiophen-2-yl-2H-pyridazine-3,5-dione (0.215 g, 0.814 mmol) and (bis-methylsulfanyl-methylene)-methyl-sulfonium tetrafluoro borate salt (prepared as described in WO 2008/011337; 0.79 g, 3.26 mmol) were combined. 1,4-Dioxane (1.06 mL) and pyridine (0.15 mL) were added. The mixture was heated at 100° C. for 1 h while stirring. Upon cooling, the mixture was diluted with ethyl acetate (30 mL) and washed with water (15 mL), saturated aqueous brine solution (15 mL), dried over sodium sulfate, filtered and concentrated in vacuo. The residue was passed through a plug of silica gel (Merck silica gel 60, 40-63 μm; eluting with 25% ethyl acetate in hexanes). Upon concentrating, 4-(bis-methylsulfanyl-methylene)-2-(3-methyl-butyl)-6-thiophen-2-yl-2H-pyridazine-3,5-dione (0.06 g, 0.163 mmol) was obtained as an orange solid. The solid was combined with 2-amino-4-(methanesulfonylamino-methyl)-thiophene-3-sulfonic acid amide (0.07 g, 0.245 mmol). Toluene (5 mL) and 1,4-dioxane (10 mL) were added and the mixture stirred at 100° C. in a sealed vial for 2 h. Upon cooling, the mixture was concentrated in vacuo to afford a thick oil. Purification by flash column chromatography (Teledyne Isco RediSep column; 5-100% ethyl acetate in hexanes) afford the desired product, N-{3-[5-hydroxy-2-(3-methyl-butyl)-3-oxo-6-thiophen-2-yl-2,3-dihydro-pyridazin-4-yl]-1,1-dioxo-1,4-dihydro-1λ⁶-thieno[2,3-e][1,2,4]thiadiazin-7-ylmethyl}-methanesulfonamide (0.018 g, 0.032 mmol, 10%) as a light orange powder. ¹H NMR (400 MHz, DMSO-$d_6$) δ: 0.95 (6H, d, J=6.2 Hz), 1.57-1.69 (3H, m), 2.97 (3H, s), 4.13 (2H, t, J=7.1 Hz), 4.27 (2H, d, J=5.5 Hz), 7.13-7.16 (1H, m), 7.31 (1H, s), 7.64-7.69 (2H, m), 7.89 (1H, d, J=4.0 Hz). LC-MS (ESI) calculated for $C_{20}H_{23}N_5O_6S_4$ 557.05. found 558.0 [M+H⁺].

150

Example 29

N-{3-[(1R,2S,7R,8S)-6-Hydroxy-4-oxo-3-(1-trifluoromethyl-cyclopropylmethyl)-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methaneulfonamide

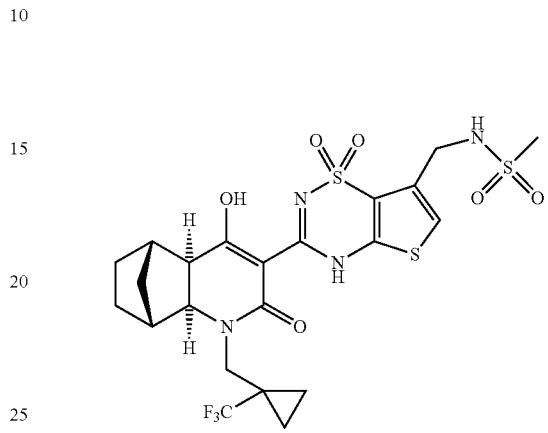

(1R,2R,3S,4S)-3-Amino-bicyclo[2.2.1]heptane-2-carboxylic acid ethyl ester (7,7-dimethyl-2-oxo-bicyclo[2.2.1]hept-1-yl)-methanesulfonate (0.3 g, 0.72 mmol, prepared as described in WO08124450A1) was dissolved in N,N-dimethylformamide (4 mL). Toluene-4-sulfonic acid 1-trifluoromethyl-cyclopropylmethyl ester (0.424 g, 1.44 mmol) was added followed by triethylamine (0.218 g, 2.16 mmol) and potassium iodide (approximately 0.05 g, 0.03 mmol). The mixture was shaken for 40 h at 75° C. Upon cooling, [7-(methanesulfonylamino-methyl)-1,1-dioxo-1,4-dihydro-1λ⁶-thieno[2,3-e][1,2,4]thiadiazin-3-yl]-acetic acid (prepared as described in Example 2c; 0.254 g, 0.72 mmol) was added followed by 1-(3-dimethylaminopropyl)-3-ethylcarbodiimide hydrochloride (0.208 g, 1.08 mmol. The mixture was shaken at 25° C. for 16 h. Triethylamine (0.290 g, 2.88 mmol) was added and the mixture was shaken for at 75° C. for 24 h. Upon cooling to 25° C., the mixture was concentrated in vacuo to afford a thick oil. The oil was partitioned between dichloromethane (6 mL) and 1.0 M aqueous hydrochloric acid solution (10 mL). The organic phase was further washed with 1.0 M aqueous hydrochloric acid solution (5 mL). The organic phase was directly purified by flash column chromatography (Teledyne Isco RediSep column; 5-100% ethyl acetate in hexanes). The resulting solid was triturated with diethyl ether, filtered and dried in vacuo to afford N-{3-[(1R,2S,7R,8S)-6-hydroxy-4-oxo-3-(1-trifluoromethyl-cyclopropylmethyl)-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide (0.006 g, 0.01 mmol, 1.4%) as an off-white powder. ¹H NMR (400 MHz, DMSO-$d_6$) δ: 0.79-0.92 (3H, m), 1.00-1.21 (3H, m), 1.37-1.60 (4H, m), 2.49-2.56 (2H, m), 2.88 (3H, s), 2.97 (1H, d, J=9.6 Hz), 3.03 (1H, d, J=15.3 Hz), 3.67 (1H, d, J=9.3 Hz), 4.17 (2H, d, J=6.2 Hz), 4.53 (1H, d, J=15.6 Hz), 7.21 (1H, s), 7.59 (1H, t, J=6.3 Hz). LC-MS (ESI—negative mode) calculated for $C_{22}H_{25}F_3N_4O_6S_3$ 594.09. found 593.25 [M−H].

Example 30

N-{3-[(1R,2S,7R,8S)-3-(2-Cyclopentyl-ethyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

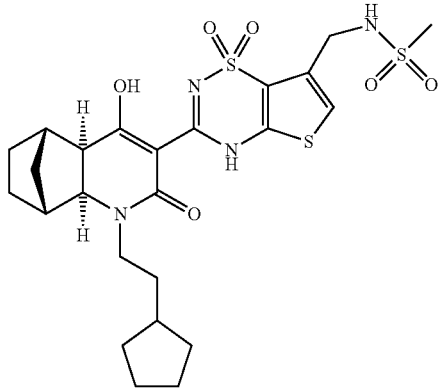

(1R,2R,3S,4S)-3-Amino-bicyclo[2.2.1]heptane-2-carboxylic acid ethyl ester (7,7-dimethyl-2-oxo-bicyclo[2.2.1]hept-1-yl)-methanesulfonate (0.15 g, 0.36 mmol, prepared as described in WO08124450A1) was dissolved in N,N-dimethylformamide (4 mL). Toluene-4-sulfonic acid 2-cyclopentyl-ethyl ester (0.193 g, 0.72 mmol) was added followed by triethylamine (0.109 g, 1.08 mmol) and potassium iodide (approximately 0.05 g, 0.03 mmol). The mixture was shaken for 40 h at 75° C. Upon cooling, [7-(methanesulfonylaminomethyl)-1,1-dioxo-1,4-dihydro-1λ$^6$-thieno[2,3-e][1,2,4]thiadiazin-3-yl]-acetic acid (prepared as described in Example 2c; 0.127 g, 0.36 mmol) was added followed by 1-(3-dimethylaminopropyl)-3-ethylcarbodiimide hydrochloride (0.104 g, 0.54 mmol. The mixture was shaken at 25° C. for 16 h. Triethylamine (0.145 g, 1.44 mmol) was added and the mixture was shaken for at 75° C. for 24 h. Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes). The resulting solid was triturated with diethyl ether, filtered and dried in vacuo to afford N-{3-[(1R,2S,7R,8S)-3-(2-cyclopentyl-ethyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.015 g, 0.026 mmol, 7.2%) as an off-white powder. $^1$H NMR (400 MHz, DMSO-d$_6$) δ: 1.11-1.18 (1H, m), 1.18-1.27 (1H, m), 1.27-1.34 (1H, m), 1.42-1.66 (10H, m), 1.67-1.81 (4H, m), 2.50-2.54 (1H, m), 2.61-2.63 (1H, m), 2.96-3.11 (5H, m), 3.58-3.68 (2H, m), 4.24 (2H, d, J=6.2 Hz), 7.28 (1H, s), 7.66 (1H, t, J=6.2 Hz). LC-MS (ESI) calculated for C$_{24}$H$_{32}$N$_4$O$_6$S$_3$ 568.1. found 569.3 [M+H$^+$].

Example 31

N-{3-[4-Hydroxy-5-methyl-5-(3-methyl-butyl)-2-oxo-1-phenyl-1,2,5,6-tetrahydro-pyridin-3-yl]-1,1-dioxo-1,4-dihydro-1λ$^6$-thieno e][1,2,4]thiadiazin-7-ylmethyl}-methanesulfonamide

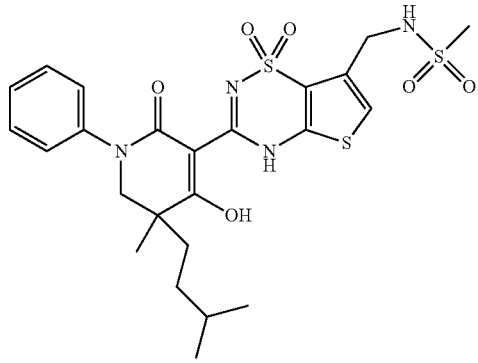

a) 2-Methyl-2-(3-methyl-butyl)malonic acid diethyl ester

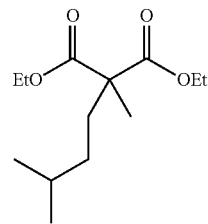

A solution of diethyl isopentylmalonate (2.31 g, 10 mmol) in a 6:2 mixture of anhydrous N,N-dimethylformamide/diethyl ether (8 mL) was stirred under a nitrogen atmosphere at 25° C. and treated with a 60% oil dispersion of sodium hydride (480 mg, 12 mmol). The reaction mixture was stirred until the evolution of hydrogen gas ceased. The reaction was then treated dropwise via syringe with iodomethane (1.87 mL, 30 mmol) and stirred for 3 h at 25° C. The reaction was quenched with a 1.0 M aqueous hydrochloric acid solution (30 mL) and extracted with diethyl ether (2×50 mL). The combined organic layers were washed with a saturated aqueous sodium bicarbonate solution (50 mL) and saturated aqueous brine solution (50 mL), dried over sodium sulfate, filtered, and concentrated in vacuo to afford the desired product, 2-methyl-2-(3-methyl-butyl)-malonic acid diethyl ester (2.09 g, 8.56 mmol, 85%), as a clear oil. $^1$H NMR (400 MHz, CDCl$_3$) δ: 0.88 (d, 6H, J=6.9 Hz), 1.06-1.12 (m, 2H), 1.24 (t, 6H, J=7.0 Hz), 1.38 (s, 3H), 1.51 (septet, 1H, J=6.6 Hz), 1.82-1.87 (m, 2H), 4.12-4.20 (m, 4H). LC-MS (ESI) calculated for C$_{13}$H$_{24}$O$_4$ 244.17. found 245.3 [M+H$^+$].

b) 2-Formyl-2,5-dimethyl-hexanoic acid ethyl ester

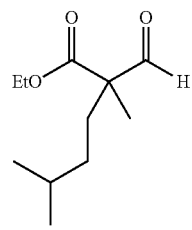

A solution of 2-methyl-2-(3-methyl-butyl)-malonic acid diethyl ester (500 mg, 2.05 mmol) in anhydrous dichloromethane (4 mL) was stirred at −78° C. under a blanket of nitrogen and treated dropwise via syringe with a 1.0 M solution of diisobutylaluminum hydride in toluene (4.1 mL, 4.1 mmol) over a period of 15 min. The reaction was stirred for 4 h at −78° C. and quenched sequentially with a saturated aqueous ammonium chloride solution (3 mL) and a 4% aqueous hydrochloric acid solution (3 mL). The resulting gelatinous suspension was allowed to warm to 25° C. and was filtered through a sintered glass funnel. The filtrate was concentrated in vacuo. The resulting crude oil was purified by flash column chromatography (Teledyne Isco RediSep column; 0-20% ethyl acetate in hexanes) to afford the desired product, 2-formyl-2,5-dimethyl-hexanoic acid ethyl ester (150 mg, 0.75 mmol, 36%), as a clear oil. $^1$H NMR (400 MHz, CDCl$_3$) δ: 0.89 (d, 6H, J=6.9 Hz), 1.07-1.15 (m, 2H), 1.23-1.26 (m, 3H), 1.28 (s, 3H), 1.52 (septet, 1H, J=6.6 Hz), 1.83-1.92 (m, 2H), 4.21 (q, 2H, J=6.9 Hz), 9.69 (s, 1H).

c) 2-[(4-Fluoro-benzylamino)-methyl]-2,5-dimethyl-hexanoic acid ethyl estr

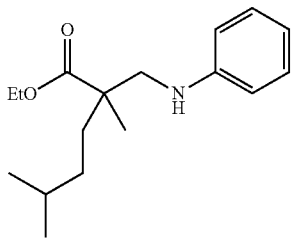

A solution of 2-formyl-2,5-dimethyl-hexanoic acid ethyl ester (300 mg, 1.50 mmol) in ethanol (5 mL) and aniline (140 mg, 1.50 mmol) was treated with glacial acetic acid (0.172 mL, 3.00 mmol) followed by sodium cyanoborohydride (189 mg, 3.00 mmol). The reaction was stirred for 4 h at 58° C., quenched with a saturated aqueous sodium bicarbonate solution and extracted with ethyl acetate (2×20 mL). The combined organic layers dried over sodium sulfate, filtered, and concentrated in vacuo. The crude oil was purified by flash column chromatography (Teledyne Isco RediSep column; 0-40% ethyl acetate in hexanes) to afford the desired product, 2-[(4-fluoro-benzylamino)-methyl]-2,5-dimethyl-hexanoic acid ethyl ester (307 mg, 1.11 mmol, 74%), as a light yellow oil. $^1$H NMR (400 MHz, CDCl$_3$) δ: 0.89-0.92 (6H, m), 1.08-1.21 (2H, m), 1.24-1.28 (7H, m), 1.47-1.58 (2H, m), 1.69-1.77 (1H, m), 3.13 (1H, d, J=12.6 Hz), 3.37 (1H, d, J=11.7 Hz), 4.12-4.20 (2H, m), 6.66-6.73 (3H, m), 7.16 (2H, dd, J$_1$=7.8 Hz, J$_2$=7.8 Hz).

d) N-{3-[4-Hydroxy-5-methyl-5-(3-methyl-butyl)-2-oxo-1-phenyl-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamie

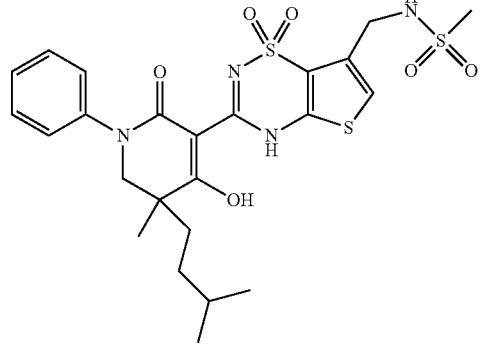

2,5-Dimethyl-2-phenylaminomethyl-hexanoic acid ethyl ester (0.10 g, 0.36 mmol) was dissolved in N,N-dimethylformamide (4 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.127 g, 0.36 mmol) was added followed by 1-(3-dimethylaminopropyl)-3-ethylcarbodiimide hydrochloride (0.083 g, 0.43 mmol). The mixture was stirred at 25° C. for 5 h. The solvent was removed in vacuo then re-dissolved in ethanol. A 21 wt. % solution of sodium ethoxide in ethanol (806 μL, 2.16 mmol) was added to the mixture and stirred at 60° C. for 16 h. Upon cooling to 25° C., the mixture was concentrated in vacuo to afford a thick oil. The oil was partitioned between dichloromethane (4 mL) and 1.0 M aqueous hydrochloric acid solution (6 mL). The organic phase was loaded directly onto a prepacked RediSep silica gel column and purified by flash column chromatography (Teledyne Isco RediSep column; 20-100% ethyl acetate in hexanes) to afford the desired product, N-{3-[4-hydroxy-5-methyl-5-(3-methyl-butyl)-2-oxo-1-phenyl-1,2,5,6-tetrahydro-pyridin-3-yl]-1,1-dioxo-1,4-dihydro-1λ$^6$-thieno[2,3-e][1,2,4]thiadiazin-7-ylmethyl}-methanesulfonamide (0.079 g, 0.1401 mmol, 39%), as an off white powder. $^1$H NMR (400 MHz, Acetone-d$_6$) δ: 0.90 (6H, d, J=8.0 Hz), 1.25-1.38 (2H, m), 1.49-1.59 (1H, m), 1.80-1.89 (2H, m), 2.08 (3H, s), 2.96 (3H, s), 3.78-3.85 (2H, m), 4.44 (2H, d, J=6.1 Hz), 6.42 (1H, t, J=6.3 Hz), 7.31-7.48 (6H, m). LC-MS (ESI) calculated for C$_{24}$H$_{30}$N$_4$O$_6$S$_3$ 566.13. found 567.2 [M+H$^+$].

Example 32

(rac-di-exo, di-exo)-N-{3-[3-(4-Fluoro-benzyl)-6-hydroxy-4-oxo-3-aza-tetracyclo[6.3.1.0$^{2,7}$.0$^{9,11}$] dodec-5-en-5-yl]-1,1-dioxo-1,4-dihydro-1λ$^6$-thieno [2,3-e][1,2,4]thiadiazin-7-ylmethyl}-methanesulfonamide

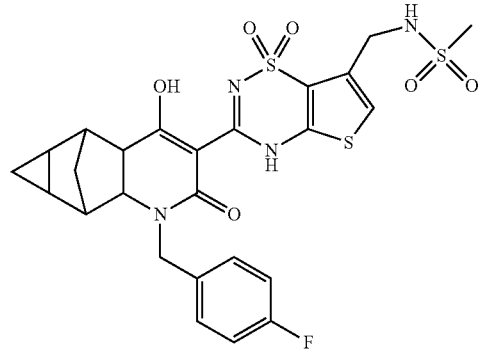

a) (rac-di-exo)-3-Aza-tricyclo[4.2.1.0$^{2,5}$]non-7-en-one

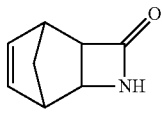

The title compound is reported in *Tetrahedron* 1984, 40, 12, 2385-2395, *Synlett* 2000, 1, 67-68 and *Chem. Commun.* 2006, 14, 1548-1550.

To a solution of bicyclo[2.2.1]hepta-2,5-diene (36.86 g, 0.40 mol) dissolved in anhydrous dichloromethane (20 mL) under an inert atmosphere of dry nitrogen was added solid anhydrous sodium carbonate (6.36 g, 60.0 mmol). The stirred suspension was cooled to 0° C. and chlorosulfonyl isocyanate (56.61 g, 0.40 mol) was slowly added dropwise over a period of 20 min. The mixture, kept at 0° C. for 2 h was gradually warmed to 25° C. and stirring was continued for 12 h. At this time the mixture was diluted with dichloromethane (40 mL) and added dropwise to a vigorously stirred mixture of sodium sulfite (145.6 g), disodium hydrogen phosphate (163 g), water (700 mL) and chloroform (580 mL) at 0° C. After the aqueous layer was separated, it was washed with dichloromethane (2×175 mL). The organic layers were combined and washed with water (100 mL), saturated aqueous brine solution (100 mL) and dried over anhydrous magnesium sulfate, filtered and concentrated in vacuo to afford the desired product, (rac-di-exo)-3-aza-tricyclo[4.2.1.0$^{2,5}$]non-7-en-one (45.9 g, 0.34 mol, 85%), as an off-white solid. $^1$H NMR (400 MHz, CDCl$_3$) δ: 1.66 (1H, d, J=9.7 Hz), 1.82 (1H, d, J=10.2 Hz), 2.89-2.91 (1H, m), 2.94-2.97 (1H, m), 3.06 (1H, dd, J$_1$=3.9 Hz, J$_2$=1.5 Hz), 3.51 (1H, d, J=3.8 Hz), 5.97 (1H, bs), 6.13 (1H, dd, J$_1$=5.5 Hz, J$_2$=3.1 Hz), 6.25 (1H, dd, J$_1$=5.3 Hz, J$_2$=3.2 Hz).

b) (rac-di-exo)-3-(4-Fluoro-benzyl)-3-aza-tricyclo[4.2.1.0$^{2,5}$]non-7-en-4-one

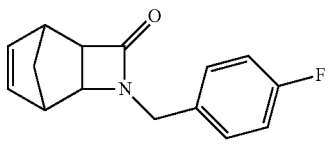

(rac-di-exo)-3-Aza-tricyclo[4.2.1.0$^{2,5}$]non-7-en-one (0.676 g, 5.0 mmol), 4-fluorobenzyl bromide (1.04 g, 5.5 mmol), and tetrabutylammonium hydrogen sulfate (0.17 g, 0.5 mmol) were dissolved in dichloromethane (8 mL) and cooled to 0° C. The solution was vigorously stirred and 50% aqueous sodium hydroxide solution (7.6 mL) was added dropwise over a period of 30 min. The biphasic mixture was warmed to 25° C. and stirred for an additional 3 h. Water (19 mL) was added and the layers were separated. Further extraction of the aqueous layer was done with dichloromethane (2×5 mL). The organic layers were combined, dried over anhydrous magnesium sulfate, filtered and concentrated in vacuo to afford a thick yellow oil. Addition of ethyl acetate to the oil precipitated a pale yellow solid. The solids were filtered, washed with ethyl acetate. The ethyl acetate solution was concentrated in vacuo and the residue was purified by flash column chromatography (Teledyne Isco RediSep column; 0-100% ethyl acetate in hexanes) to afford the desired product, (rac-di-exo)-3-(4-fluoro-benzyl)-3-aza-tricyclo[4.2.1.0$^{2,5}$]non-7-en-4-one (0.756 g, 3.1 mmol, 62%), as a pale yellow oil. $^1$H NMR (400 MHz, CDCl$_3$) δ: 1.53-1.60 (2H, m), 2.69 (1H, s), 2.96 (1H, s), 3.02 (1H, d, J=3.8 Hz), 3.38 (1H, d, J=3.8 Hz), 4.19 (1H, d, J=14.8 Hz), 4.47 (1H, d, J=14.8 Hz), 6.01 (1H, dd, J=5.6 Hz, J$_2$=5.5 Hz), 6.22 (1H, dd, J$_1$=5.3 Hz, J$_2$=5.3 Hz), 7.00-7.06 (2H, m), 7.24-7.29 (2H, m).

c) (rac-di-exo, di-exo)-3-(4-Fluoro-benzyl)-3-aza-tetracyclo [4.3.1.0$^{2,5}$.0$^{7,9}$]decan-4-one

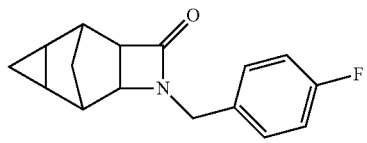

To an Erlenmeyer flask equipped with a rubber stopper (rac-di-exo)-3-(4-fluoro-benzyl)-3-aza-tricyclo[4.2.1.0$^{2,5}$]non-7-en-4-one (0.467 g, 1.92 mmol) was dissolved in anhydrous diethyl ether (8 mL). Palladium acetate (9.0 mg, 40 µmol) is added and the mixture is cooled to 0° C. To this stirred mixture is carefully added dropwise an ice cold solution of diazomethane in diethyl ether (5.76 mmol prepared from N-methyl-N-nitro-N-nitrosoguanidine and 50% aqueous potassium hydroxide solution). The yellow solution was stirred at 0° C. for 2 h. Any excess of diazomethane was evaporated by a gentle stream of nitrogen gas. The solution was further concentrated in vacuo and the residue was filtered through a plug of silica gel (Merck silica gel 60, 40-63 µm). The silica gel was washed with 10-60% ethyl acetate in hexanes and the washing were collected and concentrated in vacuo to afford the desired product, (rac-di-exo, di-exo)-3-(4-fluoro-benzyl)-3-aza-tetracyclo[4.3.1.0$^{2,5}$.0$^{7,9}$]decan-4-one (quantitative yield) as a pale yellow oil. $^1$H NMR (400 MHz, CDCl$_3$) δ: 0.27 (1H, quartet, J=7.1 Hz), 0.59-0.64 (1H, m), 0.67 (1H, dt, J$_1$=6.3 Hz, J$_2$=3.1 Hz), 0.74-0.79 (1H, m), 0.90 (2H, quartet, J=11.4 Hz), 2.21 (1H, s), 2.50 (1H, t, J=1.5 Hz), 3.17-3.18 (1H, m), 3.44 (1H, d, J=4.1 Hz), 4.15 (1H, d, J=14.8 Hz), 4.40 (1H, d, J=14.8 Hz), 6.99-7.05 (2H, m), 7.22-7.27 (2H, m).

d) (rac-di-exo, di-exo)-7-(4-Fluoro-benzylamino)-tricyclo[3.2.1.0$^{2,4}$]octane-6-carboxylic acid ethyl ester

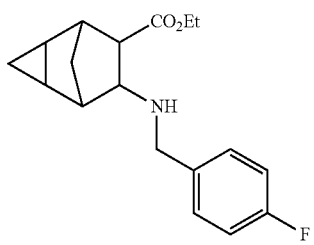

(rac-di-exo, di-exo)-3-(4-Fluoro-benzyl)-3-aza-tetracyclo[4.3.1.0$^{2,5}$.0$^{7,9}$]decan-4-one (0.257 g, 1.0 mmol) was dissolved in absolute ethanol (2 mL) and cooled to 0° C. To this was added a 2.5 M solution of hydrochloric acid in ethanol (0.8 mL). Thin layer chromatography (Merck silica gel 60, 40-63 μm; 50% ethyl acetate in hexanes) indicated the presence of starting material after stirring the mixture at 25° C. and then 40° C. for 2 h. A 4.0 M solution of hydrochloric acid in 1,4-dioxane (2×0.25 mL) was therefore added and the mixture was stirred at 60° C. for 14 h. Thin layer chromatography (Merck silica gel 60, 40-63 μm; 50% ethyl acetate in hexanes) and LC-MS showed the amino ester was formed with almost complete consumption of starting material. The solution was concentrated in vacuo and diethyl ether (7 mL) was added. The hydrochloride salt did not solidify therefore the oily residue was taken up in excess ethyl acetate and washed several times with a saturated aqueous sodium bicarbonate solution. The aqueous layers were back-extracted with ethyl acetate. The organic layers were combined, dried over anhydrous magnesium sulfate, filtered and was concentrated in vacuo to afford the desired product, (rac-di-exo, di-exo)-7-(4-fluoro-benzylamino)-tricyclo[3.2.1.0$^{2,4}$]octane-6-carboxylic acid ethyl ester, as an oil in ~95%. $^1$H NMR (400 MHz, CDCl$_3$) δ: 0.14 (1H, quartet, J=6.8 Hz), 0.56-0.59 (1H, m), 0.69 (1H, d, J=2.9 Hz), 0.71 (1H, d, J=3.0 Hz), 0.94 (1H, d, J=11.8 Hz), 1.28 (3H, t, J=7.0 Hz), 1.47 (1H, d, J=11.6 Hz), 2.33 (1H, s), 2.46 (1H, s), 2.72 (1H, dd, J$_1$=8.1 Hz, J$_2$=2.1 Hz), 3.08 (1H, d, J=7.8 Hz), 3.68 (1H, s), 3.70 (1H, d, J=11.1 Hz), 3.81 (1H, d, J=13.4 Hz), 4.14 (2H, quartet, J=7.0 Hz), 6.98 (2H, t, J=8.9 Hz), 7.23-7.29 (2H, m). LC-MS (ESI) calculated for C$_{18}$H$_{22}$FNO$_2$ 303.16. found 304.2 [M+H$^+$].

e) (rac-di-exo, di-exo)-N-{3-[3-(4-Fluoro-benzyl)-6-hydroxy-4-oxo-3-aza-tetracyclo[6.3.1.0$^{2,7}$.0$^{9,11}$] dodec-5-en-5-yl]-1,1-dioxo-1,4-dihydro-1λ$^6$-thieno[2,3-e][1,2,4]thiadiazin-7-ylmethyl}-methanesulfonamide

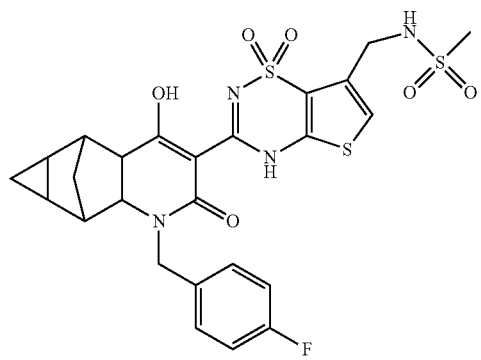

Under a dry nitrogen atmosphere (rac-di-exo)-7-(4-fluoro-benzylamino)-tricyclo[3.2.1.0$^{2,4}$]octane-6-carboxylic acid ethyl ester (0.135 g, 0.44 mmol) was dissolved in N,N-dimethylformamide (1.4 mL). To this stirred solution was added [7-(methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.157 g, 0.44 mmol) and 1-(3-dimethylaminopropyl)-3-ethylcarbodiimide hydrochloride (0.128 g, 0.67 mmol). After 1 h, triethylamine (0.27 g, 2.67 mmol) was added and the stirred mixture was heated to 75° C. for a total of 32 h. The dark mixture was cooled to 25° C. and 1.0 M aqueous hydrochloric acid solution (12 mL) was added where upon a brown solid formed. The solids were filtered, washed with water, air-dried and purified by flash column chromatography (Teledyne Isco RediSep column; 0-5% methanol in dichloromethane) to afford the desired product, (rac-di-exo, di-exo)-N-{3-[3-(4-fluoro-benzyl)-6-hydroxy-4-oxo-3-aza-tetracyclo[6.3.1.0$^{2,7}$.0$^{9,11}$]dodec-5-en-5-yl]-1,1-dioxo-1,4-dihydro-1λ$^6$-thieno[2,3-e][1,2,4]thiadiazin-7-ylmethyl}-methanesulfonamide (0.20 g, 0.34 mmol, 77%), as a beige solid. $^1$H NMR (400 MHz, DMSO-d$_6$) δ: 0.16 (1H, quartet, J=6.8 Hz), 0.51-0.53 (1H, m), 0.74-0.79 (2H, m), 0.93-1.05 (2H, m), 2.54 (1H, s), 2.66 (1H, s), 2.96 (3H, s), 3.05 (1H, d, J=9.5 Hz), 3.31 (1H, bs), 3.57 (1H, d, J=9.3 Hz), 4.24 (2H, d, J=6.0 Hz), 4.42 (1H, d, J=14.8 Hz), 4.95 (1H, d, J=15.0 Hz), 7.15 (2H, t, J=8.8 Hz), 7.26 (1H, s), 7.32-7.36 (2H, m), 7.65 (1H, t, J=6.3 Hz). LC-MS (ESI) calculated for C$_{25}$H$_{25}$FN$_4$O$_6$S$_3$ 592.09. found 593.2 [M+H$^+$].

Example 33

Cyclopropanesulfonic acid {3-[(1R,2S,7R,8S)-3-(4-fluoro-benzyl)-6-hydroxy-4-oxo-3-aza-tricyclo[6.2.1.0$^{2,7}$] undec-5-en-5-yl]-1,1-dioxo-1,4-dihydro-1λ$^6$-thieno[2,3-e][1,2,4]thiadiazin-7-ylmethyl}-amide

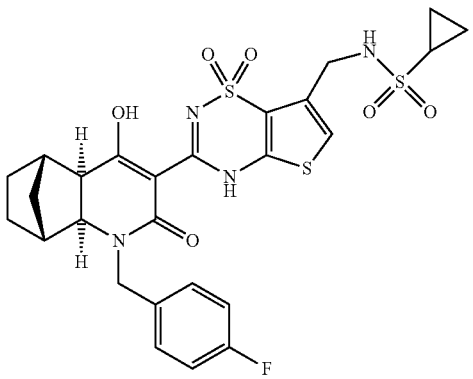

a) (7-Methoxymethoxymethyl-1,1-dioxo-1,4-dihydro-1λ$^6$-thieno[2,3-e][1,2,4]thiadiazin-3-yl)-acetic acid ethyl ester

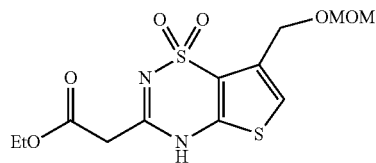

To a solution of 2-amino-4-methoxymethoxymethyl-thiophene-3-sulfonic acid amide (0.76 g, 3.01 mmol) in N,N-dimethylformamide (10 mL) at 25° C. was added 3,3-diethoxy-acrylic acid ethyl ester (0.68 g, 3.61 mmol). The reaction was stirred at 70° C. for 5 h before triethylamine (1.68 mL, 12.04 mmol) was added to the mixture. The reaction was stirred at 70° C. overnight. It was then cooled to 25° C., diluted with ethyl acetate (10 mL) and washed with 1.0 M aqueous hydrochloric acid solution (10 mL). The organic layer was dried over magnesium sulfate, filtered and concentrated in vacuo. The residue was purified via flash column chromatography (Teledyne Isco RediSep column; 0-80% ethyl acetate in hexanes) to afford the desired product, (7-methoxymethoxymethyl-1,1-dioxo-1,4-dihydro-1λ$^6$-thieno[2,3-e][1,2,4]thiadiazin-3-yl)-acetic acid ethyl ester (0.55 g, 1.57 mmol, 52%), as a brown oil. $^1$H NMR (400

MHz, CDCl₃) δ: 1.32 (3H, t, J=7.2 Hz), 3.42 (3H, s), 3.68 (2H, s), 4.26 (2H, q, J=7.2 Hz), 4.76 (2H, s), 4.80 (2H, s), 7.00 (1H, s), 8.00 (1H, s).

b) (7-Methoxymethoxymethyl-1,1-dioxo-1,4-dihydro-1λ⁶-thieno[2,3-e][1,2,4]thiadiazin-3-yl)-acetic acid

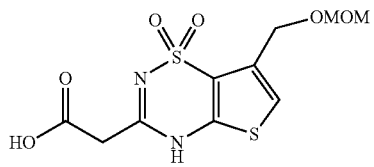

To a solution of (7-methoxymethoxymethyl-1,1-dioxo-1,4-dihydro-1λ⁶-thieno[2,3-e][1,2,4]thiadiazin-3-yl)-acetic acid ethyl ester (0.54 g, 1.55 mmol) in tetrahydrofuran (5 mL) and water (5 mL) was added lithium hydroxide monohydrate (0.33 g, 7.75 mmol). The reaction was stirred at 25° C. for 1 h before it was cooled to 0° C. The reaction was quenched via the addition of 6.0 M aqueous hydrochloric acid solution until a pH of 1-2 was reached. The resulting mixture was extracted with ethyl acetate (3×10 mL). The organic layers were combined, dried over magnesium sulfate, filtered and concentrated in vacuo to afford the crude product, (7-methoxymethoxymethyl-1,1-dioxo-1,4-dihydro-1λ⁶-thieno[2,3-e][1,2,4]thiadiazin-3-yl)-acetic acid (0.39 g, 1.21 mmol, 78%), which was used in the next step without further purification.

c) (1R,2S,7R,8S)-3-(4-Fluoro-benzyl)-6-hydroxy-5-(7-methoxymethoxymethyl-1,1-dioxo-1,4-dihydro-1λ⁶-thieno[2,3-e][1,2,4]thiadiazin-3-yl)-3-aza-tricyclo[6.2.1.0²,⁷]undec-5-en-4-one

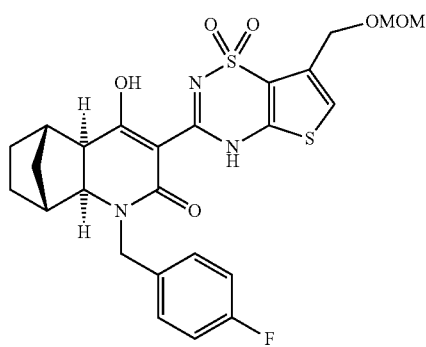

To a solution of (7-methoxymethoxymethyl-1,1-dioxo-1,4-dihydro-1λ⁶-thieno[2,3-e][1,2,4]thiadiazin-3-yl)-acetic acid (0.38 g, 1.20 mmol) and (1S,2R,3S,4R)-3-(4-fluoro-benzylamino)-bicyclo[2.2.1]heptane-2-carboxylic acid ethyl ester (0.42 g, 1.44 mmol) in N,N-dimethylformamide (4 mL) was added 1-(3-dimethylaminopropyl)-3-ethylcarbodiimide hydrochloride (0.34 g, 1.80 mmol). The reaction was stirred at 25° C. for 15 min before triethylamine (1 mL, 7.20 mmol) was added. The reaction was then stirred at 75° C. overnight. The reaction was cooled to 25° C. and quenched with 1.0 M aqueous hydrochloric acid solution (5 mL). The resulting mixture was extracted with dichloromethane (3×10 mL). The organic layers were combined, dried over magnesium sulfate, filtered and concentrated in vacuo. The residue was purified via flash column chromatography (Teledyne Isco RediSep column; 0-50% ethyl acetate in hexanes) to afford the desired product, (1R,2S,7R,8S)-3-(4-fluoro-benzyl)-6-hydroxy-5-(7-methoxymethoxymethyl-1,1-dioxo-1,4-dihydro-1λ⁶-thieno[2,3-e][1,2,4]thiadiazin-3-yl)-3-aza-tricyclo[6.2.1.0²,⁷]undec-5-en-4-one (0.44 g, 0.80 mmol, 67%), as a white solid. ¹H NMR (400 MHz, CDCl₃) δ: 1.18-1.78 (6H, m), 2.55-2.56 (1H, m), 2.82-2.86 (2H, m), 3.45 (3H, s), 4.21 (1H, d, J=15.6 Hz), 4.79 (2H, s), 4.82 (2H, s), 5.15 (1H, d, J=15.2 Hz), 7.00-7.07 (3H, m), 7.20 (2H, dd, J=5.6, 8.8 Hz).

d) (1R,2S,7R,8S)-3-(4-Fluoro-benzyl)-6-hydroxy-5-(7-hydroxymethyl-1,1-dioxo-1,4-dihydro-1λ⁶-thieno[2,3-e][1,2,4]thiadiazin-3-yl)-3-aza-tricyclo[6.2.1.0²,⁷]undec-5-en-4-one

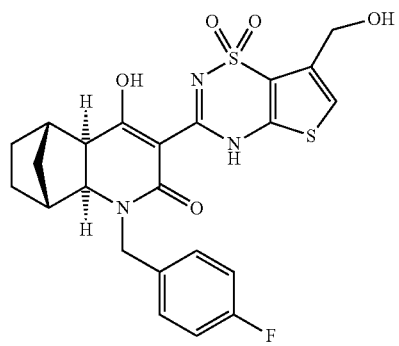

To a solution of (1R,2S,7R,8S)-3-(4-fluoro-benzyl)-6-hydroxy-5-(7-methoxymethoxymethyl-1,1-dioxo-1,4-dihydro-1λ⁶-thieno[2,3-e][1,2,4]thiadiazin-3-yl)-3-aza-tricyclo[6.2.1.0²,⁷]undec-5-en-4-one (0.42 g, 0.76 mmol) in dioxane (3 mL) was added a 4.0 M solution of hydrochloric acid in dioxane (9 mL). The reaction was stirred at 25° C. for 2 h before it was concentrated in vacuo to afford the crude product, (1R,2S,7R,8S)-3-(4-fluoro-benzyl)-6-hydroxy-5-(7-hydroxymethyl-1,1-dioxo-1,4-dihydro-1λ⁶-thieno[2,3-e][1,2,4]thiadiazin-3-yl)-3-aza-tricyclo[6.2.1.0²,⁷]undec-5-en-4-one (0.38 g, 0.76 mmol, 100%), which was used in the next step without further purification.

e) 5-(7-Azidomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0²,⁷]undec-5-en-4-one

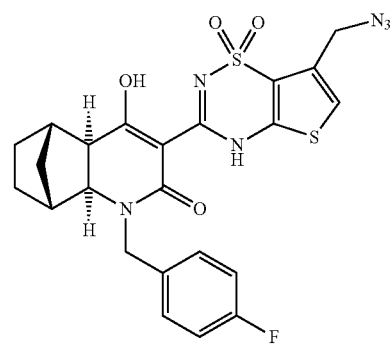

To a solution of (1R,2S,7R,8S)-3-(4-fluoro-benzyl)-6-hydroxy-5-(7-hydroxymethyl-1,1-dioxo-1,4-dihydro-1λ⁶-thieno[2,3-e][1,2,4]thiadiazin-3-yl)-3-aza-tricyclo[6.2.1.0$^{2,7}$]undec-5-en-4-one (0.38 g, 0.76 mmol) in dichloromethane (9 mL) at 0° C. was added 1,8-diazabicyclo[5.4.0]undec-7-ene (0.60 mL, 4.03 mmol) and diphenylphosphoryl azide (0.84 mL, 3.88 mmol). The reaction was stirred at 25° C. overnight. The reaction was quenched with 1.0 M aqueous hydrochloric acid solution (10 mL). The resulting mixture was extracted with dichloromethane (3×10 mL). The organic layers were combined, dried over magnesium sulfate, filtered and concentrated in vacuo. The residue was purified via flash column chromatography (Teledyne Isco RediSep column; 0-1% methanol in dichloromethane) to afford the desired product, (1R,2S,7R,8S)-5-(7-azidomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0$^{2,7}$]undec-5-en-4-one (0.21 g, 0.40 mmol, 52%), as a white solid. $^1$H NMR (400 MHz, CDCl₃) δ: 1.18-1.78 (6H, m), 2.56-2.57 (1H, m), 2.82-2.87 (2H, m), 3.47 (1H, d, J=9.6 Hz), 4.21 (1H, d, J=14.8 Hz), 4.67 (2H, s), 5.15 (1H, d, J=14.4 Hz), 7.00-7.07 (2H, m), 7.19-7.23 (2H, m), 7.32-7.36 (1H, m).

f) (1R,2S,7R,8S)-5-(7-Aminomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0$^{2,7}$]undec-5-en-4-one

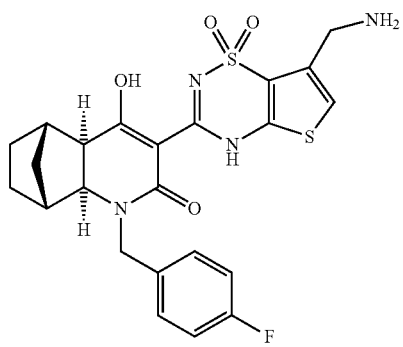

To a solution of (1R,2S,7R,8S)-5-(7-azidomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0$^{2,7}$]undec-5-en-4-one (0.10 g, 0.19 mmol) in ethanol (6 mL) and ethyl acetate (3 mL) was added 10% palladium on carbon (10 mg). The mixture was degassed and stirred under an atmosphere of hydrogen gas (balloon) overnight. The resulting mixture was diluted with N,N-dimethylformamide (10 mL) and filtered through a pad of Celite. The organic was concentrated in vacuo to afford the crude product, (1R,2S,7R,8S)-5-(7-aminomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0$^{2,7}$]undec-5-en-4-one (95 mg, 0.19 mmol, 100%), which was used in the next step without further purification.

g) Cyclopropanesulfonic acid {3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ⁶-thieno[2,3-e][1,2,4]thiadiazin-7-ylmethyl}-amide

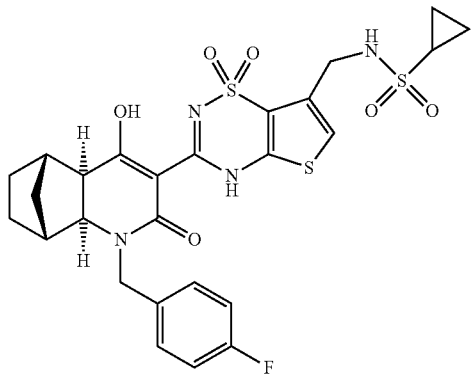

To a solution of (1R,2S,7R,8S)-5-(7-aminomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0$^{2,7}$]undec-5-en-4-one (0.10 g, 0.20 mmol) in dichloromethane (3 mL) at 0° C. was added triethylamine (56 μl, 0.40 mmol) and cyclopropanesulfonyl chloride (23 μl, 0.22 mmol). The reaction was stirred at 0° C. for 30 min, then at 25° C. for 2 h. The reaction was quenched with water (10 mL). The resulting mixture was extracted with ethyl acetate (3×10 mL). The organic layers were combined, dried over magnesium sulfate, filtered and concentrated in vacuo. The residue was purified via flash column chromatography (Teledyne Isco RediSep column; 0-1% methanol in dichloromethane) to afford the desired product, cyclopropanesulfonic acid {3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ⁶-thieno[2,3-e][1,2,4]thiadiazin-7-ylmethyl}-amide (0.10 g, 0.17 mmol, 84%), as a white solid. $^1$H NMR (400 MHz, CDCl₃) δ: 1.15-1.78 (10H, m), 2.32-2.38 (1H, m), 2.56-2.58 (1H, m), 2.84-2.88 (2H, m), 3.48 (1H, d, J=9.2 Hz), 4.21 (1H, d, J=15.6 Hz), 4.51 (2H, d, J=6.4 Hz), 5.15 (1H, d, J=14.8 Hz), 5.35 (1H, t, J=6.4 Hz), 7.02-7.07 (3H, m), 7.19-7.22 (2H, m). LC-MS (ESI) calculated for $C_{26}H_{27}FN_4O_6S_3$ 606.71. found 607.2 [M+H⁺].

Example 34

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^{6}$-thieno[2,3-e][1,2,4]thiadiazin-7-ylmethyl}-sulfamide

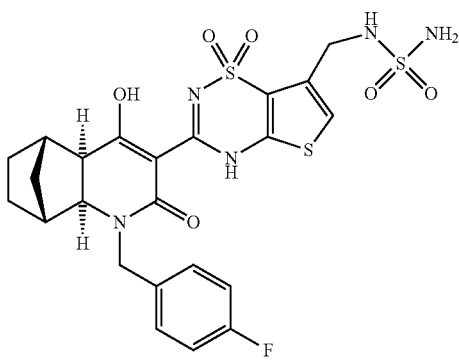

a) Benzyl (N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^{6}$-thieno[2,3-e][1,2,4]thiadiazin-7-ylmethyl}amino)sulfonylcarbamate

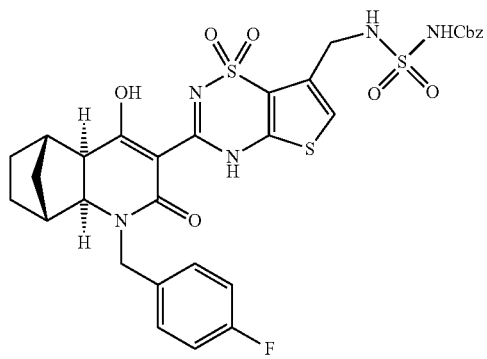

To a solution of chlorosulfonylisocyanate (28 μl, 0.32 mmol) in dichloromethane (3 mL) was added benzyl alcohol (28 μl, 0.27 mmol). The reaction was stirred at 25° C. for 30 min. A solution of (1R,2S,7R,8S)-5-(7-aminomethyl-1,1-dioxo-1,4-dihydro-1λ$^{6}$-thieno[2,3-e][1,2,4]thiadiazin-3-yl)-3-(4-fluoro-benzyl)-6-hydroxy-3-aza-tricyclo[6.2.1.0$^{2,7}$]undec-5-en-4-one (prepared as described in Example 33f; 0.10 g, 0.21 mmol) and triethylamine (125 μl, 0.90 mmol) in dichloromethane (3 mL) was then added to the above solution via cannula. The reaction was stirred at 25° C. for 1.5 h. The mixture was diluted with dichloromethane (10 mL) and washed with 1.0 M aqueous hydrochloric acid solution (10 mL). The organic was dried over magnesium sulfate, filtered and concentrated in vacuo. The residue was purified via flash column chromatography (Teledyne Isco RediSep column; 0-3% methanol in dichloromethane) to afford the desired product, benzyl (N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^{6}$-thieno[2,3-e][1,2,4]thiadiazin-7-ylmethyl}amino)sulfonylcarbamate (0.13 g, 0.18 mmol, 86%), as a white solid. $^{1}$H NMR (400 MHz, CDCl$_3$) δ: 1.19-1.77 (6H, m), 2.57-2.58 (1H, m), 2.83-2.88 (2H, m), 3.46 (1H, m), 4.22 (1H, d, J=15.6 Hz), 4.50 (2H, bs), 5.12-5.18 (3H, m), 6.06 (1H, bs), 7.02-7.07 (3H, m), 7.19-7.23 (2H, m), 7.33-7.39 (5H, m).

b) N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^{6}$-thieno[2,3-e][1,2,4]thiadiazin-7-ylmethyl}-sulfamide

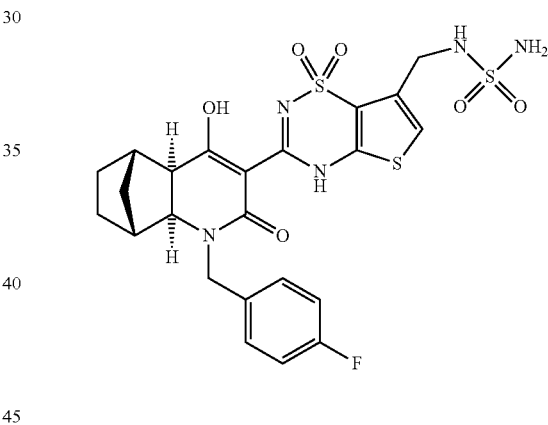

To a solution of benzyl (N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^{6}$-thieno[2,3-e][1,2,4]thiadiazin-7-ylmethyl}amino)sulfonylcarbamate (120 mg, 0.17 mmol) in methanol (20 mL) was added 10% palladium on carbon (60 mg). The mixture was degassed and stirred under an atmosphere of hydrogen gas (balloon) overnight. The resulting mixture was filtered through a pad of Celite. The organic was concentrated in vacuo. The residue was purified via flash column chromatography (Teledyne Isco RediSep column; 0-3% methanol in dichloromethane) to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^{6}$-thieno[2,3-e][1,2,4]thiadiazin-7-ylmethyl}-sulfamide (89 mg, 0.15 mmol, 88%), as a white solid. $^{1}$H NMR (400 MHz, CDCl$_3$) δ: 1.19-1.79 (6H, m), 2.57-2.58 (1H, m), 2.83-2.88 (2H, m), 3.49 (1H, d, J=9.6 Hz), 4.22 (1H, d, J=15.6 Hz), 4.48 (2H, d, J=6.4 Hz), 4.55 (2H, bs), 5.16 (1H, d, J=14.8 Hz), 5.29-5.32 (1H, m), To a solution of (1R,2S,7R,8S)-5-(7-Aminomethyl-1,1-dioxo-1,4-dihydro-1λ⁶-thieno[2,3-e][1,2,4]thiadiazin-3-yl)-3-(4-fluoro-benzyl)-6-hydroxy-3-aza-tricyclo[6.2.1.0²,⁷]undec-5-en-4-one (prepared as described in Example 33f; 56 mg, 0.11 mmol) in pyridine (3 mL) was added acetyl anhydride (12 μL, 0.12 mmol). The reaction was stirred at 25° C. overnight. The mixture was concentrated in vacuo, re-dissolved in ethyl acetate (10 mL) and washed with water (3×10 mL). The organic layers were combined, dried over magnesium sulfate, filtered and concentrated in vacuo. The residue was purified via flash column chromatography (Teledyne Isco RediSep column; 0-1% methanol in dichloromethane) to afford the desired product, N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-acetamide (49 mg, 0.09 mmol, 80%), as a white solid. ¹H NMR (400 MHz, CDCl₃) δ: 1.19-1.78 (6H, m), 1.98 (3H, s), 2.56-2.57 (1H, m), 2.83-2.87 (2H, m), 3.47 (1H, d, J=9.2 Hz), 4.20 (1H, d, J=14.4 Hz), 4.55 (2H, d, J=6.4 Hz), 5.15 (1H, d, J=14.8 Hz), 6.62-6.65 (1H, m), 7.02-7.07 (3H, m), 7.18-7.22 (2H, m). LC-MS (ESI) calculated for $C_{25}H_{25}FN_4O_5S_2$ 544.62. found 545.3 [M+H⁺].

General Procedure 1:

A 0.4 M solution of a bicyclic β-amino ester salt (selected from a list containing (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2)) in N,N-dimethylformamide (1 mL, 0.4 mmol) was combined with a 2.0 M solution of a benzyl bromide in N,N-dimethylformamide (0.2 mL, 0.4 mmol). Triethylamine (0.2 mL, 1.44 mmol) was added and the mixture was shaken at 75° C. for 44 h.

Upon cooling, the mixture was partitioned between ethyl acetate (3 mL) and saturated aqueous sodium bicarbonate solution (3 mL). The organic phase was concentrated in vacuo to afford a thick oil which was dissolved in N,N-dimethylformamide (1 mL). A 0.2 M solution of [7-(methanesulfonylamino-methyl)-1,1-dioxo-1,4-dihydro-1λ⁶-thieno[2,3-e][1,2,4]thiadiazin-3-yl]-acetic acid (prepared as described in Example 2c; 1 mL, 0.2 mmol) was added followed by a 0.4 M solution of 1-(3-dimethylaminopropyl)-3-ethylcarbodiimide hydrochloride in N,N-dimethylformamide (0.75 mL, 0.3 mmol).

The mixture was shaken at 25° C. for 16 h. Triethylamine (0.6 mL, 2.16 mmol) was added and the mixture was shaken at 75° C. for 24 h. Upon cooling to 25° C., the mixture was concentrated in vacuo to a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes) to afford the desired product.

Example 36

N-3-2S 713-(4-Fluoro-3-methoxy-benzyl)-6-hydroxy-4-oxo-3-aza-tricyclo[6.2.2.0²,⁷]dodec-5-en-5-yl]-1,1-dioxo-1,4-dihydro-1λ⁶-thieno[2,3-e],2,4]thiadiazin-7-ylmethyl}-metanesulfonamide

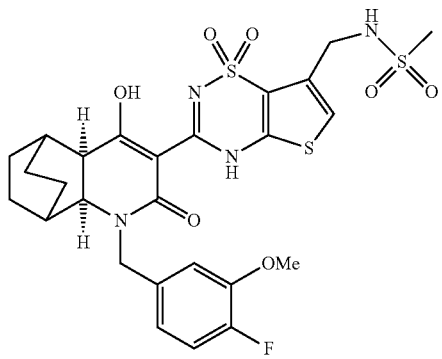

N-{3-[(2S,7R)-3-(4-Fluoro-3-methoxy-benzyl)-6-hydroxy-4-oxo-3-aza-tricyclo[6.2.2.0²,⁷]dodec-5-en-5-yl]-1,1-dioxo-1,4-dihydro-1λ⁶-thieno[2,3-e][1,2,4]thiadiazin-7-ylmethyl}-methanesulfonamide (0.017 g, 0.028 mmol, 14%), was prepared as described in general procedure 1. ¹H NMR (400 MHz, DMSO-d₆) δ: 1.37-1.61 (8H, m), 1.88-1.93 (1H, m), 2.09-2.15 (1H, m), 2.95 (3H, s), 3.23 (1H, d, J=11.1 Hz), 3.72 (1H, d, J=11.6 Hz), 3.81 (3H, s), 4.20-4.25 (3H, m), 5.02 (1H, d, J=15.7 Hz), 6.83-6.86 (1H, m), 7.06 (1H, dd, J₁=8.5 Hz, J₂=1.6 Hz), 7.13 (1H, dd, J₁=11.6 Hz, J₂=8.5 Hz), 7.28 (1H, s), 7.66 (1H, t, J=6.2 Hz). LC-MS (ESI) calculated for $C_{26}H_{29}FN_4O_7S_3$ 624.12. found 625.2 [M+H⁺].

Example 37

N-{3-[(1R,2S,7R,8S)-3-(3-Chloro-4-fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

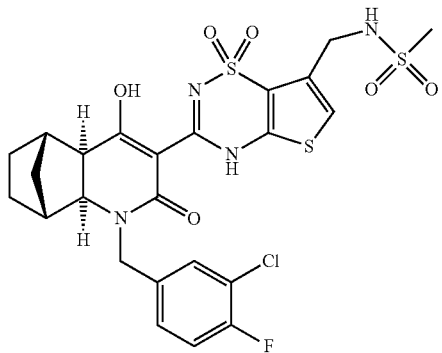

N-{3-[(1R,2S,7R,8S)-3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.017 g, 0.028 mmol, 14%) was prepared as described in general procedure 1. $^1$H NMR (400 MHz, DMSO-d$_6$) δ: 1.15-1.24 (2H, m), 1.39-1.61 (4H, m), 2.46-2.46 (1H, m), 2.61-2.61 (1H, m), 2.95 (3H, s), 2.98 (1H, d, J=9.4 Hz), 3.55 (1H, d, J=9.3 Hz), 4.24 (2H, d, J=5.2 Hz), 4.42 (1H, d, J=15.5 Hz), 4.88 (1H, d, J=16.3 Hz), 7.27-7.30 (2H, m), 7.36 (1H, t, J=8.9 Hz), 7.49 (1H, dd, J$_1$=7.0 Hz, J$_2$=1.6 Hz), 7.66 (1H, t, J=6.2 Hz). LC-MS (ESI) calculated for C$_{24}$H$_{24}$ClFN$_4$O$_6$S$_3$ 614.05. found 615.0 [M+H$^+$].

Example 38

N-{3-[(1R,2S,7R,8S)-3-(4-Fluoro-3-methoxy-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

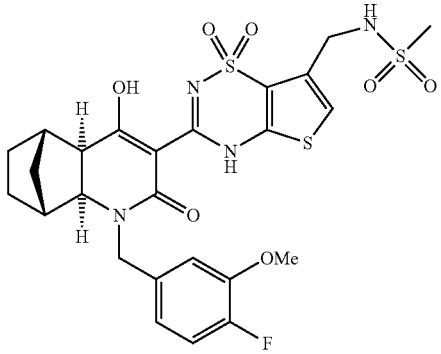

N-{3-[(1R,2S,7R,8S)-3-(4-Fluoro-3-methoxy-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.017 g, 0.028 mmol, 14%) was prepared as described in general procedure 1. $^1$H NMR (400 MHz, DMSO-d$_6$) δ: 1.15-1.22 (2H, m), 1.39-1.62 (4H, m), 2.50-2.52 (1H, m), 2.62-2.62 (1H, m), 2.95 (3H, s), 2.98 (1H, d, J=9.3 Hz), 3.52 (1H, d, J=9.3 Hz), 3.81 (3H, s), 4.24 (2H, d, J=6.3 Hz), 4.37 (1H, d, J=15.5 Hz), 4.93 (1H, d, J=15.6 Hz), 6.80-6.83 (1H, m), 7.04 (1H, dd, J$_1$=8.1 Hz, J$_2$=1.9 Hz), 7.13 (1H, dd, J$_1$=11.6 Hz, J$_2$=8.5 Hz), 7.27 (1H, s), 7.66 (1H, t, J=6.3 Hz). LC-MS (ESI) calculated for C$_{25}$H$_{27}$FN$_4$O$_7$S$_3$ 610.1. found 611.1 [M+H$^+$].

Example 39

N-[3-((1S,2S,7R,8R)-3-Benzyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

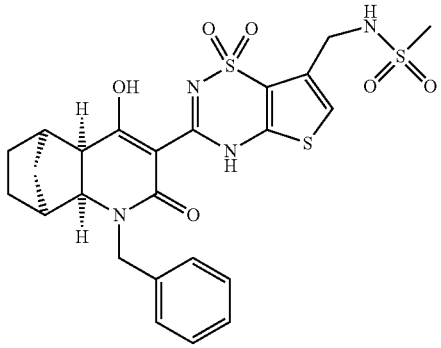

N-[3-((1S,2S,7R,8R)-3-Benzyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.018 g, 0.032 mmol, 16%) was prepared as described in general procedure 1. $^1$H NMR (400 MHz, DMSO-d$_6$) δ: 1.29-1.47 (6H, m), 2.64-2.72 (2H, m), 2.96 (3H, s), 3.20 (1H, d, J=15.4 Hz), 3.72 (1H, d, J=13.5 Hz), 4.02 (1H, d, J=14.7 Hz), 4.25 (2H, d, J=6.3 Hz), 5.17 (1H, d, J=15.6 Hz), 7.23-7.35 (6H, m), 7.67 (1H, t, J=6.2 Hz). LC-MS (ESI) calculated for C$_{24}$H$_{26}$N$_4$O$_6$S$_3$ 562.1. found 563.2 [M+H$^+$].

Example 40

N-{3-[(1S,2S,7R,8R)-3-(2,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

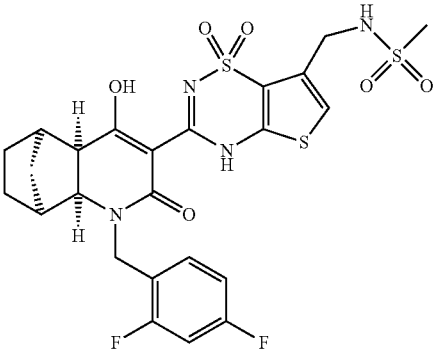

N-{3-[(1S,2S,7R,8R)-3-(2,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.017 g, 0.028 mmol, 14%) was prepared as described in general procedure 1. $^1$H NMR (400 MHz, DMSO-d$_6$) δ: 1.24-1.49 (6H, m), 2.66-2.69 (2H, m), 2.96 (3H, s), 3.21 (1H, dd, J$_1$=12.1 Hz, J$_2$=4.5 Hz), 3.77 (1H, dd, J$_1$=12.5 Hz, J$_2$=3.8 Hz), 4.09 (1H, d, J=15.5 Hz), 4.24 (2H, d, J=5.3 Hz), 5.09 (1H, d, J=15.6 Hz), 7.05 (1H, dt, J$_1$=8.6 Hz, J$_2$=2.2 Hz), 7.20-7.26 (1H, m), 7.28 (1H, s), 7.42-7.47 (1H, m), 7.66 (1H, t, J=6.2 Hz). LC-MS (ESI) calculated for C$_{24}$H$_{24}$F$_2$N$_4$O$_6$S$_3$ 598.08. found 599.1 [M+H$^+$].

Example 41

N-{3-[(1S,2S,7R,8R)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

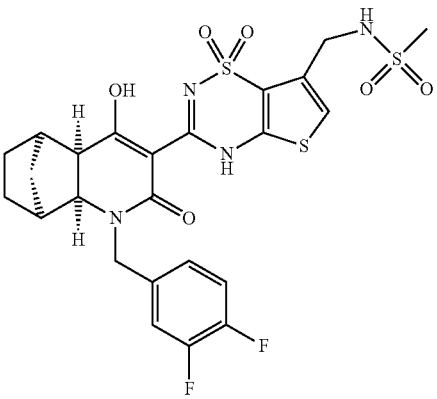

N-{3-[(1S,2S,7R,8R)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.014 g, 0.024 mmol, 12%) was prepared as described in general procedure 1. $^1$H NMR (400 MHz, DMSO-d$_6$) δ: 1.22-1.48 (6H, m), 2.68-2.72 (2H, m), 2.96 (3H, s), 3.20 (1H, dd, J$_1$=12.7 Hz, J$_2$=3.8 Hz), 3.75 (1H, dd, J$_1$=12.5 Hz, J$_2$=3.3 Hz), 4.08 (1H, d, J=15.6 Hz), 4.24 (2H, d, J=6.3 Hz), 5.05 (1H, d, J=14.9 Hz), 7.18-7.21 (1H, m), 7.29 (1H, s), 7.34-7.43 (2H, m), 7.67 (1H, t, J=6.2 Hz). LC-MS (ESI) calculated for C$_{24}$H$_{24}$F$_2$N$_4$O$_6$S$_3$ 598.08. found 599.1 [M+H$^+$].

Example 42

N-{3-[(1S,2S,7R,8R)-3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e]1,2,4 thiadiazin-7-ylmethyl}-methanesulfonamide

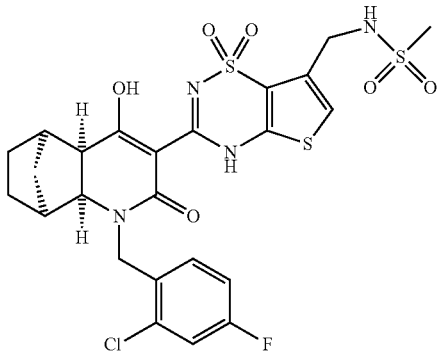

N-{3-[(1S,2S,7R,8R)-3-(2-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-yl-methyl}-methanesulfonamide (0.017 g, 0.028 mmol, 14%) was prepared as described in general procedure 1. $^1$H NMR (400 MHz, DMSO-d$_6$) δ: 1.30-1.50 (6H, m), 2.66-2.73 (2H, m), 2.96 (3H, s), 3.25 (1H, dd, J$_1$=12.5 Hz, J$_2$=4.8 Hz), 3.76 (1H, dd, J$_1$=12.4 Hz, J$_2$=3.6 Hz), 4.09 (1H, d, J=16.2 Hz), 4.24 (2H, d, J=5.6 Hz), 5.15 (1H, d, J=15.4 Hz), 7.19 (1H, dt, J$_1$=7.7 Hz, J$_2$=2.6 Hz), 7.28 (1H, s), 7.40 (1H, dd, J$_1$=8.6 Hz, J$_2$=6.3 Hz), 7.45 (1H, dd, J$_1$=8.7 Hz, J$_2$=2.5 Hz), 7.66 (1H, t, J=6.2 Hz). LC-MS (ESI) calculated for C$_{24}$H$_{24}$ClFN$_4$O$_6$S$_3$ 614.05. found 615.1 [M+H$^+$].

Example 43

N-}3-[(1S,2S,7R,8R)-3-(4-Fluoro-3-methoxy-benzyl-6-hydroxy-4-oxo-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

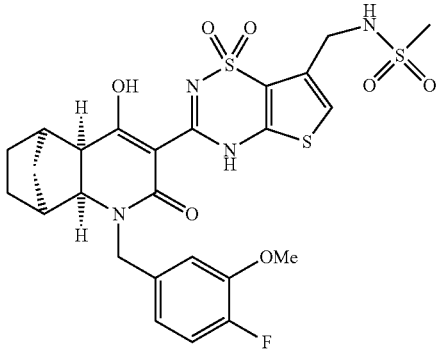

N-{3-[(1S,2S,7R,8R)-3-(4-Fluoro-3-methoxy-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.018 g, 0.03 mmol, 15%) was prepared as described in general procedure 1. $^1$H NMR (400 MHz, DMSO-d$_6$) δ: 1.24-1.48 (6H, m), 2.68-2.72 (2H, m), 2.96 (3H, s), 3.19 (1H, dd, J$_1$12.5 Hz, J$_2$=4.0 Hz), 3.72 (1H, dd, J$_1$=12.4 Hz, J$_2$=3.2 Hz), 3.81 (3H, s), 3.99-4.04 (1H, m), 4.25 (2H, d, J=6.2 Hz), 5.12 (1H, d, J=14.6 Hz), 6.87-6.90 (1H, m), 7.09-7.16 (2H, m), 7.29 (1H, s), 7.67 (1H, t, J=6.2 Hz). LC-MS (ESI) calculated for C$_{25}$H$_{27}$FN$_4$O$_7$S$_3$ 610.1. found 611.0 [M+H$^+$].

Example 44

N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

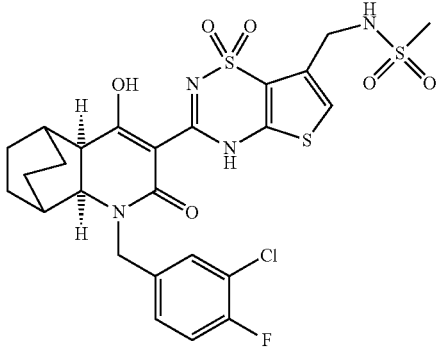

N-{3-[(2S,7R)-3-(3-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}- methanesulfonamide (0.008 g, 0.012 mmol, 6%) was prepared as described in general procedure 1. $^1$H NMR (400 MHz, DMSO-$d_6$) δ: 1.33-1.42 (2H, m), 1.49-1.66 (6H, m), 1.87-1.91 (1H, m), 2.09-2.15 (1H, m), 2.96 (3H, s), 3.23-3.31 (1H, m), 3.76 (1H, d, J=12.0 Hz), 4.25 (2H, d, J=6.2 Hz), 4.29 (1H, d, J=15.5 Hz), 4.95 (1H, d, J=15.6 Hz), 7.28-7.37 (3H, m), 7.52 (1H, dd, $J_1$=7.1 Hz, $J_2$=1.6 Hz), 7.66 (1H, t, J=6.2 Hz). LC-MS (ESI) calculated for $C_{25}H_{26}ClFN_4O_6S_3$ 628.07. found 629.2 [M+H$^+$].

Example 45

(rac-di-exo)-N-[3-(3-Benzyl-6-hydroxy-4-oxo-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

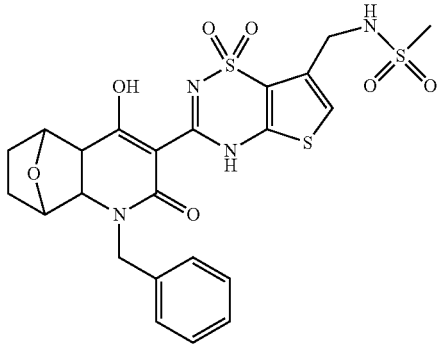

(rac-di-exo)-N-[3-(3-Benzyl-6-hydroxy-4-oxo-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.01 g, 0.018 mmol, 9%) was prepared as described in general procedure 1. $^1$H NMR (400 MHz, DMSO-$d_6$) δ: 1.45-1.73 (4H, m), 2.96 (3H, s), 3.27-3.31 (1H, m), 3.78 (1H, d, J=9.3 Hz), 4.24 (2H, d, J=5.5 Hz), 4.39 (1H, d, J=14.8 Hz), 4.72 (2H, dd, $J_1$=20.6 Hz, $J_2$=4.5 Hz), 5.05 (1H, d, J=15.6 Hz), 7.23-7.35 (6H, m), 7.66 (1H, t, J=6.2 Hz). LC-MS (ESI) calculated for $C_{23}H_{24}N_4O_7S_3$ 564.08. found 565.2 [M+H$^+$].

Example 46

(rac-di-exo)-N-[3-(3-Benzyl-6-hydroxy-4-oxo-3-aza-tricyclo[6.2.1.0$^{2,7}$]undeca-5,9-dien-5-yl)-1,1-dioxo-1,4-dihydro-1λ$^6$-thieno e][1,2,4]thiadiazin-7-ylmethyl}-methanesulfonamide

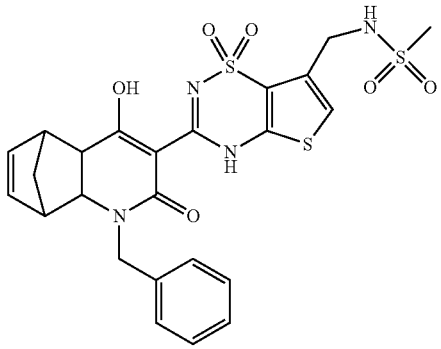

(rac-di-exo)-N-[3-(3-Benzyl-6-hydroxy-4-oxo-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide (0.011 g, 0.02 mmol, 10%) was prepared as described in general procedure 1. $^1$H NMR (400 MHz, DMSO-$d_6$) δ: 1.37 (1H, d, J=9.4 Hz), 1.65 (1H, d, J=9.5 Hz), 2.83 (1H, d, J=9.5 Hz), 2.96 (3H, s), 3.20 (1H, s), 3.27 (1H, s), 3.39 (1H, d, J=8.4 Hz), 4.24 (2H, d, J=5.6 Hz), 4.50 (1H, d, J=15.6 Hz), 5.06 (1H, d, J=15.6 Hz), 6.11-6.13 (1H, m), 6.33-6.35 (1H, m), 7.22-7.34 (6H, m), 7.66 (1H, t, J=6.2 Hz). LC-MS (ESI) calculated for $C_{24}H_{24}N_4O_6S_3$ 560.09. found 561.2 [M+H$^+$].

Example 47

(rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide

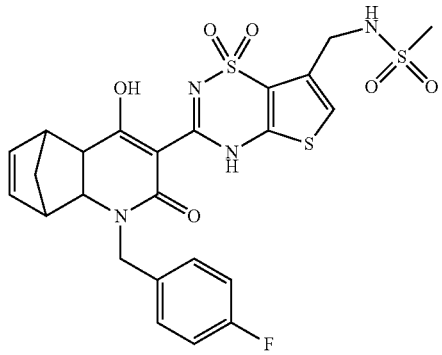

(rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide (0.02 g, 0.034 mmol, 17%) was prepared as described in general procedure 1. $^1$H NMR (400 MHz, DMSO-$d_6$) δ: 1.37 (1H, d, J=9.4 Hz), 1.63 (1H, d, J=9.3 Hz), 2.81 (1H, d, J=9.6 Hz), 2.96 (3H, s), 3.18 (1H, bs), 3.27 (1H, bs), 3.38 (1H, d, J=9.5 Hz), 4.24 (2H, d, J=6.3 Hz), 4.48 (1H, d, J=15.7 Hz), 5.02 (1H, d, J=15.7 Hz), 6.12-6.14 (1H, m), 6.33-6.35 (1H, m), 7.14 (2H, t, J=9.1 Hz), 7.26 (1H, s), 7.33 (2H, dd, J=8.5 Hz, $J_2$=5.6 Hz), 7.66 (1H, t, J=6.3 Hz). LC-MS (ESI) calculated for $C_{24}H_{23}FN_4O_6S_3$ 578.08. found 578.9 [M+H$^+$].

Example 48

N-[3-((2S,7R)-3-Benzyl-6-hydroxy-4-oxo-3-aza-tricyclo[6.2.2.0$^{2,7}$]dodec-5-en-5-yl)-1,1-dioxo-1,4-dihydro-1λ$^6$-thieno e][1,2,4]thiadiazin-7-ylmethyl}-methanesulfonamide

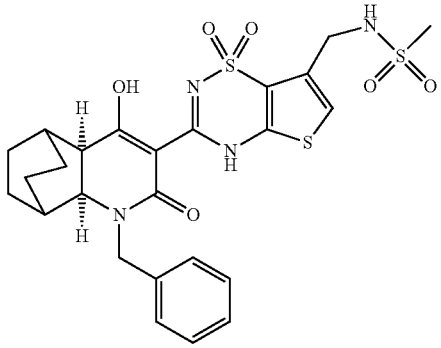

N-[3-((2S,7R)-3-Benzyl-6-hydroxy-4-oxo-3-aza-tricyclo[6.2.2.0$^{2,7}$]dodec-5-en-5-yl)-1,1-dioxo-1,4-dihydro-1λ$^6$-thieno[2,3-e][1,2,4]thiadiazin-7-ylmethyl]-methanesulfonamide (0.025 g, 0.044 mmol, 22%) was prepared as described in general procedure 1. $^1$H NMR (400 MHz, DMSO-d$_6$) δ: 1.37-1.61 (8H, m), 1.90-1.94 (1H, m), 2.12-2.14 (1H, m), 2.96 (3H, s), 3.24-3.31 (1H, m), 3.73 (1H, d, J=10.9 Hz), 4.21-4.28 (3H, m), 5.06 (1H, d, J=15.5 Hz), 7.22-7.34 (6H, m), 7.67 (1H, t, J=6.2 Hz). LC-MS (ESI) calculated for C$_{25}$H$_{28}$N$_4$O$_6$S$_3$ 576.12. found 577.2 [M+H$^+$].

Example 49

N-{3-[(1R,2S,7R,8S)-3-(2,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl]-methanesulfonamide

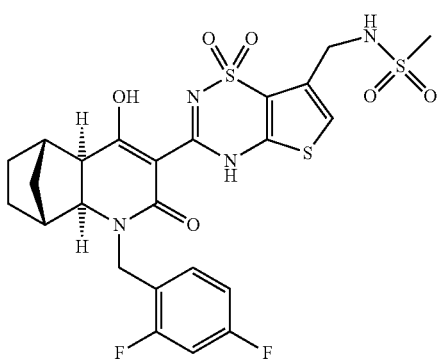

N-{3-[(1R,2S,7R,8S)-3-(2,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.031 g, 0.052 mmol, 26%) was prepared as described in general procedure 1. $^1$H NMR (400 MHz, DMSO-d$_6$) δ: 1.20-1.23 (2H, m), 1.40-1.64 (4H, m), 2.50-2.54 (1H, m), 2.62-2.62 (1H, m), 2.95 (3H, s), 3.01 (1H, d, J=9.4 Hz), 3.56 (1H, d, J=9.5 Hz), 4.23 (2H, d, J=6.3 Hz), 4.39 (1H, d, J=15.5 Hz), 4.93 (1H, d, J=15.5 Hz), 7.04 (1H, dt, J$_1$=8.6 Hz, J$_2$=2.4 Hz), 7.21-7.27 (2H, m), 7.32-7.38 (1H, m), 7.66 (1H, t, J=6.2 Hz). LC-MS (ESI) calculated for C$_{24}$H$_{24}$F$_2$N$_4$O$_6$S$_3$ 598.08. found 599.1 [M+H$^+$].

Example 50

N-[3-((1R,2S,7R,8S)-3-Benzyl-6-hydroxy-4-oxo-3-aza-tricyclo[6.2.1.0$^{2,7}$]undec-5-en-5-yl)-1,4-dihydro-1λ$^6$-thieno e][1,2,4]thiadiazin-7-ylmethyl]-methanesulfonamide

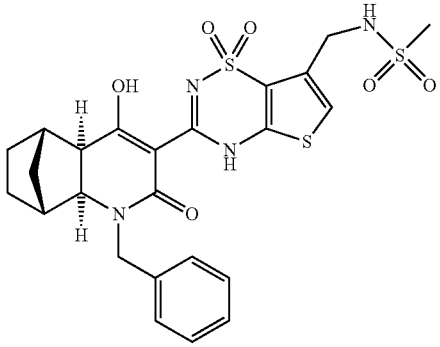

N-[3-((1R,2S,7R,8S)-3-Benzyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.021 g, 0.038 mmol, 19%) was prepared as described in general procedure 1. $^1$H NMR (400 MHz, DMSO-d$_6$) δ: 1.19-1.23 (2H, m), 1.38-1.62 (4H, m), 2.51-2.55 (1H, m), 2.62-2.62 (1H, m), 2.96 (3H, s), 2.99 (1H, d, J=8.7 Hz), 3.52 (1H, d, J=9.5 Hz), 4.24 (2H, d, J=6.2 Hz), 4.40 (1H, d, J=15.1 Hz), 4.98 (1H, d, J=15.6 Hz), 7.22-7.34 (6H, m), 7.66 (1H, t, J=6.2 Hz). LC-MS (ESI) calculated for C$_{24}$H$_{26}$N$_4$O$_6$S$_3$ 562.1. found 563.2 [M+H$^+$].

Example 51

N-{3-[2S,7R)-3-(2,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

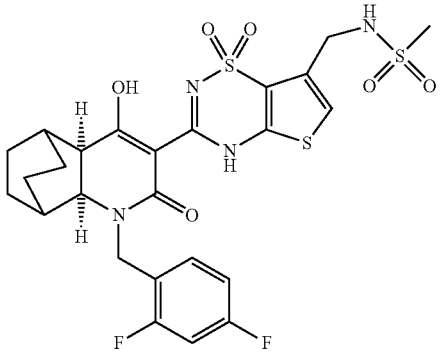

N-{3-[(2S,7R)-3-(2,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide (0.025 g, 0.04 mmol, 20%) was prepared as described in general procedure 1. $^1$H NMR (400 MHz, DMSO-d$_6$) δ: 1.33-1.46 (2H, m), 1.48-1.63 (6H, m), 1.89-1.92 (1H, m), 2.11-2.17 (1H, m), 2.95 (3H, s), 3.17-3.31 (1H, m), 3.78 (1H, d, J=10.9 Hz), 4.23-4.28 (3H, m), 5.01 (1H, d, J=15.8 Hz), 7.04 (1H, dt, J$_1$=8.5 Hz, J$_2$=1.4 Hz), 7.23 (1H, dt, J$_1$=10.0 Hz, J$_2$=2.4 Hz), 7.28 (1H, s), 7.37-7.43 (1H, m), 7.66 (1H, t, J=6.3 Hz). LC-MS (ESI) calculated for C$_{25}$H$_{26}$F$_2$N$_4$O$_6$S$_3$ 612.1. found 613.0 [M+H$^+$].

General Procedure 2:

Mixtures containing a bicyclic β-amino ester salt (selected from a list containing (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2)) at 0.2 M and sodium acetate at 0.4 M were prepared in methanol. The bicyclic β-amino ester salt/sodium acetate mixture (2 mL, 0.4 mmol of bicyclic β-amino ester salt and 0.8 mmol of sodium acetate) was combined with a 2.0 M solution of an aldehyde (0.2 mL, 0.4 mmol) in methanol. The mixture was shaken for 15 min at 25° C. A 0.4 M solution of sodium cyanoborohydride in methanol (2 mL, 0.8 mmol) was added and the mixture was shaken at 25° C. for 16 h. Saturated aqueous sodium bicarbonate solution (2 mL) was added and the mixture was shaken for 1 h.

The resulting suspension was partitioned between ethyl acetate (3 mL) and saturated aqueous sodium bicarbonate solution (3 mL). The organic phase was concentrated in vacuo to afford a thick oil which was dissolved in N,N-dimethylformamide (1 mL). A 0.2 M solution of [7-(methanesulfonylamino-methyl)-1,1-dioxo-1,4-dihydro-1λ$^6$-thieno[2,3-e][1,2,4]thiadiazin-3-yl]-acetic acid (prepared as described in Example 2c; 1 mL, 0.2 mmol) was added followed by a 0.4 M solution of 1-(3-dimethylaminopropyl)-3-ethylcarbodiimide hydrochloride in N,N-dimethylformamide (0.75 mL, 0.3 mmol). The mixture was shaken at 25° C. for 16 h. Triethylamine (0.6 mL, 2.16 mmol) was added and the mixture was shaken for at 75° C. for 24 h. Upon cooling to 25° C., the mixture was concentrated in vacuo to a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was directly purified by flash column chromatography (Teledyne Isco RediSep column; 5-100% ethyl acetate in hexanes) to afford the desired product.

Example 52

N-3-[2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

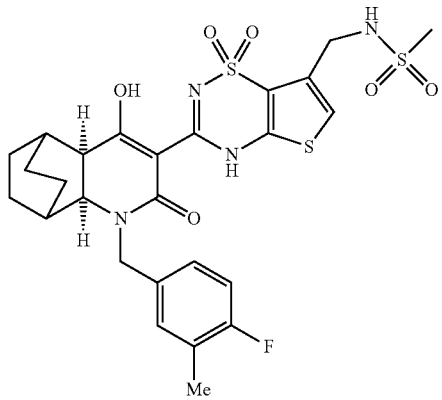

N-{3-[(2S,7R)-3-(4-Fluoro-3-methyl-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide (0.022 g, 0.036 mmol, 18%) was prepared as described in general procedure 2. $^1$H NMR (400 MHz, DMSO-d$_6$) δ: 1.30-1.66 (8H, m), 1.85-1.94 (1H, m), 2.08-2.15 (1H, m), 2.21 (3H, s), 2.96 (3H, s), 3.22 (1H, d, J=9.1 Hz), 3.72 (1H, d, J=11.7 Hz), 4.18 (1H, d, J=15.6 Hz), 4.25 (2H, d, J=6.2 Hz), 5.00 (1H, d, J=15.8 Hz), 7.06 (1H, t, J=8.9 Hz), 7.13 (1H, d, J=15.6 Hz), 7.19 (1H, d, J=7.5 Hz), 7.28 (1H, s), 7.66 (1H, t, J=6.3 Hz). LC-MS (ESI) calculated for C$_{26}$H$_{29}$FN$_4$O$_6$S$_3$ 608.12. found 609.0 [M+H$^+$].

Example 53

N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1 6-thieno[2,3-e][1,2,4]thiadiazin-7-ylmethyl}-methanesulfonamide

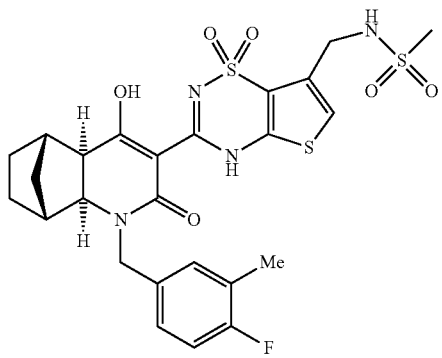

N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.021 g, 0.036 mmol, 18%) was prepared as described in general procedure 2. $^1$H NMR (400 MHz, DMSO-d$_6$) δ: 1.10-1.21 (2H, m), 1.38-1.60 (4H, m), 2.21 (3H, d, J=1.5 Hz), 2.50-2.53 (1H, m), 2.61 (1H, d, J=3.3 Hz), 2.95-2.98 (4H, m), 3.50 (1H, d, J=9.3 Hz), 4.24 (2H, d, J=6.2 Hz), 4.31 (1H, d, J=15.0 Hz), 4.93 (1H, d, J=15.8 Hz), 7.04-7.13 (2H, m), 7.17 (1H, d, J=6.9 Hz), 7.27 (1H, s), 7.66 (1H, t, J=5.8 Hz). LC-MS (ESI) calculated for $C_{25}H_{27}FN_4O_6S_3$ 594.11. found 595.1 [M+H$^+$].

Example 54

N-{3-[(1R,2S,7R,8S)-6-Hydroxy-4-oxo-3-(3,4,5-trifluoro-benzyl)-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl]-methanesulfonamide

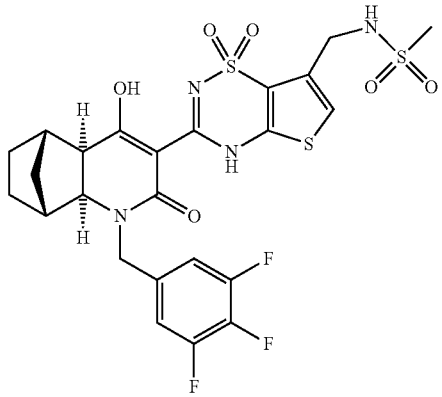

N-{3-[(1R,2S,7R,8S)-6-Hydroxy-4-oxo-3-(3,4,5-trifluoro-benzyl)-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.02 g, 0.032 mmol, 16%) was prepared as described in general procedure 2. $^1$H NMR (400 MHz, DMSO-d$_6$) δ: 1.13-1.24 (2H, m), 1.38-1.63 (4H, m), 2.42 (1H, d, J=4.0 Hz), 2.61 (1H, d, J=3.3 Hz), 2.95 (3H, s), 2.99 (1H, d, J=9.3 Hz), 3.57 (1H, d, J=9.5 Hz), 4.24 (2H, d, J=6.2 Hz), 4.44 (1H, d, J=15.9 Hz), 4.83 (1H, d, J=16.3 Hz), 7.21-7.27 (3H, m), 7.66 (1H, t, J=6.2 Hz). LC-MS (ESI) calculated for $C_{24}H_{23}F_3N_4O_6S_3$ 616.07. found 617.2 [M+H$^+$].

Example 55

N-[(1R,2S,7R,8S)-3-(6-Hydroxy-4-oxo-3-thiophen-3-ylmethyl-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

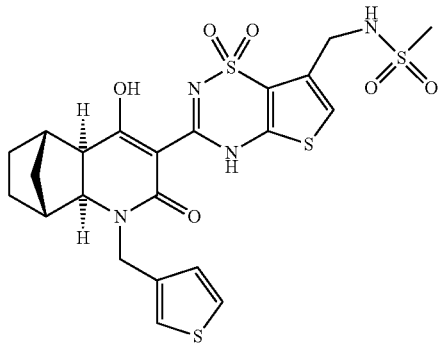

N-[(1R,2S,7R,8S)-3-(6-Hydroxy-4-oxo-3-thiophen-3-ylmethyl-3-aza-tricyclo[6.2.1.0$^{2,7}$]undec-5-yl)-1,1-dioxo-1,4-dihydro-1λ$^6$-thieno[2,3-e][1,2,4]thiadiazin-7-ylmethyl]-methanesulfonamide (0.025 g, 0.044 mmol, 22%) was prepared as described in general procedure 2. $^1$H NMR (400 MHz, DMSO-d$_6$) δ: 1.15-1.23 (2H, m), 1.39-1.60 (4H, m), 2.52-2.52 (1H, m), 2.60-2.61 (1H, m), 2.95-3.00 (4H, m), 3.54 (1H, d, J=9.5 Hz), 4.24 (2H, d, J=6.3 Hz), 4.36 (1H, d, J=15.5 Hz), 4.90 (1H, d, J=15.7 Hz), 7.04 (1H, d, J=6.3 Hz), 7.27 (1H, s), 7.38-7.38 (1H, m), 7.48 (1H, dd, J$_1$=4.6 Hz, J$_2$=3.2 Hz), 7.66 (1H, t, J=6.2 Hz). LC-MS (ESI) calculated for $C_{22}H_{24}N_4O_6S_4$ 568.06. found 569.1 [M+H$^+$].

Example 56

N-{3-[(1S,2S,7R,8R)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

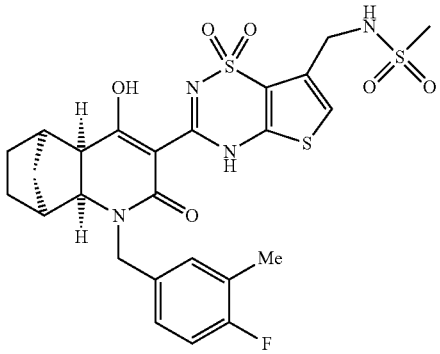

N-{3-[(1S,2S,7R,8R)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.02 g, 0.034 mmol, 17%) was prepared as described in general procedure 2. $^1$H NMR (400 MHz, DMSO-d$_6$) δ: 1.25-1.47 (6H, m), 2.21 (3H, s), 2.67-2.71 (2H, m), 2.96 (3H, s), 3.18 (1H, d, J=8.6 Hz), 3.71 (1H, d, J=12.4 Hz), 3.96 (1H, d, J=14.9 Hz), 4.24 (2H, d, J=6.3 Hz), 5.11 (1H, d, J=14.6 Hz), 7.07 (1H, t, J=8.9 Hz), 7.16-7.19 (1H, m), 7.22 (1H, d, J=5.6 Hz), 7.28 (1H, s), 7.66 (1H, t, J=6.2 Hz). LC-MS (ESI) calculated for $C_{25}H_{27}FN_4O_6S_3$ 594.11. found 595.0 [M+H$^+$].

Example 57

N-{3-[(1S,2S,7R,8R)-6-Hydroxy-4-oxo-3-(3,4,5-trifluoro-benzyl)-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

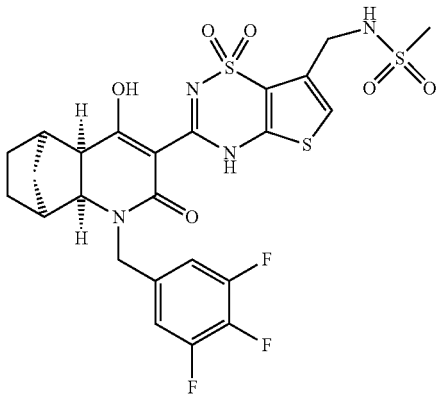

N-{3-[(1S,2S,7R,8R)-6-Hydroxy-4-oxo-3-(3,4,5-trifluorobenzyl)-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.022 g, 0.036 mmol, 18%) was prepared as described in general procedure 2. $^1$H NMR (400 MHz, DMSO-d$_6$) δ: 1.23-1.50 (6H, m), 2.64-2.71 (2H, m), 2.96 (3H, s), 3.20 (1H, dd, J$_1$=12.5 Hz, J$_2$=4.6 Hz), 3.77 (1H, dd, J$_1$=13.3 Hz, J$_2$=4.2 Hz), 4.09 (1H, d, J=15.6 Hz), 4.25 (2H, d, J=6.2 Hz), 5.02 (1H, d, J=15.6 Hz), 7.28-7.32 (3H, m), 7.66 (1H, t, J=6.3 Hz). LC-MS (ESI) calculated for C$_{24}$H$_{23}$F$_3$N$_4$O$_6$S$_3$ 616.07. found 617.2 [M+H$^+$].

Example 58

N-[3-((1S,2S,7R,8R)-6-Hydroxy-4-oxo-3-thiophen-3-1-methyl-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamie

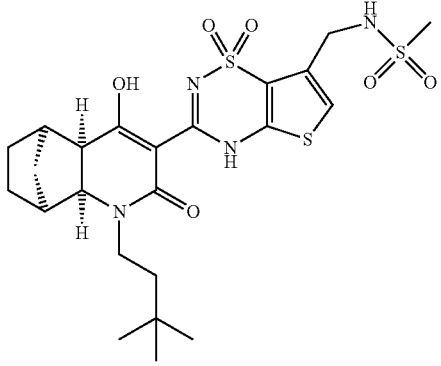

N-[3-((1S,2S,7R,8R)-6-Hydroxy-4-oxo-3-thiophen-3-ylmethyl-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.03 g, 0.052 mmol, 26%) was prepared as described in general procedure 2. $^1$H NMR (400 MHz, DMSO-d$_6$) δ: 1.23-1.49 (6H, m), 2.66-2.73 (2H, m), 2.96 (3H, s), 3.17-3.20 (1H, m), 3.77 (1H, dd, J$_1$=11.6 Hz, J$_2$=2.2 Hz), 4.10 (1H, d, J=14.9 Hz), 4.24 (2H, d, J=6.3 Hz), 5.01 (1H, d, J=14.7 Hz), 7.08 (1H, d, J=6.4 Hz), 7.29 (1H, s), 7.46-7.49 (2H, m), 7.66 (1H, t, J=6.3 Hz). LC-MS (ESI) calculated for C$_{22}$H$_{24}$N$_4$O$_6$S$_4$ 568.06. found 569.1 [M+H$^+$].

Example 59

N-{3-[(1S,2S,7R,8R)-3-(3,3-Dimethyl-butyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

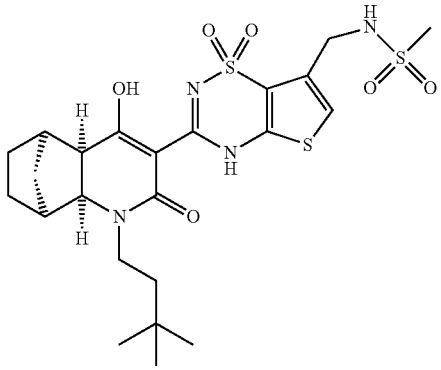

N-{3-[(1S,2S,7R,8R)-3-(3,3-Dimethyl-butyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.013 g, 0.024 mmol, 12%) was prepared as described in general procedure 2. $^1$H NMR (400 MHz, DMSO-d$_6$) δ: 0.93 (9H, s), 1.19-1.56 (8H, m), 2.62-2.69 (2H, m), 2.95-3.03 (4H, m), 3.16-3.23 (1H, m), 3.60-3.69 (1H, m), 3.87-3.91 (1H, m), 4.23-4.25 (2H, m), 7.28 (1H, s), 7.66 (1H, t, J=6.3 Hz). LC-MS (ESI) calculated for C$_{23}$H$_{32}$N$_4$O$_6$S$_3$ 556.15. found 557.1 [M+H$^+$].

Example 60

N-[3-((2S,7R)-6-Hydroxy-4-oxo-3-thiophen-3-ylmethyl-3-aza-tricyclo[6.2.2.0$^{2,7}$]dodec-5-en-5-yl)-1,1-dioxo-1,4-dihydro-1λ$^6$-thieno[2,3-e][1,2,4]thiadiazin-7-ylmethyl]-methanesulfonamide

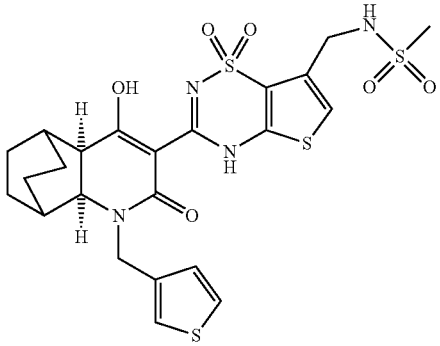

N-[3-((2S,7R)-6-Hydroxy-4-oxo-3-thiophen-3-ylmethyl-3-aza-tricyclo[6.2.2.0$^{2,7}$]dodec-5-en-5-yl)-1,1-dioxo-1,4-dihydro-1λ$^6$-thieno[2,3-e][1,2,4]thiadiazin-7-ylmethyl]-methanesulfonamide (0.028 g, 0.048 mmol, 24%) was prepared as described in general procedure 2. $^1$H NMR (400 MHz, DMSO-d$_6$) δ: 1.36-1.42 (2H, m), 1.48-1.64 (6H, m), 1.90-1.97 (1H, m), 2.11-2.14 (1H, m), 2.95 (3H, s), 3.16-3.23 (1H, m), 3.76 (1H, d, J=11.1 Hz), 4.22-4.31 (3H, m), 4.96 (1H, d, J=15.3 Hz), 7.06 (1H, d, J=6.2 Hz), 7.28 (1H, s), 7.41 (1H, s), 7.46-7.48 (1H, m), 7.66 (1H, t, J=6.3 Hz). LC-MS (ESI) calculated for C$_{23}$H$_{26}$N$_4$O$_6$S$_4$ 582.07. found 583.0 [M+H$^+$].

Example 61

(rac-di-exo)-N-[3-(6-Hydroxy-4-oxo-3-thiophen-3-ylmethyl-11-oxa-3-aza-tricyclo[6.2.1.0$^{2,7}$]undec-5-en-5-1)-1,1-dioxo-1,4-dihydro-1λ$^6$-thieno[2,3-e][1,2,4]thiadiazin-7-ylmethyl]-methanesulfonamide

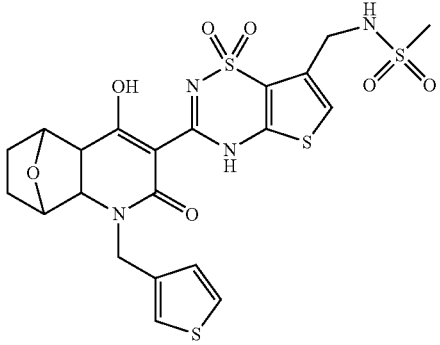

(rac-di-exo)-N-[3-(6-Hydroxy-4-oxo-3-thiophen-3-ylmethyl-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.01 g, 0.018 mmol, 9%) was prepared as described in general procedure 2. $^1$H NMR (400 MHz, DMSO-d$_6$) δ: 1.49-1.76 (4H, m), 2.95 (3H, s), 3.27 (1H, d, J=10.3 Hz), 3.80 (1H, d, J=9.3 Hz), 4.24 (2H, d, J=7.8 Hz), 4.37 (1H, d, J=15.6 Hz), 4.71 (2H, dd, J=21.6 Hz, J$_2$=4.7 Hz), 4.98 (1H, d, J=14.8 Hz), 7.06 (1H, d, J=6.3 Hz), 7.28 (1H, s), 7.41 (1H, s), 7.49-7.51 (1H, m), 7.66 (1H, t, J=6.2 Hz). LC-MS (ESI) calculated for C$_{21}$H$_{22}$N$_4$O$_7$S$_4$ 570.04. found 571.0 [M+H$^+$].

Example 62

(rac-di-exo)-N-{3-[3-(3,3-Dimethyl-butyl)-6-hydroxy-4-oxo-11-oxa-3-aza-tricyclo[6.2.1.0$^{2,7}$]undec-5-en-5-yl]-1,1-dioxo-1,4-dihydro thieno[2,3-e][1,2,4]thiadiazin-7-ylmethyl}-methanesulfonamide

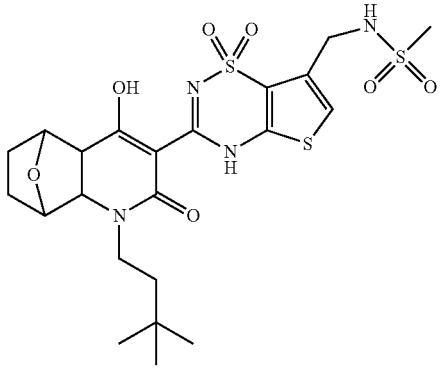

(rac-di-exo)-N-{3-[3-(3,3-Dimethyl-butyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.006 g, 0.01 mmol, 5%) was prepared as described in general procedure 2. $^1$H NMR (400 MHz, DMSO-d$_6$) δ: 0.93 (9H, s), 1.41-1.72 (6H, m), 2.95-3.21 (6H, m), 3.78-3.90 (1H, m), 4.23 (2H, d, J=5.7 Hz), 4.74 (2H, s), 7.27 (1H, s), 7.66 (1H, t, J=6.2 Hz). LC-MS (ESI) calculated for C$_{22}$H$_{30}$N$_4$O$_7$S$_3$ 558.13. found 559.1 [M+H$^+$].

Example 63

(rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

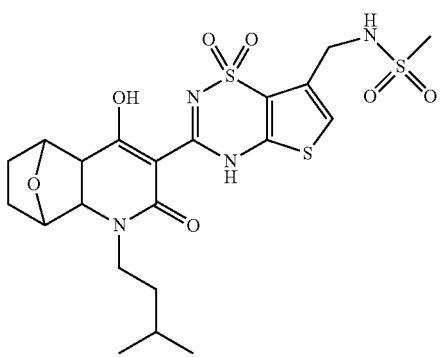

(rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.008 g, 0.014 mmol, 7%) was prepared as described in general procedure 2. $^1$H NMR (400 MHz, DMSO-d$_6$) δ: 0.91 (6H, d, J=6.3 Hz), 1.38-1.75 (7H, m), 2.95-3.08 (4H, m), 3.20-3.26 (1H, m), 3.78-3.85 (1H, m), 3.89 (1H, d, J=9.2 Hz), 4.23 (2H, d, J=6.2 Hz), 4.67-4.75 (2H, m), 7.27 (1H, s), 7.65 (1H, t, J=5.9 Hz). LC-MS (ESI) calculated for C$_{21}$H$_{28}$N$_4$O$_7$S$_3$ 544.11. found 545.2 [M+H$^+$].

Example 64

(rac-di-exo)-N-[3-(6-Hydroxy-4-oxo-3-thiophen-3-1-methyl-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide

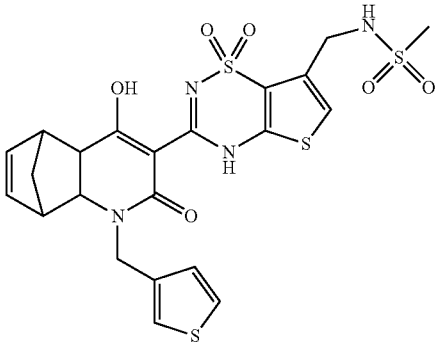

(rac-di-exo)-N-[3-(6-Hydroxy-4-oxo-3-thiophen-3-ylmethyl-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide (0.025 g, 0.044 mmol, 22%) was prepared as described in general procedure 2. $^1$H NMR (400 MHz, DMSO-d$_6$) δ: 1.36 (1H, d, J=10.1 Hz), 1.61 (1H, d, J=9.5 Hz), 2.79-2.83 (1H, m), 2.96 (3H, s), 3.18-3.23 (1H, m), 3.26-3.28 (1H, m), 3.42 (1H, d, J=9.3 Hz), 4.24 (2H, d, J=5.4 Hz), 4.47 (1H, d, J=15.7 Hz), 4.99 (1H, d, J=14.5 Hz), 6.14-6.16 (1H, m), 6.33-6.36 (1H, m), 7.06 (1H, d, J=3.9 Hz), 7.27 (1H, s), 7.40-7.42 (1H, m), 7.48 (1H, dd, J$_1$=4.9 Hz, J$_2$=2.4 Hz), 7.66 (1H, t, J=6.2 Hz). LC-MS (ESI) calculated for C$_{22}$H$_{22}$N$_4$O$_6$S$_4$ 566.04. found 567.1 [M+H$^+$].

Example 65

(rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide

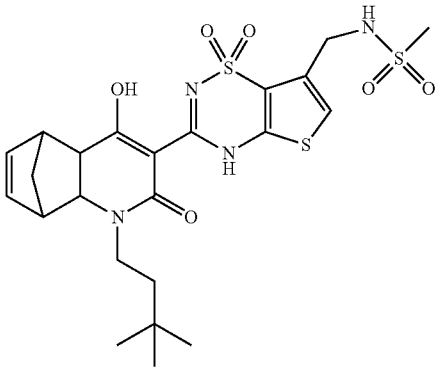

(rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide (0.01 g, 0.018 mmol, 9%) was prepared as described in general procedure 2. $^1$H NMR (400 MHz, DMSO-d$_6$) δ: 0.94 (9H, s), 1.38-1.47 (2H, m), 1.54-1.60 (2H, m), 2.75-2.84 (1H, m), 2.96 (3H, s), 3.13-3.26 (3H, m), 3.48 (1H, d, J=9.4 Hz), 3.74 (1H, dt, J$_1$=12.4 Hz, J$_2$=5.4 Hz), 4.24 (2H, d, J=6.3 Hz), 6.20-6.23 (1H, m), 6.37-6.39 (1H, m), 7.28 (1H, s), 7.66 (1H, t, J=6.3 Hz). LC-MS (ESI) calculated for C$_{23}$H$_{30}$N$_4$O$_6$S$_3$ 554.13. found 555.0 [M+H$^+$].

Example 66

(rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-thieno e][1,2,4]thiadiazin-7-ylmethyl}-methanesulfonamide

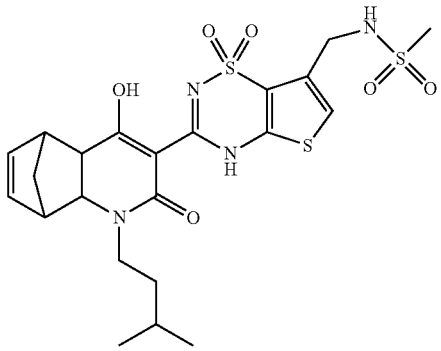

(rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide (0.015 g, 0.028 mmol, 14%) was prepared as described in general procedure 2. $^1$H NMR (400 MHz, DMSO-d$_6$) δ: 0.92 (6H, d, J=6.2 Hz), 1.34-1.62 (5H, m), 2.78-2.85 (1H, m), 2.96 (3H, s), 3.12-3.26 (3H, m), 3.48 (1H, d, J=8.4 Hz), 3.72-3.81 (1H, m), 4.24 (2H, d, J=6.2 Hz), 6.20-6.22 (1H, m), 6.37-6.39 (1H, m), 7.28 (1H, s), 7.66 (1H, t, J=6.2 Hz). LC-MS (ESI) calculated for C$_{22}$H$_{28}$N$_4$O$_6$S$_3$ 540.12. found 541.1 [M+H$^+$].

Example 67

N-{3-[(1R,2S,7R,8S)-3-(3,3-Dimethyl-butyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

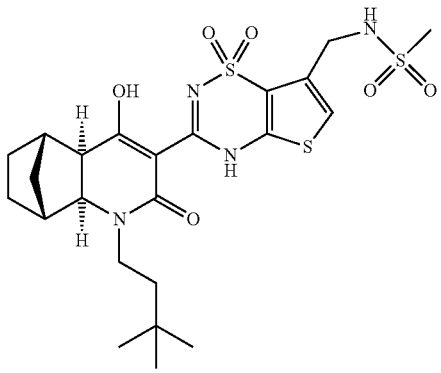

N-{3-[(1R,2S,7R,8S)-3-(3,3-Dimethyl-butyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.016 g, 0.028 mmol, 14%) was prepared as described in general procedure 2. $^1$H NMR (400 MHz, DMSO-d$_6$) δ: 0.93 (9H, s), 1.21-1.31 (2H, m), 1.37-1.63 (6H, m), 2.51-2.56 (1H, m), 2.58-2.64 (1H, m), 2.96-3.16 (5H, m), 3.60-3.67 (2H, m), 4.23 (2H, d, J=6.2 Hz), 7.28 (1H, s), 7.66 (1H, t, J=6.2 Hz). LC-MS (ESI) calculated for C$_{23}$H$_{32}$N$_4$O$_6$S$_3$ 556.15. found 557.1 [M+H$^+$].

Example 68

N-{3-[(1R,2S,7R,8S)-6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

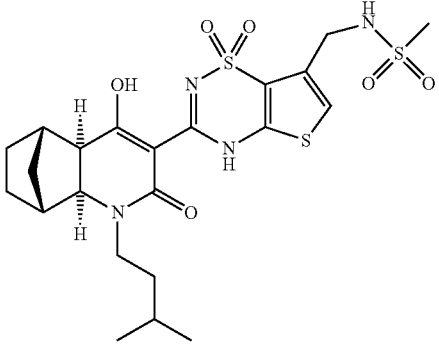

N-{3-[(1R,2S,7R,8S)-6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.014 g, 0.026 mmol, 13%) was prepared as described in general procedure 2. $^1$H NMR (400 MHz, DMSO-d$_6$) δ: 0.91 (6H, d, J=5.2 Hz), 1.20-1.66 (9H, m), 2.52-2.56 (1H, m), 2.61-2.63 (1H, m), 2.96-3.12 (5H, m), 3.61-3.68 (2H, m), 4.23 (2H, d, J=6.2 Hz), 7.28 (1H, s), 7.66 (1H, t, J=6.3 Hz). LC-MS (ESI) calculated for C$_{22}$H$_{30}$N$_4$O$_6$S$_3$ 542.13. found 543.0 [M+H$^+$].

Example 69

N-{3-[(1S,2S,7R,8R)-6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-thieno e][1,2,4]thiadiazin-7-ylmethyl}-methanesulfonamide

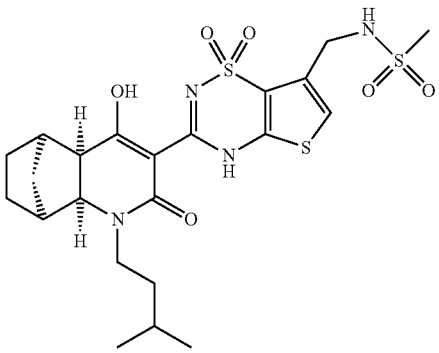

N-{3-[(1S,2S,7R,8R)-6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.021 g, 0.038 mmol, 19%) was prepared as described in general procedure 2. $^1$H NMR (400 MHz, DMSO-d$_6$) δ: 0.91 (6H, d, J=7.0 Hz), 1.23-1.35 (2H, m), 1.35-1.42 (4H, m), 1.50-1.62 (3H, m), 2.60-2.69 (2H, m), 2.95-3.03 (4H, m), 3.15-3.25 (1H, m), 3.61-3.68 (1H, m), 3.89 (1H, d, J=12.3 Hz), 4.24 (2H, d, J=6.3 Hz), 7.29 (1H, s), 7.66 (1H, t, J=6.2 Hz). LC-MS (ESI) calculated for C$_{22}$H$_{30}$N$_4$O$_6$S$_3$ 542.13. found 543.0 [M+H$^+$].

Example 70

N-{3-[(2S,7R)-6-Hydroxy-4-oxo-3-(3,4,5-trifluoro-benzyl)-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

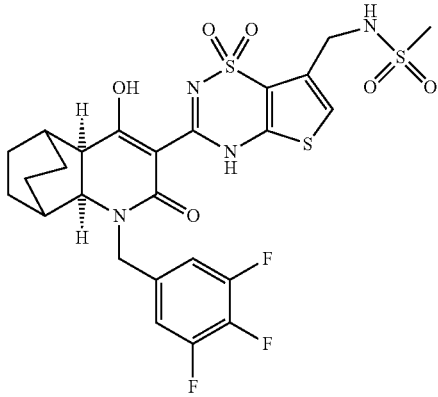

N-{3-[(2S,7R)-6-Hydroxy-4-oxo-3-(3,4,5-trifluoro-benzyl)-3-aza-tricyclo[6.2.2.0$^{2,7}$]dodec-5-en-5-yl]-dioxo-1,4-dihydro-1λ$^6$-thieno[2,3-e][1,2,4]thiadiazin-7-ylmethyl}-methanesulfonamide (0.026 g, 0.042 mmol, 21%) was prepared as described in general procedure 2. $^1$H NMR (400 MHz, DMSO-d$_6$) δ: 1.33-1.46 (2H, m), 1.49-1.60 (6H, m), 1.82-1.88 (1H, m), 2.10-2.16 (1H, m), 2.96 (3H, s), 3.22-3.27 (1H, m), 3.78 (1H, d, J=11.6 Hz), 4.24 (2H, d, J=6.3 Hz), 4.30 (1H, d, J=15.9 Hz), 4.92 (1H, d, J=16.2 Hz), 7.26-7.29 (3H, m), 7.67 (1H, t, J=6.2 Hz). LC-MS (ESI) calculated for C$_{25}$H$_{25}$F$_3$N$_4$O$_6$S$_3$ 630.09. found 631.1 [M+H$^+$].

Example 71

N-{3-[2S,7R)-6-Hydroxy-3-(3-methyl-butyl)-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

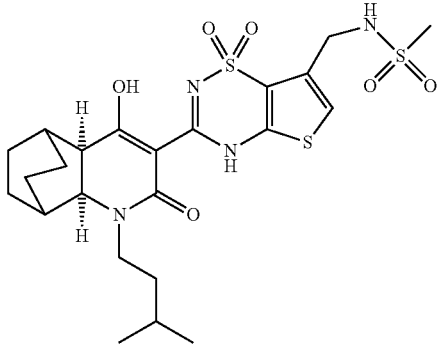

N-{3-[(2S,7R)-6-Hydroxy-3-(3-methyl-butyl)-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl]-methanesulfonamide (0.01 g, 0.018 mmol, 9%) was prepared as described in general procedure 2. $^1$H NMR (400 MHz, DMSO-d$_6$) δ: 0.90 (6H, d, J=6.2 Hz), 1.30-1.66 (11H, m), 1.82-1.90 (1H, m), 2.09-2.16 (1H, m), 2.96 (3H, s), 2.98-3.06 (1H, m), 3.21-3.30 (1H, m), 3.62-3.69 (1H, m), 3.85 (1H, d, J=12.5 Hz), 4.24 (2H, d, J=6.2 Hz), 7.29 (1H, s), 7.66 (1H, t, J=6.2 Hz). LC-MS (ESI) calculated for C$_{23}$H$_{32}$N$_4$O$_6$S$_3$ 556.15. found 557.0 [M+H$^+$].

General Procedure 3:

A mono- or bicyclic β-amino ester salt (selected from a list containing (1R,2S)-2-amino-cyclopentanecarboxylic acid ethyl ester hydrochloride (prepared as described in WO 2008/073982 A2); cis-2-amino-cyclohexanecarboxylic acid ethyl ester hydrochloride; cis-2-amino-cycloheptanecarboxylic acid methyl ester hydrochloride prepared as described in WO 2008/073982 A2; (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2); 0.5 mmol) and sodium acetate (0.082 g, 1 mmol) were combined and dissolved in methanol (4 mL). 2,4-Dimethoxy-benzaldehyde (0.083 g, 0.5 mmol) was added followed by sodium cyanoborohydride (0.062 g, 1 mmol). The mixture was shaken at 25° C. for 16 h. Saturated aqueous sodium bicarbonate solution (4 mL) was added and the mixture was shaken for 1 h.

The resulting suspension was partitioned between ethyl acetate (6 mL) and saturated aqueous sodium bicarbonate solution (6 mL). The organic phase was concentrated in vacuo to afford a thick oil. The oil was dissolved in N,N-dimethylformamide (2 mL) and [7-(methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.177 g, 0.5 mmol) was added followed by 1-(3-dimethylaminopropyl)-3-ethylcarbodiimide hydrochloride (144 g, 0.75 mmol. The mixture was shaken at 25° C. for 16 h. The mixture was diluted with ethyl acetate (10 mL) and washed with a 1.0 M aqueous hydrochloric acid solution (2×10 mL). The organic phase was concentrated in vacuo to afford an off white solid. The solid was suspended in ethanol (4 mL). A 21 wt. % solution of sodium ethoxide in ethanol (0.75 mL, 2 mmol) was added. The reaction stirred at 80° C. for 16 h. Upon cooling, 1.0 M aqueous hydrochloric acid solution (8 mL) was added and the mixture was shaken with dichloromethane (4 mL). The organic phase was directly purified by flash column chromatography (Teledyne Isco RediSep column; 5-100% ethyl acetate in hexanes) to afford the desired product.

Example 72

N-{3-[(1R,2S,7R,8S)-3-(2,4-Dimethoxy-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

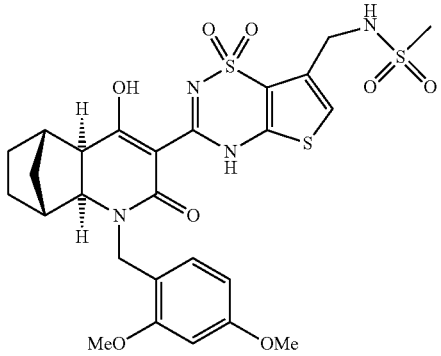

N-{3-[(1R,2S,7R,8S)-3-(2,4-Dimethoxy-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide (0.112 g, 0.18 mmol, 36%) was prepared as described in general procedure 3. ¹H NMR (400 MHz, DMSO-$d_6$) δ: 1.10-1.24 (2H, m), 1.38-1.63 (4H, m), 2.51-2.54 (1H, m), 2.61-2.64 (1H, m), 2.95-3.01 (4H, m), 3.49 (1H, d, J=9.5 Hz), 3.73 (3H, s), 3.79 (3H, s), 4.23-4.27 (3H, m), 4.85 (1H, d, J=15.8 Hz), 6.47 (1H, dd, $J_1$=8.4 Hz, $J_2$=2.3 Hz), 6.56 (1H, d, J=3.1 Hz), 7.06 (1H, d, J=8.3 Hz), 7.26 (1H, s), 7.65 (1H, t, J=6.2 Hz). LC-MS (ESI) calculated for $C_{26}H_{30}N_4O_8S_3$ 622.12. found 623.2 [M+H⁺].

Example 73

N-{3-[(1S,2S,7R,8R)-3-(2,4-Dimethoxy-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

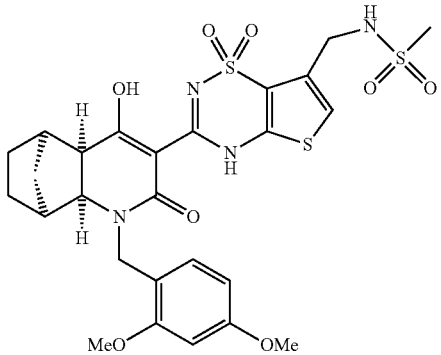

N-{3-[(1S,2S,7R,8R)-3-(2,4-Dimethoxy-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide (0.118 g, 0.19 mmol, 38%) was prepared as described in general procedure 3. ¹H NMR (400 MHz, DMSO-$d_6$) δ: 1.24-1.47 (6H, m), 2.60-2.71 (2H, m), 2.96 (3H, s), 3.19 (1H, d, J=8.7 Hz), 3.71 (1H, d, J=16.6 Hz), 3.73 (3H, s), 3.79 (3H, s), 3.93 (1H, d, J=14.1 Hz), 4.24 (2H, d, J=5.5 Hz), 5.05 (1H, d, J=15.0 Hz), 6.47 (1H, dd, $J_1$=8.7 Hz, $J_2$=2.5 Hz), 6.56 (1H, d, J=2.3 Hz), 7.12 (1H, d, J=8.3 Hz), 7.29 (1H, s), 7.66 (1H, t, J=6.2 Hz). LC-MS (ESI) calculated for $C_{26}H_{30}N_4O_8S_3$ 622.12. found 623.1 [M+H⁺].

Example 74

N-{3-[(2S,7R)-3-(2,4-Dimethoxy-benzyl)-6-hydroxy-4-oxo-3-aza-tricyclo[6.2.2.0²,⁷]dodec-5-en-5-yl]-1,1-dioxo-1,4-dihydro-1λ⁶-thieno[2,3-e][1,2,4]thiadiazin-7-ylmethyl}-methanesulfonamide

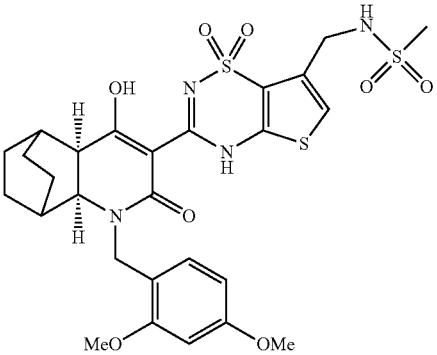

N-{3-[(2S,7R)-3-(2,4-Dimethoxy-benzyl)-6-hydroxy-4-oxo-3-aza-tricyclo[6.2.2.0²,⁷]dodec-5-en-5-yl]-1,1-dioxo-1,4-dihydro-1λ⁶-thieno[2,3-e][1,2,4]thiadiazin-7-ylmethyl}-methanesulfonamide (0.134 g, 0.21 mmol, 42%) was prepared as described in general procedure 3. ¹H NMR (400 MHz, DMSO-$d_6$) δ: 1.32-1.65 (8H, m), 1.91-1.95 (1H, m), 2.12-2.16 (1H, m), 2.96 (3H, s), 3.17-3.25 (1H, m), 3.70-3.73 (1H, m), 3.73 (3H, s), 3.78 (3H, s), 4.10 (1H, d, J=13.5 Hz), 4.24 (2H, d, J=5.4 Hz), 4.97 (1H, d, J=15.8 Hz), 6.47 (1H, dd, $J_1$=8.7 Hz, $J_2$=2.4 Hz), 6.55 (1H, d, J=2.4 Hz), 7.10 (1H, d, J=8.5 Hz), 7.29 (1H, s), 7.66 (1H, t, J=6.3 Hz). LC-MS (ESI) calculated for $C_{27}H_{32}N_4O_8S_3$ 636.14. found 637.1 [M+H⁺].

Example 75

(rac-di-exo)-N-{3-[3-(2,4-Dimethoxy-benzyl)-6-hydroxy-4-oxo-11-oxa-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

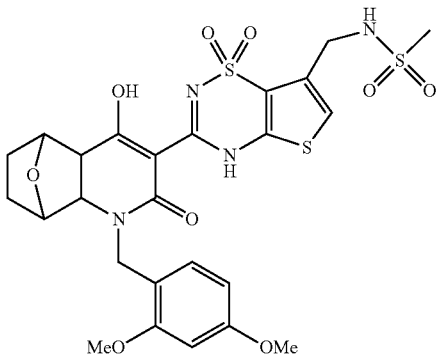

(rac-di-exo)-N-{3-[3-(2,4-Dimethoxy-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.072 g, 0.115 mmol, 23%) was prepared as described in general procedure 3. $^1$H NMR (400 MHz, DMSO-d$_6$) δ: 1.41-1.47 (1H, m), 1.56-1.73 (3H, m), 2.95 (3H, s), 3.27 (1H, d, J=9.3 Hz), 3.74 (3H, s), 3.75 (1H, d, J=10.1 Hz), 3.80 (3H, s), 4.23-4.29 (3H, m), 4.71-4.74 (2H, m), 4.90 (1H, d, J=15.3 Hz), 6.49 (1H, dd, J$_1$=8.7 Hz, J$_2$=2.4 Hz), 6.57 (1H, d, J=2.4 Hz), 7.10 (1H, d, J=8.4 Hz), 7.28 (1H, s), 7.66 (1H, t, J=6.2 Hz). LC-MS (ESI) calculated for C$_{25}$H$_{28}$N$_4$O$_9$S$_3$ 624.10. found 624.9 [M+H$^+$].

Example 76

(rac-di-exo)-N-{3-[3-(2,4-Dimethoxy-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide

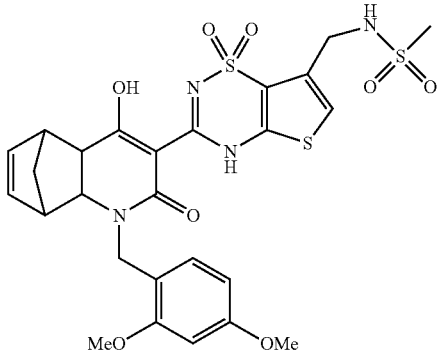

(rac-di-exo)-N-{3-[3-(2,4-Dimethoxy-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-thieno[2,3-e][1,2,4]thiadiazin-7-ylmethyl}-methanesulfonamide (0.109 g, 0.175 mmol, 35%) was prepared as described in general procedure 3. $^1$H NMR (400 MHz, DMSO-d$_6$) δ: 1.38 (1H, d, J=9.4 Hz), 1.64 (1H, d, J=9.3 Hz), 2.82 (1H, d, J=8.6 Hz), 2.96 (3H, s), 3.22-3.27 (2H, m), 3.37 (1H, d, J=9.3 Hz), 3.73 (3H, s), 3.81 (3H, s), 4.24 (2H, d, J=5.4 Hz), 4.35 (1H, d, J=15.7 Hz), 4.94 (1H, d, J=14.9 Hz), 6.13-6.15 (1H, m), 6.33-6.35 (1H, m), 6.46 (1H, dd, J$_1$=8.5 Hz, J$_2$=2.4 Hz), 6.56 (1H, d, J=2.3 Hz), 7.07 (1H, d, J=8.6 Hz), 7.28 (1H, s), 7.66 (1H, t, J=6.3 Hz). LC-MS (ESI) calculated for C$_{26}$H$_{28}$N$_4$O$_8$S$_3$ 620.11. found 621.1 [M+H$^+$].

Example 77

(4aR,7aS)-N-{3-[1-(2,4-Dimethoxy-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

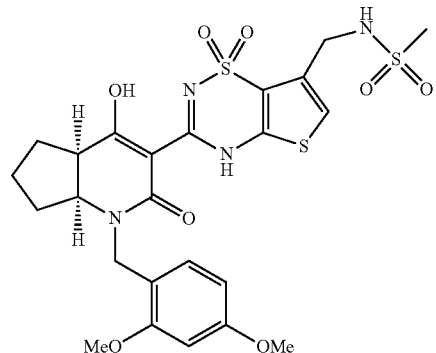

(4aR,7aS)-N-{3-[1-(2,4-Dimethoxy-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide (0.125 g, 0.21 mmol, 42%) was prepared as described in general procedure 3. $^1$H NMR (400 MHz, DMSO-d$_6$) δ: 1.45-1.60 (3H, m), 1.93-2.14 (3H, m), 2.96 (3H, s), 3.23-3.36 (1H, m), 3.74 (3H, s), 3.80 (3H, s), 3.81-3.84 (1H, m), 4.24 (2H, d, J=6.3 Hz), 4.31 (1H, d, J=18.9 Hz), 4.82 (1H, d, J=14.8 Hz), 6.48 (1H, dd, J$_1$=8.4 Hz, J$_2$=2.0 Hz), 6.57 (1H, d, J=2.3 Hz), 7.12 (1H, d, J=8.1 Hz), 7.26 (1H, s), 7.66 (1H, t, J=6.3 Hz). LC-MS (ESI) calculated for C$_{24}$H$_{28}$N$_4$O$_8$S$_3$ 596.11. found 597.1 [M+H$^+$].

Example 78

(rac-cis)-N-{3-[1-(2,4-Dimethoxy-benzyl)-4-hydroxy-2-oxo-1,2,4a,5,6,7,8,8a-octahydro-quinolin-3-yl]-1,1-dioxo-1,4-dihydro-1λ$^6$-thieno[2,3-e][1,2,4]thiadiazin-7-ylmethyl}-methanesulfonamide

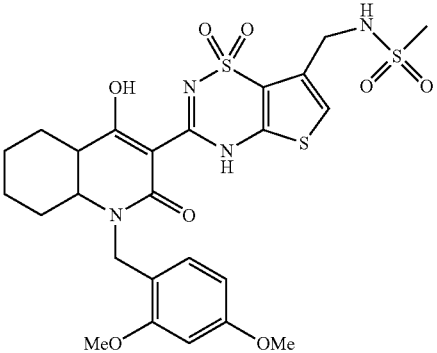

(rac-cis)-N-{3-[1-(2,4-Dimethoxy-benzyl)-4-hydroxy-2-oxo-1,2,4a,5,6,7,8,8a-octahydro-quinolin-3-yl]-1,1-dioxo-1,4-dihydro-1λ$^6$-thieno[2,3-e][1,2,4]thiadiazin-7-ylmethyl}-methanesulfonamide (0.086 g, 0.14 mmol, 28%) was prepared as described in general procedure 3. $^1$H NMR (400 MHz, DMSO-d$_6$) δ: 1.14-1.47 (6H, m), 1.63-1.81 (2H, m), 2.31 (1H, d, J=12.3 Hz), 2.95 (3H, s), 3.53-3.62 (1H, m), 3.74 (3H, s), 3.81 (3H, s), 4.16-4.23 (1H, m), 4.24 (2H, d, J=6.1 Hz), 4.86 (1H, d, J=15.5 Hz), 6.44-6.49 (1H, m), 6.55-6.57 (1H, m), 7.16 (1H, d, J=7.6 Hz), 7.24 (1H, s), 7.64 (1H, t, J=6.1 Hz). LC-MS (ESI) calculated for C$_{25}$H$_{30}$N$_4$O$_8$S$_3$ 610.12. found 611.1 [M+H$^+$].

Example 79

(rac-cis)-N-{3-[1-(2,4-Dimethoxy-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide

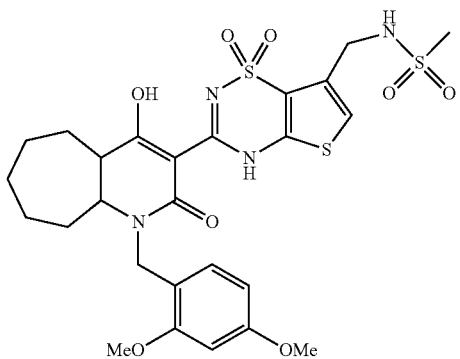

(rac-cis)-N-{3-[1-(2,4-Dimethoxy-benzyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-thieno[2,3-e][1,2,4]thiadiazin-7-ylmethyl}-methanesulfonamide (0.05 g, 0.08 mmol, 16%) was prepared as described in general procedure 3. $^1$H NMR (400 MHz, DMSO-d$_6$) δ: 1.20-1.40 (4H, m), 1.61-1.79 (6H, m), 1.92-1.98 (1H, m), 2.94 (3H, s), 3.48-3.55 (1H, m), 3.74 (3H, s), 3.81 (3H, s), 4.05-4.15 (1H, m), 4.23 (2H, d, J=5.4 Hz), 4.89 (1H, d, J=14.7 Hz), 6.49 (1H, dd, J$_1$=8.5 Hz, J$_2$=2.3 Hz), 6.57 (1H, d, J=2.5 Hz), 7.15-7.17 (2H, m), 7.59 (1H, s). LC-MS (ESI) calculated for C$_{26}$H$_{32}$N$_4$O$_8$S$_3$ 624.14. found 625.0 [M+H$^+$].

General Procedure 4:

The 2,4-dimethoxy benzyl protected pyridinone compound (prepared as described in general procedure 3, Examples 72-79; 0.1 mmol) was dissolved in mixture of 30% trifluoroacetic acid in dichloromethane (2 mL). The solution was shaken at 25° C. for 2 h. Methanol (4 mL) was added and immediate precipitation was observed. The solid was removed by vacuum filtration and discarded. The filtrate was concentrated in vacuo and the residue was triturated with diethyl ether, filtered and dried in vacuo to afford the desired product.

Example 80

N-[3-((1R,2S,7R,8S)-6-Hydroxy-4-oxo-3-aza-tricyclo[6.2.1.0$^{2,7}$]undec-5-en-5-yl)-1,1-dioxo-1,4-dihydro-1$\lambda^6$-thieno e][1,2,4]thiadiazin-7-ylmethyl]-methanesulfonamide

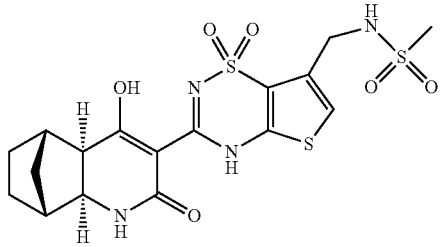

N-[3-((1R,2S,7R,8S)-6-Hydroxy-4-oxo-3-aza-tricyclo[6.2.1.0$^{2,7}$]undec-5-en-5-yl)-1,1-dioxo-1,4-dihydro-1$\lambda^6$-thieno[2,3-e][1,2,4]thiadiazin-7-ylmethyl]-methanesulfonamide (0.005 g, 0.0108 mmol, 6%) was prepared as described in general procedure 4. $^1$H NMR (400 MHz, DMSO-d$_6$) δ: 1.20-1.25 (2H, m), 1.34-1.62 (4H, m), 2.22-2.32 (1H, m), 2.52-2.61 (1H, m), 2.95 (3H, s), 3.29-3.42 (1H, m), 3.53-3.66 (1H, m), 4.23 (2H, d, J=6.2 Hz), 7.26 (1H, s), 7.66 (1H, t, J=6.3 Hz). LC-MS (ESI) calculated for C$_{17}$H$_{20}$N$_4$O$_6$S$_3$ 472.05. found 472.9 [M+H$^+$].

Example 81

N-[3-((1S,2S,7R,8R)-6-Hydroxy-4-oxo-3-aza-tricyclo[6.2.1.0$^{2,7}$]undec-5-en-5-yl)-1,1-dioxo-1,4-dihydro-1$\lambda^6$-thieno e][1,2,4]thiadiazin-7-ylmethyl]-methanesulfonamide

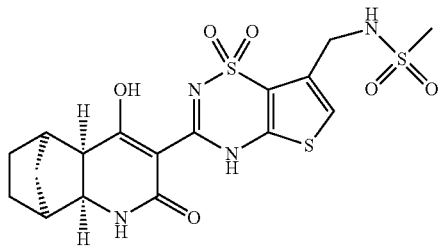

N-[3-((1S,2S,7R,8R)-6-Hydroxy-4-oxo-3-aza-tricyclo[6.2.1.0$^{2,7}$]undec-5-en-5-yl)-1,1-dioxo-1,4-dihydro-1$\lambda^6$-thieno[2,3-e][1,2,4]thiadiazin-7-ylmethyl]-methanesulfonamide (0.008 g, 0.0171 mmol, 9%) was prepared as described in general procedure 4. $^1$H NMR (400 MHz, DMSO-d$_6$) δ: 1.18-1.25 (2H, m), 1.35-1.50 (4H, m), 2.38 (1H, bs), 2.64 (1H, bs), 2.96 (3H, s), 3.46 (1H, bs), 3.79 (1H, bs), 4.24 (2H, d, J=6.3 Hz), 7.26 (1H, s), 7.66 (1H, t, J=6.3 Hz). LC-MS (ESI) calculated for C$_{17}$H$_{20}$N$_4$O$_6$S$_3$ 472.05. found 473.0 [M+H$^+$].

Example 82

N-[3-((2S,7R)-6-Hydroxy-4-oxo-3-aza-tricyclo[6.2.2.0$^{2,7}$]dodec-5-en-5-yl)-1,1-dioxo-1,4-dihydro-1$\lambda^6$-thieno[2,3-e][1,2,4]thiadiazin-7-ylmethyl]-methanesulfonamide

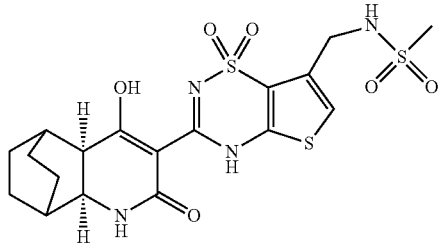

N-[3-((2S,7R)-6-Hydroxy-4-oxo-3-aza-tricyclo[6.2.2.0$^{2,7}$]dodec-5-en-5-yl)-1,1-dioxo-1,4-dihydro-1$\lambda^6$-thieno[2,3-e][1,2,4]thiadiazin-7-ylmethyl]-methanesulfonamide (0.005 g, 0.01092 mmol, 5.2%) was prepared as described in general procedure 4. $^1$H NMR (400 MHz, DMSO-d$_6$) δ: 1.29-1.72 (9H, m), 1.98-2.12 (1H, m), 2.95 (3H, s), 3.25-3.40 (1H, m), 3.77-3.99 (1H, m), 4.24 (2H, d, J=6.2 Hz), 7.25 (1H, s), 7.65 d, J=8.6 Hz), 7.28 (1H, s), 7.66 (1H, t, J=6.3 Hz). LC-MS (ESI) calculated for C$_{26}$H$_{28}$N$_4$O$_8$S$_3$ 620.11. found 621.1 [M+H$^+$].

(1H, t, J=6.3 Hz). LC-MS (ESI) calculated for $C_{18}H_{22}N_4O_6S_3$ 486.07. found 487.0 [M+H$^+$].

Example 83

(rac-di-exo)-N-[3-(6-Hydroxy-4-oxo-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

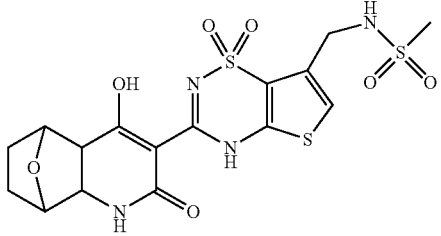

(rac-di-exo)-N-[3-(6-Hydroxy-4-oxo-11-oxa-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.002 g, 0.0046 mmol, 4%) was prepared as described in general procedure 4. $^1$H NMR (400 MHz, DMSO-d$_6$) δ: 1.17-1.75 (4H, m), 2.95 (3H, s), 3.18-3.32 (2H, m), 3.61-3.86 (2H, m), 4.21 (2H, d, J=6.2 Hz), 7.22 (1H, s), 7.62-7.66 (1H, m). LC-MS (ESI) calculated for $C_{16}H_{18}N_4O_7S_3$ 474.03. found 475.3 [M+H$^+$].

Example 84

(rac-di-exo)-N-[3-(6-Hydroxy-4-oxo-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide

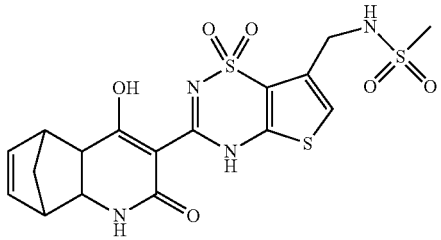

(rac-di-exo)-N-[3-(6-Hydroxy-4-oxo-3-aza-tricyclo[6.2.1.0$^{2,7}$]undeca-5,9-dien-5-yl)-1,1-dioxo-1,4-dihydro-1λ$^6$-thieno[2,3-e][1,2,4]thiadiazin-7-ylmethyl]-methanesulfonamide (0.004 g, 0.009275 mmol, 5.3%) was prepared as described in general procedure 4. $^1$H NMR (400 MHz, DMSO-d$_6$) δ: 1.33-1.44 (1H, m), 1.48-1.56 (1H, m), 2.59-2.72 (1H, m), 2.96 (3H, s), 2.97-3.01 (1H, m), 3.16-3.25 (1H, m), 3.45 (1H, d, J=8.6 Hz), 4.24 (2H, d, J=6.3 Hz), 6.15-6.17 (1H, m), 6.37-6.39 (1H, m), 7.26 (1H, s), 7.66 (1H, t, J=6.2 Hz). LC-MS (ESI) calculated for $C_{17}H_{18}N_4O_6S_3$ 470.04. found 471.0 [M+H$^+$].

Example 85

(4aR,7aS)-N-[3-(4-Hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide

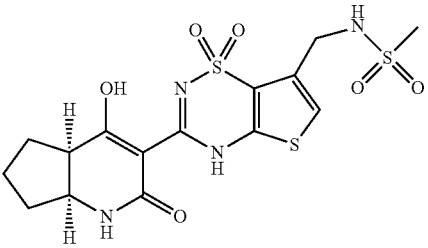

(4aR,7aS)-N-[3-(4-Hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide (0.007 g, 0.0147 mmol, 7%) was prepared as described in general procedure 4. $^1$H NMR (400 MHz, DMSO-d$_6$) δ: 1.60-1.74 (2H, m), 1.77-1.93 (3H, m), 1.98-2.15 (1H, m), 2.78-2.90 (1H, m), 2.95 (3H, s), 3.99-4.03 (1H, m), 4.23 (2H, d, J=6.3 Hz), 7.24 (1H, s), 7.65 (1H, t, J=6.2 Hz). LC-MS (ESI) calculated for $C_{15}H_{18}N_4O_6S_3$ 446.04. found 446.9 [M+H$^+$].

Example 86

(rac-cis)-N-[3-(4-Hydroxy-2-oxo-1,2,4a 5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide

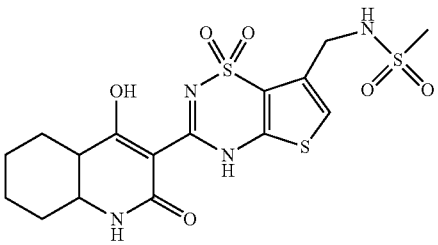

(rac-cis)-N-[3-(4-Hydroxy-2-oxo-1,2,4a,5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide (0.003 g, 0.007 mmol, 5%) was prepared as described in general procedure 4. $^1$H NMR (400 MHz, DMSO-d$_6$) δ: 1.23-1.58 (6H, m), 1.73-1.79 (2H, m), 2.64-2.66 (1H, m), 2.95 (3H, s), 3.69-3.78 (1H, m), 4.23 (2H, d, J=6.3 Hz), 7.24 (1H, s), 7.65 (1H, t, J=6.2 Hz). LC-MS (ESI) calculated for $C_{16}H_{20}N_4O_6S_3$ 460.05. found 461.0 [M+H$^+$].

Example 87

(rac-cis)-N-[3-(4-Hydroxy-2-oxo-2,4a,5,6,7,8,9,9a-octahydro-1H-cyclohepta[b]pyridin-3-yl)-1,1-dioxo-1,4-dihydro-1λ⁶-thieno e][1,2,4]thiadiazin-7-ylmethyl}-methanesulfonamide

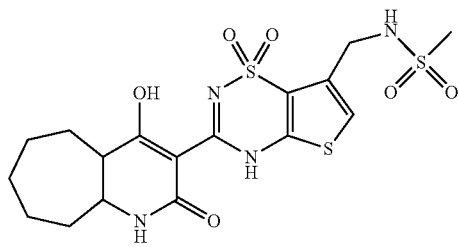

(rac-cis)-N-[3-(4-Hydroxy-2-oxo-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl}-methanesulfonamide (0.003 g, 0.00736 mmol, 9.2%) was prepared as described in general procedure 4. $^1$H NMR (400 MHz, DMSO-d$_6$) δ: 1.32-1.53 (4H, m), 1.54-1.85 (6H, m), 2.67-2.70 (1H, m), 2.95 (3H, s), 3.86-3.90 (1H, m), 4.23 (2H, d, J=6.3 Hz), 7.24 (1H, s), 7.65 (1H, t, J=6.3 Hz). LC-MS (ESI) calculated for $C_{17}H_{22}N_4O_6S_3$ 474.07. found 474.9 [M+H$^+$].

General Procedure 5:

A mixture of a bicyclic β-amino ester salt (selected form a list containing (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2); 1.0 mmol) with an aldehyde (1.0 mmol), sodium cyanoborohydride (2.0 mmol) and 4 Å molecular sieves (200 mg) were mixed in 15 mL of ethanol (or methanol dependent on the bicyclic β-amino ester salt used) for 16 h after which time the solvent was removed in vacuo. The mixture was then re-dissolved in 1.0 M aqueous sodium hydroxide solution (15 mL) and extracted two times with diethyl ether. The organic layers were combined, dried with sodium sulfate, filtered and concentrated in vacuo.

The crude material was purified by flash column chromatography (Teledyne Isco RediSep column; 0-30% ethyl acetate in hexanes) to afford the N-substituted bicyclic β-amino ester intermediate. 1-(3-Dimethylaminopropyl)-3-ethylcarbodiimide hydrochloride (0.424 mmol) was added to a solution containing [7-(methanesulfonyl-amino-methyl)-1,1-dioxo-1,4-dihydro-1λ⁶-thieno[2,3-e][1,2,4]thiadiazin-3-yl]-acetic acid (prepared as described in Example 2c; 0.282 mmol) and the N-substituted bicyclic β-amino ester intermediate (0.282 mmol) in N,N-dimethylformamide (4 mL) and allowed to stir at 25° C. for 16 h. Triethylamine (1.69 mmol) was added and the mixture was stirred at 70° C. for 16 h. Upon cooling to 25° C., the mixture was concentrated in vacuo to a thick oil. The oil was partitioned between dichloromethane (2 mL) and 1.0 M aqueous hydrochloric acid solution (6 mL). The organic phase was loaded directly onto a prepacked RediSep silica gel column and purified by flash column chromatography (Teledyne Isco RediSep column; 20-100% ethyl acetate in hexanes) to afford the desired final product.

Example 88

N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ⁶-thieno[2,3-e][1,2,4]thiadiazin-7-ylmethyl}-methanesulfonamide

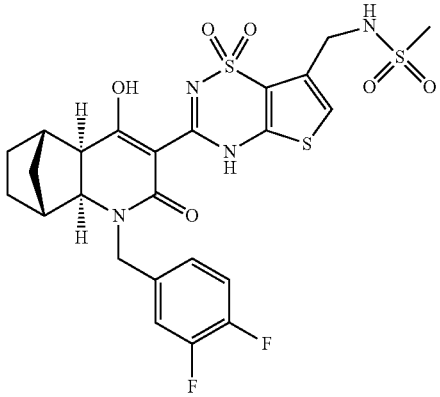

N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ⁶-thieno[2,3-e][1,2,4]thiadiazin-7-ylmethyl}-methanesulfonamide (0.112 g, 0.1866 mmol, 19%) was prepared as described in general procedure 5. $^1$H NMR (400 MHz, Acetone-d$_6$) δ: 1.28-1.34 (2H, m), 1.48-1.75 (4H, m), 2.60-2.60 (1H, m), 2.76 (1H, d, J=2.3 Hz), 2.97 (3H, s), 3.07 (1H, d, J=9.3 Hz), 3.73 (1H, d, J=9.3 Hz), 4.45 (1H, d, J=6.4 Hz), 4.52 (1H, d, J=15.6 Hz), 5.03 (1H, d, J=15.6 Hz), 6.43 (1H, t, J=6.3 Hz), 7.20-7.36 (4H, m). LC-MS (ESI) calculated for $C_{24}H_{24}F_2N_4O_6S_3$ 598.08. found 599.4 [M+H$^+$].

Example 89

N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ⁶-thieno[2,3-e][1,2,4]thiadiazin-7-ylmethyl}-methanesulfonamide

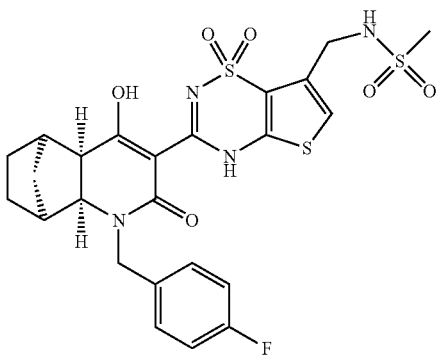

N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.042 g, 0.0727 mmol, 7%) was prepared as described in general procedure 5. $^1$H NMR (400 MHz, Acetone-d$_6$) δ: 1.40-1.59 (6H, m), 2.77-2.79 (H, m), 2.97 (H, s), 3.24-3.28 (H, m), 3.89 (1H, dd, J$_1$=12.5 Hz, J$_2$=3.2 Hz), 4.16 (1H, d, J=15.0 Hz), 4.46 (2H, d, J=7.9 Hz), 5.23 (1H, d, J=15.0 Hz), 6.44 (1H, t, J=6.3 Hz), 7.08 (2H, t, J=9.0 Hz), 7.37 (1H, s), 7.42-7.45 (2H, m). LC-MS (ESI) calculated for C$_{24}$H$_{25}$FN$_4$O$_6$S$_3$ 580.09. und 581.2 [M+H$^+$].

Example 90

(rac-di-exo)-N-{3-[3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide

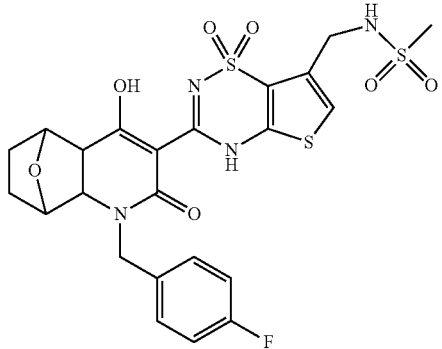

(rac-di-exo)-N-{3-[3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.049 g, 0.0839 mmol, 8%) was prepared as described in general procedure 5. $^1$H NMR (400 MHz, Acetone-d$_6$) δ: 1.60-1.82 (4H, m), 2.97 (3H, s), 3.33-3.35 (1H, m), 3.98 (1H, d, J=9.3 Hz), 4.44-4.49 (2H, m), 4.82 (2H, dd, J$_1$=34.4 Hz, J$_2$=3.9 Hz), 5.17 (1H, d, J=15.5 Hz), 6.43 (1H, t, J=6.4 Hz), 7.07-7.11 (2H, m), 7.37-7.41 (3H, m). LC-MS (ESI) calculated for C$_{23}$H$_{23}$FN$_4$O$_7$S$_3$ 582.07. found 582.9 [M+H$^+$].

Example 91

N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

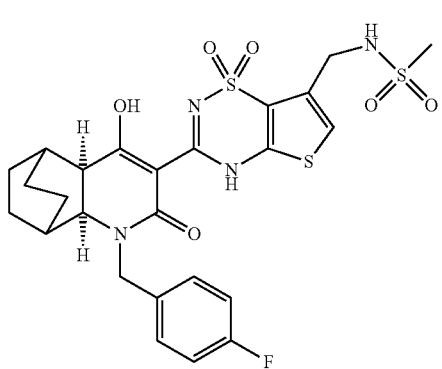

N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide (0.112 g, 0.1890 mmol, 19%) was prepared as described in general procedure 5. $^1$H NMR (400 MHz, Acetone-d$_6$) δ: 1.45-1.70 (8H, m), 2.01 (1H, m), 2.24 (1H, m), 3.27-3.30 (1H, m), 3.91 (1H, d, J=11.7 Hz), 4.32 (1H, d, J=15.6 Hz), 4.45 (2H, d, J=5.3 Hz), 5.16 (1H, d, J=15.8 Hz), 6.43 (1H, t, J=6.2 Hz), 7.07 (2H, t, J=8.7 Hz), 7.36-7.42 (3H, m). LC-MS (ESI) calculated for C$_{25}$H$_{27}$FN$_4$O$_6$S$_3$ 594.11. found 595.1 [M+H$^+$].

Example 92

N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl]-methanesulfonaide

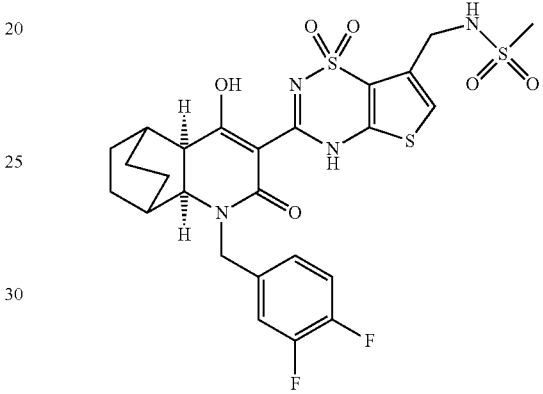

N-{3-[(2S,7R)-3-(3,4-Difluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide (0.123 g, 0.1999 mmol, 20%) was prepared as described in general procedure 5. $^1$H NMR (400 MHz, Acetone-d$_6$) δ: 1.46-1.69 (8H, m), 1.99 (1H, m), 2.25 (1H, m), 2.97 (3H, s), 3.31-3.34 (1H, m), 3.96 (1H, d, J=11.7 Hz), 4.38 (1H, d, J=15.7 Hz), 4.46 (2H, d, J=6.3 Hz), 5.10 (1H, d, J=15.6 Hz), 6.43 (1H, t, J=6.2 Hz), 7.20-7.36 (4H, m). LC-MS (ESI) calculated for C$_{25}$H$_{26}$F$_2$N$_4$O$_6$S$_3$ 612.1. found 613.3 [M+H$^+$].

Example 93

N-{3-[(2S,7R)-3-(3,3-Dimethyl-butyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide

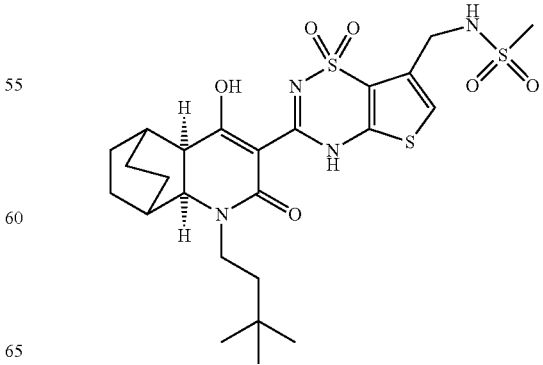

N-{3-[(2S,7R)-3-(3,3-Dimethyl-butyl)-6-hydroxy-4-oxo-3-aza-tricyclo[6.2.2.0²,⁷]dodec-5-en-5-yl]-1,1-dioxo-1,4-dihydro-1λ⁶-thieno[2,3-e][1,2,4]thiadiazin-7-ylmethyl}-methanesulfonamide (0.114 g, 0.2003 mmol, 20%) was prepared as described in general procedure 5. $^1$H NMR (400 MHz, Acetone-$d_6$) δ: 0.96 (9H, s), 1.46-1.71 (10H, m), 1.96 (2H, s), 2.24 (1H, m), 2.97 (3H, s), 3.11-3.30 (1H, m), 3.73-3.81 (1H, m), 3.98-4.01 (1H, m), 4.45 (2H, d, J=6.1 Hz), 6.42 (1H, t, J=6.3 Hz), 7.35 (1H, s). LC-MS (ESI) calculated for $C_{24}H_{34}N_4O_6S_3$ 570.16. found 571.4 [M+H$^+$].

General Procedure 6:

To a solution of a bicyclic β-amino ester salt (selected from a list containing (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2); 1.0 mmol) and a benzyl bromide (1.0 mmol) in N,N-dimethylformamide (15 mL), triethylamine was added to the mixture and stirred at 70° C. for 16 h. After which time the solvent was removed in vacuo. The mixture was then re-dissolved in 1.0 M aqueous sodium hydroxide solution (15 mL) and extracted two times with diethyl ether (15 mL). The organic layers were combined, dried with sodium sulfate, filtered and concentrated in vacuo.

The crude material was purified by flash column chromatography (Teledyne Isco RediSep column; 0-30% ethyl acetate in hexanes) to afford the N-substituted bicyclic β-amino ester intermediate. 1-(3-Dimethylamino-propyl)-3-ethylcarbodiimide hydrochloride (0.424 mmol) was added to a solution containing [7-(methanesulfonyl-amino-methyl)-1,1-dioxo-1,4-dihydro-1λ⁶-thieno[2,3-e][1,2,4]thiadiazin-3-yl]-acetic acid (prepared as described in Example 2c; 0.282 mmol) and the N-substituted bicyclic β-amino ester intermediate (0.282 mmol) in N,N-dimethylformamide (4 mL) and allowed to stir at 25° C. for 16 h. Triethylamine (1.69 mmol) was added and the mixture was stirred at 70° C. for 16 h. Upon cooling to 25° C., the mixture was concentrated in vacuo to a thick oil. The oil was partitioned between dichloromethane (2 mL) and 1.0 M aqueous hydrochloric acid solution (6 mL). The organic phase was loaded directly onto a prepacked RediSep silica gel column and purified by flash column chromatography (Teledyne Isco RediSep column; 20-100% ethyl acetate in hexanes) to afford the desired final product.

Example 94

N-{3-[(1R,2S,7R,8S)-3-(2-Chloro-4-fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

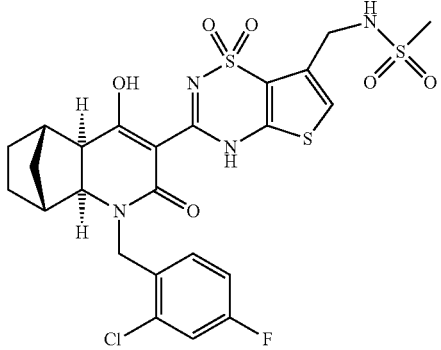

N-{3-[(—R,2S,7R,8S)-3-(2-Chloro-4-fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide (0.073 g, 0.1190 mmol, 12%) was prepared as described in general procedure 6. $^1$H NMR (400 MHz, Acetone-$d_6$) δ: 1.30-1.34 (2H, m), 1.50-1.81 (4H, m), 2.61-2.61 (1H, m), 2.79-2.79 (1H, m), 2.97 (3H, s), 3.11 (1H, d, J=8.8 Hz), 3.74 (1H, d, J=9.5 Hz), 4.45 (2H, d, J=6.2 Hz), 4.57 (1H, d, J=15.4 Hz), 5.04 (1H, d, J=16.3 Hz), 6.43 (1H, t, J=6.2 Hz), 7.07-7.12 (1H, m), 7.30 (1H,dd, $J_1$=8.6 Hz, $J_2$=2.5 Hz), 7.36 (H, s), 7.44 (1H, dd, $J_1$=8.3 Hz, $J_2$=6.4 Hz). LC-MS (ESI) calculated for $C_{24}H_{24}ClFN_4O_6S_3$ 614.05. found 615.4 [M+H$^+$].

Example 95

N-{3-[(1S,2S,7R,8R)-3-(3 Chloro-4-fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

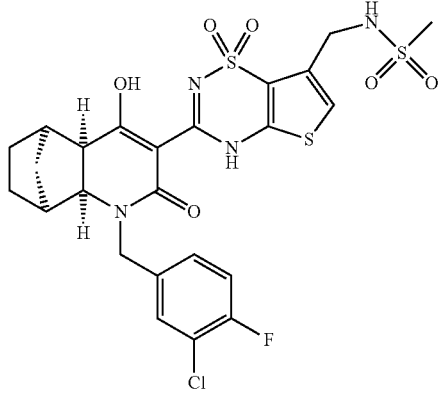

N-{3-[(1 S,2S,7R,8R)-3-(3-Chloro-4-fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide (0.127 g, 0.2069 mmol, 21%) was prepared as described in general procedure 6. $^1$H NMR (400 MHz, Acetone-$d_6$) δ: 1.36-1.59 (6H, m), 2.79-2.79 (2H, m), 2.97 (3H, s), 3.25-3.30 (1H, m), 3.94 (1H, dd, $J_1$=12.8 Hz, $J_2$=3.7 Hz), 4.20 (1H, d, J=14.8 Hz), 4.45 (2H, d, J=5.3 Hz), 5.20 (1H, d, J=15.3 Hz), 6.43 (1H, t, J=6.1 Hz), 7.25 (1H, t, J=9.0 Hz), 7.37 (1H, s), 7.39-7.43 (1H, m), 7.56 (1H, dd, $J_1$=7.0 Hz, $J_2$=2.3 Hz). LC-MS (E [M+H$^+$].

Example 96

N-{3-[(2S,7R)-3-(2-Chloro-4-fluoro-benzyl)-6-hydroxy-4-oxo-3-aza-tricyclo[6.2.2.0²,⁷]dodec-5-en-5-yl]-1,1-dioxo-1,4-dihydro-1λ⁶-thieno[2,3-e][1,2,4]thiadiazin-7-ylmethyl}-methanesulfonamide

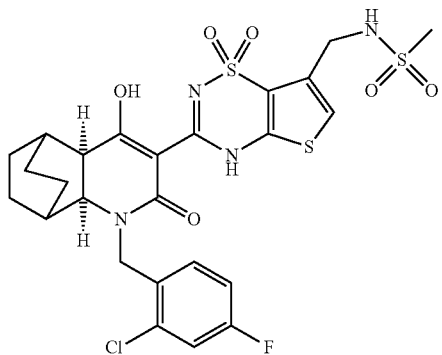

N-{3-[(2S,7R)-3-(2-Chloro-4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide (0.097 g, 0.1534 mmol, 15%) was prepared as described in general procedure 6. $^1$H NMR (400 MHz, Acetone-d$_6$) δ: 1.44-1.78 (6H, m), 1.96 (2H, s), 1.98 (1H, m), 2.28-2.29 (1H, m), 2.97 (3H, s), 3.38-3.41 (1H, m), 3.95 (1H, d, J=12.5 Hz), 4.39 (1H, d, J=16.7 Hz), 4.45 (2H, d, J=5.5 Hz), 5.16 (1H, d, J=16.5 Hz), 6.43 (1H, t, J=6.3 Hz), 7.07-7.11 (1H, m), 7.27-7.28 (1H, m), 7.27-7.30 (1H, m), 7.36 (1H, s), 7.46-7.49 (1H, m). LC-MS (ESI) calculated for C$_{25}$H$_{26}$ClFN$_4$O$_6$S$_3$ 628.07. found 629.4 [M+H$^+$].

General Procedure 7:

A mixture of a mono- or bicyclic β-amino ester salt (selected from a list containing (1R,2S)-2-amino-cyclopentanecarboxylic acid ethyl ester hydrochloride (prepared as described in WO 2008/073982 A2); cis-2-amino-cyclohexanecarboxylic acid ethyl ester hydrochloride; cis-2-amino-cycloheptanecarboxylic acid methyl ester hydrochloride prepared as described in WO 2008/073982 A2; (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2); 0.455 mmol) with cyclohexanone (0.455 mmol), sodium cyanoborohydride (1.37 mmol) and 4 Å molecular sieves (100 mg) were mixed in 6 mL of ethanol (or methanol dependent on the mono- or bicyclic β-amino ester salt used) for 16 h after which time the solvent was removed in vacuo. The mixture was then re-dissolved in 1.0 M aqueous sodium hydroxide solution (4 mL) and extracted two times with diethyl ether (4 mL).

The organic layers were combined, dried with sodium sulfate, filtered and concentrated in vacuo to afford the N-substituted mono- or bicyclic β-amino ester intermediate. 1-(3-Dimethylaminopropyl)-3-ethylcarbodiimide hydrochloride (0.273 mmol) was added to a solution containing [7-(methanesulfonyl-amino-methyl)-1,1-dioxo-1,4-dihydro-1λ$^6$-thieno[2,3-e][1,2,4]thiadiazin-3-yl]-acetic acid (prepared as described in Example 2c; 0.228 mmol) and the N-substituted mono- or bicyclic β-amino ester intermediate in N,N-dimethylformamide (4 mL) and allowed to stir at 25° C. for 5 h. Triethylamine (2.73 mmol) was added and the mixture was stirred at 70° C. for 16 h. Upon cooling to 25° C., the mixture was concentrated in vacuo to a thick oil. The oil was partitioned between dichloromethane (2 mL) and 1.0 M aqueous hydrochloric acid solution (6 mL). The organic phase was loaded directly onto a prepacked RediSep silica gel column and purified by flash column chromatography (Teledyne Isco RediSep column; 20-100% ethyl acetate in hexanes) to afford the desired final product.

Example 97

N-[3-((1R,2S,7R,8S)-3-Cyclohexyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

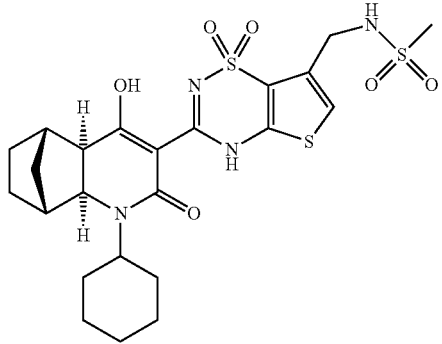

N-[3-((1R,2S,7R,8S)-3-Cyclohexyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.061 g, 0.1100 mmol, 48%) was prepared as described in general procedure 7. $^1$H NMR (400 MHz, Acetone-d$_6$) δ: 1.17-1.91 (16H, m), 2.12-2.21 (1H, m), 2.58 (1H, m), 2.70-2.71 (1H, m), 2.96 (3H, s), 3.55-3.60 (1H, m), 3.73 (1H, d, J=9.2 Hz), 4.44 (2H, d, J=6.2 Hz), 6.41 (1H, t, J=6.2 Hz), 7.33 (1H, s). LC-MS (ESI) calculated for C$_{23}$H$_{30}$N$_4$O$_6$S$_3$ 554.13. found 555.0 [M+H$^+$].

Example 98

N-[3-((1S,2S,7R,8R)-3-Cyclohexyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

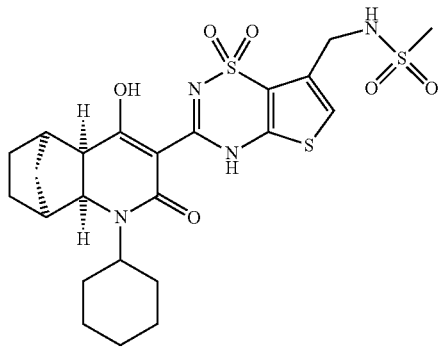

N-[3-((1S,2S,7R,8R)-3-Cyclohexyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.028 g, 0.0505 mmol, 21%) was prepared as described in general procedure 7. $^1$H NMR (400 MHz, Acetone-$d_6$) δ: 1.16-1.87 (16H, m), 2.70 (1H, m), 2.76 (1H, m), 2.97 (3H, s), 3.23-3.26 (1H, m), 3.76-3.82 (1H, m), 3.97-4.01 (1H, m), 4.44 (2H, d, J=5.3 Hz), 6.42 (1H, t, J=6.3 Hz), 7.35 (1H, s). LC-MS (ESI) calculated for $C_{23}H_{30}N_4O_6S_3$ 554.13. found 555.0 [M+H$^+$].

Example 99

(4aR,7aS)-N-[3-(1-Cyclohexyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide

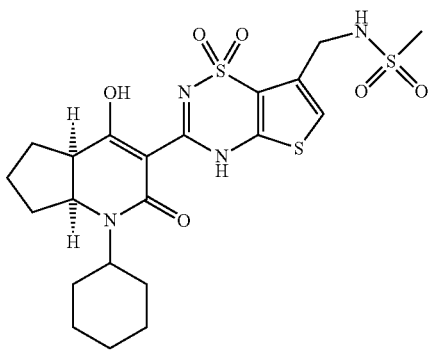

(4aR,7aS)-N-[3-(1-Cyclohexyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide (0.046 g, 0.0866 mmol, 33%) was prepared as described in general procedure 7. $^1$H NMR (400 MHz, Acetone-$d_6$) δ: 1.18-1.83 (14H, m), 2.11-2.16 (1H, m), 2.42 (1H, m), 2.97 (3H, s), 3.31 (1H, m), 4.05 (1H, m), 4.33 (1H, m), 4.44 (2H, d, J=6.2 Hz), 6.42 (1H, t, J=5.9 Hz), 7.34 (1H, s). LC-MS (ESI) calculated for $C_{21}H_{28}N_4O_6S_3$ 528.12. found 528.9 [M+H$^+$].

Example 100

(rac-cis)-N-[3-(1-Cyclohexyl-4-hydroxy-2-oxo-1,2,4a 5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide

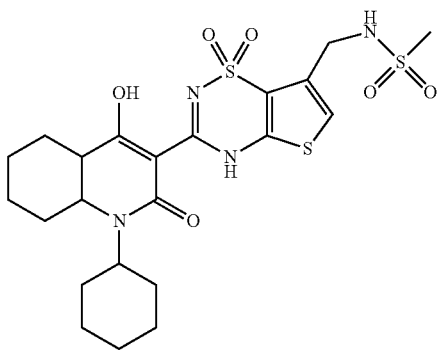

(rac-cis)-N-[3-(1-Cyclohexyl-4-hydroxy-2-oxo-1,2,4a,5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide (0.055 g, 0.1013 mmol, 42%) was prepared as described in general procedure 7. $^1$H NMR (400 MHz, Acetone-$d_6$) δ: 1.14-1.84 (16H, m), 2.43-2.46 (1H, m), 2.82 (1H, m), 2.96 (3H, s), 3.30 (1H, m), 3.74-3.93 (1H, m), 4.28 (1H, m), 4.44 (2H, d, J=6.2 Hz), 6.42 (1H, m), 7.34 (1H, s). LC-MS (ESI) calculated for $C_{22}H_{30}N_4O_6S_3$ 542.13. found 543.0 [M+H$^+$].

General Procedure 8:

A mixture of a mono- or bicyclic β-amino ester salt (selected from a list containing (1R,2S)-2-amino-cyclopentanecarboxylic acid ethyl ester hydrochloride (prepared as described in WO 2008/073982 A2); cis-2-amino-cyclohexanecarboxylic acid ethyl ester hydrochloride; cis-2-amino-cycloheptanecarboxylic acid methyl ester hydrochloride prepared as described in WO 2008/073982 A2; (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2); 0.455 mmol) with cyclohexylcarboxaldehyde (0.455 mmol), sodium cyanoborohydride (1.37 mmol) and 4 Å molecular sieves (100 mg) were mixed in 6 mL of ethanol (or methanol dependent on the a mono- or bicyclic β-amino ester salt used) for 16 h after which time the solvent was removed in vacuo.

The mixture was then re-dissolved in 1.0 M aqueous sodium hydroxide solution (4 mL) and extracted two times with diethyl ether (4 mL). The organic layers were combined, dried with sodium sulfate, filtered and concentrated in vacuo to afford the N-substituted mono- or bicyclic β-amino ester intermediate. 1-(3-Dimethylaminopropyl)-3-ethylcarbodiimide hydrochloride (0.273 mmol) was added to a solution containing [7-(methanesulfonyl-amino-methyl)-1,1-dioxo-1,4-dihydro-1λ$^6$-thieno[2,3-e][1,2,4]thiadiazin-3-yl]-acetic acid (prepared as described in Example 2c; 0.228 mmol) and the N-substituted mono- or bicyclic β-amino ester intermediate in N,N-dimethylformamide (4 mL) and allowed to stir at 25° C. for 5 h. Triethylamine (2.73 mmol) was added and the mixture was stirred at 70° C. for 16 h. Upon cooling to 25° C., the mixture was concentrated in vacuo to a thick oil. The oil was partitioned between dichloromethane (2 mL) and 1.0 M aqueous hydrochloric acid solution (6 mL). The organic phase was loaded directly onto a prepacked RediSep silica gel column and purified by flash column chromatography (Teledyne Isco RediSep column; 20-100% ethyl acetate in hexanes) to afford the desired final product.

Example 101

N-[3-((1R,2S,7R,8S)-3-Cyclohexylmethyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

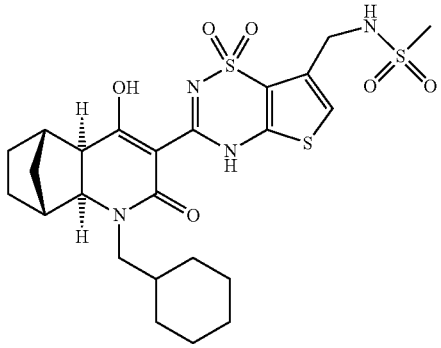

N-[3-(([1R,2S,7R,8S)-3-Cyclohexylmethyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.109 g, 0.1909 mmol, 84%) was prepared as described in general procedure 8. $^1$H NMR (400 MHz, Acetone-d$_6$) δ: 0.88-1.92 (17H, m), 2.62 (1H, m), 2.70-2.71 (1H, m), 2.79-2.86 (1H, m), 2.96 (3H, s), 3.02-3.04 (1H, m), 3.72 (1H, d, J=9.3 Hz), 3.86 (1H, dd, J$_1$=13.6 Hz, J$_2$=7.4 Hz), 4.44 (2H, d, J=6.2 Hz), 6.41 (1H, t, J=6.2 Hz), 7.33 (1H, s). LC-MS (ESI) calculated for C$_{24}$H$_{32}$N$_4$O$_6$S$_3$ 568.15. found 569.1 [M+H$^+$].

Example 102

N-[3-((1S,2S,7R,8R)-3-Cyclohexylmethyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide

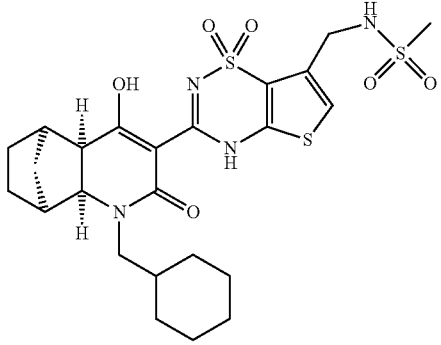

N-[3-((1S,2S,7R,8R)-3-Cyclohexylmethyl-6-hydroxy-4-oxo-3-aza-tricyclo[6.2.1.0$^{2,7}$]undec-5-en-5-yl)-1,1-dioxo-1,4-dihydro-1λ$^6$-thieno[2,3-e][1,2,4]thiadiazin-7-ylmethyl]-methanesulfonamide (0.092 g, 0.1625 mmol, 68%) was prepared as described in general procedure 8. $^1$H NMR (400 MHz, Acetone-d$_6$) δ: 0.87-1.87 (17H, m), 2.72-2.85 (3H, m), 2.96 (3H, s), 3.25-3.27 (1H, m), 3.88 (1H, dd, J$_1$=13.4 Hz, J$_2$=7.9 Hz), 4.03 (1H, dd, J$_1$=12.5 Hz, J$_2$=4.0 Hz), 4.45 (2H, d, J=7.9 Hz), 6.41 (1H, t, J=6.5 Hz), 7.34 (1H, s). LC-MS (ESI) calculated for C$_{24}$H$_{32}$N$_4$O$_6$S$_3$ 568.15. found 569.3 [M+H$^+$].

Example 103

4aR,7aS)-N-[3-(1-Cyclohexylmethyl-4-hydroxy-2-oxo 2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide

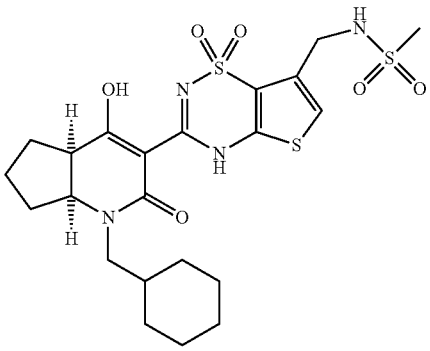

(4aR,7aS)-N-[3-(1-Cyclohexylmethyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide (0.065 g, 0.1203 mmol, 46%) was prepared as described in general procedure 8. $^1$H NMR (400 MHz, Acetone-d$_6$) δ: 0.92-1.29 (6H, m), 1.67-1.80 (9H, m), 2.21-2.31 (2H, m), 2.82 (1H, m), 2.96 (3H, s), 3.41 (1H, m), 3.80 (1H, dd, J$_1$=13.2 Hz, J$_2$=6.9 Hz), 3.98-3.99 (1H, m), 4.44 (2H, d, J=6.2 Hz), 6.42 (1H, t, J=6.4 Hz), 7.34 (1H, s). LC-MS (ESI) calculated for C$_{22}$H$_{30}$N$_4$O$_6$S$_3$ 542.13. found 543.1 [M+H$^+$].

Example 104

(rac-cis)-N-[3-(1-Cyclohexylmethyl-4-hydroxy-2-oxo-1,2,4a,5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide

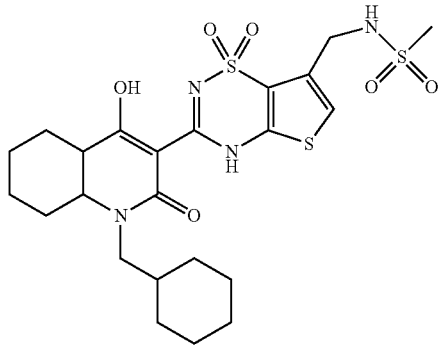

(rac-cis)-N-[3-(1-Cyclohexylmethyl-4-hydroxy-2-oxo-1,2,4a,5,6,7,8,8a-octahydro-quinolin-3-yl)-1,1-dioxo-1,4-dihydro-1λ$^6$-thieno[2,3-e][1,2,4]thiadiazin-7-ylmethyl]-methanesulfonamide (0.093 g, 0.1670 mmol, 70%) was prepared as described in general procedure 8. ¹H NMR (400 MHz, Acetone-$d_6$) δ: 0.98-1.93 (17H, m), 2.47 (1H, m), 2.72-2.83 (1H, m), 2.96 (3H, s), 3.13 (1H, m), 3.44 (1H, m), 3.59-3.77 (1H, m), 3.86 (1H, dd, $J_1$=13.4 Hz, $J_2$=7.1 Hz), 4.44 (2H, d, J=6.2 Hz), 6.41 (1H, m), 7.33 (1H, s). LC-MS (ESI) calculated for $C_{23}H_{32}N_4O_6S_3$ 556.15. found 557.1 [M+H⁺].

Example 105

(rac-cis)-N-[3-(1-Cyclohexylmethyl-4-hydroxy-2-oxo-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl]-methanesulfonamide

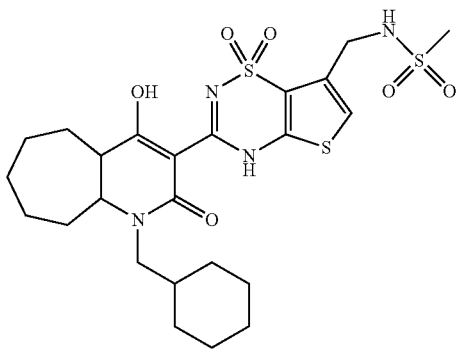

(rac-cis)-N-[3-(1-Cyclohexylmethyl-4-hydroxy-2-oxo-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl]-methanesulfonamide (0.029 g, 0.0503 mmol, 21%) was prepared as described in general procedure 8. ¹H NMR (400 MHz, Acetone-$d_6$) δ: 0.91-1.85 (19H, m), 2.68 (1H, m), 2.83 (1H, m), 2.98 (3H, s), 3.31 (1H, m), 3.64-3.78 (2H, m), 3.93 (1H, dd, $J_1$=13.0 Hz, $J_2$=6.6 Hz), 4.46 (2H, d, J=6.2 Hz), 6.43 (1H, m), 7.36 (1H, s). LC-MS (ESI) calculated for $C_{24}H_{34}N_4O_6S_3$ 570.16. found 571.1 [M+H⁺].

General Procedure 9:

A mixture of a bicyclic β-amino ester salt (selected from a list containing (1R,2S,3R,4S)-3-ethoxycarbonyl-bicyclo[2.2.1]hept-2-yl-aminium (1'S)-(+)-10-camphorsulfonate (prepared as described in Example 1m); (1S,2R,3S,4R)-3-amino-bicyclo[2.2.1]heptane-2-carboxylic acid ethyl ester hydrochloride (prepared from Example 1n); (1R,2R,3S,4S)-3-amino-bicyclo[2.2.1]heptane-2-carboxylic acid methyl ester hydrochloride (prepared as described in WO 2008/073982 A2); (rac-di-exo)-3-amino-7-oxa-bicyclo[2.2.1]heptane-2-carboxylic acid methyl ester hydrochloride; (rac-di-exo)-3-amino-bicyclo[2.2.1]hept-5-ene-2-carboxylic acid ethyl ester hydrochloride; (2R,3S)-3-amino-bicyclo[2.2.2]octane-2-carboxylic acid methyl ester hydrochloride (prepared as described in WO 2008/073982 A2); 0.455 mmol) with a terminal alkyl tosylate (0.455 mmol), and triethylamine (1.37 mmol) were mixed in 4 mL of N,N-dimethylformamide at 70° C. for 16 h after which time the solvent was removed in vacuo.

The mixture was then re-dissolved in 1.0 M aqueous sodium hydroxide solution (4 mL) and extracted two times with ethyl acetate (4 mL). The organic layers were combined, dried with sodium sulfate, filtered and concentrated in vacuo to afford the N-substituted bicyclic β-amino ester intermediate. 1-(3-Dimethylaminopropyl)-3-ethylcarbodiimide hydrochloride (0.273 mmol) was added to a solution containing [7-(methanesulfonyl-amino-methyl)-1,1-dioxo-1,4-dihydro-1λ⁶-thieno[2,3-e][1,2,4]thiadiazin-3-yl]-acetic acid (prepared as described in Example 2c; 0.228 mmol) and the N-substituted bicyclic β-amino ester intermediate in N,N-dimethylformamide (4 mL) and allowed to stir at 25° C. for 5 h. Triethylamine (2.73 mmol) was added and the mixture was stirred at 70° C. for 16 h. Upon cooling to 25° C., the mixture was concentrated in vacuo to a thick oil. The oil was partitioned between dichloromethane (2 mL) and 1.0 M aqueous hydrochloric acid solution (6 mL). The organic phase was loaded directly onto a prepacked RediSep silica gel column and purified by flash column chromatography (Teledyne Isco RediSep column; 20-100% ethyl acetate in hexanes) to afford the desired final product.

Example 106

N-{3-[(1R,2S,7R,8S)-3-(2-Cyclopropyl-ethyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

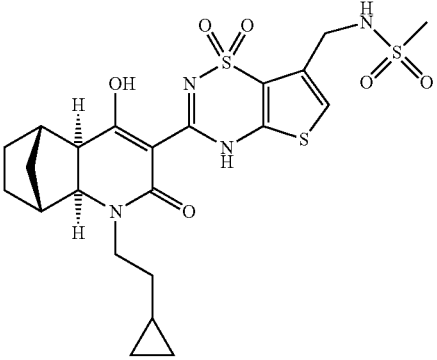

N-{3-[(1R,2S,7R,8S)-3-(2-Cyclopropyl-ethyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide (0.014 g, 0.0250 mmol, 11%) was prepared as described in general procedure 9. ¹H NMR (400 MHz, Acetone-$d_6$) δ: 0.08-0.12 (2H, m), 0.43-0.47 (2H, m), 0.70-0.77 (1H, m), 1.28-1.41 (3H, m), 1.47-1.54 (2H, m), 1.61-1.72 (4H, m), 2.64 (1H, m), 2.72-2.73 (1H, m), 2.96 (3H, s), 2.99-3.01 (1H, m), 3.26 (1H, m), 3.80 (1H, d, J=10.0 Hz), 4.44 (2H, d, J=6.3 Hz), 6.42 (1H, t, J=6.2 Hz), 7.34 (1H, s). LC-MS (ESI) calculated for $C_{22}H_{28}N_4O_6S_3$ 540.12. found 541.2 [M+H⁺].

Example 107

N-{3-[(1S,2S,7R,8R)-3-(2-Cyclopropyl-ethyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide

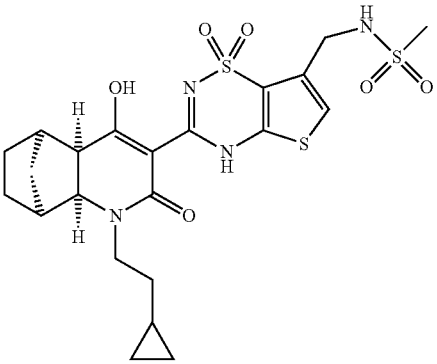

N-{3-[(1S,2S,7R,8R)-3-(2-Cyclopropyl-ethyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylm-ethyl}-methanesulfonamide (0.026 g, 0.0479 mmol, 20%) was prepared as described in general procedure 9. $^1$H NMR (400 MHz, Acetone-d$_6$) δ: 0.09-0.12 (2H, m), 0.42-0.47 (2H, m), 0.69-0.76 (1H, m), 1.37-1.52 (7H, m), 1.60-1.63 (2H, m), 2.77-2.81 (1H, m), 2.97 (3H, s), 3.19-3.27 (2H, m), 3.78-3.85 (1H, m), 4.05 (1H, dd, J$_1$=12.9 Hz, J$_2$=3.3 Hz), 4.45 (H, d, J=6.2 Hz), 6.42 (H, t, J=6.2 Hz), 7.35 (H, s). LC-MS (ESI) calculated for C$_{22}$H$_{28}$N$_4$O$_6$S$_3$ 540.12. found 541.1 [M+H$^+$].

Example 108

N-{3-[3-(2-Cyclopropyl-ethyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylm-ethyl}-methanesulfonamide

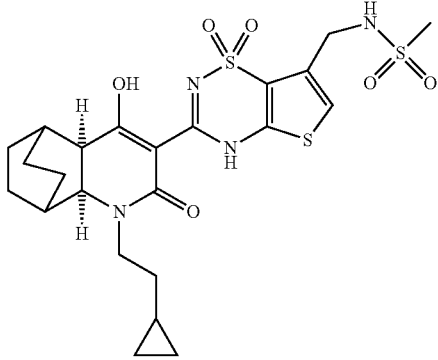

N-{3-[3-(2-Cyclopropyl-ethyl)-6-hydroxy-4-oxo-3-aza-tricyclo[6.2.2.0$^{2,7}$]dodec-5-en-5-yl]-1,1-dioxo-1,4-dihydro-1λ$^6$-thieno[2,3-e][1,2,4]thiadiazin-7-ylmethyl}-methanesulfonamide (0.006 g, 0.0106 mmol, 5%) was prepared as described in general procedure 9. $^1$H NMR (400 MHz, Acetone-d$_6$) δ: 0.09-0.10 (2H, m), 0.41-0.47 (2H, m), 0.70-0.78 (1H, m), 1.15-1.71 (10H, m), 1.97 (1H, m), 2.24 (1H, m), 2.79 (1H, m), 2.96 (3H, s), 3.18-3.31 (2H, m), 3.81-3.88 (1H, m), 4.04 (1H, d, J=11.5 Hz), 4.45 (2H, d, J=6.2 Hz), 6.42 (1H, t, J=6.2 Hz), 7.34 (1H, s). LC-MS (ESI) calculated for C$_{23}$H$_{30}$N$_4$O$_6$S$_3$ 554.13. found 554.8 [M+H$^+$].

Example 109

N-(3-{6-Hydroxy-3-[2-(1 methyl-cyclopropyl)ethyl]-4-oxo-3-aza-tricyclo[6.2.2.0$^{2,7}$]dodec-5-en-5-yl}-1,1-dioxo-1,4-dihydro-1λ$^6$-thieno[2,3-e][1,2,4]thiadiazin-7-ylmethyl]-methanesulfonamide

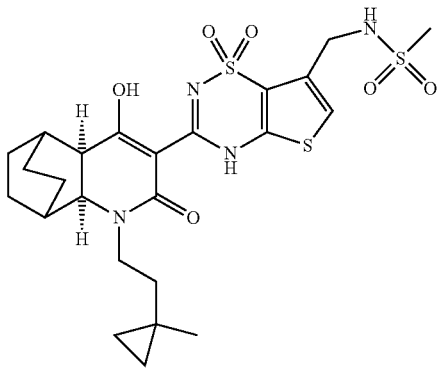

N-(3-{6-Hydroxy-3-[2-(1-methyl-cyclopropyl)-ethyl]-4-oxo-3-aza-tricyclo[6.2.2.0$^{2,7}$]dodec-5-en-5-yl}-1,1-dioxo-1,4-dihydro-1λ$^6$-thieno[2,3-e][1,2,4]thiadiazin-7-ylmethyl)-methanesulfonamide (0.003 g, 0.0051 mmol, 5%) was prepared as described in general procedure 9. $^1$H NMR (400 MHz, Acetone-d$_6$) δ: 0.27-0.36 (4H, m), 1.09 (3H, s), 1.29-1.69 (9H, m), 1.97 (1H, m), 2.24-2.25 (1H, m), 2.76 (1H, m), 2.96 (3H, s), 3.24 (2H, m), 3.81-3.88 (1H, m), 4.00 (1H, d, J=11.7 Hz), 4.44 (2H, d, J=5.4 Hz), 6.42 (1H, t, J=6.3 Hz), 7.34 (1H, s). LC-MS (ESI) calculated for C$_{24}$H$_{32}$N$_4$O$_6$S$_3$ 568.15. found 569.2 [M+H$^+$].

General Procedure 10:

(1R,2S)-2-Amino-cyclopentanecarboxylic acid ethyl ester hydrochloride (prepared as described in WO 2008/073982 A2; 100 mg, 0.518 mmol) was dissolved in anhydrous N,N-dimethylformamide (10 mL). A benzylic halide (1.1 eq., 0.570 mmol) was added followed by triethylamine (3 eq., 1.554 mmol, 216 μl) and the mixtures were agitated at 70° C. for 16 h. The solvent was removed in vacuo (Savant Speed-Vac), a 1.0 M aqueous solution of sodium hydroxide (2 mL) was added to the residues and the resulting solutions were extracted with diethyl ether (2×5 mL). The organic layers were dried over sodium sulfate, filtered and concentrated in vacuo to afford the crude products, which were purified by flash column chromatography (Teledyne Isco RediSep Column; 0-30% ethyl acetate in hexanes) to afford the N-substituted (1R,2S)-2-amino-cyclopentanecarboxylic acid ethyl ester intermediates.

[7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 1 eq.) was dissolved in anhydrous N,N-dimethylformamide (2 mL). The N-substituted (1R,2S)-2-amino-cyclopentanecarboxylic acid ethyl ester intermediates (1 eq.) were added followed by 1-(3-dimethylaminopropyl)-3-ethylcarbodiimide hydrochloride (1.5 eq.). The mixtures were agitated at 25° C. for 6 h. The mixtures were concentrated in vacuo and the crude residues were dissolved in ethanol (4 mL). A 21 wt. % solution of sodium ethoxide in ethanol (4 eq.) was added into the above solutions. The mixtures were agitated at 60° C. for 16 h and allowed to cool to 25° C. The mixtures were concentrated in vacuo and the residues were dissolved in dichloromethane (2 mL) and extracted with a 1.0 M aqueous hydrochloric acid solution (2 mL). The organic layers were dried over sodium sulfate, filtered and purified by flash column chromatography (Teledyne Isco RediSep Column; 20-100% ethyl acetate in hexanes) to afford the desired final products.

Example 110

(4aR,7aS)-N-{3-[1-(4-Fluoro-benzyl)-4-hydroxy-2-oxo-2,4-a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

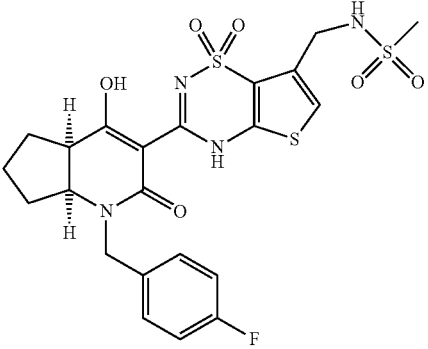

(4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide (yellow oil, 10.4 mg, 0.019 mmol, 13.6% over 2 steps) was prepared as described in general procedure 10. $^1$H NMR (400 MHz, DMSO-d$_6$) δ: 7.58-7.61 (1H, m), 7.35-7.38 (2H, m), 7.12-7.16 (3H, m), 4.85 (1H, d, J=15.6 Hz), 4.43 (1H, d, J=15.7 Hz), 4.24 (2H, d, J=5.4 Hz), 3.71-3.79 (1H, br), 2.99-3.11 (1H, br), 2.95 (3H, s), 2.05-2.19 (1H, m), 1.83-1.96 (H, m), 1.42-1.57 (H, m), 0.83-1.26 (H, m) 0.83-1.26 (1H, m), 1.42-1.57 (3H, m), 1.83-1.96 (2H, m), 2.05-2.19 (1H, m), 2.95 (3H, s), 2.99-3.11 (1H, br), 3.71-3.79 (1H, br), 4.24 (2H, d, J=5.4 Hz), 4.43 (1H, d, J=15.7 Hz), 4.85 (1H, d, J=15.6 Hz), 7.12-7.16 (3H, m), 7.35-7.38 (2H, m), 7.58-7.61 (1H, m). LC-MS (ESI) calculated for C$_{22}$H$_{23}$FN$_4$O$_6$S$_3$ 554.08. found 555.0 [M+H$^+$].

Example 111

(4aR,7aS)-N-{3-[1-(2-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

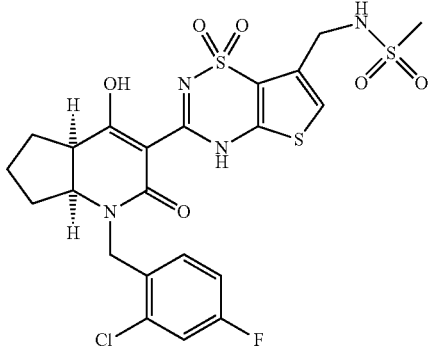

(4aR,7aS)-N-{3-[1-(2-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide (white solid, 56.3 mg, 0.096 mmol, 35.6% over 2 steps) was prepared as described in general procedure 10. $^1$H NMR (400 MHz, DMSO-d$_6$) d: 1.45-1.65 (3H, m), 1.97-2.18 (3H, m), 2.95 (3H, s), 3.81-3.89 (1H, m), 4.24 (2H, d, J=5.3 Hz), 4.46 (1H, d, J=16.4 Hz), 4.93 (1H, d, J=15.5 Hz), 7.16-7.21 (1H, m), 7.26 (1H, bs), 7.38-7.41 (1H, m), 7.45-7.48 (1H, m), 7.63-7.67 (1H, m). LC-MS (ESI) calculated for C$_{22}$H$_{22}$ClFN$_4$O$_6$S$_3$ 588.04. found 589.2 [M+H$^+$].

Example 112

(4aR,7aS)-N-{3-[1-(2,4-Difluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

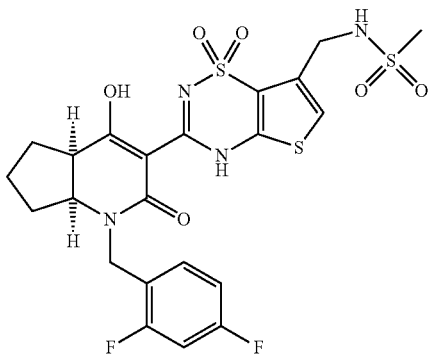

(4aR,7aS)-N-{3-[1-(2,4-Difluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide (yellow oil, 38.4 mg, 0.067 mmol, 31.3% over 2 steps) was prepared as described in general procedure 10. $^1$H NMR (400 MHz, DMSO-d$_6$) δ: 1.43-1.82 (3H, m), 1.91-2.05 (2H, m), 2.05-2.19 (1H, m), 2.96 (3H, s), 3.20 (1H, br), 3.77-3.90 (1H, m), 4.24 (2H, d, J=5.2 Hz), 4.45 (1H, d, J=15.5 Hz), 4.89 (1H, d, J=15.7 Hz), 7.03-7.08 (1H, m), 7.21-7.26 (2H, m), 7.39-7.45 (1H, m), 7.61-7.64 (1H, m). LC-MS (ESI) calculated for C$_{22}$H$_{22}$F$_2$N$_4$O$_6$S$_3$ 572.07. found 573.0 [M+H$^+$].

Example 113

(4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1λ6-thieno[2,3-e][1,2,4]thiadiazin-7-ylmethyl}-methanesulfonamide

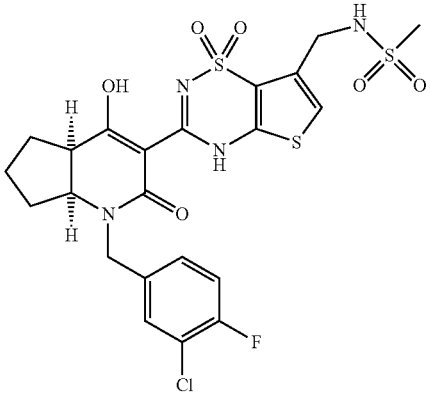

(4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide (off-white solid, 66.8 mg, 0.114 mmol, 45.0% over 2 steps) was prepared as described in general procedure 10. $^1$H NMR (400 MHz, DMSO-d$_6$) δ: 1.45-1.62 (3H, m), 1.96-2.14 (3H, m), 2.96 (3H, s), 3.85-3.91 (1H, m), 4.25 (2H, d, J=5.4 Hz), 4.46 (1H, d, J=15.8 Hz), 4.87 (1H, d, J=15.4 Hz), 7.29 (1H, bs), 7.36-7.40 (2H, m), 7.56 (1H, d, J=7.8 Hz), 7.66-7.69 (1H, m). LC-MS (ESI) calculated for C$_{22}$H$_{22}$ClFN$_4$O$_6$S$_3$ 588.04. found 589.1 [M+H$^+$].

Example 114

(4aR,7aS)-N-{3-[1-(4-Fluoro-3-methoxy-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

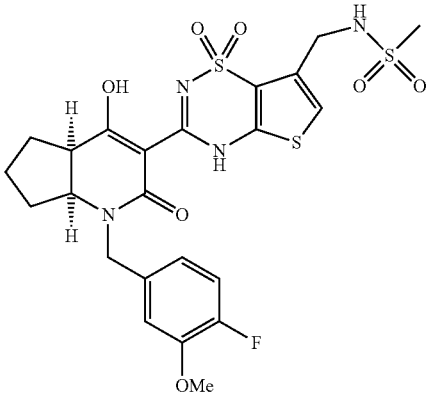

(4aR,7aS)-N-{3-[1-(4-Fluoro-3-methoxy-benzyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (yellow oil, 6.3 mg, 0.011 mmol, 15.5% over 2 steps) was prepared as described in general procedure 10. ¹H NMR (400 MHz, DMSO-$d_6$) δ: 0.81-0.96 (1H, m), 1.09-1.28 (1H, m), 1.37-1.57 (3H, m), 1.70-1.94 (2H, m), 2.10-2.20 (1H, m), 2.94 (3H, s), 3.59-3.73 (1H, m), 3.81 (3H, s), 4.23 (2H, d, J=5.3 Hz), 4.33 (1H, d, J=15.6 Hz), 4.86 (1H, d, J=15.3 Hz), 6.81-6.89 (1H, m), 7.03-7.17 (3H, m), 7.48-7.57 (1H, m). LC-MS (ESI) calculated for $C_{23}H_{25}FN_4O_7S_3$ 584.09. found 584.9 [M+H⁺].

Example 115

(4aR,7aS)-N-{3-[4-Hydroxy-2-oxo-1-(2,3,3-trifluoro-benzyl)-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide

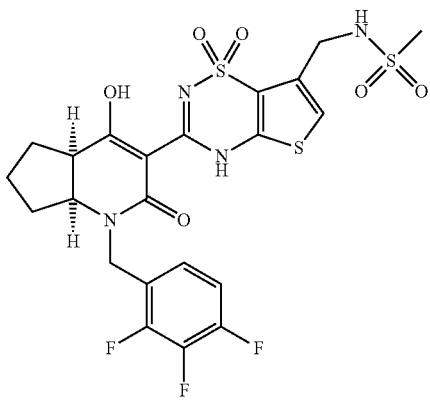

(4aR,7aS)-N-{3-[4-Hydroxy-2-oxo-1-(2,3,4-trifluoro-benzyl)-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (yellow oil, 27.4 mg, 0.046 mmol, 39.2% over 2 steps) was prepared as described in general procedure 10. ¹H NMR (400 MHz, DMSO-$d_6$) δ: 1.40-1.57 (3H, m), 1.69-1.94 (2H, m), 2.14-2.21 (1H, m), 2.84-2.94 (1H, m), 2.94 (3H, s), 3.66-3.77 (1H, m), 4.23 (2H, d, J=6.1 Hz), 4.44 (1H, d, J=15.6 Hz), 4.87 (1H, d, J=15.6 Hz), 7.05 (1H, bs), 7.15-7.30 (2H, m), 7.50-7.54 (1H, m). LC-MS (ESI) calculated for $C_{22}H_{21}F_3N_4O_6S_3$ 590.06. found 591.2 [M+H⁺].

General Procedure 11:

Ethyl cis-2-amino-1-cyclohexanecarboxylate hydrochloride (100 mg, 0.483 mmol) was dissolved in anhydrous N,N-dimethylformamide (10 mL). A benzylic halide (1.1 eq., 0.570 mmol) was added followed by triethylamine (3 eq., 1.449 mmol, 202 μL) and the mixtures were agitated at 70° C. for 16 h. The solvent was removed in vacuo (Savant Speed-Vac), a 1.0 M aqueous solution of sodium hydroxide (2 mL) was added to the residues and the resulting solutions were extracted with diethyl ether (2×5 mL). The organic layers were dried over sodium sulfate, filtered and concentrated in vacuo to afford the crude products, which were purified by flash column chromatography (Teledyne Isco RediSep Column; 0-30% ethyl acetate in hexanes) to afford the N-substituted (1R,2S)-2-amino-cyclohexanecarboxylic acid ethyl ester intermediates.

[7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 1 eq.) was dissolved in anhydrous N,N-dimethylformamide (2 mL). The N-substituted cis-2-amino-cyclohexanecarboxylic acid ethyl ester intermediates (1 eq.) were added followed by 1-(3-dimethylaminopropyl)-3-ethylcarbodiimide hydrochloride (1.5 eq.). The mixtures were agitated at 25° C. for 6 h. The mixtures were concentrated in vacuo and the crude residues were dissolved in ethanol (4 mL). A 21 wt. % solution of sodium ethoxide in ethanol (4 eq.) was added into the above solutions. The mixtures were agitated at 60° C. for 16 h and allowed to cool to 25° C. The mixtures were concentrated in vacuo and the residues were dissolved in dichloromethane (2 mL) and extracted with a 1.0 M aqueous hydrochloric acid solution (2 mL). The organic layers were dried over sodium sulfate, filtered and purified by flash column chromatography (Teledyne Isco RediSep Column; 20-100% ethyl acetate in hexanes) to afford the desired final products.

Example 116

(rac-cis)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ⁶-thieno e][1,2,4]thiadiazin-7-ylmethyl}-methanesulfonamide

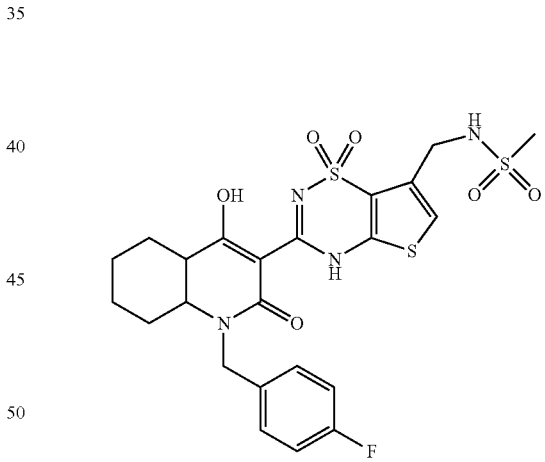

(rac-cis)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ⁶-thieno[2,3-e][1,2,4]thiadiazin-7-ylmethyl}-methanesulfonamide (yellow oil, 11.3 mg, 0.020 mmol, 19.1% over 2 steps) was prepared as described in general procedure 11. ¹H NMR (400 MHz, DMSO-$d_6$) δ: 1.04-1.37 (3H, m), 1.37-1.52 (2H, m), 1.56-1.78 (2H, m), 2.31 (1H, d, J=14.8 Hz), 2.95 (3H, s), 3.22-3.47 (3H, m), 4.24-4.25 (3H, m), 4.99 (1H, d, J=15.7 Hz), 7.11-7.18 (3H, m), 7.36-7.40 (2H, m), 7.53-7.62 (1H, m). LC-MS (ESI) calculated for $C_{23}H_{25}FN_4O_6S_3$ 568.09. found 569.0 [M+H⁺].

Example 117

(rac-cis)-N-{3-[1-(2-Chloro-4-fluoro-benzyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide

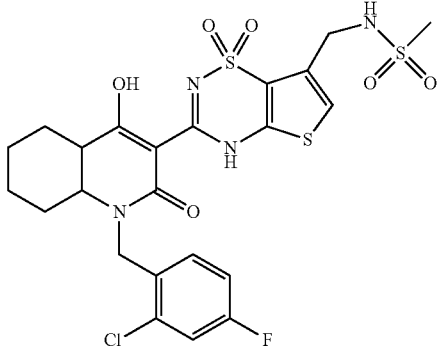

(rac-cis)-N-{3-[1-(2-Chloro-4-fluoro-benzyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide (yellow oil, 27.2 mg, 0.045 mmol, 17.4% over 2 steps) was prepared as described in general procedure 11. $^1$H NMR (400 MHz, DMSO-d$_6$) δ: 1.10-1.31 (3H, m), 1.32-1.58 (3H, m), 1.60-1.77 (1H, m), 1.79-1.93 (1H, m), 2.28-2.37 (1H, m), 2.96 (3H, s), 3.52-3.61 (1H, m), 4.24 (2H, d, J=5.4 Hz), 4.32 (1H, d, J=15.8 Hz), 5.04 (1H, d, J=16.5 Hz), 7.16-7.31 (2H, m), 7.44-7.48 (2H, m), 7.63-7.66 (1H, m). LC-MS (ESI) calculated for C$_{23}$H$_{24}$ClFN$_4$O$_6$S$_3$ 602.05. found 603.0 [M+H$^+$].

Example 118

(rac-cis)-N-{3-[1-(2,4-Difluoro-benzyl)-4-hydroxy-2-oxo-1,2,4a,5,6,7,8,8a-octahydro-quinolin-3-yl]-1,1-dioxo-1,4-dihydro-1$\lambda^6$-thieno e][1,2,4]thiadiazin-7-ylmethyl}-methanesulfonamide

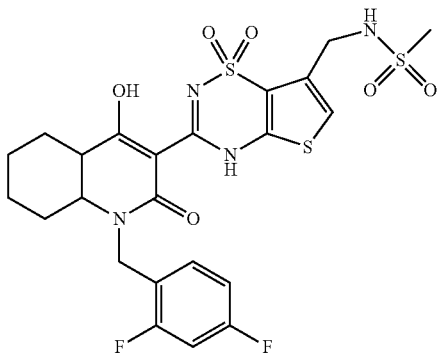

(rac-cis)-N-{3-[1-(2,4-Difluoro-benzyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide (off-white solid, 17.8 mg, 0.030 mmol, 14.3% over 2 steps) was prepared as described in general procedure 11. $^1$H NMR (400 MHz, DMSO-d$_6$) δ: 1.08-1.30 (3H, m), 1.33-1.56 (3H, m), 1.58-1.88 (2H, m), 2.26-2.36 (1H, m), 2.96 (3H, s), 3.54-3.63 (1H, m), 4.24 (2H, d, J=6.1 Hz), 4.34 (1H, d, J=15.6 Hz), 4.99 (1H, d, J=15.7 Hz), 7.02-7.07 (1H, m), 7.22-7.27 (2H, m), 7.44-7.50 (1H, m), 7.65 (1H, t, J=6.3 Hz). LC-MS (ESI) calculated for C$_{23}$H$_{24}$F$_2$N$_4$O$_6$S$_3$ 586.08. found 587.0 [M+H$^+$].

Example 119

(rac-cis)-N-{3-[1-(3-Chloro-4-fluoro-benzyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide

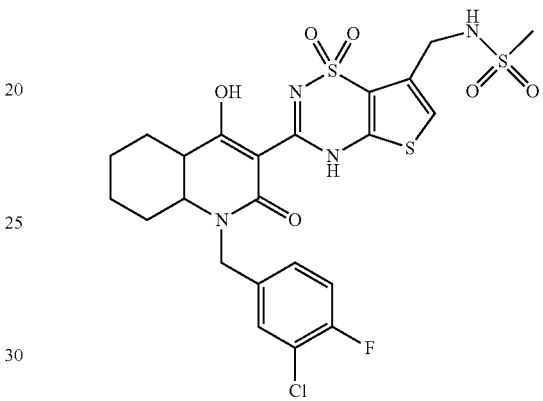

(rac-cis)-N-{3-[1-(3-Chloro-4-fluoro-benzyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide (off-white solid, 37.1 mg, 0.062 mmol, 27.8% over 2 steps) was prepared as described in general procedure 11. $^1$H NMR (400 MHz, DMSO-d$_6$) δ: 1.09-1.31 (3H, m), 1.34-1.56 (3H, m), 1.59-1.85 (2H, m), 2.23-2.36 (1H, m), 2.96 (3H, s), 3.51-3.61 (1H, m), 4.24-4.30 (3H, m), 4.98 (1H, d, J=15.4 Hz), 7.24 (1H, bs), 7.36-7.38 (2H, m), 7.58 (1H, d, J=7.7 Hz), 7.64 (1H, t, J=5.8 Hz). LC-MS (ESI) calculated for C$_{23}$H$_{24}$ClFN$_4$O$_6$S$_3$ 602.05. found 603.1 [M+H$^+$].

General Procedure 12:

cis-2-Amino-cycloheptanecarboxylic acid methyl ester hydrochloride (prepared as described in WO 2008/073982 A2; 100 mg, 0.483 mmol) was dissolved in anhydrous N,N-dimethylformamide (10 mL). A benzylic halide (1.1 eq., 0.570 mmol) was added followed by triethylamine (3 eq., 1.449 mmol, 202 μl) and the mixtures were agitated at 70° C. for 16 h. The solvent was removed in vacuo (Savant Speed-Vac), a 1.0 M aqueous solution of sodium hydroxide (2 mL) was added to the residues and the resulting solutions were extracted with diethyl ether (2×5 mL). The organic layers were dried over sodium sulfate, filtered and concentrated in vacuo to afford the crude products, which were purified by flash column chromatography (Teledyne Isco RediSep Column; 0-30% ethyl acetate in hexanes) to afford the N-substituted cis-2-amino-cycloheptanecarboxylic acid ethyl ester intermediates.

[7-(Methanesulfonylamino-methyl)-1,1-dioxo-1,4-dihydro-1$\lambda^6$-thieno[2,3-e][1,2,4]thiadiazin-3-yl]-acetic acid (prepared as described in Example 2c; 1 eq.) was dissolved in anhydrous N,N-dimethylformamide (2 mL). The N-substituted cis-2-amino-cycloheptanecarboxylic acid ethyl ester intermediates (1 eq.) were added followed by 1-(3-dimethylaminopropyl)-3-ethylcarbodiimide hydrochloride (1.5 eq.). The mixtures were agitated at 25° C. for 6 h. The mixtures were concentrated in vacuo and the crude residues were dissolved in ethanol (4 mL). A 21 wt. % solution of sodium ethoxide in ethanol (4 mL) was added into the above solutions. The mixtures were agitated at 60° C. for 16 h and allowed to cool to 25° C. The mixtures were concentrated in vacuo and the residues were dissolved in dichloromethane (2 mL) and extracted with a 1.0 M aqueous hydrochloric acid solution (2 mL). The organic layers were dried over sodium sulfate, filtered and purified by flash column chromatography (Teledyne Isco RediSep Column; 20-100% ethyl acetate in hexanes) to afford the desired final products.

Example 120

(rac-cis)-N-{3-[1-(4-Fluoro-benzyl)-4-hydroxy-2-oxo-2,4-a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonmide

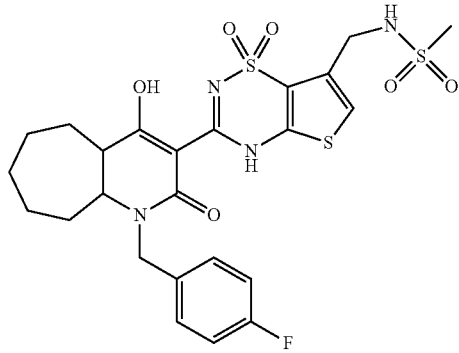

(rac-cis)-N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide (yellow oil, 6.0 mg, 0.010 mmol, 14.0% over 2 steps) was prepared as described in general procedure 12. $^1$H NMR (400 MHz, DMSO-d$_6$) δ: 1.09-1.39 (5H, m), 1.41-1.78 (6H, m), 1.91-2.02 (1H, m), 2.71-2.79 (1H, m), 2.93 (3H, s), 3.23-3.28 (1H, m), 4.03 (1H, d, J=14.9 Hz), 4.22 (2H, d, J=6.1 Hz), 5.01 (1H, d, J=15.7 Hz), 6.93 (1H, bs), 7.09-7.14 (2H, m), 7.32-7.36 (2H, m), 7.45 (1H, t, J=6.2 Hz). LC-MS (ESI) calculated for C$_{24}$H$_{27}$FN$_4$O$_6$S$_3$ 582.11. found 583.0 [M+H$^+$].

Example 121

(rac-cis)-N-{3-[1-(3-Chloro-4-fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide

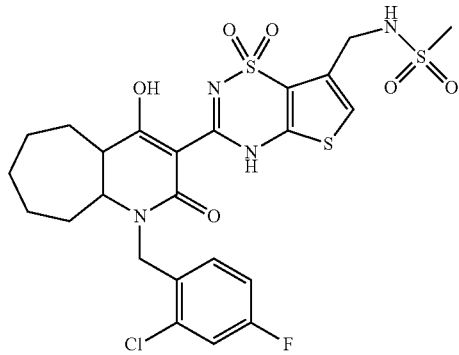

(rac-cis)-N-{3-[1-(2-Chloro-4-fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide (yellow oil, 24.4 mg, 0.040 mmol, 22.0% over 2 steps) was prepared as described in general procedure 12. $^1$H NMR (400 MHz, DMSO-d$_6$) δ: 1.21-1.44 (4H, m), 1.52-1.82 (6H, m), 1.95-2.04 (1H, m), 2.93 (3H, s), 2.98-3.03 (1H, m), 4.06 (1H, d, J=15.5 Hz), 4.22 (2H, d, J=4.7 Hz), 5.08 (1H, d, J=15.5 Hz), 6.97 (1H, bs), 7.16-7.21 (1H, m), 7.37-7.43 (2H, m), 7.47 (1H, t, J=6.3 Hz). LC-MS (ESI) calculated for C$_{24}$H$_{26}$ClFN$_4$O$_6$S$_3$ 616.07. found 617.2 [M+H$^+$].

Example 122

(rac-cis)-N-{3-[1-(2,4-Difluoro-benzyl)-4-hydroxy-2-oxo-2,4-a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamde

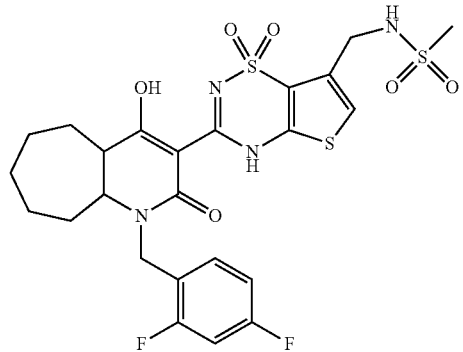

(rac-cis)-N-{3-[1-(2,4-Difluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide (yellow oil, 21.6 mg, 0.036 mmol, 25.9% over 2 steps) was prepared as described in general procedure 12. $^1$H NMR (400 MHz, DMSO-d$_6$) δ: 1.21-1.45 (4H, m), 1.50-1.80 (7H, m), 1.94-2.04 (1H, m), 2.94 (3H, s), 3.35-3.44 (1H, m), 4.14 (1H, d, J=15.5 Hz), 4.22 (2H, d, J=5.2 Hz), 5.00 (1H, d, J=15.4 Hz), 7.01-7.06 (2H, m), 7.18-7.24 (1H, m), 7.38-7.44 (1H, m), 7.51 (1H, t, J=6.2 Hz). LC-MS (ESI) calculated for C$_{24}$H$_{26}$F$_2$N$_4$O$_6$S$_3$ 600.1. found 601.1 [M+H$^+$].

Example 123

(rac-cis)-N-{3-[1-(3-Chloro-4-fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide

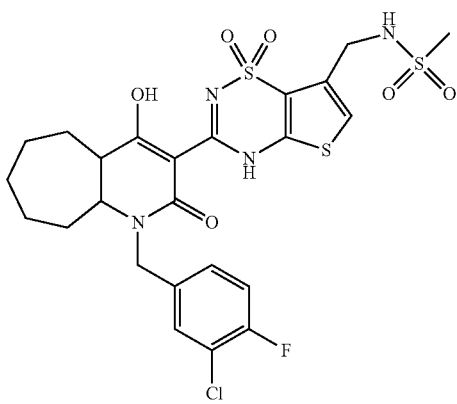

(rac-cis)-N-{3-[1-(3-Chloro-4-fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-thieno[2,3-e][1,2,4]thiadiazin-7-ylmethyl}-methanesulfonamide (off-white solid, 29.2 mg, 0.047 mmol, 28.7% over 2 steps) was prepared as described in general procedure 12. $^1$H NMR (400 MHz, DMSO-d$_6$) δ: 1.19-1.44 (4H, m), 1.49-1.77 (7H, m), 1.91-2.00 (1H, m), 2.94 (3H, s), 3.36-3.46 (1H, m), 4.12 (1H, d, J=15.6 Hz), 4.23 (2H, d, J=5.2 Hz), 4.97 (1H, d, J=15.1 Hz), 7.04 (1H, bs), 7.34-7.36 (2H, m), 7.51-7.53 (2H, m). LC-MS (ESI) calculated for $C_{24}H_{26}ClFN_4O_6S_3$ 616.07. found 617.2 [M+H$^+$].

General Procedure 13:

(1R,2S)-2-Amino-cyclopentanecarboxylic acid ethyl ester hydrochloride (prepared as described in WO 2008/073982 A2; 100 mg, 0.518 mmol) was dissolved in methanol (10 mL). Sodium acetate (2 eq., 85 mg, 1.036 mmol) was added followed by an aldehyde (1 eq., 0.518 mmol). Sodium cyanoborohydride (2 eq., 65 mg, 1.036 mmol) was added and the mixtures were agitated at 25° C. for 16 h. The solvent was removed in vacuo (Savant SpeedVac), a 1.0 M aqueous solution of sodium hydroxide (2 mL) was added to the residues and the resulting solutions were extracted with diethyl ether (2×5 mL). The organic layers were dried over sodium sulfate, filtered and concentrated in vacuo to afford the crude N-substituted (1R,2S)-2-amino-cyclopentanecarboxylic acid ethyl ester intermediates, which were used without further purification.

The crude N-substituted (1R,2S)-2-amino-cyclopentanecarboxylic acid ethyl ester intermediates (1 eq.) were dissolved in anhydrous N,N-dimethylformamide (2 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 1 eq., 183 mg, 0.518 mmol) was added followed by 1-(3-dimethylaminopropyl)-3-ethylcarbodiimide hydrochloride (1.5 eq., 149 mg, 0.777 mmol). The mixtures were agitated at 25° C. for 6 h. The mixtures were concentrated in vacuo and the crude residues were dissolved in ethanol (4 mL). A 21 wt. % solution of sodium ethoxide in ethanol (4 eq., 774 μL, 2.072 mmol) was added into the above solutions. The mixtures were agitated at 60° C. for 16 h and allowed to cool to 25° C. The mixtures were concentrated in vacuo and the residues were dissolved in dichloromethane (2 mL) and extracted with a 1.0 M aqueous hydrochloric acid solution (2 mL). The organic layers were dried over sodium sulfate, filtered and purified by flash column chromatography (Teledyne Isco RediSep Column; 20-100% ethyl acetate in hexanes) to afford the desired final products.

Example 124

(4aR,7aS)-N-[3-(1-Benzyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide

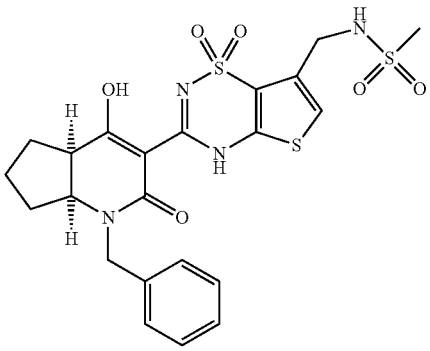

(4aR,7aS)-N-[3-(1-Benzyl-4-hydroxy-2-oxo-2,4a,5,6,7,7a-hexahydro-1H-[1]pyrindin-3-yl)-1,1-dioxo-1,4-dihydro-1λ$^6$-thieno[2,3-e][1,2,4]thiadiazin-7-ylmethyl]-methanesulfonamide (yellow oil; 121.9 mg, 0.227 mmol, 43.9% over 3 steps) was prepared as described in general procedure 13. $^1$H NMR (400 MHz, DMSO-d$_6$) δ: 1.45-1.61 (3H, m), 1.92-2.05 (3H, m), 2.96 (3H, s), 3.82-3.88 (1H, m), 4.25 (2H, d, J=6.2 Hz), 4.46 (1H, d, J=15.5 Hz), 4.93 (1H, d, J=14.8 Hz), 7.25-7.28 (2H, m), 7.33-7.36 (4H, m), 7.67 (1H, t, J=6.2 Hz). LC-MS (ESI) calculated for $C_{22}H_{24}N_4O_6S_3$ 536.09. found 537.2 [M+H$^+$].

Example 125

(4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ$^6$-thieno[2,3-e][1,2,4]thiadiazin-7-ylmethyl}-methanesulfonamide

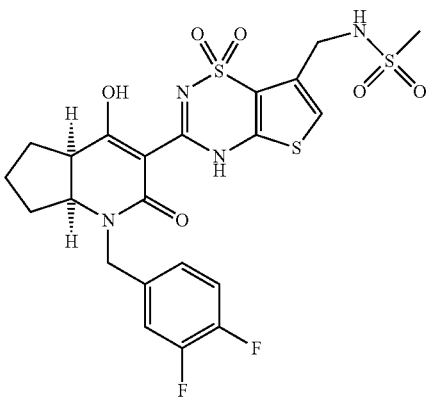

(4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (yellow oil; 152.2 mg, 0.266 mmol, 51.4% over 3 steps) was prepared as described in general procedure 13. ¹H NMR (400 MHz, DMSO-$d_6$) δ: 1.44-1.62 (3H, m), 1.92-2.08 (3H, m), 2.96 (3H, s), 3.81-3.92 (1H, m), 4.25 (2H, d, J=5.5 Hz), 4.46 (1H, d, J=15.4 Hz), 4.86 (1H, d, J=15.8 Hz), 7.17-7.21 (1H, m), 7.28 (1H, bs), 7.35-7.43 (2H, m), 7.66 (1H, t, J=6.2 Hz). LC-MS (ESI) calculated for $C_{22}H_{22}F_2N_4O_6S_3$ 572.07. found 573.0 [M+H⁺].

Example 126

(4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro thieno[2,3-e][1,2,4]thiadiazin-7-ylmethyl}-methanesulfonamide

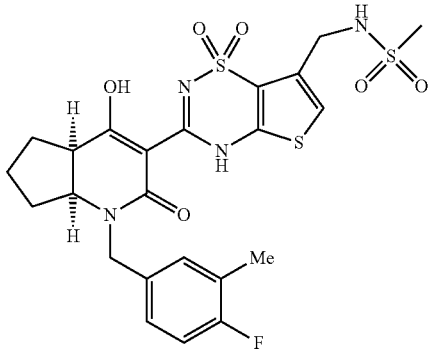

(4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (yellow oil; 134.1 mg, 0.236 mmol, 45.6% over 3 steps) was prepared as described in general procedure 13. ¹H NMR (400 MHz, DMSO-$d_6$) δ: 1.45-1.63 (3H, m), 1.93-2.08 (3H, m), 2.23 (3H, s), 2.96 (3H, s), 3.79-3.89 (1H, m), 4.25 (2H, d, J=6.2 Hz), 4.39 (1H, d, J=15.0 Hz), 4.88 (1H, d, J=14.5 Hz), 7.06-7.11 (1H, m), 7.16-7.20 (1H, m), 7.24 (1H, d, J=6.3 Hz), 7.29 (1H, bs), 7.67 (1H, t, J=6.3 Hz). LC-MS (ESI) calculated for $C_{23}H_{25}FN_4O_6S_3$ 568.09. found 569.0 [M+H⁺].

Example 127

(4aR,7S)-N-[3-(4-Hydroxy-2-oxo-1-thiophen-3-ylmethyl-2,4-a,5,6,7,7a-hexahydro-1H-[1]pyrindin-3-yl)-1,1-dioxo-1,4-dihydro-1λ⁶-thieno[2,3-e][1,2,4]thiadiazin-7-ylmethyl]-methanesulfonamide

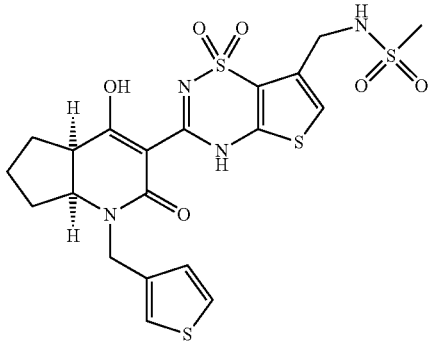

(4aR,7aS)-N-[3-(4-Hydroxy-2-oxo-1-thiophen-3-ylmethyl-2,4a,5,6,7,7a-hexahydro-1H-[1]pyrindin-3-yl)-1,1-dioxo-1,4-dihydro-1λ⁶-thieno[2,3-e][1,2,4]thiadiazin-7-ylmethyl]-methanesulfonamide (yellow oil; 105.9 mg, 0.195 mmol, 37.7% over 3 steps) was prepared as described in general procedure 13. ¹H NMR (400 MHz, DMSO-$d_6$) δ: 1.42-1.62 (3H, m), 1.93-2.08 (3H, m), 2.96 (3H, s), 3.85-3.91 (1H, m), 4.25 (2H, d, J=5.2 Hz), 4.47 (1H, d, J=15.0 Hz), 4.87 (1H, d, J=15.7 Hz), 7.10 (1H, d, J=4.8 Hz), 7.29 (1H, bs), 7.46 (1H, bs), 7.50-7.51 (1H, m), 7.67 (1H, t, J=6.2 Hz). LC-MS (ESI) calculated for $C_{20}H_{22}N_4O_6S_4$ 542.04. found 543.0 [M+H⁺].

Example 128

(4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide

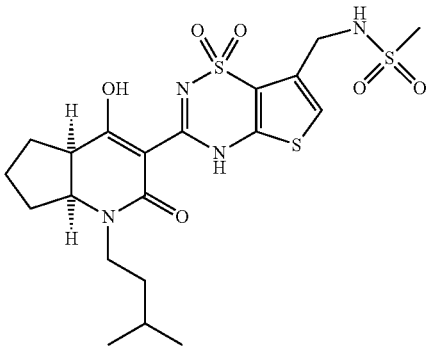

(4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (yellow oil; 45.9 mg, 0.089 mmol, 17.2% over 3 steps) was prepared as described in general procedure 13. ¹H NMR (400 MHz, DMSO-$d_6$) δ: 0.92 (3H, s), 0.93 (3H, s), 1.38-1.68 (6H, m), 1.94-2.06 (1H, m), 2.09-2.22 (2H, m), 2.96 (3H, s), 3.16-3.30 (1H, m), 3.61-3.73 (1H, m), 3.87-3.97 (1H, m), 4.24 (2H, d, J=5.4 Hz), 7.27 (1H, bs), 7.66 (1H, t, J=6.3 Hz). LC-MS (ESI) calculated for $C_{20}H_{28}N_4O_6S_3$ 516.12. found 517.0 [M+H⁺].

Example 129

(4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide

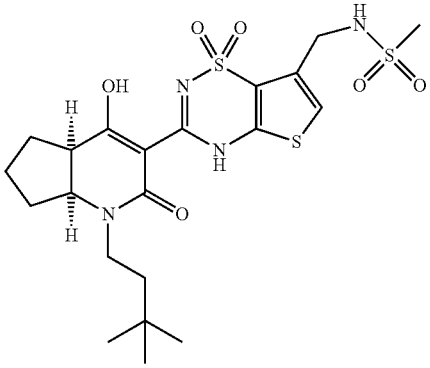

(4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ⁶-thieno[2,3-e][1,2,4]thiadiazin-7-ylmethyl}-methanesulfonamide (yellow oil; 78.8 mg, 0.149 mmol, 28.7% over 3 steps) was prepared as described in general procedure 13. $^1$H NMR (400 MHz, DMSO-$d_6$) δ: 0.95 (9H, s), 1.38-1.67 (5H, m), 2.12-2.19 (2H, m), 2.96 (3H, s), 3.06-3.31 (2H, m), 3.60-3.70 (1H, m), 3.85-3.93 (1H, m), 4.24 (2H, d, J=6.1 Hz), 7.28 (1H, bs), 7.66 (1H, t, J=5.8 Hz). LC-MS (ESI) calculated for $C_{21}H_{30}N_4O_6S_3$ 530.13. found 531.0 [M+H$^+$].

General Procedure 14:

cis-2-Amino-cyclohexanecarboxylic acid ethyl ester hydrochloride (100 mg, 0.483 mmol) was dissolved in methanol (10 mL). Sodium acetate (2 eq., 79 mg, 0.966 mmol) was added followed by an aldehyde (1 eq., 0.483 mmol). Sodium cyanoborohydride (2 eq., 61 mg, 0.966 mmol) was added and the mixtures were agitated at 25° C. for 16 h. The solvent was removed in vacuo (Savant SpeedVac), a 1.0 M aqueous solution of sodium hydroxide (2 mL) was added to the residues and the resulting solutions were extracted with diethyl ether (2×5 mL). The organic layers were dried over sodium sulfate, filtered and concentrated in vacuo to afford the crude N-substituted cis-2-amino-cyclohexanecarboxylic acid ethyl ester intermediates, which were used without further purification.

The crude N-substituted cis-2-amino-cyclohexanecarboxylic acid ethyl ester intermediates (1 eq.) were dissolved in anhydrous N,N-dimethylformamide (2 mL). [7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 1 eq., 171 mg, 0.483 mmol) was added followed by 1-(3-dimethylaminopropyl)-3-ethylcarbodiimide hydrochloride (1.5 eq., 139 mg, 0.725 mmol). The mixtures were agitated at 25° C. for 6 h. The mixtures were concentrated in vacuo and the crude residues were dissolved in ethanol (4 mL). A 21 wt. % solution of sodium ethoxide in ethanol (4 eq., 721 µL, 1.932 mmol) was added into the above solutions. The mixtures were agitated at 60° C. for 16 h and allowed to cool to 25° C. The mixtures were concentrated in vacuo and the residues were dissolved in dichloromethane (2 mL) and extracted with a 1.0 M aqueous hydrochloric acid solution (2 mL). The organic layers were dried over sodium sulfate, filtered and purified by flash column chromatography (Teledyne Isco RediSep Column; 20-100% ethyl acetate in hexanes) to afford the desired final products.

Example 130

(rac-cis)-N-[3-(1-Benzyl-4-hydroxy-2-oxo-1,2,4a,5,6,7,8,8a-octahydro-quinolin-3-yl)-1,1-dioxo-1,4-dihydro-1λ⁶-thieno[2,3-e][1,2,4]thiadiazin-7-ylmethyl]-methanesulfonamide

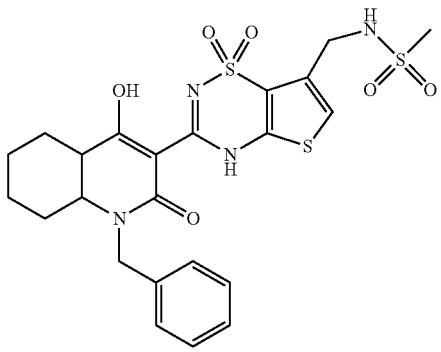

(rac-cis)-N-[3-(1-Benzyl-4-hydroxy-2-oxo-1,2,4a,5,6,7,8,8a-octahydro-quinolin-3-yl)-1,1-dioxo-1,4-dihydro-1λ⁶-thieno[2,3-e][1,2,4]thiadiazin-7-ylmethyl]-methanesulfonamide (yellow oil; 7.7 mg, 0.014 mmol, 2.9% over 3 steps) was prepared as described in general procedure 14. $^1$H NMR (400 MHz, DMSO-$d_6$) δ: 1.07-1.29 (3H, m), 1.31-1.55 (3H, m), 1.56-1.68 (1H, m), 1.77-1.84 (1H, m), 2.24-2.34 (1H, m), 2.96 (3H, s), 3.48-3.63 (1H, m), 4.25 (2H, d, J=6.2 Hz), 4.32 (1H, d, J=15.5 Hz), 5.03 (1H, d, J=15.4 Hz), 7.23-7.30 (2H, m), 7.32-7.38 (4H, m), 7.65 (1H, t, J=6.2 Hz). LC-MS (ESI) calculated for $C_{23}H_{26}N_4O_6S_3$ 550.1. found 551.1 [M+H$^+$].

Example 131

(rac-cis)-N-{3-[1-(4-Fluoro-3-methyl-benzyl)-4-hydroxy-2-oxo-1,2,4a,5,6,7,8,8a-octahydro-quinolin-3-yl]-1,1-dioxo-1,4-dihydro-1λ⁶-thieno[2,3-e][1,2,4]thiadiazin-7-ylmethyl]-methanesulfonamide

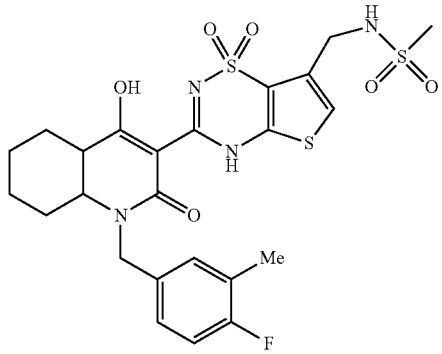

(rac-cis)-N-{3-[1-(4-Fluoro-3-methyl-benzyl)-4-hydroxy-2-oxo-1,2,4a,5,6,7,8,8a-octahydro-quinolin-3-yl]-1,1-dioxo-1,4-dihydro-1λ⁶-thieno[2,3-e][1,2,4]thiadiazin-7-ylmethyl}-methanesulfonamide (yellow oil; 83.0 mg, 0.143 mmol, 29.5% over 3 steps) was prepared as described in general procedure 14. $^1$H NMR (400 MHz, DMSO-$d_6$) δ: 1.07-1.29 (3H, m), 1.33-1.53 (3H, m), 1.62-1.70 (1H, m), 1.75-1.81 (1H, m), 2.08 (3H, s), 2.25-2.33 (1H, m), 2.96 (3H, s), 3.55 (1H, bs), 4.24-4.26 (3H, m), 4.98 (1H, d, J=15.8 Hz), 7.06-7.11 (1H, m), 7.19-7.22 (1H, m), 7.25-7.27 (2H, m), 7.66 (1H, t, J=6.2 Hz). LC-MS (ESI) calculated for $C_{24}H_{27}FN_4O_6S_3$ 582.11. found 583.0 [M+H$^+$].

Example 132

(rac-cis)-N-{3-[4-Hydroxy-1-(3-methyl-butyl)-2-oxo-1,2,4a,5,6,7,8,8a-octahydro-quinolin-3-yl]-1,1-dioxo-1,4-dihydro-1λ⁶-thieno[2,3-e][1,2,4]thiadiazin-7-ylmethyl}-methanesulfonamide

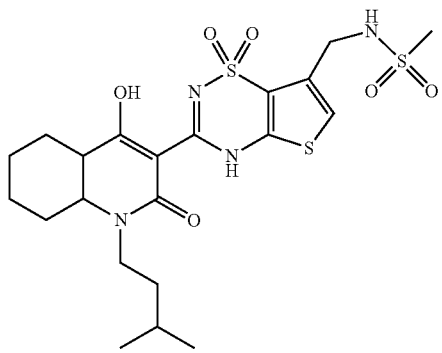

(rac-cis)-N-{3-[4-Hydroxy-1-(3-methyl-butyl)-2-oxo-1,2, 4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide (yellow oil; 8.9 mg, 0.017 mmol, 3.5% over 3 steps) was prepared as described in general procedure 14. $^1$H NMR (400 MHz, DMSO-$d_6$) δ: 0.92 (3H, s), 0.94 (3H, s), 1.03-1.72 (8H, m), 1.76-1.90 (1H, m), 2.24-2.38 (1H, m), 2.96 (3H, s), 2.96-3.15 (1H, m), 3.50-3.68 (1H, m), 3.78-3.86 (1H, m), 4.24 (2H, d, J=6.4 Hz), 7.23 (1H, bs), 7.64 (1H, t, J=6.4 Hz). LC-MS (ESI) calculated for $C_{21}H_{30}N_4O_6S_3$ 530.13. found 531.0 [M+H$^+$].

Example 133

(rac-cis)-N-{3-[1-(3,3-Dimethyl-butyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide

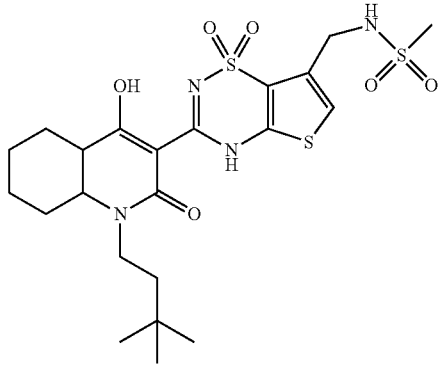

(rac-cis)-N-{3-[1-(3,3-Dimethyl-butyl)-4-hydroxy-2-oxo-1, 2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide (yellow oil; 5.0 mg, 0.009 mmol, 1.9% over 3 steps) was prepared as described in general procedure 14. $^1$H NMR (400 MHz, DMSO-$d_6$) δ: 0.95 (9H, s), 1.04-1.61 (8H, m), 1.61-1.71 (1H, m), 1.78-1.91 (1H, m), 2.25-2.36 (1H, m), 2.96 (3H, s), 3.00-3.15 (1H, m), 3.51-3.65 (1H, m), 3.74-3.85 (1H, m), 4.24 (2H, d, J=6.1 Hz), 7.22 (1H, bs), 7.63 (1H, t, J=6.4 Hz). LC-MS (ESI) calculated for $C_{22}H_{32}N_4O_6S_3$ 544.15. found 545.3 [M+H$^+$].

Example 134

(rac-cis)-N-{3-[1-(3,4-Difluoro-benzyl)-4-hydroxy-2-oxo-1,2,4a 5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide

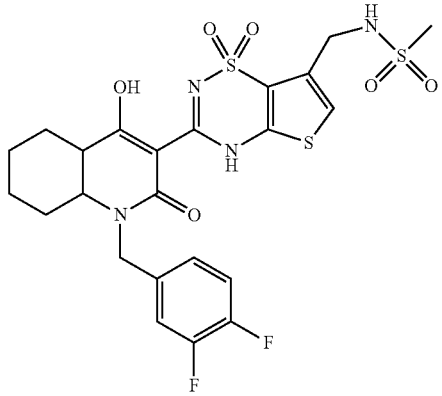

(rac-cis)-N-{3-[1-(3,4-Difluoro-benzyl)-4-hydroxy-2-oxo-1,2,4a,5,6,7,8,8a-octahydro-quinolin-3-yl]-1,1-dioxo-1,4-dihydro-1$\lambda^6$-thieno[2,3-e][1,2,4]thiadiazin-7-ylmethyl}-methanesulfonamide (yellow oil; 96.1 mg, 0.164 mmol, 33.9% over 3 steps) was prepared as described in general procedure 14. $^1$H NMR (400 MHz, DMSO-$d_6$) δ: 1.26-1.65 (4H, m), 1.68-2.20 (2H, m), 2.95 (3H, s), 2.98-3.12 (1H, m), 3.32-3.38 (1H, m), 3.66-3.90 (1H, m), 3.95-4.14 (1H, m), 4.18-4.36 (1H, m), 4.64-4.69 (2H, m), 4.97 (1H, d, J=15.7 Hz), 7.00-7.09 (1H, m), 7.17-7.47 (2H, m), 7.58-7.65 (1H, m), 12.94 (1H, bs). LC-MS (ESI) calculated for $C_{23}H_{24}F_2N_4O_6S_3$ 586.08. found 587.0 [M+H$^+$].

Example 135

(rac-cis)-N-[3-(4-Hydroxy-2-oxo-1-thiophen-3-ylmethyl-1,2,4a,5,6,7,8,8a-octahydro-quinolin-3-yl)-1,1-dioxo-1,4-dihydro-1$\lambda^6$-thieno[2,3-e][1,2,4]thiadiazin-7-ylmethyl]-methanesulfonamide

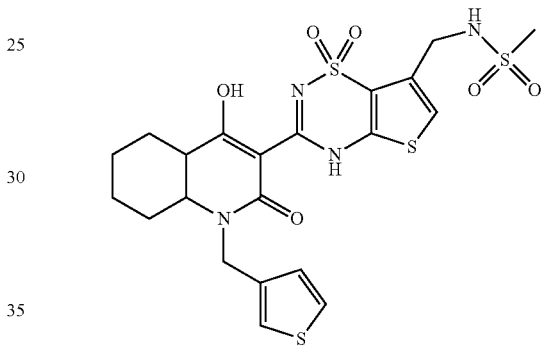

(rac-cis)-N-[3-(4-Hydroxy-2-oxo-1-thiophen-3-ylmethyl-1, 2,4a,5,6,7,8,8a-octahydro-quinolin-3-yl)-1,1-dioxo-1,4-dihydro-1$\lambda^6$-thieno[2,3-e][1,2,4]thiadiazin-7-ylmethyl]-methanesulfonamide (yellow oil; 107.1 mg, 0.193 mmol, 39.9% over 3 steps) was prepared as described in general procedure 14. $^1$H NMR (400 MHz, DMSO-$d_6$) δ: 1.01-2.19 (6H, m), 2.96 (3H, s), 2.99-3.09 (1H, m), 3.39-3.79 (1H, m), 3.83-4.33 (2H, m), 4.60-4.69 (3H, m), 6.94-7.37 (3H, m), 7.54-7.65 (2H, m), 12.94 (1H, bs). LC-MS (ESI) calculated for $C_{21}H_{24}N_4O_6S_4$ 556.06. found 557.0 [M+H$^+$].

General Procedure 15:

cis-2-Amino-cycloheptanecarboxylic acid methyl ester hydrochloride (100 mg, 0.483 mmol) was dissolved in methanol (10 mL). Sodium acetate (2 eq., 79 mg, 0.966 mmol) was added followed by an aldehyde (1 eq., 0.483 mmol). Sodium cyanoborohydride (2 eq., 61 mg, 0.966 mmol) was added and the mixtures were agitated at 25° C. for 16 h. The solvent was removed in vacuo (Savant SpeedVac), a 1.0 M aqueous solution of sodium hydroxide (2 mL) was added to the residues and the resulting solutions were extracted with diethyl ether (2×5 mL). The organic layers were dried over sodium sulfate, filtered and concentrated in vacuo to afford the crude N-substituted cis-2-amino-cycloheptanecarboxylic acid methyl ester intermediates, which were used without further purification.

The crude N-substituted cis-2-amino-cycloheptanecarboxylic acid methyl ester intermediates (1 eq.) were dissolved in anhydrous N,N-dimethylformamide (2 mL). [7-(Methanesulfonylamino-methyl)-1,1-dioxo-1,4-dihydro-1λ⁶-thieno[2,3-e][1,2,4]thiadiazin-3-yl]-acetic acid (prepared as described in Example 2c; 1 eq., 171 mg, 0.483 mmol) was added followed by 1-(3-dimethylaminopropyl)-3-ethylcarbodiimide hydrochloride (1.5 eq., 139 mg, 0.725 mmol). The mixtures were agitated at 25° C. for 6 h. The mixtures were concentrated in vacuo and the crude residues were dissolved in ethanol (4 mL). A 21 wt. % solution of sodium ethoxide in ethanol (4 eq., 721 µL, 1.932 mmol) was added into the above solutions. The mixtures were agitated at 60° C. for 16 h and allowed to cool to 25° C. The mixtures were concentrated in vacuo and the residues were dissolved in dichloromethane (2 mL) and extracted with a 1.0 M aqueous hydrochloric acid solution (2 mL). The organic layers were dried over sodium sulfate, filtered and purified by flash column chromatography (Teledyne Isco RediSep Column; 20-100% ethyl acetate in hexanes) to afford the desired final products.

Example 136

(rac-cis)-N-[3-(1-Benzyl-4-hydroxy-2-oxo-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl]-methanesulfonamide

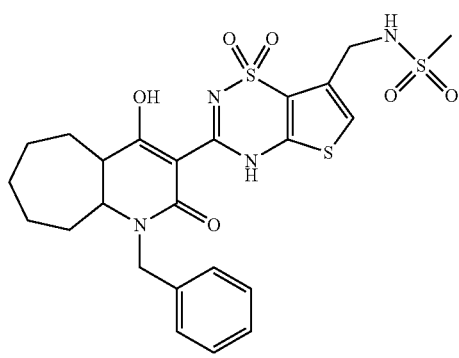

(rac-cis)-N-[3-(1-Benzyl-4-hydroxy-2-oxo-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl]-methanesulfonamide (yellow oil; 4.3 mg, 0.008 mmol, 1.6% over 3 steps) was prepared as described in general procedure 15. ¹H NMR (400 MHz, DMSO-d₆) δ: 1.21-1.48 (4H, m), 1.55-1.84 (6H, m), 1.89-2.02 (1H, m), 2.96 (3H, s), 3.52-3.61 (1H, m), 4.24-4.28 (3H, m), 5.06 (1H, d, J=15.5 Hz), 7.20-7.30 (2H, m), 7.32-7.35 (4H, m), 7.64 (1H, t, J=6.0 Hz). LC-MS (ESI) calculated for C₂₄H₂₈N₄O₆S₃ 564.12. found 565.3 [M+H⁺].

Example 137

(rac-cis)-N-{3-[1-(3,4-Difluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide

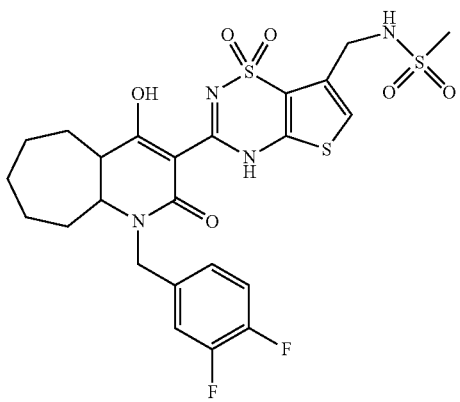

(rac-cis)-N-{3-[1-(3,4-Difluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide (yellow oil; 7.0 mg, 0.012 mmol, 2.4% over 3 steps) was prepared as described in general procedure 15. ¹H NMR (400 MHz, DMSO-d₆) δ: 1.21-1.43 (4H, m), 1.57-1.77 (8H, m), 1.91-2.00 (1H, m), 2.94 (3H, s), 3.43 (1H, bs), 4.13 (1H, d, J=15.5 Hz), 4.23 (2H, d, J=5.4 Hz), 4.99 (1H, d, J=14.9 Hz), 7.01-7.13 (1H, m), 7.15-7.22 (1H, m), 7.33-7.42 (2H, m), 7.54-7.58 (1H, m). LC-MS (ESI) calculated for C₂₄H₂₆F₂N₄O₆S₃ 600.1. found 600.9 [M+H⁺].

Example 138

(rac-cis)-N-{3-[4-Hydroxy-1-(3-methyl-butyl)-2-oxo-2,4-a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide

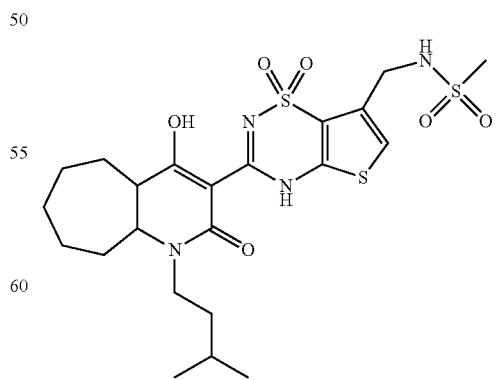

(rac-cis)-N-{3-[4-Hydroxy-1-(3-methyl-butyl)-2-oxo-2,4a,5,6,7,8,9,9a-octahydro-1H-cyclohepta[b]pyridin-3-yl]-1,1- dioxo-1,4-dihydro-1λ⁶-thieno[2,3-e][1,2,4]thiadiazin-7-ylmethyl}-methanesulfonamide (yellow oil; 2.6 mg, 0.005 mmol, 1.0% over 3 steps) was prepared as described in general procedure 15. ¹H NMR (400 MHz, DMSO-d₆) δ: 0.92 (3H, s), 0.94 (3H, s), 1.20-1.87 (13H, m), 1.93-2.03 (1H, m), 2.95 (3H, s), 3.60 (1H, bs), 3.83-3.90 (1H, m), 4.23 (2H, d, J=6.2 Hz), 7.20 (1H, bs), 7.62 (1H, t, J=5.5 Hz). LC-MS (ESI) calculated for $C_{22}H_{32}N_4O_6S_3$ 544.15. found 545.3 [M+H⁺].

Example 139

(rac-cis)-N-{3-[1-(4-Fluoro-3-methyl-benzyl)-4-hydroxy-2-oxo-2,4a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide

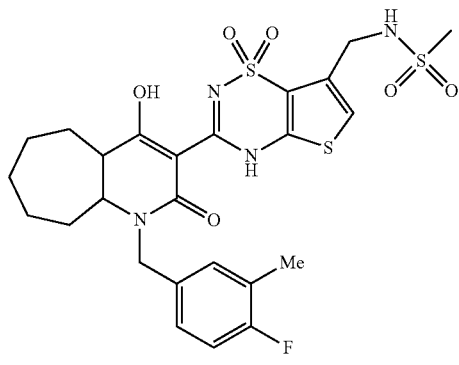

(rac-cis)-N-{3-[1-(4-Fluoro-3-methyl-benzyl)-4-hydroxy-2-oxo-2,4a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide (yellow oil; 5.0 mg, 0.008 mmol, 1.7% over 3 steps) was prepared as described in general procedure 15. ¹H NMR (400 MHz, DMSO-d₆) δ: 1.14-1.75 (10H, m), 1.90-2.01 (1H, m), 2.22 (3H, s), 2.94 (3H, s), 4.01-4.14 (1H, m), 4.23 (2H, d, J=5.4 Hz), 5.01 (1H, d, J=14.8 Hz), 7.04-7.10 (2H, m), 7.14-7.22 (2H, m), 7.48-7.56 (1H, m). LC-MS (ESI) calculated for $C_{25}H_{29}FN_4O_6S_3$ 596.12. found 597.3 [M+H⁺].

Example 140

(rac-cis)-N-{3-[4-Hydroxy-2-oxo-1-(3,4,5-trifluoro-benzyl)-2,4a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide

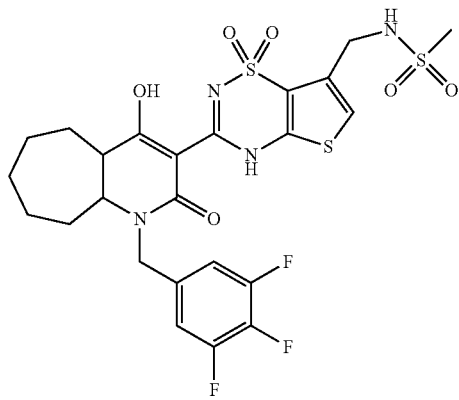

(rac-cis)-N-{3-[4-Hydroxy-2-oxo-1-(3,4,5-trifluoro-benzyl)-2,4a,5,6,7,8,9,9a-octahydro-1H-cyclohepta[b]pyridin-3-yl]-1,1-dioxo-1,4-dihydro-1λ⁶-thieno[2,3-e][1,2,4]thiadiazin-7-ylmethyl}-methanesulfonamide (yellow oil; 12.2 mg, 0.020 mmol, 4.1% over 3 steps) was prepared as described in general procedure 15. ¹H NMR (400 MHz, DMSO-d₆) δ: 1.20-1.83 (10H, m), 1.90-2.02 (1H, m), 2.94 (3H, s), 3.47-3.58 (1H, m), 4.15 (1H, d, J=15.8 Hz), 4.23 (2H, d, J=6.3 Hz), 4.99 (1H, d, J=15.5 Hz), 7.16 (1H, bs), 7.27-7.31 (2H, m), 7.55-7.63 (1H, m). LC-MS (ESI) calculated for $C_{24}H_{25}F_3N_4O_6S_3$ 618.09. found 619.3 [M+H⁺].

Example 141

(rac-cis)-N-[3-(4-Hydroxy-2-oxo-1-thiophen-3-ylmethyl-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl}-methanesulfonamide

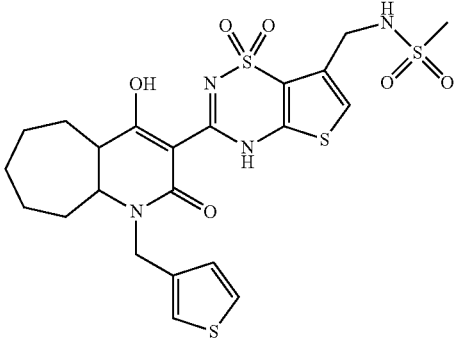

(rac-cis)-N-[3-(4-Hydroxy-2-oxo-1-thiophen-3-ylmethyl-2,4a,5,6,7,8,9,9a-octahydro-1H-cyclohepta[b]pyridin-3-yl)-1,1-dioxo-1,4-dihydro-1λ⁶-thieno[2,3-e][1,2,4]thiadiazin-7-ylmethyl]-methanesulfonamide (off-white solid; 3.9 mg, 0.007 mmol, 1.4% over 3 steps) was prepared as described in general procedure 15. ¹H NMR (400 MHz, DMSO-d₆) δ: 1.15-1.76 (10H, m), 1.90-2.00 (1H, m), 2.94 (3H, s), 2.97-2.99 (1H, m), 4.08-4.20 (1H, m), 4.24 (2H, d, J=6.2 Hz), 4.97 (1H, d, J=14.6 Hz), 7.03-7.08 (1H, m), 7.40 (1H, bs), 7.46-7.49 (1H, m), 7.49-7.54 (2H, m). LC-MS (ESI) calculated for $C_{22}H_{26}N_4O_6S_4$ 570.07. found 571.0 [M+H⁺].

Example 142

(rac-di-exo)-N-{3-[3-(4-Fluoro-benzyl)-6-hydroxy-4-oxo-3-aza-tricyclo[6.3.2.0²,⁷]tridec-5-en-5-yl]-1,1-dioxo-1,4-dihydro-1λ⁶-thieno[2,3-e][1,2,4]thiadiazin-7-ylmethyl}-methanesulfonamide

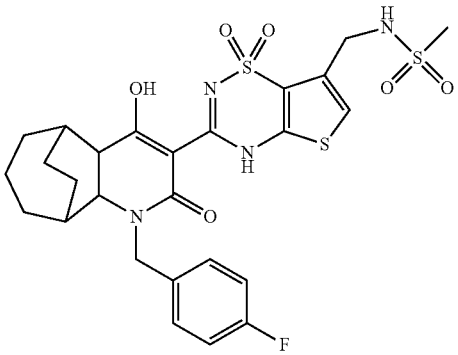

a) (di-exo)-4-Oxa-tricyclo[5.3.2.0²,⁶]dodec-11-ene-3,5-dione

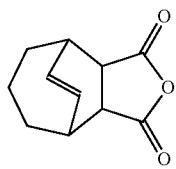

1,3-Cycloheptadiene (5 g, 53.1 mmol) and maleic anhydride (4.73 g, 48.3 mmol) were combined in benzene (7 mL). A trace amount of hydroquinone (~1 mg) was added and the mixture was heated in a sealed tube at 150° C. for 18 h. Upon cooling, the mixture was concentrated in vacuo to afford the crude product, (di-exo)-4-oxa-tricyclo[5.3.2.0²,⁶]dodec-11-ene-3,5-dione (9.25 g, 48.1 mmol, 99%) as a white solid which was used directly in the next step without further purification.

b) (rac-di-exo)-Bicyclo[3.2.2]non-8-ene-6,7-dicarboxylic acid monomethyl ester

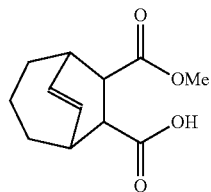

(di-exo)-4-Oxa-tricyclo[5.3.2.0²,⁶]dodec-11-ene-3,5-dione (5 g, 26.01 mmol) was suspended in methanol (200 mL) and stirred at 25° C. for 2 h. The mixture was heated to reflux for 1 min. Upon cooling, the remaining solids were removed by vacuum filtration and discarded. The resulting solution was stirred at 25° C. for 10 days. The mixture was concentrated in vacuo to afford the desired product, (rac-di-exo)-bicyclo[3.2.2]non-8-ene-6,7-dicarboxylic acid monomethyl ester (5.2 g, 23.2 mmol, 89%) as a thick oil which was used directly in the next step without further purification or characterization.

c) (rac-di-exo)-7-Benzyloxycarbonylamino-bicyclo[3.2.2]non-8-ene-6-carboxylic acid methyl ester

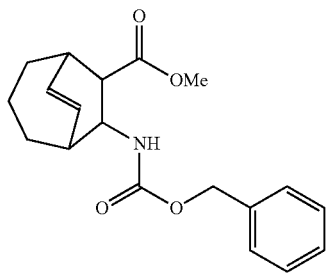

(rac-di-exo)-Bicyclo[3.2.2]non-8-ene-6,7-dicarboxylic acid monomethyl ester (5.2 g, 23.2 mmol) was dissolved in d product, (rac-di-exo)-7-benzyloxycarbonylamino-bicyclo[3.2.2]non-8-ene-6-carboxylic acid methyl ester (2.55 g, 7.74 mmol, 33%) as a white solid. LC-MS (ESI) calculated for $C_{19}H_{23}NO_4$ 329.16. found 330.1 [M+H⁺].

d) (rac-di-exo)-7-Amino-bicyclo[3.2.2]nonane-6-carboxylic acid methyl ester hydrochloride

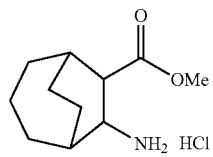

(rac-di-exo)-7-Benzyloxycarbonylamino-bicyclo[3.2.2]non-8-ene-6-carboxylic acid methyl ester (2.55 g, 7.74 mmol) was dissolved in ethyl acetate (150 mL). 10% Palladium on carbon (0.5 g) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (20 mL) and with vigorous stirring, a 1.0 M solution of hydrochloric acid in diethyl ether (20 mL, 20 mmol) was added dropwise. The resulting suspension was concentrated in vacuo to afford the desired product, (rac-di-exo)-7-amino-bicyclo[3.2.2]nonane-6-carboxylic acid methyl ester hydrochloride (1.45 g, 6.2 mmol, 80%) as a brittle foam. LC-MS (ESI) calculated for $C_{11}H_{19}NO_2$ (free amine) 197.14. found 198.2 [M+H⁺].

e) (rac-di-exo)-7-(4-Fluoro-benzylamino)-bicyclo[3.2.2]nonane-6-carboxylic acid methyl ester

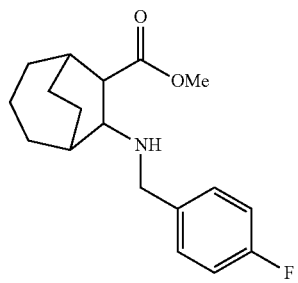

(rac-di-exo)-7-Amino-bicyclo[3.2.2]nonane-6-carboxylic acid methyl ester (0.4 g, 1.71 mmol) was dissolved in methyl alcohol (19 mL). Sodium acetate (0.28 g, 3.42 mmol) was added followed by 4-fluoro benzaldehyde (0.212 g, 1.71 mmol). The mixture was shaken for 15 min. at 25° C. Sodium cyanoborohydride (0.215 g, 3.42 mmol) was added and the mixture was shaken at 25° C. for 16 h. Saturated aqueous sodium bicarbonate solution (10 mL) was added and the mixture was shaken for 1 h. The resulting suspension was partitioned between ethyl acetate (40 mL) and saturated aqueous sodium bicarbonate solution (20 mL). The organic phase was dried over magnesium sulfate, filtered, and concentrated in vacuo to afford the desired product, (rac-di-exo)-7-(4-fluoro-benzylamino)-bicyclo[3.2.2]nonane-6-carboxylic acid methyl ester (0.22 g, 0.72 mmol, 42%) as a clear oil. LC-MS (ESI) calculated for $C_{18}H_{24}FNO_2$ 305.18. found 306.2 [M+H$^+$].

f) (rac-di-exo)-N-{3-[3-(4-Fluoro-benzyl)-6-hydroxy-4-oxo-3-aza-tricyclo[6.3.2.0$^{2,7}$]tridec-5-en-5-yl]-1,1-dioxo-1,4-dihydro-1λ$^6$-thieno[2,3-e][1,2,4]thiadiazin-7-ylmethyl}-methanesulfonamide

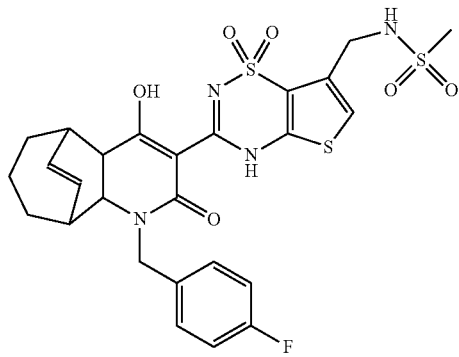

(rac-di-exo)-7-(4-Fluoro-benzylamino)-bicyclo[3.2.2]nonane-6-carboxylic acid methyl ester (0.15 g, 0.491 mmol) was dissolved in N,N-dimethylformamide (4 mL). [7-(Methanesulfonylamino-methyl)-1,1-dioxo-1,4-dihydro-1λ$^6$-thieno[2,3-e][1,2,4]thiadiazin-3-yl]-acetic acid (prepared as described in Example 2c; 0.174 g, 0.491 mmol) was added followed by 1-(3-dimethylaminopropyl)-3-ethylcarbodiimide hydrochloride (0.142 g, 0.737 mmol. The mixture was shaken at 25° C. for 5 h. Triethylamine (1.1 mL, 3.9 mmol) was added and the mixture was shaken for at 75° C. for 16 h.

Upon cooling to 25° C., the mixture was concentrated in vacuo to afford a thick oil. The oil was partitioned between dichloromethane (4 mL) and 1.0 M aqueous hydrochloric acid solution (6 mL). The organic phase was further washed with 1.0 M aqueous hydrochloric acid solution (2 mL). The organic phase was purified by flash column chromatography (Teledyne Isco RediSep Column; 5-100% ethyl acetate in hexanes) to afford the desired product, (rac-di-exo)-N-{3-[3-(4-Fluoro-benzyl)-6-hydroxy-4-oxo-3-aza-tricyclo[6.3.2.0$^{2,7}$]tridec-5-en-5-yl]-1,1-dioxo-1,4-dihydro-1λ$^6$-thieno[2,3-e][1,2,4]thiadiazin-7-ylmethyl}-methanesulfonamide (0.014 g, 0.023 mmol, 4.7% yield) as an off-white powder. $^1$H NMR (400 MHz, DMSO-d$_6$) δ: 1.49-1.79 (10H, m), 1.79-1.87 (1H, m), 1.96-2.04 (1H, m), 2.56-2.64 (1H, m), 2.95 (3H, s), 3.77 (1H, d, J=10.1 Hz), 4.15 (1H, d, J=15.7 Hz), 4.24 (2H, d, J=5.5 Hz), 5.07 (1H, d, J=15.8 Hz), 7.14 (2H, t, J=8.4 Hz), 7.21 (1H, s), 7.34 (2H, dd, J$_1$=8.3 Hz, J$_2$=5.7 Hz), 7.58-7.63 (1H, m). LC-MS (ESI) calculated for $C_{26}H_{29}FN_4O_6S_3$ 608.12. found 609.2 [M+H$^+$].

Biological Testing

The ability of compounds of the invention to inhibit HCV replication was demonstrated in the following in vitro assays.

Luciferase-Based HCV Replicon Assay Protocol (EC$_{50}$ (1b))

The cell culture component of the assay was performed essentially as described by Bartenschlager et al., *Hepatology* 2002, 35, 694-703, wherein exponentially growing HCV Huh-luc/neo-ET replicon cells were seeded at 6×10$^3$ cells/well in 96 well assay plate. 24 hours later the cells were treated with various concentrations of compound in triplicate. After 72 hours exposure to the compound, the luciferase activity in the wells was determined using Bright-Glo reagent (Promega, Madison, Wis.) with a luminometer (Wallac 1420 Multilabel HTS Counter Victor 2). The background control was replicon cells treated with 100 nM BILN-2061, an inhibitor of the HCV protease. % Inhibition was determined for each compound concentration in relation to the negative (no compound) control to calculate the EC$_{50}$ (1b).

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention.

Test results (EC$_{50}$ (1b) values) for compounds of Formula I are summarized in Table 1, wherein +++++ means HCV replicon inhibition with EC$_{50}$ (1b) values less than or equal to 0.005 μM, ++++ means EC$_{50}$ (1b) values between 0.005 μM and 0.02 μM, +++ means EC$_{50}$ (1b) values between 0.02 μM and 0.1 μM, ++ means EC$_{50}$ (1b) values between 0.1 μM and 1 μM, and + means EC$_{50}$ (1b) values greater than 1 μM.

TABLE 1

| Example # | EC$_{50}$ (1b) |
|---|---|
| 1 | +++++ |
| 2 | ++++ |
| 3 | ++ |
| 4 | ++ |
| 5 | ++ |
| 6 | ++ |
| 7 | ++ |
| 8 | +++ |
| 9 | ++ |
| 10 | ++ |
| 11 | + |
| 12 | + |
| 13 | ++ |
| 14 | ++++ |
| 15 | ++ |
| 16 | +++ |
| 17 | ++ |
| 18 | ++ |
| 19 | ++ |
| 20 | ++ |
| 21 | ++ |
| 22 | +++++ |
| 23 | +++++ |
| 24 | +++++ |
| 25 | +++++ |
| 26 | +++ |
| 27 | + |
| 28 | ++ |
| 29 | ++++ |
| 30 | +++ |
| 31 | + |
| 32 | +++++ |
| 33 | ++++ |
| 34 | ++ |
| 35 | ++++ |
| 36 | +++++ |
| 37 | ++++ |
| 38 | ++++ |
| 39 | ++++ |
| 40 | +++ |
| 41 | ++++ |
| 42 | ++ |
| 43 | +++ |
| 44 | +++++ |
| 45 | +++ |
| 46 | +++++ |
| 47 | +++++ |

TABLE 1-continued

| Example # | EC$_{50}$ (1b) |
|---|---|
| 48 | +++++ |
| 49 | +++ |
| 50 | +++++ |
| 51 | +++ |
| 52 | +++++ |
| 53 | ++++ |
| 54 | ++++ |
| 55 | +++++ |
| 56 | +++ |
| 57 | ++++ |
| 58 | ++++ |
| 59 | +++ |
| 60 | +++++ |
| 61 | +++ |
| 62 | ++++ |
| 63 | +++ |
| 64 | +++++ |
| 65 | +++++ |
| 66 | ++++ |
| 67 | ++++ |
| 68 | ++++ |
| 69 | +++ |
| 70 | +++++ |
| 71 | ++++ |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | +++++ |
| 89 | +++++ |
| 90 | ++++ |
| 91 | +++++ |
| 92 | +++++ |
| 93 | +++++ |
| 94 | +++ |
| 95 | +++ |
| 96 | +++ |
| 97 | ++ |
| 98 | ++ |
| 99 | ++ |
| 100 | ++ |
| 101 | +++ |
| 102 | +++ |
| 103 | +++ |
| 104 | ++ |
| 105 | ++ |
| 106 | ++++ |
| 107 | +++ |
| 108 | ++++ |
| 109 | ++++ |
| 110 | ++++ |
| 111 | ++ |
| 112 | +++ |
| 113 | +++ |
| 114 | ++ |
| 115 | ++ |
| 116 | +++ |
| 117 | ++ |
| 118 | ++ |
| 119 | ++ |
| 120 | +++ |
| 121 | + |
| 122 | + |
| 123 | ++ |
| 124 | ++++ |
| 125 | +++ |

TABLE 1-continued

| Example # | EC$_{50}$ (1b) |
|---|---|
| 126 | +++ |
| 127 | ++++ |
| 128 | +++ |
| 129 | ++++ |
| 130 | ++ |
| 131 | ++ |
| 132 | +++ |
| 133 | +++ |
| 134 | + |
| 135 | + |
| 136 | +++ |
| 137 | ++ |
| 138 | +++ |
| 139 | + |
| 140 | + |
| 141 | + |
| 142 | +++ |

What is claimed is:

1. A compound of Formula I that is:

(Formula I)

2. A method of making a compound of Formula I comprising:

(a) acylating an amide of Formula II with a chloride compound of Formula III to form an amide intermediate:

Formula II

Formula III (b) treating the amide intermediate obtained in step (a) with sodium hydroxide; and (c) obtaining the compound of Formula I by hydrolysing the product obtained in step (b) with hydrochloric acid

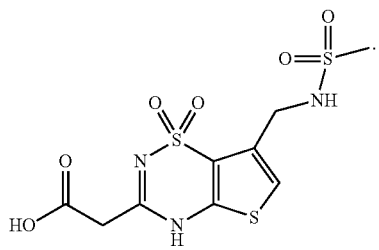

Formula I

3. The method according to claim 2, wherein the acylation of step (a) is carried out in tetrahydrofuran.

4. The method according to claim 3, wherein step (a) is conducted at a temperature of about 25° Celsius.

5. The method according to claim 2, wherein step (b) is conducted at a temperature of about 100° Celsius.

6. A method of making the compound of Formula I comprising:
  (a) reacting an amide of Formula II with an ester of Formula IV

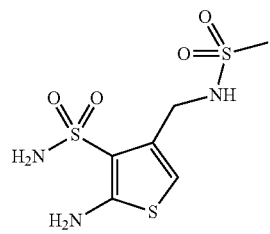

Formula II

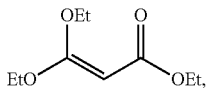

Formula IV followed by triethylamine, to form an ethyl ester of a cyclic intermediate;
  (b) hydrolysing the ester intermediate obtained in step (a) with lithium hydroxide; and
  (c) obtaining the compound of Formula I by treating the product obtained in step (b) with an aqueous hydrochloric acid solution

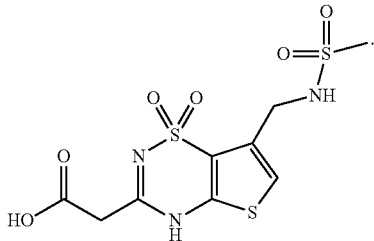

Formula I

7. The method according to claim 6, wherein the reaction of step (a) is carried out in dimethylformamide.

8. The method according to claim 7, wherein the reaction of step (a) is conducted at a temperature of about 70° Celsius.

9. The method according to claim 6, wherein the hydrolysis of step (b) is conducted at a temperature of about 25° Celsius.

10. The method according to claim 6, wherein step (c) is conducted at a temperature of about 0° Celsius.

* * * * *